(12) United States Patent
Hunter et al.

(10) Patent No.: US 6,846,841 B2
(45) Date of Patent: Jan. 25, 2005

(54) ANTI-ANGIOGENIC COMPOSITIONS AND METHODS OF USE

(75) Inventors: William L. Hunter, Vancouver (CA); Lindsay S. Machan, Vancouver (CA); A. Larry Arsenault, Paris (CA)

(73) Assignee: Angiotech Pharmaceuticals, Inc., Vancouver (CA)

( * ) Notice: Subject to any disclaimer, the term of this patent is extended or adjusted under 35 U.S.C. 154(b) by 0 days.

(21) Appl. No.: 10/112,921

(22) Filed: Mar. 28, 2002

(65) Prior Publication Data

US 2003/0004209 A1 Jan. 2, 2003

Related U.S. Application Data

(63) Continuation of application No. 09/013,765, filed on Jan. 27, 1998, now abandoned, which is a continuation of application No. 08/478,914, filed on Jun. 7, 1995, now Pat. No. 5,994, 341, which is a division of application No. 08/417,160, filed as application No. PCT/CA94/00373 on Jul. 19, 1994, now abandoned, which is a continuation-in-part of application No. 08/094,536, filed on Jul. 19, 1993, now abandoned.

(51) Int. Cl.[7] ............................................. A61K 31/335
(52) U.S. Cl. ....................... 514/449; 514/210; 514/250; 514/825; 514/826
(58) Field of Search .................................. 514/210, 250, 514/825, 826, 449; 424/424, 501, 502, 426

(56) References Cited

U.S. PATENT DOCUMENTS

| | | | |
|---|---|---|---|
| 4,542,025 A | 9/1985 | Tice et al. | 424/78 |
| 5,039,521 A | 8/1991 | Bolton et al. | 424/85.8 |
| 5,061,724 A | 10/1991 | Gertner | 514/420 |
| 5,171,217 A | 12/1992 | March et al. | 604/53 |
| 5,260,066 A | 11/1993 | Wood et al. | 424/447 |
| 5,362,831 A | 11/1994 | Mongelli et al. | 526/304 |
| 5,439,686 A | 8/1995 | Desai et al. | 424/451 |
| 5,511,563 A | 4/1996 | Diamond | 128/848 |
| 5,529,786 A | 6/1996 | Moore | 424/464 |
| 5,530,003 A | 6/1996 | Yanagawa | 514/256 |
| 5,560,933 A | 10/1996 | Soon-Shiong et al. | 424/489 |
| 5,583,153 A | 12/1996 | Brahn | 514/449 |
| 5,616,608 A | 4/1997 | Kinsella et al. | 514/449 |
| 5,626,862 A | 5/1997 | Brem et al. | 424/426 |
| 5,643,575 A | 7/1997 | Martinez et al. | 424/194.1 |
| 5,648,506 A | 7/1997 | Desai et al. | 549/510 |
| 5,651,986 A | 7/1997 | Brem et al. | 424/484 |
| 5,667,764 A | 9/1997 | Kopia et al. | 424/1.45 |
| 5,719,265 A | 2/1998 | Mongelli et al. | 530/329 |
| 5,733,925 A | 3/1998 | Kunz et al. | 514/449 |
| 5,801,191 A | 9/1998 | Bressi et al. | 514/449 |
| 5,811,447 A | 9/1998 | Kunz et al. | 514/411 |
| 5,886,026 A | 3/1999 | Hunter et al. | 514/449 |
| 5,981,568 A | 11/1999 | Kunz et al. | 514/411 |
| 5,994,341 A | 11/1999 | Hunter et al. | 514/210 |
| 6,074,659 A | 6/2000 | Kunz et al. | 424/423 |
| 6,171,609 B1 | 1/2001 | Kunz | 424/422 |
| 6,506,411 B2 * | 1/2003 | Hunter et al. | 424/501 |
| 6,544,544 B2 * | 4/2003 | Hunter et al. | 424/424 |

FOREIGN PATENT DOCUMENTS

| | | |
|---|---|---|
| DE | 3825374 | 2/1990 |
| EP | 616813 A2 | 9/1994 |
| EP | 0470569 B1 | 11/1995 |
| FR | 2693193 | 1/1994 |
| WO | WO 91/10424 | 7/1991 |
| WO | WO 91/11193 | 8/1991 |
| WO | WO 92/12717 | 8/1992 |
| WO | WO 93/18793 | 9/1993 |
| WO | WO 93/23075 | 11/1993 |
| WO | WO 95/03036 | 2/1995 |
| WO | WO 99/48536 | 9/1999 |

OTHER PUBLICATIONS

Brandwein et al., "Fatal Pulmonary Lipid Embolism Associated with Taxol Therapy," *The Mount Sinai Journal of Medicine* 55(2):187–189, Mar. 1988.

Kamei et al., "Antitumor Effects of Angiogenesis Inhibitor TNP–470 in Rabbits Bearing VX–2 Carcinoma by Arterial Administration of Microspheres and Oil Solution," *The Journal of Pharmacology and Experimental Therapeutics* 264(1):469–474, Jan. 1993.

Kato et al., "The Role of Embolization/Chemoembolization in the Treatment of Renal Cell Carcinoma," *Therapeutic Progress in Urological Cancers*, Murphy and Khoury, eds., pp. 697–705, Alan R. Liss, Inc., NY, 1989.

Pazdur et al., "The taxoids: paclitaxel (Taxol®) and docetaxel®)," *Cancer Treatment Reviews* 19(4):351–386, Oct. 1993.

Weissleder et al., "A Drug System (PDH) for Interventional Radiology," *Investigative Radiology* 28(12):1083–1089, Dec. 1993.

Asako et al., "Colchicine and Methotrexate Reduce Leukocyte Adherence and Emigration in Rat Mesenteric Venules," *Inflammation* 16(1): 43, 1992.

Tang et al., "Regression of Collagen–Induced Arthritis with Taxol, A Microtubule Stabilizer," *Arthritis & Rheumatism* 36(9, Suppl.): S45, Abstract No. 42, Sep. 1993.

Brahn et al., "Regression of Collagen–Induced Arthritis with Taxol, A Microtubule Stabilizer," *Arthritis & Rheumatism* 37(6): 839–845, Jun. 1994.

Sloboda et al., "Studies of the Effect of Mitoxantrone on Adjuvant Induced Arthritis in Rats," *Clinical Immunology and Immunopathology* 40: 236–243, 1986.

(List continued on next page.)

Primary Examiner—Shailendra Kumar
(74) Attorney, Agent, or Firm—Seed IP Law Group PLLC

(57) ABSTRACT

The present invention provides compositions comprising an anti-angiogenic factor, and a polymeric carrier. Representative examples of anti-angiogenic factors include Anti-Invasive Factor, Retinoic acids and derivatives thereof, and paclitaxel. Also provided are methods for embolizing blood vessels, and eliminating biliary, urethral, esophageal, and tracheal/bronchial obstructions.

15 Claims, 76 Drawing Sheets

OTHER PUBLICATIONS

Oliver et al., "Suppression of Collagen–Induced Arthritis Using an Angiogenesis Inhibitor, AGM–1470, and a Microtubule Stabilizer, Taxol," *Cellular Immunology 157*: 291–299, 1994.

Beckett et al., "Matrix Metalloproteinase Inhibitors in the Treatment of Rheumatoid Arthritis and Cancer," *Abstracts of Papers, 205th ACS National Meeting, American Chemical Society, Denver, Colorado*, Mar. 28–Apr. 2, 1993, Abstract No. 147, MEDI.

Grinstaff et al., "Intravenous Targeted Delivery of Taxol in Protein Microspheres," *American Chemical Society, 207th National Meeting*, Mar. 13–17, 1994, Abstract No. 91, MEDI.

Ratcliffe et al., "Preparation and evaluation of biodegradable polymeric systems for the intra–articular delivery of drugs," *J. Pharm. Pharmacol. 36*: 431–436, 1984.

Ratcliffe et al., "Albumin microspheres for intra–articular drug delivery: investigation of their retention in normal and arthritic knee joints of rabbits," *J. Pharm. Pharamacol. 39*: 290–295, 1987.

Hunneyball, I.M., "Intra–articular administration of drugs," *Pharmacy International*: 118–122, May 1986.

Menkes, C.J., "Intraarticular Treatment of Osteoarthritis and Guidelines to its Assessment," *The Journal of Rheumatology 21*: 74–76, 1994.

Mönkkönen et al., "Studies on liposome formulations for intra–articular delivery of clodronate," *Journal of Controlled Release 35*: 145–154, 1995.

English Abstract of French Patent FR 2693193, Jan. 7, 1994.

English Abstract of German Patent DE 3825374, Feb. 1, 1990.

Dahlberg et al., "Intraarticular Injections of Hyaluronan in Patients with Cartilage Abnormalities and Knee Pain," *Arthritis & Rheumatism 37*(4): 521–528, Apr. 1994.

Innocenti et al., "Plasma and Tissue Disposition of Paclitaxel (Taxol) After Intraperitoneal Administration in Mice," *Drug Metabolism and Disposition 23*(7): 713–717, 1995.

Walter et al., "Interstitial Taxol Delivered from a Biodegradable Polymer Implant against Experimental Malignant Glioma," *Cancer Research 54*: 2207–2212, Apr. 15, 1994.

Smith et al., "Intratumoral chemotherapy with a sustained–release drug delivery system inhibits growth of human pancreatic cancer xenografts," *Anti–Cancer Drugs 6*: 717–726, 1995.

Burt et al., "Controlled delivery of taxol from microspheres composed of a blend of ethylene–vinyl acetate copolymer and poly (d,l–lactic acid)," *Cancer Letters 88*: 73–79, 1995.

Pesenti et al., "Synthesis and biological activity of water soluble polymer–bound taxol derivatives," *Proceedings of the American Association for Cancer Research 36*: Abstract No. 1824, Mar. 1995.

Durdunoo et al., "Taxol encapsulation in poly($\epsilon$–caprolactone) microspheres," *Cancer Chemother. Pharmacol. 36*: 279–282, 1995.

Bartoli et al., "In vitro and in vivo antitumoral activity of free, and encapsulated taxol," *J. Microencapsulation 7*(2): 191–197, 1990.

Jampel et al., "In Vitro Release of Hydrophobic Drugs From Polyanhydride Disks," *Ophthalmic Surgery 22*(11): 676–680, 1991.

Ike et al., "Biodegradation and antitumor effect of adriamycin–containing poly(L–Lactic acid) microspheres," *Biomaterials 12*: 757–762, Oct. 1991.

* cited by examiner c-FOS expression:
Northern RNA hybridization

1 TNF-alpha
2 C
3 taxol 10(−8)M + TNF-alpha
4 taxol 10(−7)M + TNF-alpha
5 taxol 10(−6)M + TNF-alpha RNA gel electrophoresis Tubulin expression Collagenase expression:
Northern RNA hybridization 1 C
2 IL-1
3 taxol 10(-6)M + IL-1
3 taxol 10(-6)M + IL-1

Gel electrophoresis

18 S band

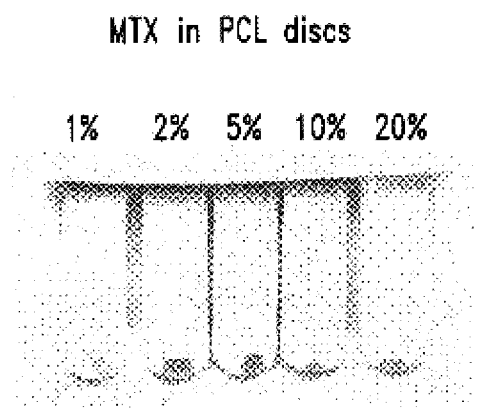 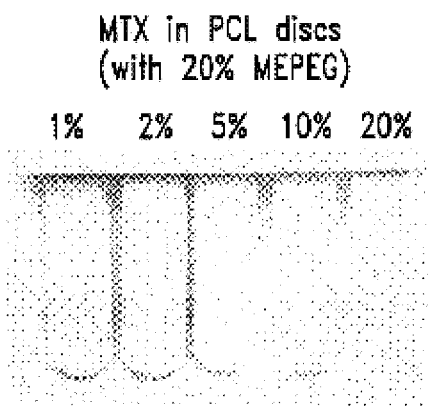
Fig. 47D
Fig. 47E

ANTI-ANGIOGENIC COMPOSITIONS AND METHODS OF USE

CROSS-REFERENCE TO RELATED APPLICATIONS

This application is a continuation of U.S. patent application Ser. No. 09/013,765, filed Jan. 27, 1998, now abandoned which is a continuation of U.S. patent application Ser. No. 08/478,914, filed Jun. 7, 1995, and issued as U.S. Pat. No. 5,994,341, on Nov. 30, 1998; which application is a divisional of U.S. application Ser. No. 08/417,160, filed Apr. 3, 1995, now abandoned; which application claims priority under 35 U.S.C. §§ 119 and 365 from PCT Application No. PCT/CA94/00373, filed Jul. 19, 1994, and in addition is a continuation-in-part of U.S. application Ser. No. 08/094,536, filed Jul. 19, 1993, now abandoned.

TECHNICAL FIELD

The present invention relates generally to compositions and methods for treating cancer and other angiogenic-dependent diseases, and more specifically, to compositions comprising anti-angiogenic factors and polymeric carriers, stents which have been coated with such compositions, as well as method for utilizing these stents and compositions.

BACKGROUND OF THE INVENTION

Angiogenesis-dependent diseases (i.e., those diseases which require or induce vascular growth) represent a significant portion of all diseases for which medical treatment is sought. For example, cancer is the second leading cause of death in the United States, and accounts for over one-fifth of the total mortality. Briefly, cancer is characterized by the uncontrolled division of a population of cells which, most typically, leads to the formation of one or more tumors. Such tumors are also characterized by the ingrowth of vasculature which provide various factors that permit continued tumor growth. Although cancer is generally more readily diagnosed than in the past, many forms, even if detected early, are still incurable.

A variety of methods are presently utilized to treat cancer, including for example, various surgical procedures. If treated with surgery alone however, many patients (particularly those with certain types of cancer, such as breast, brain, colon and hepatic cancer) will experience recurrence of the cancer. Therefore, in addition to surgery, many cancers are also treated with a combination of therapies involving cytotoxic chemotherapeutic drugs (e.g., vincristine, vinblastine, cisplatin, methotrexate, 5-FU, etc.) and/or radiation therapy. One difficulty with this approach, however, is that radiotherapeutic and chemotherapeutic agents are toxic to normal tissues, and often create life-threatening side effects. In addition, these approaches often have extremely high failure/remission rates.

In addition to surgical, chemo- and radiation therapies, others have attempted to utilize an individual's own immune system in order to eliminate cancerous cells. For example, some have suggested the use of bacterial or viral components as adjuvants in order to stimulate the immune system to destroy tumor cells. (See generally "Principles of Cancer Biotherapy," Oldham (ed.), Raven Press, New York, 1987.) Such agents have generally been useful as adjuvants and as nonspecific stimulants in animal tumor models, but have not as of yet proved to be generally effective in humans.

Lymphokines have also been utilized in the treatment of cancer. Briefly, lymphokines are secreted by a variety of cells, and generally have an effect on specific cells in the generation of an immune response. Examples of lymphokines include Interleukins (IL)-1, -2, -3, and -4, as well as colony stimulating factors such as G-CSF, GM-CSF, and M-CSF. Recently, one group has utilized IL-2 to stimulate peripheral blood cells in order to expand and produce large quantities of cells which are cytotoxic to tumor cells (Rosenberg et al., N Engl. J Med. 313:1485–1492, 1985).

Others have suggested the use of antibodies in the treatment of cancer. Briefly, antibodies may be developed which recognize certain cell surface antigens that are either unique, or more prevalent on cancer cells compared to normal cells. These antibodies, or "magic bullets," may be utilized either alone or conjugated with a toxin in order to specifically target and kill tumor cells (Dillman, "Antibody Therapy," Principles of Cancer Biotherapy, Oldham (ed.), Raven Press, Ltd., New York, 1987). However, one difficulty is that most monoclonal antibodies are of murine origin, and thus hypersensitivity against the murine antibody may limit its efficacy, particularly after repeated therapies. Common side effects include fever, sweats and chills, skin rashes, arthritis, and nerve palsies.

One additional difficulty of present methods is that local recurrence and local disease control remains a major challenge in the treatment of malignancy. In particular, a total of 630,000 patients annually (in the U.S.) have localized disease (no evidence of distant metastatic spread) at the time of presentation; this represents 64% of al those patients diagnosed with malignancy (this does not include nonmelanoma skin cancer or carcinoma in situ). For the vast majority of these patients, surgical resection of the disease represents the greatest chance for a cure and indeed 428,000 will be cured after the initial treatment—428,000. Unfortunately, 202,000 (or 32% of all patients with localized disease) will relapse after the initial treatment. Of those who relapse, the number who will relapse due to local recurrence of the disease amounts to 133,000 patients annually (or 21% of all those with localized disease). The number who will relapse due to distant metastases of the disease is 68,000 patients annually (11% of all those with localized disease). Another 102,139 patients annually will die as a direct result of an inability to control the local growth of the disease.

Nowhere is this problem more evident than in breast cancer, which affects 186,000 women annually in the U.S. and whose mortality rate has remained unchanged for 50 years. Surgical resection of the disease through radical mastectomy, modified radical mastectomy, or lumpectomy remains the mainstay of treatment for this condition. Unfortunately, 39% of those treated with lumpectomy alone will develop a recurrence of the disease, and surprisingly, so will 25% of those in which the resection margin is found to be clear of tumor histologically. As many as 90% of these local recurrences will occur within 2 cm of the previous excision site.

Similarly, in 1991, over 113,000 deaths and 238,600 new cases of liver metastasis were reported in North America alone. The mean survival time for patients with liver metastases is only 6.6 months once liver lesions have developed. Non-surgical treatment for hepatic metastases include systemic chemotherapy, radiation, chemoembolization, hepatic arterial chemotherapy, and intraarterial radiation. However, despite evidence that such treatments can transiently decrease the size of the hepatic lesions (e.g., systemic chemotherapy and hepatic arterial chemotherapy initially reduces lesions in 15–20%, and 80% of patients, respectively), the lesions invariably reoccur. Surgical resection of liver metastases represents the only possibility for a cure, but such a procedure is possible in only 5% of patients with metastases, and in only 15–20% of patients with primary hepatic cancer.

One method that has been attempted for the treatment of tumors with limited success is therapeutic embolization. Briefly, blood vessels which nourish a tumor are deliberately blocked by injection of an embolic material into the vessels. A variety of materials have been attempted in this regard, including autologous substances such as fat, blood clot, and chopped muscle fragments, as well as artificial materials such as wool, cotton, steel balls, plastic or glass beads, tantalum powder, silicone compounds, radioactive particles, sterile absorbable gelatin sponge (Sterispon, Gelfoam), oxidized cellulose (Oxycel), steel coils, alcohol, lyophilized human dura mater (Lyodura), microfibrillar collagen (Avitene), collagen fibrils (Tachotop), polyvinyl alcohol sponge (PVA; Ivalon), Barium-impregnated silicon spheres (Biss) and detachable balloons. The size of liver metastases may be temporarily decreased utilizing such methods, but tumors typically respond by causing the growth of new blood vessels into the tumor.

A related problem to tumor formation is the development of cancerous blockages which inhibit the flow of material through body passageways, such as the bile ducts, trachea, esophagus, vasculature and urethra. One device, the stent, has been developed in order to hold open passageways which have been blocked by tumors or other substances. Representative examples of common stents include the Wallstent, Strecker stent, Gianturco stent, and the Palmaz stent. The major problem with stents, however, is that they do not prevent the ingrowth of tumor or inflammatory material through the interstices of the stent. If this material reaches the inside of a stent and compromises the stent lumen, it may result in blockage of the body passageway into which it has been inserted. In addition, presence of a stent in the body may induce reactive or inflammatory tissue (e.g., blood vessels, fibroblasts, white blood cells) to enter the stent lumen, resulting in partial or complete closure of the stent.

The present invention provides compositions and methods suitable for treating cancers, as well as other non-tumorigenic angiogenesis-dependent diseases, and further provides other related advantages.

SUMMARY OF THE INVENTION

Briefly stated, the present invention provides anti-angiogenic compositions, as well as methods and devices which utilize such compositions for the treatment of cancer and other angiogenesis-dependent diseases. Within one aspect of the present invention, compositions are provided (anti-angiogenic compositions) comprising (a) an anti-angiogenic factor and (b) a polymeric carrier. A wide variety of molecules may be utilized within the scope of the present invention as anti-angiogenic factors, including for example Anti-Invasive Factor, retinoic acids and their derivatives, paclitaxel including analogues and derivatives thereof, Suramin, Tissue Inhibitor of Metalloproteinase-1, Tissue Inhibitor of Metalloproteinase-2, Plasminogen Activator Inhibitor-I and Plasminogen Activator Inhibitor-2, and lighter "d group" transition metals. Similarly, a wide variety of polymeric carriers may be utilized, representative examples of which include poly (ethylene-vinyl acetate) (40% cross-linked), poly (D,L-lactic acid) oligomers and polymers, poly (L-lactic acid) oligomers and polymers, poly (glycolic acid), copolymers of lactic acid and glycolic acid, poly (caprolactone), poly (valerolactone), poly (anhydrides), copolymers of poly (caprolactone) or poly (lactic acid) with polyethylene glycol, and blends thereof.

Within certain preferred embodiments, the compositions comprise a compound which disrupts microtubule function, such as, for example, paclitaxel, estramustine, colchicine, methotrexate, curacin-A, epothilone, vinblastine or tBCEV. Within other preferred embodiments, the compositions comprise a polymeric carrier and a lighter d gropu transition metal (e.g., a vanadium species, molybdenum species, tungsten species, titanium species, niobium species or tantalum species) which inhibits the formation of new blood vessels.

Within one embodiment of the invention, the composition has an average size of 15 to 200 $\mu$m, within other embodiments, the polymeric carrier of the composition has a molecular weight ranging from less than 1,000 daltons to greater than 200,000 to 300,000 daltons. Within yet other embodiments, the compositions provided herein may be formed into films with a thickness of betweem 100 $\mu$m and 2 mm, or thermologically active compositions which are liquid at one temperature (e.g., above 45° C.) and solid or semi-solid at another (e.g., 37° C.).

Within another aspect of the present invention methods for embolizing blood vessel are provided, comprising the step of delivering into the vessel a therapeutically effective amount of an anti-angiogenic composition (as described above), such that the blood vessel is effectively occluded. Within one embodiment, the anti-angiogenic composition is delivered to a blood vessel which nourishes a tumor.

Within yet another aspect of the present invention, stents are provided comprising a generally tubular structure, the surface being coated with one or more anti-angiogenic compositions. Within other aspects of the present invention, methods are provided for expanding the lumen of a body passageway, comprising inserting a stent into the passageway, the stent having a generally tubular structure, the surface of the structure being coated with an anti-angiogenic composition as described above, such that the passageway is expanded. Within various embodiments of the invention, methods are provided for eliminating biliary obstructions, comprising inserting a biliary stent into a biliary passageway; for eliminating urethral obstructions, comprising inserting a urethral stent into a urethra; for eliminating esophageal obstructions, comprising inserting an esophageal stent into an esophagus; and for eliminating tracheal/bronchial obstructions, comprising inserting a tracheal/bronchial stent into the trachea or bronchi. In each of these embodiments, the stent has a generally tubular structure, the surface of which is coated with an anti-angiogenic composition as described above.

Within another aspect of the present invention, methods are provided for treating tumor excision sites, comprising administering an anti-angiogenic composition as described above to the resection margins of a tumor subsequent to excision, such that the local recurrence of cancer and the formation of new blood vessels at the site is inhibited. Within yet another aspect of the invention, methods for treating corneal neovascularization are provided, comprising the step of administering to a patient a therapeutically effective amount of an anti-angiogenic composition as described above to the cornea, such that the formation of blood vessels is inhibited. Within one embodiment, the anti-angiogenic composition further comprises a topical corticosteroid.

Within another aspect of the present invention, methods are provided for inhibiting angiogenesis in patients with non-tumorigenic, angiogenesis-dependent diseases, comprising administering to a patient a therapeutically effective amount of paclitaxel to a patient with a non-tumorigenic angiogenesis-dependent disease, such that the formation of new blood vessels is inhibited. Within other aspects, methods are provided for embolizing blood vessels in non-tumorigenic, angiogenesis-dependent diseases, comprising delivering to the vessel a therapeutically effective amount of a composition comprising paclitaxel, such that the blood vessel is effectively occluded.

Within yet other aspects of the present invention, methods are provided for expanding the lumen of a body passageway, comprising inserting a stent into the passageway, the stent having a generally tubular structure, the surface of the structure being coated with a composition comprising paclitaxel, such that the passageway is expanded. Within various embodiments of the invention, methods are provided for eliminating biliary obstructions, comprising inserting a biliary stent into a biliary passageway; for eliminating urethral obstructions, comprising inserting a urethral stent into a urethra; for eliminating esophageal obstructions, comprising inserting an esophageal stent into an esophagus; and for eliminating tracheal/bronchial obstructions, comprising inserting a tracheal/bronchial stent into the trachea or bronchi. Within each of these embodiments the stent has a generally tubular structure, the surface of the structure being coated with a composition comprising paclitaxel.

Within another aspect of the present invention, methods are provided for treating a tumor excision site, comprising administering a composition comprising paclitaxel to the resection margin of a tumor subsequent to excision, such that the local recurrence of cancer and the formation of new blood vessels at the site is inhibited. Within other aspects, methods are provided for treating neovascular diseases of the eye, comprising administering to a patient a therapeutically effective amount of an anti-angiogenic factor (such as a compound which disrupts microtubule function) to the eye, such that the formation of new vessels is inhibited.

Within other aspects of the present invention, methods are provided for treating inflammatory arthritis, comprising administering to a patient a therapeutically effective amount of an anti-angiogenic factor (such as a compound which disrupts microtubule function), or a composition comprising an anti-angiogenic factor and a polymeric carrier to a joint. Within preferred embodiments, the anti-angiogenic factor may be a compound which disrupts microtubule function such as paclitaxel, or an element from the lighter 'd group' transition metals, such as a vanadium species.

Within yet another aspect of the invention, pharmaceutical products are provided, comprising (a) a compound which disrupts microtubule function, in a container, and (b) a notice associated with the container in form prescribed by a governmental agency regulating the manufacture, use, or sale of pharmaceuticals, which notice is reflective of approval by the agency of a compound which disrupts microtubule function, for human or veterinary administration to treat non-tumorigenic angiogenesis-dependent diseases such as, for example, inflammatory arthritis or neovascular diseases of the eye. Briefly, Federal Law requires that the use of a pharmaceutical agent in the therapy of humans be approved by an agency of the Federal government. Responsibility for enforcement (in the United States) is with the Food and Drug Administration, which issues appropriate regulations for securing such approval, detailed in 21 U.S.C. §§301-392. Regulation for biological materials comprising products made from the tissues of animals, is also provided under 42 U.S.C. §262. Similar approval is required by most countries, although, regulations may vary from country to country.

These and other aspects of the present invention will become evident upon reference to the following detailed description and attached drawings. In addition, various references are set forth below which describe in more detail certain procedures, devices or compositions, and are therefore incorporated by reference in their entirety.

BRIEF DESCRIPTION OF THE DRAWINGS

FIG. 2D illustrates the typical "elbowing" effect (arrowheads) of both small and large vessels being redirected away from the periphery of the avascular zone.

FIGS. 3A, 3B and 3C are a series of photographs of 0.5 mm thick plastic sections transversely cut through a paclitaxel-treated CAM at three different locations within the avascular zone.

FIG. 4A (Mag=2,200×) shows a small capillary lying subjacent to the ectodermal layer (Ec) possessing three endothelial cells arrested in mitosis (*). Several other cell types in both the ectoderm and mesoderm are also arrested in mitosis. FIG. 4B (Mag=2,800×) shows the early avascular phase contains extravasated blood cells subjacent to the ectoderm; these blood cells are intermixed with presumptive endothelial cells (*) and their processes. Degrative cellular vacuoles (arrowhead). FIG. 4C (Mag=2,800×) shows that in response to paclitaxel, the ecto-mesodermal interface has become populated with cells in various stages of degradation containing dense vacuoles and granules (arrowheads).

FIG. 15F is a photograph similar to that of 15E at increased magnification.

FIG. 20B is an underside view of the CAM shown in 20A. Briefly, this view demonstrates the radial appearance of the blood vessels which enter the tumor like the spokes of a wheel. Note that the blood vessel density is greater in the vicinity of the tumor than it is in the surrounding normal CAM tissue. FIG. 20D is taken from the underside of the CAM shown in 20C, and demonstrates the disruption of blood flow into the tumor when compared to control tumor tissue. Note that the blood vessel density is reduced in the vicinity of the tumor and is sparser than that of the normal surrounding CAM tissue.

FIG. 66A illustrates the obliteration of the stent lumen by the process of benign epithelial overgrowth. At higher magnification (66B), the fibrous and inflammatory tissue is evident with little luminal space remaining. The paclitaxel-treated biliary duct remains patent (66C). At higher magnification, normal biliary tract epithelium is present with only minimal alteration of the mucosal lining by the coated stent tines (t).

DETAILED DESCRIPTION OF THE INVENTION

Figure 1A:
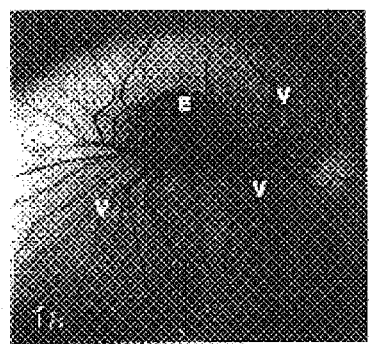
FIG. 1A is a photograph which shows a shell-less egg culture on day 6.
Figure 1B:
FIG. 1B is a digitized computer-displayed image taken with a stereomicroscope of living, unstained capillaries (1040×).
Figure 1C:
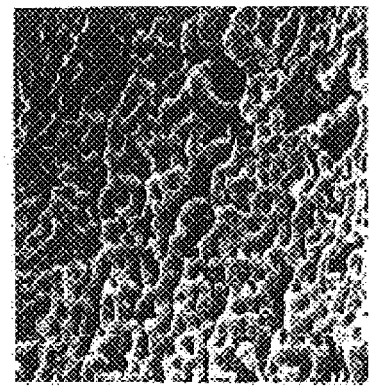
FIG. 1C is a photograph of a corrosion casting which shows CAM microvasculature that are fed by larger, underlying vessels (arrows; 1300×).

As noted above, the present invention provides methods and compositions which utilize anti-angiogenic factors. Briefly, within the context of the present invention, anti-angiogenic factors should be understood to include any protein, peptide, chemical, or other molecule, which acts to inhibit vascular growth. A variety of methods may be readily utilized to determine the anti-angiogenic activity of a given factor, including for example, chick chorioallantoic membrane ("CAM") assays. Briefly, as described in more detail below in Examples 2A and 2C, a portion of the shell from a freshly fertilized chicken egg is removed, and a methyl cellulose disk containing a sample of the anti-angiogenic factor to be tested is placed on the membrane. After several days (e.g., 48 hours), inhibition of vascular growth by the sample to be tested may be readily determined by visualization of the chick chorioallantoic membrane in the region surrounding the methyl cellulose disk. Inhibition of vascular growth may also be determined quantitatively, for example, by determining the number and size of blood vessels surrounding the methyl cellulose disk, as compared to a control methyl cellulose disk. Although anti-angiogenic factors as described herein are considered to inhibit the formation of new blood vessels if they do so in merely a statistically significant manner, as compared to a control, within preferred aspects such anti-angiogenic factors will completely inhibit the formation of new blood vessels, as well as reduce the size and number of previously existing vessels.

In addition to the CAM assay described above, a variety of other assays may also be utilized to determine the efficacy of anti-angiogenic factors in vivo, including for example, mouse models which have been developed for this purpose (see Roberston et al., *Cancer. Res.* 51:1339–1344, 1991). In addition, a variety of representative in vivo assays relating to various aspects of the inventions described herein have also been described in more detail below in Examples 5 to 7, and 17 to 19.

As noted above, the present invention provides compositions comprising an anti-angiogenic factor, and a polymeric carrier. Briefly, a wide variety of anti-angiogenic factors may be readily utilized within the context of the present invention. Representative examples include Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals. These and other anti-angiogenic factors will be discussed in more detail below.

Briefly, Anti-Invasive Factor, or "AIF" which is prepared from extracts of cartilage, contains constituents which are responsible for inhibiting the growth of new blood vessels. These constituents comprise a family of 7 low molecular weight proteins (<50,000 daltons) (Kuettner and Pauli, "Inhibition of neovascularization by a cartilage factor" in *Development of the Vascular System,* Pitman Books (CIBA Foundation Symposium 100), pp. 163–173, 1983), including a variety of proteins which have inhibitory effects against a variety of proteases (Eisentein et al, *Am. J Pathol.* 81:337–346, 1975; Langer et al., *Science* 193:70–72, 1976; and Horton et al., *Science* 199:1342–1345, 1978). AIF suitable for use within the present invention may be readily prepared utilizing techniques known in the art (e.g., Eisentein et al, supra; Kuettner and Pauli, supra; and Langer et al., supra). Purified constituents of AIF such as Cartilage-Derived Inhibitor ("CDI") (see Moses et al., *Science* 248:1408–1410, 1990) may also be readily prepared and utilized within the context of the present invention.

Retinoic acids alter the metabolism of extracellular matrix components, resulting in the inhibition of angiogenesis. Addition of proline analogs, angiostatic steroids, or heparin may be utilized in order to synergistically increase the anti-angiogenic effect of transretinoic acid. Retinoic acid, as well as derivatives thereof which may also be utilized in the context of the present invention, may be readily obtained from commercial sources, including for example, Sigma Chemical Co. (# R2625).

Paclitaxel is a highly derivatized diterpenoid (Wani et al., *J. Am. Chem. Soc.* 93:2325, 1971) which has been obtained from the harvested and dried bark of *Taxis brevifolia* (Pacific Yew.) and *Taxomyces Andreanae* and Endophytic Fungus of the Pacific Yew (Stierle et al., *Science* 60:214–216, 1993). Generally, paclitaxel acts to stabilize microtubular structures by binding tubulin to form abnormal mitotic spindles. "Paclitaxel" (which should be understood herein to include analogues and derivatives such as, for example, TAXOL®, TAXOTERE®, 10-desacetyl analogues of paclitaxel and 3'N-desbenzoyl-3'N-t-butoxy carbonyl analogues of paclitaxel) may be readily prepared utilizing techniques known to those skilled in the art (see also WO 94/07882, WO 94/07881, WO 94/07880, WO 94/07876, WO 93/23555, WO 93/10076, U.S. Pat. Nos. 5,294,637, 5,283, 253, 5,279,949, 5,274,137, 5,202,448, 5,200,534, 5,229,529, and EP 590267), or obtained from a variety of commercial sources, including for example, Sigma Chemical Co., St. Louis, Mo. (T7402-from *Taxus brevifolia*).

Suramin is a polysulfonated naphthylurea compound that is typically used as a trypanocidal agent. Briefly, Suramin blocks the specific cell surface binding of various growth factors such as platelet derived growth factor ("PDGF"), epidermal growth factor ("EGF"), transforming growth factor ("TGF-β"), insulin-like growth factor ("IGF-1"), and fibroblast growth factor ("βFGF"). Suramin may be prepared in accordance with known techniques, or readily obtained from a variety of commercial sources, including for example Mobay Chemical Co., New York. (see Gagliardi et al., *Cancer Res.* 52:5073–5075, 1992; and Coffey, Jr., et al., *J. of Cell. Phys.* 132:143–148, 1987).

Tissue Inhibitor of Metalloproteinases-1 ("TIMP") is secreted by endothelial cells which also secrete MTPases. TIMP is glycosylated and has a molecular weight of 28.5 kDa. TIMP-1 regulates angiogenesis by binding to activated metalloproteinases, thereby suppressing the invasion of blood vessels into the extracellular matrix. Tissue Inhibitor of Metalloproteinases-2 ("TIMP-2") may also be utilized to inhibit angiogenesis. Briefly, TIMP-2 is a 21 kDa nonglycosylated protein which binds to metalloproteinases in both the active and latent, proenzyme forms. Both TIMP-1 and TIMP-2 may be obtained from commercial sources such as Synergen, Boulder, Colo.

Plasminogen Activator Inhibitor-1 (PA) is a 50 kDa glycoprotein which is present in blood platelets, and can also be synthesized by endothelial cells and muscle cells. PAI-I inhibits t-PA and urokinase plasminogen activator at the basolateral site of the endothelium, and additionally regulates the fibrinolysis process. Plasminogen Activator Inhibitor-2 (PAI-2) is generally found only in the blood under certain circumstances such as in pregnancy, and in the presence of tumors. Briefly, PAI-2 is a 56 kDa protein which is secreted by monocytes and macrophages. It is believed to regulate fibrinolytic activity, and in particular inhibits urokinase plasminogen activator and tissue plasminogen activator, thereby preventing fibrinolysis.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate (i.e., $VO_3^-$) and orthovanadate (i.e., $VO_4^{3-}$) complexes such as, for example, ammonium metavanadate (i.e., $NH_4VO_3$), sodium metavanadate (i.e., $NaVO_3$), and sodium orthovanadate (i.e., $Na_3VO_4$). Suitable vanadyl (i.e., $VO^{2+}$) complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate (i.e., $WO_4^{2-}$) complexes include ammonium tungstate (i.e., $(NH_4)_2WO_4$), calcium tungstate (i.e., $CaWO_4$), sodium tungstate dihydrate (i.e., $Na_2WO_4.2H_2O$), and tungstic acid (i.e., $H_2WO_4$). Suitable tungsten oxides include tungsten (IV) oxide (i.e., $WO_2$) and tungsten (VI) oxide (i.e., $WO_3$). Suitable oxo molybdenum complexes include molybdate, molybdenum oxide, and molybdenyl complexes. Suitable molybdate (i.e., $MoO_4^{2-}$) complexes include ammonium molybdate (i.e., $(NH_4)_2MoO_4$) and its hydrates, sodium molybdate (i.e., $Na_2MoO_4$) and its hydrates, and potassium molybdate (i.e., $K_2MoO_4$) and its hydrates. Suitable molybdenum oxides include molybdenum (VI) oxide (i.e., $MoO_2$), molybdenum (VI) oxide (i.e., $MoO_3$), and molybdic acid. Suitable molybdenyl (i.e., $MoO_2^{2+}$) complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include Platelet Factor 4 (Sigma Chemical Co., #F1385); Protamine Sulphate (Clupeine) (Sigma Chemical Co., #P4505); Sulphated Chitin Derivatives (prepared from queen crab shells), (Sigma Chemical Co., #C3641; Murata et al., *Cancer Res.* 51:22–26, 1991); Sulphated Polysaccharide Peptidoglycan Complex (SP-PG) (the function of this compound may be enhanced by the presence of steroids such as estrogen, and tamoxifen citrate); Staurosporine (Sigma Chemical Co., #S4400); Modulators of Matrix Metabolism, including for example, proline analogs {[(L-azetidine-2-carboxylic acid (LACA) (Sigma Chemical Co., #A0760)), cishydroxyproline, d,L-3,4-dehydroproline (Sigma Chemical Co., #D0265), Thiaproline (Sigma Chemical Co., #T0631)], α,α-dipyridyl (Sigma Chemical Co., #D7505), β-aminopropionitrile fumarate (Sigma Chemical Co., #A3134)]}; MDL 27032 (4-propyl-5-(4-pyridinyl)-2(3H)-oxazolone; Merion Merrel Dow Research Institute); Methotrexate (Sigma Chemical Co., #A6770; Hirata et al., *Arthritis and Rheumatism* 32:1065–1073, 1989); Mitoxantrone (Polverini and Novak, *Biochem. Biophys. Res. Comm.* 140:901–907); Heparin (Folkman, *Bio. Phar.* 34:905–909, 1985; Sigma Chemical Co., #P8754); Interferons (e.g., Sigma Chemical Co., #13265); 2 Macroglobulin-serum (Sigma Chemical Co., #M7151); ChIMP-3 (Pavloff et al., *J. Bio. Chem.* 267:17321–17326, 1992); Chymostatin (Sigma Chemical Co., #C7268; Tomkinson et al., *Biochem J.* 286:475–480, 1992); β-Cyclodextrin Tetradecasulfate (Sigma Chemical Co., #C4767); Eponemycin; Camptothecin; Fumagillin (Sigma Chemical Co., #F6771; Canadian Patent No. 2,024, 306; Ingber et al., *Nature* 348:555–557, 1990); Gold Sodium Thiomalate ("GST"; Sigma:G4022; Matsubara and Ziff, *J. Clin. Invest.* 79:1440–1446, 1987); (D-Penicillamine ("CDPT"; Sigma Chemical Co., #P4875 or P5000(HCl));

β-1-anticollagenase-serum; α2-antiplasmin (Sigma Chem. Co.:A0914; Holmes et al., *J. Biol. Chem.* 262(4) :1659–1664, 1987); Bisantrene (National Cancer Institute); Lobenzarit disodium (N-(2)-carboxyphenyl-4-chloroanthronilic acid disodium or "CCA"; Takeuchi et al., *Agents Actions* 36:312–316, 1992); Thalidomide; Angostatic steroid; AGM-1470; carboxynaminolmidazole; metalloproteinase inhibitors such as BB94 and the peptide CDPGYIGSR-NH$_2$ (SEQUENCE ID NO. 1) (Iwaki Glass, Tokyo, Japan).

Although the above anti-angiogenic factors have been provided for the purposes of illustration, it should be understood that the present invention is not so limited. In particular, although certain anti-angiogenic factors are specifically referred to above, the present invention should be understood to include analogues, derivatives and conjugates of such anti-angiogenic factors. For example, paclitaxel should be understood to refer to not only the common chemically available form of paclitaxel, but analogues (e.g., taxotere, as noted above) and paclitaxel conjugates (e.g., paclitaxel-PEG, paclitaxel-dextran, or paclitaxel-xylos).

Anti-angiogenic compositions of the present invention may additionally comprise a wide variety of compounds in addition to the anti-angiogenic factor and polymeric carrier. For example, anti-angiogenic compositions of the present invention may also, within certain embodiments of the invention, also comprise one or more antibiotics, anti-inflammatories, anti-viral agents, anti-fungal agents and/or anti-protozoal agents. Representative examples of antibiotics included within the compositions described herein include: penicillins; cephalosporins such as cefadroxil, cefazolin, cefaclor; aminoglycosides such as gentamycin and tobramycin; sulfonamides such as sulfamethoxazole; and metronidazole. Representative examples of anti-inflammatories include: steroids such as prednisone, prednisolone, hydrocortisone, adrenocorticotropic hormone, and sulfasalazine; and non-steroidal anti-inflammatory drugs ("NSAIDS") such as aspirin, ibuprofen, naproxen, fenoprofen, indomethacin, and phenylbutazone. Representative examples of antiviral agents include acyclovir, ganciclovir, zidovudine. Representative examples of antifungal agents include: nystatin, ketoconazole, griseofulvin, flucytosine, miconazole, clotrimazole. Representative examples of antiprotozoal agents include: pentamidine isethionate, quinine, chloroquine, and mefloquine.

Anti-angiogenic compositions of the present invention may also contain one or more hormones such as thyroid hormone, estrogen, progesterone, cortisone and/or growth hormone, other biologically active molecules such as insulin, as well as T$_H$1 (e.g., Interleukins-2, -12, and -15, gamma interferon) or T$_H$2 (e.g., Interleukins-4 and -10) cytokines.

Within certain preferred embodiments of the invention, anti-angiogenic compositions are provided which contain one or more compounds which disrupt microtubule function. Representative examples of such compounds include paclitaxel (discussed above), estramustine (available from Sigma; Wang and Stearns *Cancer Res.* 48:6262–6271, 1988), epothilone, curacin-A, colchicine, methotrexate, vinblastine and 4-tert-butyl-[3-(2-chloroethyl) ureido] benzene ("tBCEU").

Anti-angiogenic compositions of the present invention may also contain a wide variety of other compounds, including for example: α-adrenergic blocking agents, angiotensin II receptor antagonists and receptor antagonists for histamine, serotonin, endothelin; inhibitors of the sodium/hydrogen antiporter (e.g., amiloride and its derivatives); agents that modulate intracellular Ca$^{2+}$ transport such as L-type (e.g., diltiazem, nifedipine, verapamil) or T-type Ca$^{2+}$ channel blockers (e.g., amiloride), calmodulin antagonists (e.g., H$_7$) and inhibitors of the sodium/calcium antiporter (e.g., amiloride); ap-1 inhibitors (for tyrosine kinases, protein kinase C, myosin light chain kinase, Ca$^{2+}$/calmodulin kinase II, casein kinase II); anti-depressants (e.g. amytriptyline, fluoxetine, LUVOX® and PAXIL®); cytokine and/or growth factors, as well as their respective receptors, (e.g., the interleukins, α, β or γ-IFN, GM-CSF, G-CSF, epidermal growth factor, transforming growth factors alpha and beta, TNF, and antagonists of vascular epithelial growth factor, endothelial growth factor, acidic or basic fibroblast growth factors, and platelet dervived growth factor); inhibitors of the IP3 receptor (e.g., heparin); protease and collagenase inhibitors (e.g., TIMPs, discussed above); nitrovasodilators (e.g., isosorbide dinitrate); antimitotic agents (e.g., colchicine, anthracyclines and other antibiotics, folate antagonists and other anti-metabolites, vinca alkaloids, nitrosoureas, DNA alkylating agents, topoisomerase inhibitors, purine antagonists and analogs, pyrimidine antagonists and analogs, alkyl sulfonates); immunosuppressive agents (e.g., adrenocorticosteroids, cyclosporine); sense or antisense oligonucleotides (e.g., DNA, RNA, nucleic acid analogues (e.g., peptide nucleic acids) or any combinations of these); and inhibitors of transcription factor activity (e.g., lighter d group transition metals).

Anti-angiogenic compositions of the present invention may also comprise additional ingredients such as surfactants (either hydrophilic or hydrophobic; see Example 13), antineoplastic or chemotherapeutic agents (e.g., 5-fluorouracil, vincristine, vinblastine, cisplatin, doxyrubicin, adriamycin, or tamocifen), radioactive agents (e.g., Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212 and Bi-212) or toxins (e.g., ricin, abrin, diphtheria toxin, cholera toxin, gelonin, pokeweed antiviral protein, tritin, Shigella toxin, and Pseudomonas exotoxin A).

As noted above, anti-angiogenic compositions of the present invention comprise an anti-angiogenic factor and a polymeric carrier. In addition to the wide array of anti-angiogenic factors and other compounds discussed above, anti-angiogenic compositions of the present invention are provided in a wide variety of polymeric carriers, including for example both biodegradable and non-biodegradable compositions. Representative examples of biodegradable compositions include albumin, gelatin, starch, cellulose, dextrans, polysaccharides, fibrinogen, poly (D,L lactide), poly (D,L-lactide-co-glycolide), poly (glycolide), poly (hydroxybutyrate), poly (alkylcarbonate) and poly (orthoesters) (see generally, Illum, L., Davids, S. S. (eds.) "Polymers in controlled Drug Delivery" Wright, Bristol, 1987; Arshady, *J. Controlled Release* 17:1–22, 1991; Pitt, *Int. J. Phar.* 59:173–196, 1990; Holland et al., *J. Controlled Release* 4:155–0180, 1986). Representative examples of nondegradable polymers include EVA copolymers, silicone rubber and poly (methylmethacrylate). Particularly preferred polymeric carriers include poly (ethylene-vinyl acetate)(40% cross-linked), poly (D,L-lactic acid) oligomers and polymers, poly (L-lactic acid) oligomers and polymers, poly (glycolic acid), copolymers of lactic acid and glycolic acid, poly (caprolactone), poly (valerolactone), polyanhydrides, copolymers of poly (caprolactone) or poly (lactic acid) with polyethylene glycol and blends thereof.

Polymeric carriers may be fashioned in a variety of forms, including for example, rod-shaped devices, pellets, slabs, or capsules (see, e.g., Goodell et al., *Am. J. Hosp. Pharm.* 43:1454–1461, 1986; Langer et al., "Controlled release of macromolecules from polymers", in *Biomedical polymers, Polymeric materials and pharmaceuticals for biomedical use*, Goldberg, E. P., Nakagim, A. (eds.) Academic Press, pp. 113–137, 1980; Rhine et al., *J. Pharm. Sci.* 69:265–270, 1980; Brown et al., *J. Pharm. Sci.* 72:1181–1185, 1983; and Bawa et al., *J. Controlled Release* 1:259–267, 1985). Anti-angiogenic factors may be linked by occlusion in the matrices of the polymer, bound by covalent linkages, or encapsulated in microcapsules. Within certain preferred embodiments of the invention, anti-angiogenic compositions are provided in non-capsular formulations such as microspheres (ranging from nanometers to micrometers in size), pastes, threads of various size, films and sprays.

Preferably, anti-angiogenic compositions of the present invention (which comprise one or more anti-angiogenic factors, and a polymeric carrier) are fashioned in a manner appropriate to the intended use. Within certain aspects of the present invention, the anti-angiogenic composition should be biocompatible, and release one or more anti-angiogenic factors over a period of several days to months. For example, "quick release" or "burst" anti-angiogenic compositions are provided that release greater than 10%, 20%, or 25% (w/v) of an anti-angiogenic factor (e.g., paclitaxel) over a period of 7 to 10 days. Such "quick release" compositions should, within certain embodiments, be capable of releasing chemotherapeutic levels (where applicable) of a desired anti-angiogenic factor. Within other embodiments, "low release" anti-angiogenic compositions are provided that release less than 1% (w/v) of an anti-angiogenic factor over a period of 7 to 10 days. Further, anti-angiogenic compositions of the present invention should preferably be stable for several months and capable of being produced and maintained under sterile conditions.

Within certain aspects of the present invention, anti-angiogenic compositions may be fashioned in any size ranging from 50 nm to 500 $\mu$m, depending upon the particular use. For example, when used for the purpose of tumor embolization (as discussed below), it is generally preferable to fashion the anti-angiogenic composition in microspheres of between 15 and 500 $\mu$m, preferably between 15 and 200 $\mu$m, and most preferably, between 25 and 150 $\mu$m. Alternatively, such compositions may also be readily applied as a "spray", which solidifies into a film or coating. Such sprays may be prepared from microspheres of a wide array of sizes, including for example, from 0.1 $\mu$m to 3 $\mu$m, from 10 $\mu$m to 30 $\mu$m, and from 30 $\mu$m to 100 $\mu$m (see Example 8).

Anti-angiogenic compositions may also be prepared, given the disclosure provided herein, for a variety of other applications. For example, for administration to the cornea, the anti-angiogenic factors of the present invention may be incorporated into muco-adhesive polymers (e.g., polyacrylic acids such as (CARBOPOL®, dextron, polymethacrylate, or starch (see LeYung and Robinson, *J. of Controlled Rel.* 5:223, 1988)), or nanometer-sized microspheres (see generally, Kreuter *J. Controlled Release* 16:169–176, 1991; Couvreur and Vauthier, *J. Controlled Release* 17:187–198, 1991).

Anti-angiogenic compositions of the present invention may also be prepared in a variety of "paste" or gel forms. For example, within one embodiment of the invention, anti-angiogenic compositions are provided which are liquid at one temperature (e.g., temperature greater than 37° C., such as 40° C., 45° C., 50° C., 55° C. or 60° C.), and solid or semi-solid at another temperature (e.g., ambient body temperature, or any temperature lower than 37° C.). Such "thermopastes" may be readily made given the disclosure provided herein (see, e.g., Examples 10 and 14).

Within yet other aspects of the invention, the anti-angiogenic compositions of the present invention may be formed as a film. Preferably, such films are generally less than 5, 4, 3, 2, or 1, mm thick, more preferably less than 0.75 mm or 0.5 mm thick, and most preferably less than 500 $\mu$m to 100 $\mu$m thick. Such films are preferably flexible with a good tensile strength (e.g., greater than 50, preferably greater than 100, and more preferably greater than 150 or 200 N/cm$^2$), good adhesive properties (i.e., readily adheres to moist or wet surfaces), and has controlled permeability. Representative examples of such films are set forth below in the Examples (see e.g., Example 13).

Representative examples of the incorporation of anti-angiogenic factors such as those described above into a polymeric carriers is described in more detail below in Examples 3, 4 and 8–15.

Polymeric Carriers for the Release of Hydrophobic Compounds

Within further aspects of the present invention, polymeric carriers are provided which are adapted to contain and release a hydrophobic compound, the carrier containing the hydrophobic compound in combination with a carbohydrate, protein or polypeptide. Within certain embodiments, the polymeric carrier contains or comprises regions, pockets, or granules of one or more hydrophobic compounds. For example, within one embodiment of the invention, hydrophobic compounds may be incorporated within a matrix which contains the hydrophobic compound, followed by incorporation of the matrix within the polymeric carrier. A variety of matrices can be utilized in this regard, including for example, carbohydrates and polysaccharides such as starch, cellulose, dextran, methylcellulose, and hyaluronic acid, proteins or polypeptides such as albumin, collagen and gelatin (see e.g., Example 31). Within alternative embodiments, hydrophobic compounds may be contained within a hydrophobic core, and this core contained within a hydrophilic shell. For example, as described in Example 38, paclitaxel may be incorporated into a hydrophobic core (e.g., of the poly D,L lactic acid-PEG or MePEG aggregate) which has a hydrophilic shell.

A wide variety of hydrophobic compounds may be released from the polymeric carriers described above, including for example: certain hydrophobic compounds which disrupt microtubule function such as paclitaxel and estramustine; hydrophobic proteins such as myelin basic protein, proteolipid proteins of CNS myelin, hydrophobic cell wall protein, porins, membrane proteins (*EMBO J.* 12(9):3409–3415, 1993), myelin oligodendrocyte glycoprotein ("MOG") (*Biochem. and Mol. Biol. Int.* 30(5):945–958, 1993, P27 *Cancer Res.* 53(17):4096–4101, 1913, bacterioopsin, human surfactant protein ("HSB"; *J. Biol. Chem.* 268(15):11160–11166, 1993), and SP-B or SP-C (*Biochimica et Biophysica Acta* 1105(1):161–169, 1992).

Arterial Embolization

Figure 13A:
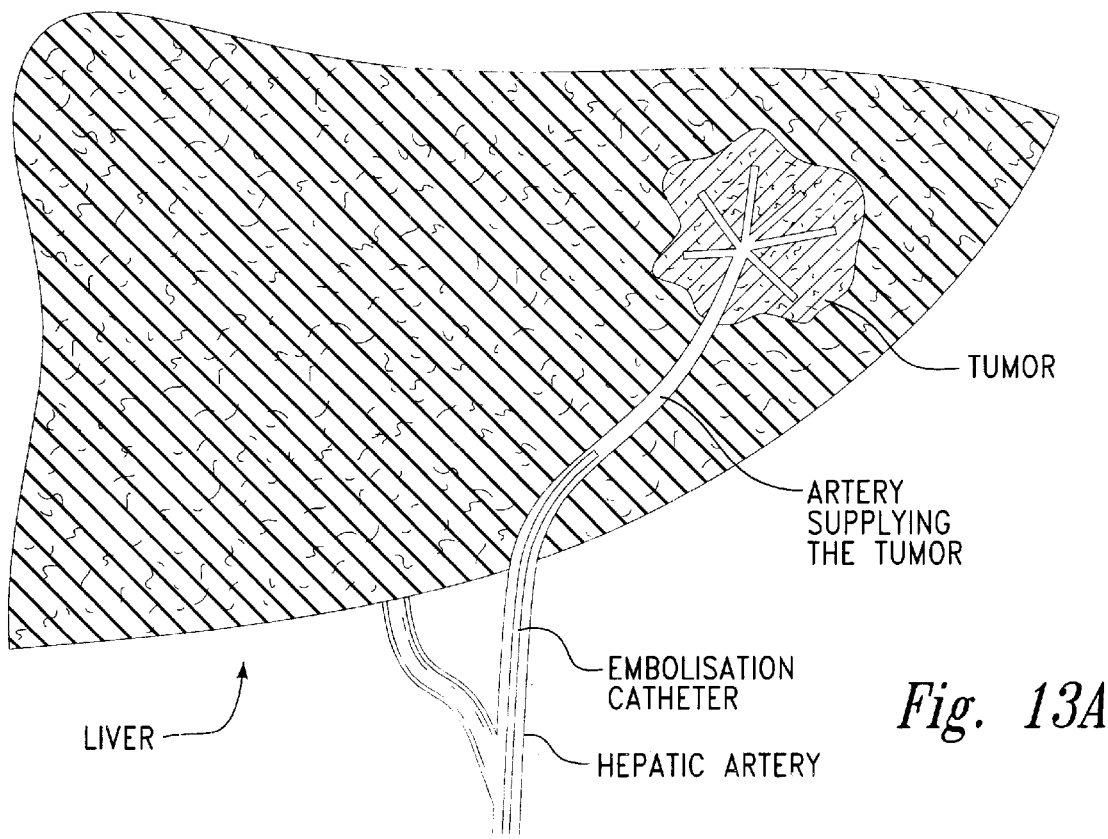
FIGS. 13A and 13B are an illustration of a representative embodiment of hepatic tumor embolization.
Figure 13B:
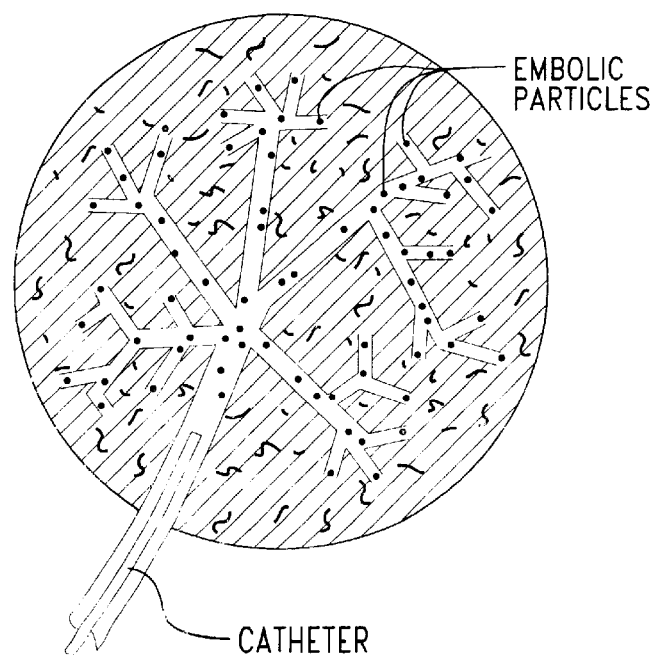
Figure 14A:
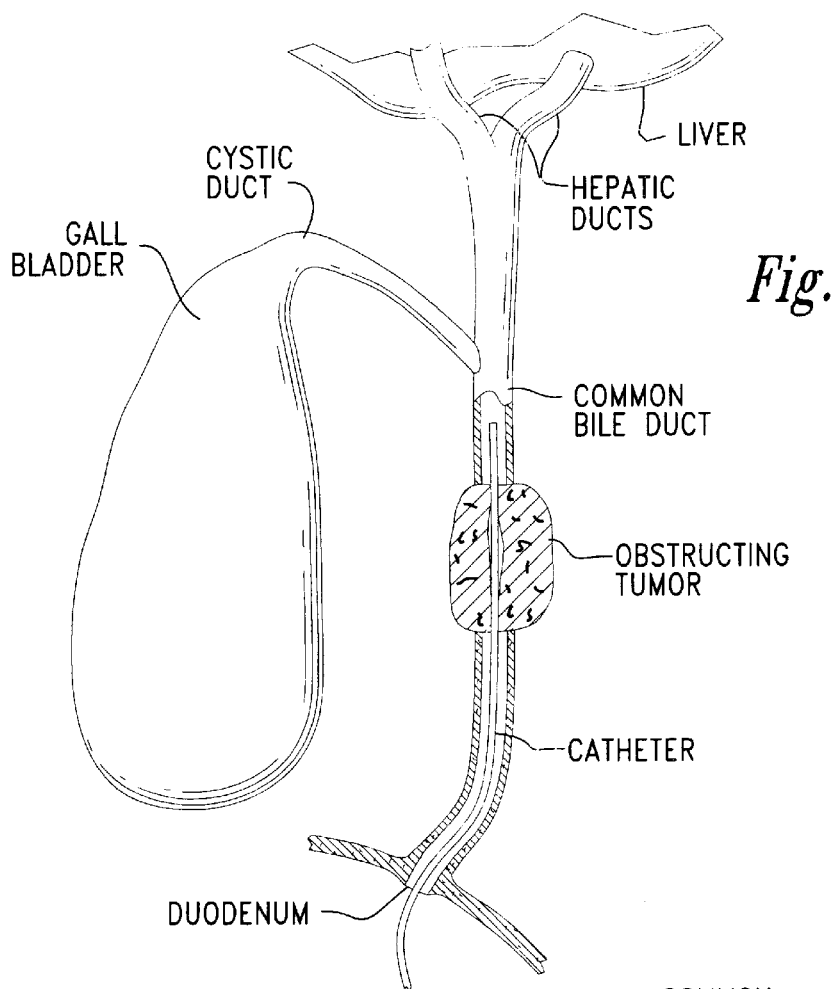
FIGS. 14A and 14B are an illustration of the insertion of a representative stent coated with an anti-angiogenic composition.
Figure 14B:
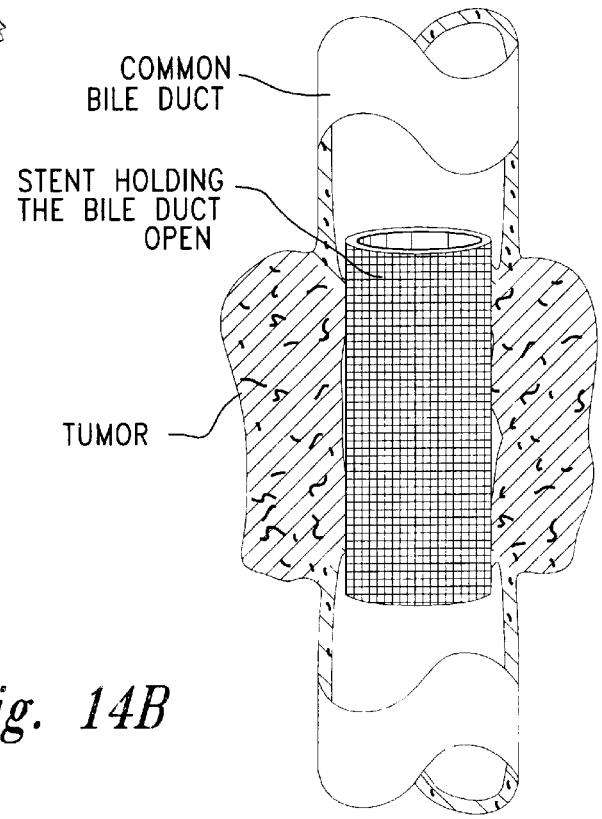

In addition to the compositions described above, the present invention also provides a variety of methods which utilize the above-described anti-angiogenic compositions. In particular, within one aspect of the present invention methods are provided for embolizing a blood vessel, comprising the step of delivering into the vessel a therapeutically effective amount of an anti-angiogenic composition (as described above), such that the blood vessel is effectively occluded. Therapeutically effective amounts suitable for occluding blood vessels may be readily determined given the disclosure provided below, and as described in Example 6. Within a particularly preferred embodiment, the anti-angiogenic composition is delivered to a blood vessel which nourishes a tumor (see FIG. 13).

Briefly, there are a number of clinical situations (e.g., bleeding, tumor development) where it is desirable to reduce or abolish the blood supply to an organ or region. As described in greater detail below, this may be accomplished by injecting anti-angiogenic compositions of the present invention into a desired blood vessel through a selectively positioned catheter (see FIG. 13). The composition travels via the blood stream until it becomes wedged in the vasculature, thereby physically (or chemically) occluding the blood vessel. The reduced or abolished blood flow to the selected area results in infarction (cell death due to an inadequate supply of oxygen and nutrients) or reduced blood loss from a damaged vessel.

For use in embolization therapy, anti-angiogenic compositions of the present invention are preferably non-toxic, thrombogenic, easy to inject down vascular catheters, radio-opaque, rapid and permanent in effect, sterile, and readily available in different shapes or sizes at the time of the procedure. In addition, the compositions preferably result in the slow (ideally, over a period of several weeks to months) release of an anti-angiogenic factor. Particularly preferred anti-angiogenic compositions should have a predictable size of 15–200 $\mu$m after being injected into the vascular system. Preferably, they should not clump into larger particles either in solution or once injected. In addition, preferable compositions should not change shape or physical properties during storage prior to use.

Embolization therapy may be utilized in at least three principal ways to assist in the management of neoplasms: (1) definitive treatment of tumors (usually benign); (2) for preoperative embolization; and (3) for palliative embolization. Briefly, benign tumors may sometimes be successfully treated by embolization therapy alone. Examples of such tumors include simple tumors of vascular origin (e.g., haemangiomas), endocrine tumors such as parathyroid adenomas, and benign bone tumors.

For other tumors, (e.g., renal adenocarcinoma), preoperative embolization may be employed hours or days before surgical resection in order to reduce operative blood loss, shorten the duration of the operation, and reduce the risk of dissemination of viable malignant cells by surgical manipulation of the tumor. Many tumors may be successfully embolized preoperatively, including for example nasopharyngeal tumors, glomus jugular tumors, meningiomas, chemodectomas, and vagal neuromas.

Embolization may also be utilized as a primary mode of treatment for inoperable malignancies, in order to extend the survival time of patients with advanced disease. Embolization may produce a marked improvement in the quality of life of patients with malignant tumors by alleviating unpleasant symptoms such as bleeding, venous obstruction and tracheal compression. The greatest benefit from palliative tumor embolization, however, may be seen in patients suffering from the humoral effects of malignant endocrine tumors, wherein metastases from carcinoid tumors and other endocrine neoplasms such as insulinomas and glucagonomas may be slow growing, and yet cause great distress by virtue of the endocrine syndromes which they produce.

In general, embolization therapy utilizing anti-angiogenic compositions of the present invention is typically performed in a similar manner, regardless of the site. Briefly, angiography (a road map of the blood vessels) of the area to be embolized is first performed by injecting radiopaque contrast through a catheter inserted into an artery or vein (depending on the site to be embolized) as an X-ray is taken. The catheter may be inserted either percutaneously or by surgery. The blood vessel is then embolized by refluxing anti-angiogenic compositions of the present invention through the catheter, until flow is observed to cease. Occlusion may be confirmed by repeating the angiogram.

Embolization therapy generally results in the distribution of compositions containing anti-angiogenic factors throughout the interstices of the tumor or vascular mass to be treated. The physical bulk of the embolic particles clogging the arterial lumen results in the occlusion of the blood supply. In addition to this effect, the presence of an anti-angiogenic factor(s) prevents the formation of new blood vessels to supply the tumor or vascular mass, enhancing the devitalizing effect of cutting off the blood supply.

Therefore, it should be evident that a wide variety of tumors may be embolized utilizing the compositions of the present invention. Briefly, tumors are typically divided into two classes: benign and malignant. In a benign tumor the cells retain their differentiated features and do not divide in a completely uncontrolled manner. In addition, the tumor is localized and nonmetastatic. In a malignant tumor, the cells become undifferentiated, do not respond to the body's growth and hormonal signals, and multiply in an uncontrolled manner; the tumor is invasive and capable of spreading to distant sites (metastasizing).

Within one aspect of the present invention, metastases (secondary tumors) of the liver may be treated utilizing embolization therapy. Briefly, a catheter is inserted via the femoral or brachial artery and advanced into the hepatic artery by steering it through the arterial system under fluoroscopic guidance. The catheter is advanced into the hepatic arterial tree as far as necessary to allow complete blockage of the blood vessels supplying the tumor(s), while sparing as many of the arterial branches supplying normal structures as possible. Ideally this will be a segmental branch of the hepatic artery, but it could be that the entire hepatic artery distal to the origin of the gastroduodenal artery, or even multiple separate arteries, will need to be blocked depending on the extent of tumor and its individual blood supply. Once the desired catheter position is achieved, the artery is embolized by injecting anti-angiogenic compositions (as described above) through the arterial catheter until flow in the artery to be blocked ceases, preferably even after observation for 5 minutes. Occlusion of the artery may be confirmed by injecting radiopaque contrast through the catheter and demonstrating by fluoroscopy or X-ray film that the vessel which previously filled with contrast no longer does so. The same procedure may be repeated with each feeding artery to be occluded.

As noted above, both benign and malignant tumors may be embolized utilizing compositions of the present invention. Representative examples of benign hepatic tumors include Hepatocellular Adenoma, Cavernous Haemangioma, and Focal Nodular Hyperplasia. Other benign tumors, which are more rare and often do not have clinical manifestations, may also be treated. These include Bile Duct Adenomas, Bile Duct Cystadenomas, Fibromas, Lipomas, Leiomyomas, Mesotheliomas, Teratomas, Myxomas, and Nodular Regenerative Hyperplasia.

Malignant Hepatic Tumors are generally subdivided into two categories: primary and secondary. Primary tumors arise directly from the tissue in which they are found. Thus, a primary liver tumor is derived originally from the cells which make up the liver tissue (such as hepatocytes and biliary cells). Representative examples of primary hepatic malignancies which may be treated by arterial embolization include Hepatocellularcarcinoma, Cholangiocarcinoma, Angiosarcoma, Cystadenocarcinoma, Squamous Cell Carcinoma, and Hepatoblastoma.

A secondary tumor, or metastasis, is a tumor which originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.). Secondary hepatic tumors are one of the most common causes of death in the cancer patient and are by far and away the most common form of liver tumor. Although virtually any malignancy can metastasize to the liver, tumors which are most likely to spread to the liver include: cancer of the stomach, colon, and pancreas; melanoma; tumors of the lung, oropharynx, and bladder; Hodgkin's and non-Hodgkin's lymphoma; tumors of the breast, ovary, and prostate. Each one of the above-named primary tumors has numerous different tumor types which may be treated by arterial embolization (for example, there are over 32 different types of ovarian cancer).

As noted above, embolization therapy utilizing anti-angiogenic compositions of the present invention may also be applied to a variety of other clinical situations where it is desired to occlude blood vessels. Within one aspect of the present invention, arteriovenous malformation may be treated by administration of one of the above-described compositions. Briefly, arteriovenous malformations (vascular malformations) refers to a group of diseases wherein at least one (and most typically, many) abnormal communications between arteries and veins occur, resulting in a local tumor-like mass composed predominantly of blood vessels. Such disease may be either congenital or acquired.

Within one embodiment of the invention, an arteriovenous malformation may be treated by inserting a catheter via the femoral or brachial artery, and advancing it into the feeding artery under fluoroscopic guidance. The catheter is preferably advanced as far as necessary to allow complete blockage of the blood vessels supplying the vascular malformation, while sparing as many of the arterial branches supplying normal structures as possible (ideally this will be a single artery, but most often multiple separate arteries may need to be occluded, depending on the extent of the vascular malformation and its individual blood supply). Once the desired catheter position is achieved, each artery may be embolized utilizing anti-angiogenic compositions of the present invention.

Within another aspect of the invention, embolization may be accomplished in order to treat conditions of excessive bleeding. For example, menorrhagia (excessive bleeding with menstruation) may be readily treated by embolization of uterine arteries. Briefly, the uterine arteries are branches of the internal iliac arteries bilaterally. Within one embodiment of the invention, a catheter may be inserted via the femoral or brachial artery, and advanced into each uterine artery by steering it through the arterial system under fluoroscopic guidance. The catheter should be advanced as far as necessary to allow complete blockage of the blood vessels to the uterus, while sparing as many arterial branches that arise from the uterine artery and supply normal structures as possible. Ideally a single uterine artery on each side may be embolized, but occasionally multiple separate arteries may need to be blocked depending on the individual blood supply. Once the desired catheter position is achieved, each artery may be embolized by administration of the anti-angiogenic compositions as described above.

In a like manner, arterial embolization may be accomplished in a variety of other conditions, including for example, for acute bleeding, vascular abnormalities, central nervous system disorders, and hypersplenism.

Use of Anti-Angiogenic Compositions as Coatings for Stents

As noted above, the present invention also provides stents, comprising a generally tubular structure (which includes for example, spiral shapes), the surface of which is coated with a composition as described above. Briefly, a stent is a scaffolding, usually cylindrical in shape, that may be inserted into a body passageway (e.g., bile ducts) or a portion of a body passageway, which has been narrowed, irregularly contured, obstructed, or occluded by a disease process (e.g., ingrowth by a tumor) in order to prevent closure or reclosure of the passageway. Stents act by physically holding open the walls of the body passage into which they are inserted.

A variety of stents may be utilized within the context of the present invention, including for example, esophageal stents, vascular stents, biliary stents, pancreatic stents, ureteric and urethral stents, lacrimal stents, Eustachian tube stents, fallopian tube stents and tracheal/bronchial stents.

Stents may be readily obtained from commercial sources, or constructed in accordance with well-known techniques. Representative examples of stents include those described in U.S. Pat. No. 4,768,523, entitled "Hydrogel Adhesive;" U.S. Pat. No. 4,776,337, entitled "Expandable Intraluminal Graft, and Method and Apparatus for Implanting and Expandable Intraluminal Graft;" U.S. Pat. No. 5,041,126 entitled "Endovascular Stent and Delivery System;" U.S. Pat. No. 5,052,998 entitled "Indwelling Stent and Method of Use;" U.S. Pat. No. 5,064,435 entitled "Self-Expanding Prosthesis Having Stable Axial Length;" U.S. Pat. No. 5,089,606, entitled "Water-insoluble Polysaccharide Hydrogel Foam for Medical Applications;" U.S. Pat. No. 5,147,370, entitled "Nitinol Stent for Hollow Body Conduits;" U.S. Pat. No. 5,176,626, entitled "Indwelling Stent;" U.S. Pat. No. 5,213,580, entitled "Biodegradable polymeric Endoluminal Sealing Process;" and U.S. Pat. No. 5,328,471, entitled "Method and Apparatus for Treatment of Focal Disease in Hollow Tubular Organs and Other Tissue Lumens."

Stents may be coated with anti-angiogenic compositions or anti-angiogenic factors of the present invention in a variety of manners, including for example: (a) by directly affixing to the stent an anti-angiogenic composition (e.g., by either spraying the stent with a polymer/drug film, or by dipping the stent into a polymer/drug solution), (b) by coating the stent with a substance such as a hydrogel which will in turn absorb the anti-angiogenic composition (or anti-angiogenic factor above), (c) by interweaving anti-angiogenic composition coated thread (or the polymer itself formed into a thread) into the stent structure, (d) by inserting the stent into a sleeve or mesh which is comprised of or coated with an anti-angiogenic composition, or (e) constructing the stent itself with an anti-angiogenic composition. Within preferred embodiments of the invention, the composition should firmly adhere to the stent during storage and at the time of insertion, and should not be dislodged from the stent when the diameter is expanded from its collapsed size to its full expansion size. The anti-angiogenic composition should also preferably not degrade during storage, prior to insertion, or when warmed to body temperature after expansion inside the body. In addition, it should preferably coat the stent smoothly and evenly, with a uniform distribution of angiogenesis inhibitor, while not changing the stent contour. Within preferred embodiments of the invention, the anti-angiogenic composition should provide a uniform, predictable, prolonged release of the anti-angiogenic factor into the tissue surrounding the stent once it has been deployed. For vascular stents, in addition to the above properties, the composition should not render the stent thrombogenic (causing blood clots to form), or cause significant turbulence in blood flow (more than the stent itself would be expected to cause if it was uncoated).

Within another aspect of the present invention, methods are provided for expanding the lumen of a body passageway, comprising inserting a stent into the passageway, the stent having a generally tubular structure, the surface of the structure being coated with an anti-angiogenic composition (or, an anti-angiogenic factor alone), such that the passageway is expanded. A variety of embodiments are described below wherein the lumen of a body passageway is expanded in order to eliminate a biliary, esophageal, tracheal/bronchial, urethral or vascular obstruction. In addition, a representative example is described in more detail below in Example 7.

Generally, stents are inserted in a similar fashion regardless of the site or the disease being treated. Briefly, a preinsertion examination, usually a diagnostic imaging procedure, endoscopy, or direct visualization at the time of surgery, is generally first performed in order to determine the appropriate positioning for stent insertion. A guidewire is then advanced through the lesion or proposed site of insertion, and over this is passed a delivery catheter which allows a stent in its collapsed form to be inserted. Typically, stents are capable of being compressed, so that they can be inserted through tiny cavities via small catheters, and then expanded to a larger diameter once they are at the desired location. Once expanded, the stent physically forces the walls of the passageway apart and holds them open. As such, they are capable of insertion via a small opening, and yet are still able to hold open a large diameter cavity or passageway. The stent may be self-expanding (e.g., the Wallstent and Gianturco stents), balloon expandable (e.g., the Palmaz stent and Strecker stent), or implanted by a change in temperature (e.g. the Nitinol stent).

Stents are typically maneuvered into place under radiologic or direct visual control, taking particular care to place the stent precisely across the narrowing in the organ being treated. The delivery catheter is then removed, leaving the stent standing on its own as a scaffold. A post insertion examination, usually an x-ray, is often utilized to confirm appropriate positioning.

Within a preferred embodiment of the invention, methods are provided for eliminating biliary obstructions, comprising inserting a biliary stent into a biliary passageway, the stent having a generally tubular structure, the surface of the structure being coated with a composition as described above, such that the biliary obstruction is eliminated. Briefly, tumor overgrowth of the common bile duct results in progressive cholestatic jaundice which is incompatible with life. Generally, the biliary system which drains bile from the liver into the duodenum is most often obstructed by (1) a tumor composed of bile duct cells (cholangiocarcinoma), (2) a tumor which invades the bile duct (e.g., pancreatic carcinoma), or (3) a tumor which exerts extrinsic pressure and compresses the bile duct (e.g., enlarged lymph nodes).

Both primary biliary tumors, as well as other tumors which cause compression of the biliary tree may be treated utilizing the stents described herein. One example of primary biliary tumors are adenocarcinomas (which are also called Klatskin tumors when found at the bifurcation of the common hepatic duct). These tumors are also referred to as biliary carcinomas, choledocholangiocarcinomas, or adenocarcinomas of the biliary system. Benign tumors which affect the bile duct (e.g., adenoma of the biliary system), and, in rare cases, squamous cell carcinomas of the bile duct and adenocarcinomas of the gallbladder, may also cause compression of the biliary tree and therefore, result in biliary obstruction.

Compression of the biliary tree is most commonly due to tumors of the liver and pancreas which compress and therefore obstruct the ducts. Most of the tumors from the pancreas arise from cells of the pancreatic ducts. This is a highly fatal form of cancer (5% of all cancer deaths; 26,000 new cases per year in the U.S.) with an average of 6 months survival and a 1 year survival rate of only 10%. When these tumors are located in the head of the pancreas they frequently cause biliary obstruction, and this detracts significantly from the quality of life of the patient. While all types of pancreatic tumors are generally referred to as "carcinoma of the pancreas" there are histologic subtypes including: adenocarcinoma, adenosquamous carcinoma, cystadenocarcinoma, and acinar cell carcinoma. Hepatic tumors, as discussed above, may also cause compression of the biliary tree, and therefore cause obstruction of the biliary ducts.

Within one embodiment of the invention, a biliary stent is first inserted into a biliary passageway in one of several ways: from the top end by inserting a needle through the abdominal wall and through the liver (a percutaneous transhepatic cholangiogram or "PTC"); from the bottom end by cannulating the bile duct through an endoscope inserted through the mouth, stomach, and duodenum (an endoscopic retrograde cholangiogram or "ERCP"); or by direct incision during a surgical procedure. A preinsertion examination, PTC, ERCP, or direct visualization at the time of surgery should generally be performed to determine the appropriate position for stent insertion. A guidewire is then advanced through the lesion, and over this a delivery catheter is passed to allow the stent to be inserted in its collapsed form. If the diagnostic exam was a PTC, the guidewire and delivery catheter is inserted via the abdominal wall, while if the original exam was an ERCP the stent may be placed via the mouth. The stent is then positioned under radiologic, endoscopic, or direct visual control taking particular care to place it precisely across the narrowing in the bile duct. The delivery catheter is then removed leaving the stent standing as a scaffolding which holds the bile duct open. A further cholangiogram may be performed to document that the stent is appropriately positioned.

Within yet another embodiment of the invention, methods are provided for eliminating esophageal obstructions, comprising inserting an esophageal stent into an esophagus, the stent having a generally tubular structure, the surface of the structure being coated with an anti-angiogenic composition as described above, such that the esophageal obstruction is eliminated. Briefly, the esophagus is the hollow tube which transports food and liquids from the mouth to the stomach. Cancer of the esophagus or invasion by cancer arising in adjacent organs (e.g. cancer of the stomach or lung) results in the inability to swallow food or saliva. Within this embodiment, a preinsertion examination, usually a barium swallow or endoscopy should generally be performed in order to determine the appropriate position for stent insertion. A catheter or endoscope may then be positioned through the mouth, and a guidewire is advanced through the blockage. A stent delivery catheter is passed over the guidewire under radiologic or endoscopic control, and a stent is placed precisely across the narrowing in the esophagus. A post insertion examination, usually a barium swallow x-ray, may be utilized to confirm appropriate positioning.

Within other embodiments of the invention, methods are provided for eliminating tracheal/bronchial obstructions, comprising inserting a tracheal/bronchial stent into the trachea or bronchi, the stent having a generally tubular structure, the surface of which is coated with an anti-angiogenic composition as described above, such that the tracheal/bronchial obstruction is eliminated. Briefly, the trachea and bronchi are tubes which carry air from the mouth and nose to the lungs. Blockage of the trachea by cancer, invasion by cancer arising in adjacent organs (e.g., cancer of the lung), or collapse of the trachea or bronchi due to chondromalacia (weakening of the cartilage rings) results in inability to breathe. Within this embodiment of the invention, preinsertion examination, usually an endoscopy, should generally be performed in order to determine the appropriate position for stent insertion. A catheter or endoscope is then positioned through the mouth, and a guidewire advanced through the blockage. A delivery catheter is then passed over the guidewire in order to allow a collapsed stent to be inserted. The stent is placed under radiologic or endoscopic control in order to place it precisely across the narrowing. The delivery catheter may then be removed leaving the stent standing as a scaffold on its own. A post insertion examination, usually a bronchoscopy may be utilized to confirm appropriate positioning.

Within another embodiment of the invention, methods are provided for eliminating urethral obstructions, comprising inserting a urethral stent into a urethra, the stent having a generally tubular structure, the surface of the structure being coated with an anti-angiogenic composition as described above, such that the urethral obstruction is eliminated. Briefly, the urethra is the tube which drains the bladder through the penis. Extrinsic narrowing of the urethra as it passes through the prostate, due to hypertrophy of the prostate, occurs in virtually every man over the age of 60 and causes progressive difficulty with urination. Within this embodiment, a preinsertion examination, usually an endoscopy or urethrogram should generally first be performed in order to determine the appropriate position for stent insertion, which is above the external urinary sphincter at the lower end, and close to flush with the bladder neck at the upper end. An endoscope or catheter is then positioned through the penile opening and a guidewire advanced into the bladder. A delivery catheter is then passed over the guidewire in order to allow stent insertion. The delivery catheter is then removed, and the stent expanded into place. A post insertion examination, usually endoscopy or retrograde urethrogram, may be utilized to confirm appropriate position.

Within another embodiment of the invention, methods are provided for eliminating vascular obstructions, comprising inserting a vascular stent into a blood vessel, the stent having a generally tubular structure, the surface of the structure being coated with an anti-angiogenic composition as described above, such that the vascular obstruction is eliminated. Briefly, stents may be placed in a wide array of blood vessels, both arteries and veins, to prevent recurrent stenosis at the site of failed angioplasties, to treat narrowings that would likely fail if treated with angioplasty, and to treat post surgical narrowings (e.g., dialysis graft stenosis). Representative examples of suitable sites include the iliac, renal, and coronary arteries, the superior vena cava, and in dialysis grafts. Within one embodiment, angiography is first performed in order to localize the site for placement of the stent. This is typically accomplished by injecting radiopaque contrast through a catheter inserted into an artery or vein as an x-ray is taken. A catheter may then be inserted either percutaneously or by surgery into the femoral artery, brachial artery, femoral vein, or brachial vein, and advanced into the appropriate blood vessel by steering it through the vascular system under fluoroscopic guidance. A stent may then be positioned across the vascular stenosis. A post insertion angiogram may also be utilized in order to confirm appropriate positioning.

Use of Anti-Angiogenic Compositions in Surgical Procedures

As noted above, anti-angiogenic compositions may be utilized in a wide variety of surgical procedures. For example, within one aspect of the present invention an anti-angiogenic compositions (in the form of, for example, a spray or film) may be utilized to coat or spray an area prior to removal of a tumor, in order to isolate normal surrounding tissues from malignant tissue, and/or to prevent the spread Of disease to surrounding tissues. Within other aspects of the present invention, anti-angiogenic compositions (e.g., in the form of a spray) may be delivered via endoscopic procedures in order to coat tumors, or inhibit angiogenesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh ladened with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering an anti-angiogenic composition as described above to the resection margins of a tumor subsequent to excision, such that the local recurrence of cancer and the formation of new blood vessels at the site is inhibited. Within one embodiment of the invention, the anti-angiogenic composition(s) (or anti-angiogenic factor(s) alone) are administered directly to the tumor excision site (e.g., applied by swabbing, brushing or otherwise coating the resection margins of the tumor with the anti-angiogenic composition(s) or factor(s)). Alternatively, the anti-angiogenic composition(s) or factor(s) may be incorporated into known surgical pastes prior to administration. Within particularly preferred embodiments of the invention, the anti-angiogenic compositions are applied after hepatic resections for malignancy, and after neurosurgical operations.

Within one aspect of the present invention, anti-angiogenic compositions (as described above) may be administered to the resection margin of a wide variety of tumors, including for example, breast, colon, brain and hepatic tumors. For example, within one embodiment of the invention, anti-angiogenic compositions may be administered to the site of a neurological tumor subsequent to excision, such that the formation of new blood vessels at the site are inhibited. Briefly, the brain is highly functionally localized; i.e., each specific anatomical region is specialized to carry out a specific function. Therefore it is the location of brain pathology that is often more important than the type. A relatively small lesion in a key area can be far more devastating than a much larger lesion in a less important area. Similarly, a lesion on the surface of the brain may be easy to resect surgically, while the same tumor located deep in the brain may not (one would have to cut through too many vital structures to reach it). Also, even benign tumors can be dangerous for several reasons: they may grow in a key area and cause significant damage; even though they would be cured by surgical resection this may not be possible; and finally, if left unchecked they can cause increased intracranial pressure. The skull is an enclosed space incapable of expansion. Therefore, if something is growing in one location, something else must be being compressed in another location—the result is increased pressure m the skull or increased intracranial pressure. If such a condition is left untreated, vital structures can be compressed, resulting in death. The incidence of CNS (central nervous system) malignancies is 8–16 per 100,000. The prognosis of primary malignancy of the brain is dismal, with a median survival of less than one year, even following surgical resection. These tumors, especially gliomas, are predominantly a local disease which recur within 2 centimeters of the original focus of disease after surgical removal.

Representative examples of brain tumors which may be treated utilizing the compositions and methods described herein include Glial Tumors (such as Anaplastic Astrocytoma, Glioblastoma Multiform, Pilocytic Astrocytoma, Oligodendroglioma, Ependymoma, Myxopapillary Ependymoma, Subependymoma, Choroid Plexus Papilloma); Neuron Tumors (e.g., Neuroblastoma, Ganglioneuroblastoma, Ganglioneuroma, and Medulloblastoma); Pineal Gland Tumors (e.g., Pineoblastoma and Pineocytoma); Menigeal Tumors (e.g., Meningioma, Meningeal Hemangiopericytoma, Meningeal Sarcoma); Tumors of Nerve Sheath Cells (e.g., Schwannoma (Neurolemmoma) and Neurofibroma); Lymphomas (e.g., Hodgkin's and Non-Hodgkin's Lymphoma (including numerous subtypes, both primary and secondary); Malformative Tumors (e.g., Craniopharyngioma, Epidermoid Cysts, Dermoid Cysts and Colloid Cysts); and Metastatic Tumors (which can be derived from virtually any tumor, the most common being from lung, breast, melanoma, kidney, and gastrointestinal tract tumors).

Inflammatory Arthritis

Inflammatory arthritis is a serious health problems in developed countries, particularly given the increasing number of aged individuals. For example, one form of inflammatory arthritis, rheumatoid arthritis (RA) is a multisystem chronic, relapsing, inflammatory disease of unknown cause. Although many organs can be affected, RA is basically a severe form of chronic synovitis that sometimes leads to destruction and ankylosis of affected joints (taken from *Robbins Pathological Basis of Disease*, by R. S. Cotran, V. Kumar, and S. L. Robbins, W. B. Saunders Co., 1989). Pathologically the disease is characterized by a marked thickening of the synovial membrane which forms villous projections that extend into the joint space, multilayering of the synoviocyte lining (synoviocyte proliferation), infiltration of the synovial membrane with white blood cells (macrophages, lymphocytes, plasma cells, and lymphoid follicles; called an "inflammatory synovitis"), and deposition of fibrin with cellular necrosis within the synovium. The tissue formed as a result of this process is called pannus and eventually the pannus grows to fill the joint space. The pannus develops an extensive network of new blood vessels through the process of angiogenesis which is essential to the evolution of the synovitis. Release of digestive enzymes [matrix metalloproteinases (e.g., collagenase, stromelysin)] and other mediators of the inflammatory process (e.g., hydrogen peroxide, superoxides, lysosomal enzymes, and products of arachadonic acid metabolism) from the cells of the pannus tissue leads to the progressive destruction of the cartilage tissue. The pannus invades the articular cartilage leading to erosions and fragmentation of the cartilage tissue. Eventually there is erosion of the subchondral bone with fibrous ankylosis and ultimately bony ankylosis, of the involved joint.

It is generally believed, but not conclusively proven, that RA is an autoimmune disease, and that many different arthriogenic stimuli activate the immune response in the immunogenetically susceptible host. Both exogenous infectious agents (Ebstein-Barr Virus, Rubella virus, Cytomegalovirus, Herpes Virus, Human T-cell Lymphotropic Virus, Mycoplasma, and others) and endogenous proteins (collagen, proteoglycans, altered immunoglobulins) have been implicated as the causative agent which triggers an inappropriate host immune response. Regardless of the inciting agent, autoimmunity plays a role in the progression of the disease. In particular, the relevant antigen is ingested by antigen-presenting cells (macrophages or dendritic cells in the synovial membrane), processed, and presented to T lymphocytes. The T cells initiate a cellular immune response and stimulate the proliferation and differentiation of B lymphocytes into plasma cells. The end result is the production of an excessive inappropriate immune response directed against the host tissues [e.g., antibodies directed against Type II collagen, antibodies directed against the Fc portion of autologous IgG (called "Rheumatoid Factor")]. This further amplifies the immune response and hastens the destruction of the cartilage tissue. Once this cascade is initiated numerous mediators of cartilage destruction are responsible for the progression of rheumatoid arthritis.

Thus, within one aspect of the present invention, methods are provided for treating or preventing inflammatory arthritis (e.g., rheumatoid arthritis) comprising the step of administering to a patient a therapeutically effective amount of an anti-angiogenic factor or anti-angiogenic composition to a joint. Within a preferred embodiment of the invention, anti-angiogenic factors (including anti-angiogenic compositions, as described above) may be administered directly by intra-articular injection, as a surgical paste, or as an oral agent (e.g. containing the anti-angiogenic factor thalidomide). One representative example of such a method is set forth in more detail below in Example 19.

As utilized within the context of the present invention, it should be understood that efficatious administration of the anti-angiogenic factors and compositions described herein may be assessed in several ways, including: (1) by preventing or lessening the pathological and/or clinical symptoms associated with rheumatoid arthritis; (2) by downregulating the white blood cell response which initiates the inflammatory cascade and results in synovitis, swelling, pain, and tissue destruction; (3) by inhibiting the "tumor-like" proliferation of synoviocytes that leads to the development of a locally invasive and destructive pannus tissue; (4) by decreasing the production/activity of matrix metalloproteinases produced by white blood cells, synoviocytes, chondrocytes, and endothelial cells, which degrade the cartilage matrix and result in irreversible destruction of the articular cartilage; and (5) by inhibiting blood vessel formation which provides the framework and nutrients necessary for the growth and development of the pannus tissue. Furthermore, the anti-angiogenic factors or compositions should not be toxic to normal chondrocytes at therapeutic levels. Each of these aspects will be discussed in more detail below.

A. Inflammatory Response

Neutrophils are found in abundance in the synovial fluid, but only in small numbers in the synovial membrane itself It is estimated that more than 1 billion neutrophils enter a moderately inflamed rheumatoid knee joint each day (Hollingsworth et al., 1967) and remain there because no pathway exists by which they can leave the joint. These cells release reactive free radicals and lysosomal enzymes which degrade the cartilage tissue. Other PMN products such as prostaglandins and leukotrienes augment the inflammatory response and recruit more inflammatory cells into the joint tissue.

Lymphocytes, particularly T cells, are present in abundance in the diseased synovial tissue. Activated T cells produce a variety of lymphokines and cooperate with B cells to produce autoantibodies. T cells products result in the activation macrophages, a cell which is thought to have an important role in the pathology of the disease. The macrophages produce a variety destructive lysosomal enzymes, prostaglandins, and monokines and are also capable of stimulating angiogenesis. One of the more important monokines secreted by macrophages is IL-1. Briefly, IL-1 is known to: stimulate synthesis and release of collagenase by synoviocytes and synovial fibroblasts, inhibit proteoglycan synthesis by chondrocytes, activate osteoclasts, induce changes in the endothelium of the synovial vasculature [stimulation of endothelial production of plasminogen activator and colony stimulating factor, expression of leukocyte adhesion molecules, promotion of procoagulant activity (Wider et al., 1991)], and act as a chemoattractant for lymphocytes and neutrophils.

Within one embodiment, downregulation of the white blood cell response, or inhibition of the inflammatory response, may be assessed by determination of the effect of the anti-angiogenic factor or anti-angiogenic composition on the response of neutrophils stimulated with opsonized CPPD crystals or opsonized zyrosan. Such methods are illustrated in more detail below in Example 22.

B. Synoviocyte Hyperplasia

During the development of RA, the synovial lining cells become activated by products of inflammation or through phagocytosis of immune complexes. Several subtypes of synovial lining cells have been identified and all of them become intensely activated and undergo excessive hyperplasia and growth when stimulated. As the synovial tissue organizes to form a pannus, the number of synoviocytes, blood vessels, connective tissue elements, and inflammatory cells increases to form a mass 100 times its original size. In many ways, the synovitis in rheumatoid arthritis behaves much like a localized neoplasia (Harris, 1990). In fact, cultured rheumatoid synovial cells develop the phenotypic characteristics of anchorage-independent growth usually associated with neoplastic cells if they given sufficient plateletderived growth factor (Lafyatis et al., 1989). In addition, the synoviocytes also produce large amounts of collagenase, stromelysin, prostaglandins, and Interleukin-1.

The tumor-like proliferation of the cells of the synovial connective tissue stroma (synoviocytes, fibroblast-like cells and neovascular tissue) produces a pannus with many features of a localized malignancy. Supporting this tumor analogy are several findings: the pannus expresses high levels of oncoproteins such as c-myc and c-fos, produces metalloproteinases to facilitate surrounding tissue invasion, express cytoskeletal markers characteristic of poorly differentiated mesenchymal tissue (e.g., vimentin); synoviocytes in vitro grow rapidly, do not contact inhibit, form foci, and can be grown under anchorage-independent conditions in soft agarose; and pannus tissue is capable of inducing the growth of a supporting vasculature (i.e. angiogenesis). All these findings are suggestive of a tissue in which normal growth regulation as been lost.

Within one embodiment, inhibition of synoviocyte proliferation may be determined by, for example, analysis of $^3$H-thymidine incorporation into synoviocytes, or in vitro synoviocyte proliferation. Such methods are illustrated in more detail below in Example 23.

C. Matrix Metalloproteinases (MMP)

Irreparable degradation of the cartilage extracellular matrix is believed to be largely due to the enzymatic action of matrix metalloproteinases on the components of the cartilage matrix. Although numerous other enzymes are likely involved in the development of RA, collagenase (MMP-1) and stromelysin (MMP-3) play an important role (Vincetti et al., 1994) in disease progression. These enzymes are capable of degrading type 11 collagen and proteoglycans respectively; the 2 major extracellular components of cartilage tissue. Cytokines such as IL-1, epidermal growth factor (EGF), platelet-derived growth factor, and tumor necrosis factor are all potent stimulators of collagenase and stromelysin production. As described above, numerous cell types found in the arthritic joint (white blood cells, synoviocytes, endothelial cells, and chondrocytes) are capable of synthesizing and secreting MMPS.

In proliferating rheumatoid synovial tissue, collagenase and stromelysin become the major gene products of the pannus and may comprise as much as 2% of the messenger RNAs produced by the synovial fibroblasts (Brinkerhoff and Auble, 1990). Increased levels of collagenase and stromelysin are present in the cartilage of patients with RA and the level of enzyme activity in the joint correlates well with the severity of the lesion (Martel-Pelletier et al., 1993; Walakovitis et al., 1992). Because these enzymes are fundamental to the pathology of RA and result in irreversible cartilage damage, many therapeutic strategies have been devised to inhibit their effects.

Numerous naturally present inhibitors of MMP activity have been identified and named "TIMPS" for Tissue Inhibitors of Metalloproteinases. Many of these protein inhibitors bind with the active MMPs to form 1:1 noncovalent complexes which inactivate the MMP enzymes. The TIMPs are produced locally by chondrocytes and synovial fibroblasts and are likely responsible for the normal regulation of connective tissue degradation. It is thought that much of the damage to the cartilage matrix is due to a local imbalance between MMP and TIMP activity. This is probably due to increased production of metalloproteinases while the production of TIMPs remains at a normal or constant level (Vincetti et al., 1994). To overcome this, therapeutic strategies have been designed to add exogenous TIMPs (e.g., the chemically modified tetracycline molecules, collagen substrate analogues) or to upregulate TIMP production (retinoids, transforming growth factor β, IL-6, IL-11, oncostatin M) in an effort to restore the enzymatic balance. However this approach has yet to translate into significant clinical results.

An alternative approach is to inhibit or downregulate the production of the MMPs to restore a normal balance of activity. Naturally occurring compounds (TNFβ, all-trans retinoic acid) and synthetic compounds (retinoids, glucocorticoid hormones) have been demonstrated to inhibit MMP activity by suppressing transcription and synthesis of these proteins. A post-transcriptional method of blocking MMP release could also be expected to result in a decrease in the amount of MMP produced and an improved balance between MMP and TIMP activity in the joint.

Within one embodiment, a decrease in the production or activity of MMP's may be determined by, for example, analysis of IL-1 induced collagenase expression. One such method is illustrated in more detail below in Example 24.

D. Angiogenesis

The development of an extensive network of new blood vessels is essential to the development of the synovitis present in rheumatoid arthritis (Harris, 1990; Folkman et al., 1989; Sano et al., 1990). Several local mediators such as plateletderived growth factor (PDGF), TGF-β, and fibroblast growth factor (FGF) are likely responsible for the induction and perpetuation of neovascularization within the synovium. Pannus tissue composed of new capillaries and synovial connective tissue invades and destroys the articular cartilage. The migrating angiogenic vessels themselves produce and secrete increased levels of metalloproteinases such as collagenase and stromelysin capable of degrading the cartilage matrix (Case et al., 1989). The newly formed vessels are also quite "leaky" with gaps present between the microvascular endothelial cells. This facilitates the exudation of plasma proteins into the synovium (which increases swelling), enhances WBCs movement from the circulation into the pannus tissue (which increases inflammation), and leads to the perivascular accumulation of mononuclear inflammatory cells (Wilder et al., 1991).

In summary, the endothelial tissue plays an important role in the development of this disease by expressing the necessary surface receptors to allow inflammatory cells to leave the circulation and enter the developing pannus, secreting proteolytic enzymes capable of degrading the cartilage matrix, and proliferating to form the new vessels (angiogenesis) required for the pannus tissue to increase in size and invade adjacent tissues.

Within one embodiment, inhibition of new blood vessel formation may be readily determined in a variety of asays, including the CAM assay described above and within Example 2.

Neovascular Diseases of the Eye

As noted above, the present invention also provides methods for treating neovascular diseases of the eye, including for example, corneal neovascularization, neovascular glaucoma, proliferative diabetic retinopathy, retrolental fibroblasia and macular degeneration.

Briefly, corneal neovascularization as a result of injury to the anterior segment is a significant cause of decreased visual acuity and blindness, and a major risk factor for rejection of corneal allografts. As described by Burger et al., Lab. Invest. 48:169–180, 1983, corneal angiogenesis involves three phases: a pre-vascular latent period, active neovascularization, and vascular maturation and regression. The identity and mechanism of various angiogenic factors, including elements of the inflammatory response, such as leukocytes, platelets, cytokines, and eicosanoids, or unidentified plasma constituents have yet to be revealed.

Currently no clinically satisfactory therapy exists for inhibition of corneal neovascularization or regression of existing corneal new vessels. Topical corticosteroids appear to have some clinical utility, presumably by limiting stromal inflammation.

Thus, within one aspect of the present invention methods are provided for treating neovascular diseases of the eye such as corneal neovascularization (including corneal graft neovascularization), comprising the step of administering to a patient a therapeutically effective amount of an anti-angiogenic composition (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates.

Blood vessels can enter the cornea in a variety of patterns and depths, depending upon the process which incites the neovascularization. These patterns have been traditionally defined by ophthalmologists in the following types: pannus trachomatosus, pannus leprosus, pannus phylctenulosus, pannus degenerativus, and glaucomatous pannus. The corneal stroma may also be invaded by branches of the anterior ciliary artery (called interstitial vascularization) which causes several distinct clinical lesions: terminal loops, a "brush-like" pattern, an umbel form, a lattice form, interstitial arcades (from episcleral vessels), and aberrant irregular vessels.

A wide variety of disorders can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali burns, trauma, inflammation (of any cause), toxic and nutritional deficiency states, and as a complication of wearing contact lenses.

While the cause of corneal neovascularization may vary, the response of the cornea to the insult and the subsequent vascular ingrowth is similar regardless of the cause. Briefly, the location of the injury appears to be of importance as only those lesions situated within a critical distance of the limbus will incite an angiogenic response. This is likely due to the fact that the angiogenic factors responsible for eliciting the vascular invasion are created at the site of the lesion, and must diffuse to the site of the nearest blood vessels (the limbus) in order to exert their effect. Past a certain distance from the limbus, this would no longer be possible and the limbic endothelium would not be induced to grow into the cornea. Several angiogenic factors are likely involved in this process, many of which are products of the inflammatory response. Indeed, neovascularization of the cornea appears to only occur in association with an inflammatory cell infiltrate, and the degree of angiogenesis is proportional to the extent of the inflammatory reaction. Corneal edema further facilitates blood vessel ingrowth by loosening the corneal stromal framework and providing a pathway of "least resistance" through which the capillaries can grow.

Following the initial inflammatory reaction, capillary growth into the cornea proceeds in the same manner as it occurs in other tissues. The normally quiescent endothelial cells of the limbic capillaries and venules are stimulated to divide and migrate. The endothelial cells project away from their vessels of origin, digest the surrounding basement membrane and the tissue through which they will travel, and migrate towards the source of the angiogenic stimulus. The blind ended sprouts acquire a lumen and then anastomose together to form capillary loops. The end result is the establishment of a vascular plexus within the corneal stroma.

Anti-angiogenic factors and compositions of the present invention are useful by blocking the stimulatory effects of angiogenesis promoters, reducing endothelial cell division, decreasing endothelial cell migration, and impairing the activity of the proteolytic enzymes secreted by the endothelium.

Within particularly preferred embodiments of the invention, an anti-angiogenic factor may be prepared for topical administration in saline (combined with any of the preservatives and antimicrobial agents commonly used in ocular preparations), and administered in eyedrop form. The anti-angiogenic factor solution or suspension may be prepared in its pure form and administered several times daily. Alternatively, anti-angiogenic compositions, prepared as described above, may also be administered directly to the cornea. Within preferred embodiments, the anti-angiogenic composition is prepared with a muco-adhesive polymer which binds to cornea. Within further embodiments, the anti-angiogenic factors or anti-angiogenic compositions may be utilized as an adjunct to conventional steroid therapy.

Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the anti-angiogenic compositions described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2–3 times per year. A steroid could also be added to the injection solution to reduce inflammation resulting from the injection itself.

Within another aspect of the present invention, methods are provided for treating neovascular glaucoma, comprising the step of administering to a patient a therapeutically effective amount of an anti-angiogenic composition to the eye, such that the formation of blood vessels is inhibited.

Briefly, neovascular glaucoma is a pathological condition wherein new capillaries develop in the iris of the eye. The angiogenesis usually originates from vessels located at the pupillary margin, and progresses across the root of the iris and into the trabecular meshwork. Fibroblasts and other connective tissue elements are associated with the capillary growth and a fibrovascular membrane develops which spreads across the anterior surface of the iris. Eventually this tissue reaches the anterior chamber angle where it forms synechiae. These synechiae in turn coalesce, scar, and contract to ultimately close off the anterior chamber angle. The scar formation prevents adequate drainage of aqueous humor through the angle and into the trabecular meshwork, resulting in an increase in intraocular pressure that may result in blindness.

Neovascular glaucoma generally occurs as a complication of diseases in which retinal ischemia is predominant. In particular, about one third of the patients with this disorder have diabetic retinopathy and 28% have central retinal vein occlusion. Other causes include chronic retinal detachment, end-stage glaucoma, carotid artery obstructive disease, retrolental fibroplasia, sickle-cell anemia, intraocular tumors, and carotid cavernous fistulas. In its early stages, neovascular glaucoma may be diagnosed by high magnification slitlamp biomicroscopy, where it reveals small, dilated, disorganized capillaries (which leak fluorescein) on the surface of the iris. Later gonioscopy demonstrates progressive obliteration of the anterior chamber angle by fibrovascular bands. While the anterior chamber angle is still open, conservative therapies may be of assistance. However, once the angle closes surgical intervention is required in order to alleviate the pressure.

Therefore, within one embodiment of the invention anti-angiogenic factors (either alone or in an anti-angiogenic composition, as described above) may be administered topically to the eye in order to treat early forms of neovascular glaucoma.

Within other embodiments of the invention, anti-angiogenic compositions may be implanted by injection of the composition into the region of the anterior chamber angle. This provides a sustained localized increase of anti-angiogenic factor, and prevents blood vessel growth into the area. Implanted or injected anti-angiogenic compositions which are placed between the advancing capillaries of the iris and the anterior chamber angle can "defend" the open angle from neovascularization. As capillaries will not grow within a significant radius of the anti-angiogenic composition, patency of the angle could be maintained. Within other embodiments, the anti-angiogenic composition may also be placed in any location such that the anti-angiogenic factor is continuously released into the aqueous humor. This would increase the anti-angiogenic factor concentration within the humor, which in turn bathes the surface of the iris and its abnormal capillaries, thereby providing another mechanism by which to deliver the medication. These therapeutic modalities may also be useful prophylactically and in combination with existing treatments.

Within another aspect of the present invention, methods are provided for treating proliferative diabetic retinopathy, comprising the step of administering to a patient a therapeutically effective amount of an anti-angiogenic composition to the eyes, such that the formation of blood vessels is inhibited.

Briefly, the pathology of diabetic retinopathy is thought to be similar to that described above for neovascular glaucoma. In particular, background diabetic retinopathy is believed to convert to proliferative diabetic retinopathy under the influence of retinal hypoxia. Generally, neovascular tissue sprouts from the optic nerve (usually within 10 mm of the edge), and from the surface of the retina in regions where tissue perfusion is poor. Initially the capillaries grow between the inner limiting membrane of the retina and the posterior surface of the vitreous. Eventually, the vessels grow into the vitreous and through the inner limiting membrane. As the vitreous contracts, traction is applied to the vessels, often resulting in shearing of the vessels and blinding of the vitreous due to hemorrhage. Fibrous traction from scarring in the retina may also produce retinal detachment.

The conventional therapy of choice is panretinal photocoagulation to decrease retinal tissue, and thereby decrease retinal oxygen demands. Although initially effective, there is a high relapse rate with new lesions forming in other parts of the retina. Complications of this therapy include a decrease in peripheral vision of up to 50% of patients, mechanical abrasions of the cornea, laser-induced cataract formation, acute glaucoma, and stimulation of subretinal neovascular growth (which can result in loss of vision). As a result, this procedure is performed only when several risk factors are present, and the risk-benefit ratio is clearly in favor of intervention.

Therefore, within particularly preferred embodiments of the invention, proliferative diabetic retinopathy may be treated by injection of an anti-angiogenic factor(s) (or anti-angiogenic composition) into the aqueous humor or the vitreous, in order to increase the local concentration of anti-angiogenic factor in the retina. Preferably, this treatment should be initiated prior to the acquisition of severe disease requiring photocoagulation. Within other embodiments of the invention, arteries which feed the neovascular lesions may be embolized (utilizing anti-angiogenic compositions, as described above)

Within another aspect of the present invention, methods are provided for treating retrolental fibroblasia, comprising the step of administering to a patient a therapeutically effective amount of an anti-angiogenic factor (or anti-angiogenic composition) to the eye, such that the formation of blood vessels is inhibited.

Briefly, retrolental fibroblasia is a condition occurring in premature infants who receive oxygen therapy. The peripheral retinal vasculature, particularly on the temporal side, does not become fully formed until the end of fetal life. Excessive oxygen (even levels which would be physiologic at term) and the formation of oxygen free radicals are thought to be important by causing damage to the blood vessels of the immature retina. These vessels constrict, and then become structurally obliterated on exposure to oxygen. As a result, the peripheral retina fails to vascularize and retinal ischemia ensues. In response to the ischemia, neovascularization is induced at the junction of the normal and the ischemic retina.

In 75% of the cases these vessels regress spontaneously. However, in the remaining 25% there is continued capillary growth, contraction of the fibrovascular component, and traction on both the vessels and the retina. This results in vitreous hemorrhage and/or retinal detachment which can lead to blindness. Neovascular angle-closure glaucoma is also a complication of this condition.

As it is often impossible to determine which cases will spontaneously resolve and which will progress in severity, conventional treatment (i.e., surgery) is generally initiated only in patients with established disease and a well developed pathology. This "wait and see" approach precludes early intervention, and allows the progression of disease in the 25% who follow a complicated course. Therefore, within one embodiment of the invention, topical administration of anti-angiogenic factors (or anti-angiogenic compositions, as described above) may be accomplished in infants which are at high risk for developing this condition in an attempt to cut down on the incidence of progression of retrolental fibroplasia. Within other embodiments, intravitreous injections and/or intraocular implants of an anti-angiogenic composition may be utilized. Such methods are particularly preferred in cases of established disease, in order to reduce the need for surgery.

Other Therapeutic Uses of Anti-Angiogenic Compositions

Anti-angiogenic factors and compositions of the present invention may be utilized in a variety of additional methods in order to therapeutically treat a cancer or tumor. For example, anti-angiogenic factors or compositions described herein may be formulated for topical delivery, in order to treat cancers such as skin cancer, head and neck tumors, breast tumors, and Kaposi's sarcoma. Within yet other aspects, the anti-angiogenic factors or compositions provided herein may be utilized to treat superficial forms of bladder cancer by, for example, intravesical administration.

In addition to cancer, however, numerous other non-tumorigenic angiogenesis-dependent diseases which are characterized by the abnormal growth of blood vessels may also be treated with the anti-angiogenic factors or compositions of the present invention. Representative examples of such non-tumorigenic angiogenesis-dependent diseases include hypertrophic scars and keloids, proliferative diabetic retinopathy (discussed above), rheumatoid arthritis (discussed above), arteriovenous malformations (discussed above), atherosclerotic plaques, delayed wound healing, hemophilic joints, nonunion fractures, Osler-Weber syndrome, psoriasis, pyogenic granuloma, scleroderma, tracoma, menorrhagia (discussed above) and vascular adhesions.

For example, within one aspect of the present invention methods are provided for treating hypertrophic scars and keloids, comprising the step of administering one of the above-described anti-angiogenic compositions to a hypertrophic scar or keloid.

Briefly, healing of wounds and scar formation occurs in three phases: inflammation, proliferation, and maturation. The first phase, inflammation, occurs in response to an injury which is severe enough to break the skin. During this phase, which lasts 3 to 4 days, blood and tissue fluid form an adhesive coagulum and fibrinous network which serves to bind the wound surfaces together. This is then followed by a proliferative phase in which there is ingrowth of capillaries and connective tissue from the wound edges, and closure of the skin defect. Finally, once capillary and fibroblastic proliferation has ceased, the maturation process begins wherein the scar contracts and becomes less cellular, less vascular, and appears flat and white. This final phase may take between 6 and 12 months.

If too much connective tissue is produced and the wound remains persistently cellular, the scar may become red and raised. If the scar remains within the boundaries of the original wound it is referred to as a hypertrophic scar, but if it extends beyond the original scar and into the surrounding tissue, the lesion is referred to as a keloid. Hypertrophic scars and keloids are produced during the second and third phases of scar formation. Several wounds are particularly prone to excessive endothelial and fibroblastic proliferation, including burns, open wounds, and infected wounds. With hypertrophic scars, some degree of maturation occurs and gradual improvement occurs. In the case of keloids however, an actual tumor is produced which can become quite large. Spontaneous improvement in such cases rarely occurs.

Therefore, within one embodiment of the present invention either anti-angiogenic factors alone, or anti-angiogenic compositions as described above, are directly injected into a hypertrophic scar or keloid, in order to prevent the progression of these lesions. The frequency of injections will depend upon the release kinetics of the polymer used (if present), and the clinical response. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development.

As noted above, within yet another aspect of the present invention, vascular grafts are provided comprising a synthetic tube, the surface of which is coated with an anti-angiogenic composition as described above. Briefly, vascular grafts are synthetic tubes, usually made of Dacron or Gortex, inserted surgically to bypass arterial blockages, most frequently from the aorta to the femoral, or the femoral to the popliteal artery. A major problem which particularly complicates femoral-popliteal bypass grafts is the formation of a subendothelial scar-like reaction in the blood vessel wall called neointimal hyperplasia, which narrows the lumen within and adjacent to either end of the graft, and which can be progressive. A graft coated with or containing anti-angiogenic factors (or anti-angiogenic compositions, as described above) may be utilized to limit the formation of neointimal hyperplasia at either end of the graft. The graft may then be surgically placed by conventional bypass techniques.

Anti-angiogenic compositions of the present invention may also be utilized in a variety of other manners. For example, they may be incorporated into surgical sutures in order to prevent stitch granulomas, implanted in the uterus (in the same manner as an IUD) for the treatment of menorrhagia or as a form of female birth control, administered as either a peritoneal lavage fluid or for peritoneal implantation in the treatment of endometriosis, attached to a monoclonal antibody directed against activated endothelial cells as a form of systemic chemotherapy, or utilized in diagnostic imaging when attached to a radioactively labeled monoclonal antibody which recognizes activated endothelial cells.

Formulation and Administration

As noted above, anti-angiogenic compositions of the present invention may be formulated in a variety of forms (e.g., microspheres, pastes, films or sprays). Further, the compositions of the present invention may be formulated to contain more than one anti-angiogenic factor, to contain a variety of additional compounds, to have certain physical properties (e.g., elasticity, a particular melting point, or a specified release rate). Within certain embodiments of the invention, compositions may be combined in order to achieve a desired effect (e.g., several preparations of microspheres may be combined in order to achieve both a quick and a slow or prolonged release of one or more anti-angiogenic factor).

Anti-angiogenic factors and compositions of the present invention may be administered either alone, or in combination with pharmaceutically or physiologically acceptable carrier, excipients or diluents. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

As noted above, anti-angiogenic factors, anti-angiogenic compositions, or pharmaceutical compositions provided herein may be prepared for administration by a variety of different routes, including for example intrartricularly, intraocularly, intranasally, intradermally, sublingually, orally, topically, intravesically, intrathecally, topically, intravenously, intraperitoneally, intracranially, intramuscularly, subcutaneously, or even directly into a tumor or disease site. Other representative routes of administration include gastroscopy, ECRP and colonoscopy, which do not require full operating procedures and hospitalization, but may require the presence of medical personnel.

The anti-angiogenic factors, anti-angiogenic compositions and pharmaceutical compositions provided herein may be placed within containers, along with packaging material which provides instructions regarding the use of such materials. Generally, such instructions will include a tangible expression describing the reagent concentration, as well as within certain embodiments, relative amounts of excipient ingredients or diluents (e.g., water, saline or PBS) which may be necessary to reconstitute the anti-angiogenic factor, anti-angiogenic composition, or pharmaceutical composition.

The following examples are offered by way of illustration, and not by way of limitation.

EXAMPLES

Example 1

Preparation of Anti-Invasive Factor

The shoulder girdle and skull from a dogfish is excised, then scraped with a scalpel in order to remove all muscle and associated connective tissue from the cartilage. The cartilage is then homogenized with a tissue grinder, and extracted by continuous stirring at room temperature for 2 to 5 days in a solution containing 2.0 M guanidium hydrochloride and 0.02 M MES at pH 6.0.

After 2 to 5 days, the cartilage extract is passed through gauze netting in order to remove the larger constituents. The filtrate is then passed through an Amicon ultrafiltration unit which utilizes spiral-wound cartridges, with a molecular weight cutoff of 100,000. The filtrate (containing proteins with a molecular weight of less than 100,000 daltons) is then dialyzed against 0.02 M MES buffer (pH 6) with an Amicon ultrafiltration unit which retains proteins with a molecular weight of greater than 3,000 daltons. Utilizing this method, low molecular weight proteins and constituents are removed, as well as excessive amounts of guanidium HCl. The dialysate is concentrated to a final concentration 9 mg/ml.

Example 2

Analysis of Various Agents for Anti-Angiogenic Activity

A. Chick Chorioallantoic Membrane ("Cam") Assays

Fertilized, domestic chick embryos were incubated for 3 days prior to shell-less culturing. In this procedure, the egg contents were emptied by removing the shell located around the air space. The interior shell membrane was then severed and the opposite end of the shell was perforated to allow the contents of the egg to gently slide out from the blunted end. The egg contents were emptied into round-bottom sterilized glass bowls and covered with petri dish covers. These were then placed into an incubator at 90% relative humidity and 3% $CO_2$ and incubated for 3 days.

Paclitaxel (Sigma, St. Louis, Mich.) was mixed at concentrations of 1, 5, 10, 30 µg per 10 ml aliquot of 0.5% aqueous methylcellulose. Since paclitaxel is insoluble in water, glass beads were used to produce fine particles. Ten microliter aliquots of this solution were dried on parafilm for 1 hour forming disks 2 mm in diameter. The dried disks containing paclitaxel were then carefully placed at the growing edge of each CAM at day 6 of incubation. Controls were obtained by placing paclitaxel-free methylcellulose disks on the CAMs over the same time course. After a 2 day exposure (day 8 of incubation) the vasculature was examined with the aid of a stereomicroscope. Liposyn II, a white opaque solution, was injected into the CAM to increase the visibility of the vascular details. The vasculature of unstained, living embryos were imaged using a Zeiss stereomicroscope which was interfaced with a video camera (Dage-MTI Inc., Michigan City, Ind.). These video signals were then displayed at 160 times magnification and captured using an image analysis system (Vidas, Kontron; Etching, Germany). Image negatives were then made on a graphics recorder (Model 3000; Matrix Instruments, Orangeburg, N.Y.).

The membranes of the 8 day-old shell-less embryo were flooded with 2% glutaraldehyde in 0.1 M Na cacodylate buffer; additional fixative was injected under the CAM. After 10 minutes in situ, the CAM was removed and placed into fresh fixative for 2 hours at room temperature. The tissue was then washed overnight in cacodylate buffer containing 6% sucrose. The areas of interest were postfixed in 1% osmium tetroxide for 1.5 hours at 4° C. The tissues were then dehydrated in a graded series of ethanols, solvent exchanged with propylene oxide, and embedded in Spurr resin. Thin sections were cut with a diamond knife, placed on copper grids, stained, and examined in a Joel 1200EX electron microscope. Similarly, 0.5 mm sections were cut and stained with toluene blue for light microscopy.

At day 11 of development, chick embryos were used for the corrosion casting technique. Mercox resin (Ted Pella, Inc., Redding, Calif.) was injected into the CAM vasculature using a 30-gauge hypodermic needle. The casting material consisted of 2.5 grams of Mercox CL-2B polymer and 0.05 grams of catalyst (55% benzoyl peroxide) having a 5 minute polymerization time. After injection, the plastic was allowed to sit in situ for an hour at room temperature and then overnight in an oven at 65° C. The CAM was then placed in 50% aqueous solution of sodium hydroxide to digest all organic components. The plastic casts were washed extensively in distilled water, air-dried, coated with gold/palladium, and viewed with the Philips 501B scanning electron microscope.

Results of the above experiments are shown in FIGS. 1–4. Briefly, the general features of the normal chick shell-less egg culture are shown in FIG. 1A. At day 6 of incubation, the embryo is centrally positioned to a radially expanding network of blood vessels; the CAM develops adjacent to the embryo. These growing vessels lie close to the surface and are readily visible malting this system an idealized model for the study of angiogenesis. Living, unstained capillary networks of the CAM can be imaged noninvasively with a stereomicroscope. FIG. 1B illustrates such a vascular area in which the cellular blood elements within capillaries were recorded with the use of a video/computer interface. The 3-dimensional architecture of such CAM capillary networks is shown by the corrosion casting method and viewed in the scanning electron microscope (FIG. 1C). These castings revealed underlying vessels which project toward the CAM surface where they form a single layer of anastomotic capillaries.

Figure 1D:
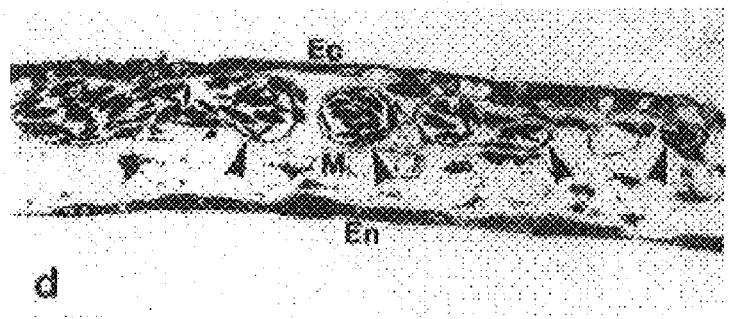
FIG. 1D is a photograph which depicts a 0.5 mm thick plastic section cut transversely through the CAM, and recorded at the light microscope level. This photograph shows the composition of the CAM, including an outer double-layered ectoderm (Ec), a mesoderm (M) containing capillaries (arrows) and scattered adventitila cells, and a single layered endoderm (En) (400×).
Figure 1E:
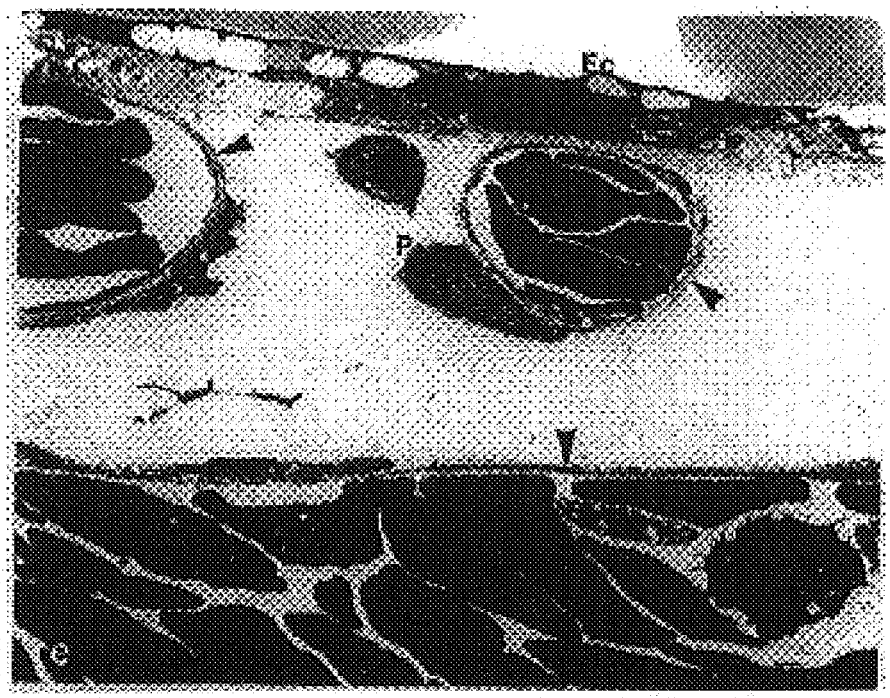
FIG. 1E is a photograph at the electron microscope level (3500×) wherein typical capillary structure is presented showing thin-walled endothelial cells (arrowheads) and an associated pericyte.

Transverse sections through the CAM show an outer ectoderm consisting of a double cell layer, a broader mesodermal layer containing capillaries which lie subjacent to the ectoderm, adventitial cells, and an inner, single endodermal cell layer (FIG. 1D). At the electron microscopic level, the typical structural details of the CAM capillaries are demonstrated. Typically, these vessels lie in close association with the inner cell layer of ectoderm (FIG. 1E)

After 48 hours exposure to paclitaxel at concentrations of 0.25, 0.5, 1, 5, 10, or 30 ug, each CAM was examined under living conditions with a stereomicroscope equipped with a video/computer interface in order to evaluate the effects on angiogenesis. This imaging setup was used at a magnification of 160 times which permitted the direct visualization of blood cells within the capillaries; thereby blood flow in areas of interest could be easily assessed and recorded. For this study, the inhibition of angiogenesis was defined as an area of the CAM lacking a capillary network and vascular blood flow. Throughout the experiments, avascular zones were assessed on a 4 point avascular gradient (Table I). This scale represents the degree of overall inhibition with maximal inhibition represented as a 3 on the avascular gradient scale. Paclitaxel was very consistent and induced a maximal avascular zone (6 mm in diameter or a 3 on the avasculare gradient scale) within 48 hours depending on its concentration.

TABLE I

AVASCULAR GRADIENT

| | |
|---|---|
| 0 | normal vascularity |
| 1 | lacking some microvascular movement |
| 2* | small avascular zone approximately 2 mm in diameter |
| 3* | avascularity extending beyond the disk (6 mm in diameter) |

The dose-dependent, experimental data of the effects of paclitaxel at different concentrations are shown in Table II.

TABLE II

Angiogenic Inhibition by Paclitaxel

| Paclitaxel in Methylcellulose Disks (µg) | Embryos Evaluated positive/total) | % Inhibition |
|---|---|---|
| 0.25 | 2/11 | 18 |
| 0.5 | 6/11 | 54 |
| 1 | 6/15 | 40 |
| 5 | 20/27 | 76 |
| 10 | 16/21 | 76 |
| 30 | 31/31 | 100 |
| 0 (control) | 0/40 | 0 |

TABLE III

Angiogenic Inhibition of Paclitaxel-Loaded Thermopaste

| Paclitaxel-loaded Thermopaste (%) | Embryos Evaluated (positive/n) |
|---|---|
| 0.25 | 4/4 |
| 0.5 | 4/4 |
| 1 | 8/8 |
| 5 | 4/4 |
| 10 | 5/5 |
| 20 | 6/6 |
| 0 (control) | 0/30 |

Figure 2A:
FIGS. 2A, 2B, 2C and 2D are a series of digitized images of four different, unstained CAMs taken after a 48 hour exposure to digitized images of four different living, unstained CAMs were taken after a 48 h exposure to 10 paclitaxel per 10 ml of methylcellulose. The transparent methylcellulose disk (*) containing paclitaxel is present on each CAM and is positioned over a singular avascular zone (A) with surrounding blood islands (Is). These avascular areas extend beyond the disk and typically have a diameter of 6 mm.
Figure 2B:
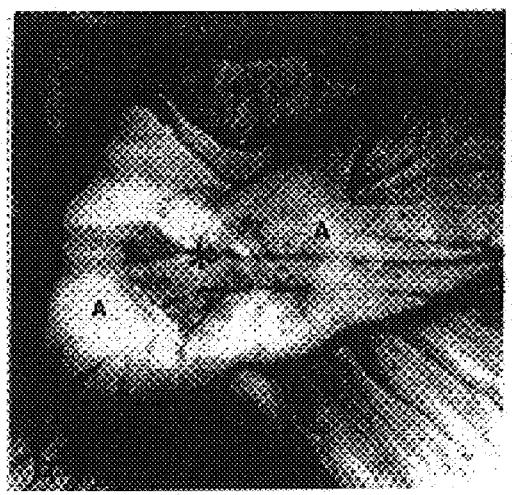
Figure 2C:
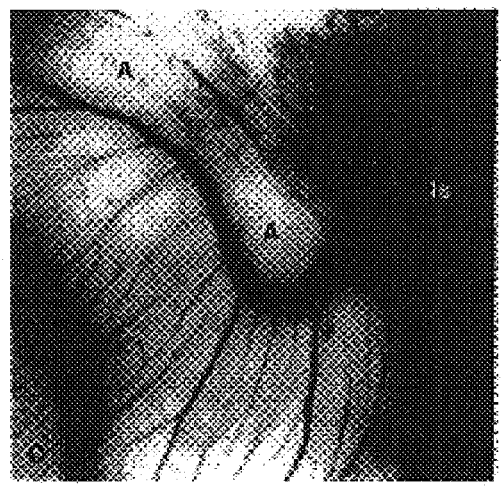
Figure 2D:
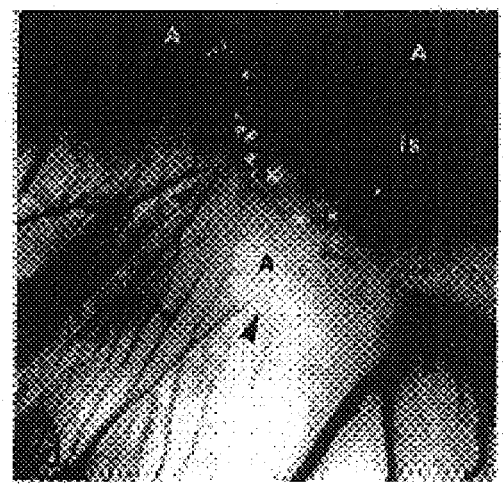

Typical paclitaxel-treated CAMs are also shown with the transparent methylcellulose disk centrally positioned over the avascular zone measuring 6 mm in diameter. At a slightly higher magnification, the periphery of such avascular zones is clearly evident (FIG. 2C); the surrounding functional vessels were often redirected away from the source of paclitaxel (FIGS. 2C and 2D). Such angular redirecting of blood flow was never observed under normal conditions. Another feature of the effects of paclitaxel was the formation of blood islands within the avascular zone representing the aggregation of blood cells.

Figure 3A:
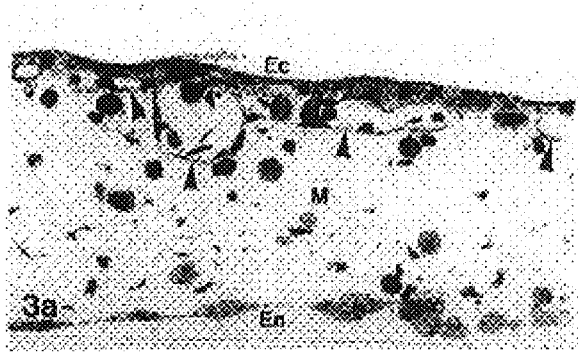
FIG. 3A is a photograph (Mag=400×) which shows just peripheral to the avascular zone, that capillaries (arrowheads) exhibit numerous endothelial cells arrested in mitosis. Ectoderm (Ec); Mesoderm (M); Endoderm (En).
Figure 3B:
FIG. 3B (Mag=400×) shows that within the avascular zone proper the typical capillary structure has been eliminated and there are numerous extravasated blood cells (arrowheads).
Figure 3C:
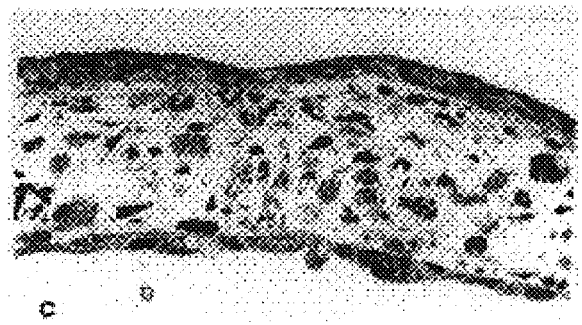
FIG. 3C (Mag=400×) shows that in the central area of the avascular zone, red blood cells are dispersed throughout the mesoderm.
Figure 4A:
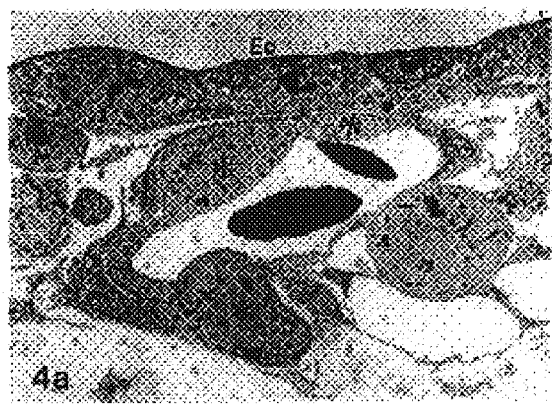
FIGS. 4A, 4B and 4C are series of electron micrographs which were taken from locations similar to that of FIGS. 3A, 3B and 3C (respectively) above.
Figure 4B:
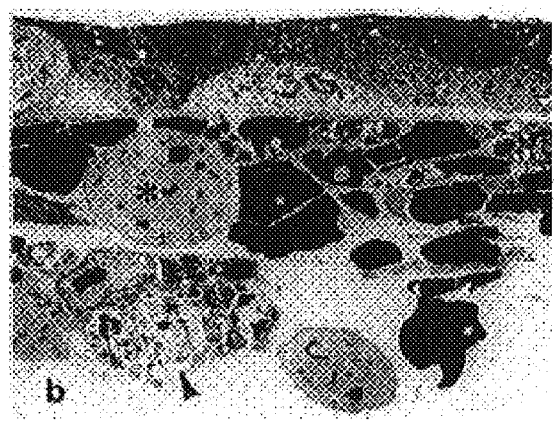
Figure 4C:
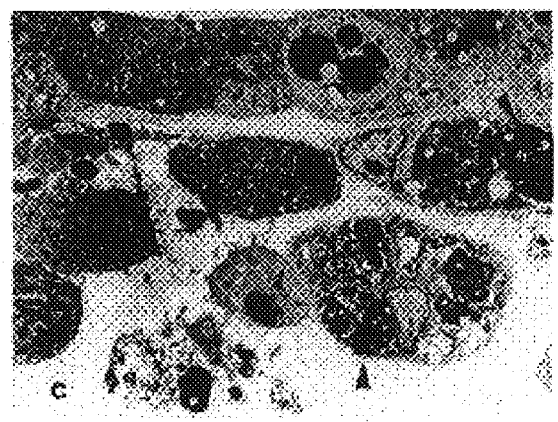
Figure 5:
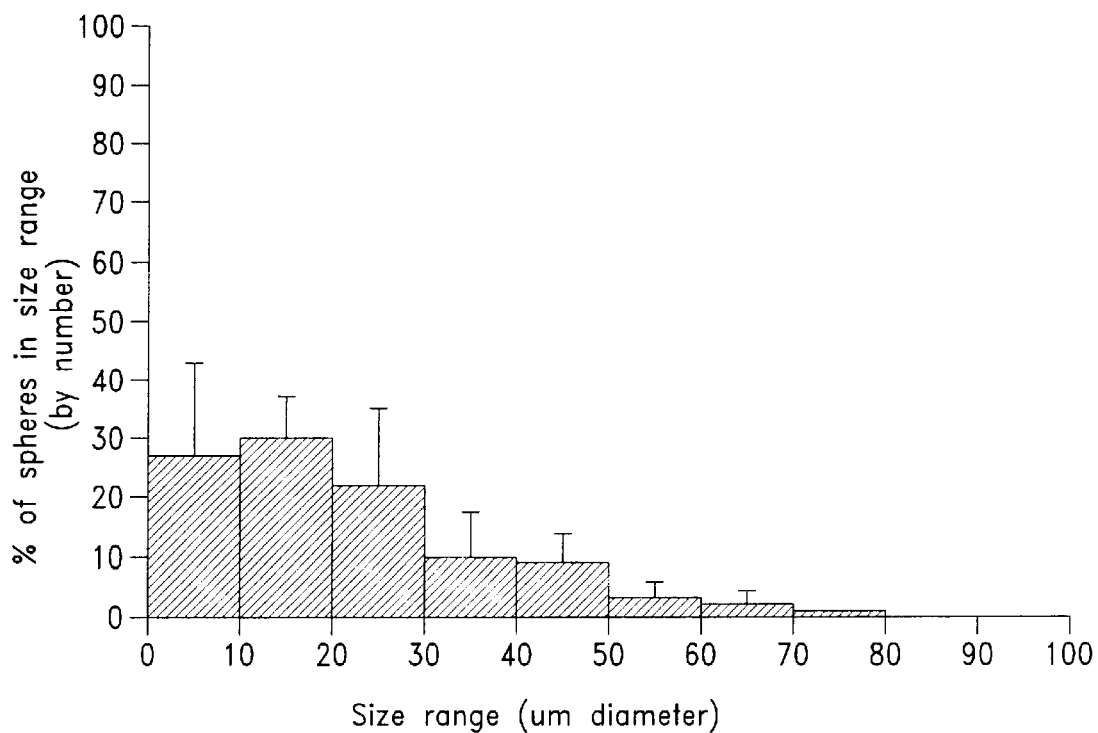
FIG. 5 is a bar graph which depicts the size distribution of microspheres by number (5% poly (ethylene-vinyl acetate) with 10 mg sodium suramin into 5% PVA).
Figure 6:
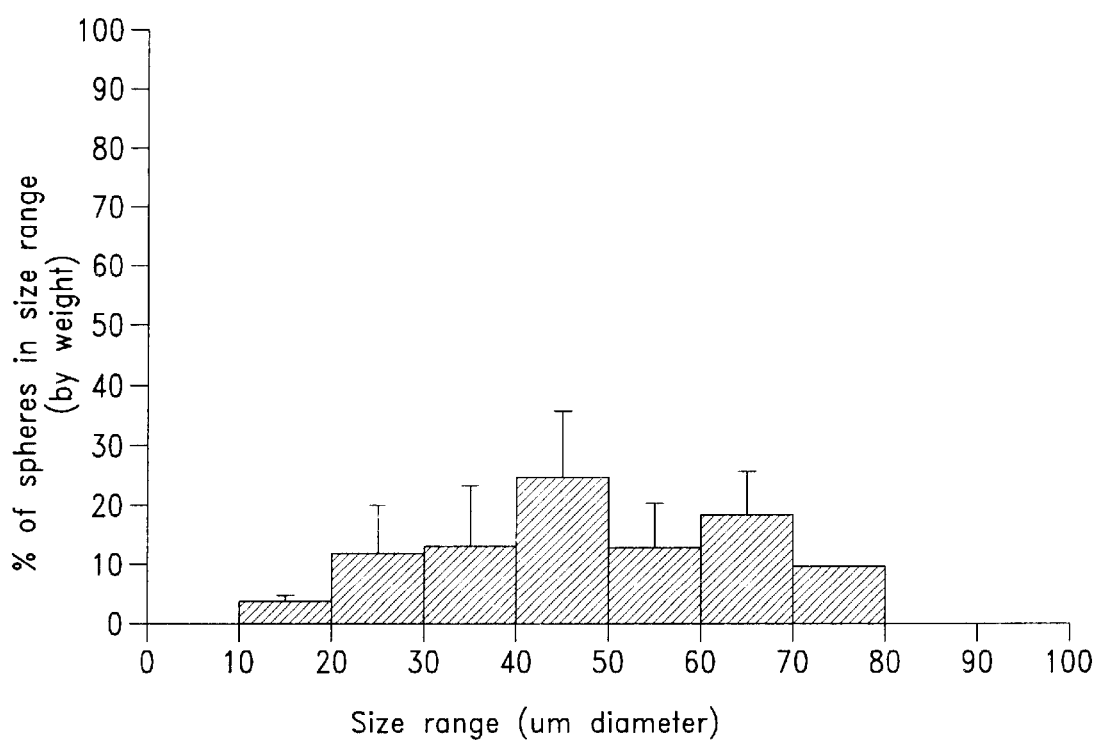
FIG. 6 is a bar graph which depicts the size distribution of microspheres by weight (5% poly (ethylene-vinyl acetate) with 10 mg sodium suramin into 5% PVA).

The associated morphological alterations of the paclitaxel-treated CAM are readily apparent at both the light and electron microscopic levels. For the convenience of presentation, three distinct phases of general transition from the normal to the avascular state are shown. Near the periphery of the avascular zone the CAM is hallmarked by an abundance of mitotic cells within all three germ layers (FIGS. 3A and 4A). This enhanced mitotic division was also a consistent observation for capillary endothelial cells. However, the endothelial cells remained junctionally intact with no extravasation of blood cells. With further degradation, the CAM is characterized by the breakdown and dissolution of capillaries (FIGS. 3B and 4B). The presumptive endothelial cells, typically arrested in mitosis, still maintain a close spatial relationship with blood cells and lie subjacent to the ectoderm; however, these cells are not junctionally linked. The most central portion of the avascular zone was characterized by a thickened ectodermal and endodermal layer (FIGS. 3C and 4C). Although these layers were thickened, the cellular junctions remained intact and the layers maintained their structural characteristics. Within the mesoderm, scattered mitotically arrested cells were abundant; these cells did not exhibit the endothelial cell polarization observed in the former phase. Also, throughout this avascular region, degenerating cells were common as noted by the electron dense vacuoles and cellular debris (FIG. 4C).

In summary, this study demonstrated that 48 hours after paclitaxel application to the CAM, angiogenesis was inhibited. The blood vessel inhibition formed an avascular zone which was represented by three transitional phases of paclitaxel's effect. The central, most affected area of the avascular zone contained disrupted capillaries with extravasated red blood cells; this indicated that intercellular junctions between endothelial cells were absent. The cells of the endoderm and ectoderm maintained their intercellular junctions and therefore these germ layers remained intact; however, they were slightly thickened. As the normal vascular area was approached, the blood vessels retained their junctional complexes and therefore also remained intact. At the periphery of the paclitaxel-treated zone, further blood vessel growth was inhibited which was evident by the typical redirecting or "elbowing" effect of the blood vessels (FIG. 2D).

Paclitaxel-treated avascular zones also revealed an abundance of cells arrested in mitosis in all three germ layers of the CAM; this was unique to paclitaxel since no previous study has illustrated such an event. By being arrested in mitosis, endothelial cells could not undergo their normal metabolic functions involved in angiogenesis. In comparison, the avascular zone formed by suramin and cortisone acetate do not produce mitotically arrested cells in the CAM; they only prevented further blood vessel growth into the treated area. Therefore, even though these agents are anti-angiogenic, there are many points in which the angiogenesis process may be targeted.

The effects of paclitaxel over the 48 hour duration were also observed. During this period of observation it was noticed that inhibition of angiogenesis occurs as early as 9 hours after application. Histological sections revealed a similar morphology as seen in the first transition phase of the avascular zone at 48 hours illustrated in FIGS. 3A and 4A. Also, we observed in the revascularization process into the avascular zone previously observed. It has been found that the avascular zone formed by heparin and angiostatic steroids became revascularized 60 hours after application. In one study, paclitaxel-treated avascular zones did not revascularize for at least 7 days after application implying a more potent long-term effect.

Example 3

Encapsulation of Suramin

One milliliter of 5% ELVAX (poly(ethylene-vinyl acetate) cross-linked with 5% vinyl acetate) in dichloromethane ("DCM") is mixed with a fixed weight of submicron ground sodium suramin. This mixture is injected into 5 ml of 5% Polyvinyl Alcohol ("PVA") in water in a 30 ml flat bottomed test tube. Tubes containing different weights of the drug are then suspended in a multi-sample water bath at 40° for 90 minutes with automated stirring. The mixtures are removed, and microsphere samples taken for size analysis. Tubes are centrifuged at 1000 g for 5 min. The PVA supernatant is removed and saved for analysis (nonencapsulated drug). The microspheres are then washed (vortexed) in 5 ml of water and recentrifuged. The 5 ml wash is saved for analysis (surface bound drug). Microspheres are then wetted in 50 ul of methanol, and vortexed in 1 ml of DCM to dissolve the ELVAX. The microspheres are then warmed to 40° C., and 5 ml of 50° C. water is slowly added with stirring. This procedure results in the immediate evaporation of DCM, thereby causing the release of sodium suramin into the 5 ml of water.

All samples were assayed for drug content by quantification of fluorescence. Briefly, sodium suramin absorbs uv/vis with a lambda max of 312 nm. This absorption is linear in the 0 to 100 ug/ml range in both water and 5% PVA. Sodium suramin also fluoresces strongly with an excitation maximum at 312 nm, and emission maximum at 400 nm. This fluorescence is quantifiable in the 0 to 25 ug/ml range.

The results of these experiments is shown in FIGS. 5–11. Results are shown in FIGS. 5–10. Briefly, the size distribution of microspheres by number (FIG. 5) or by weight (FIG. 6) appears to be unaffected by inclusion of the drug in the DCM. Good yields of microspheres in the 20 to 60 μm range may be obtained.

Figure 7:
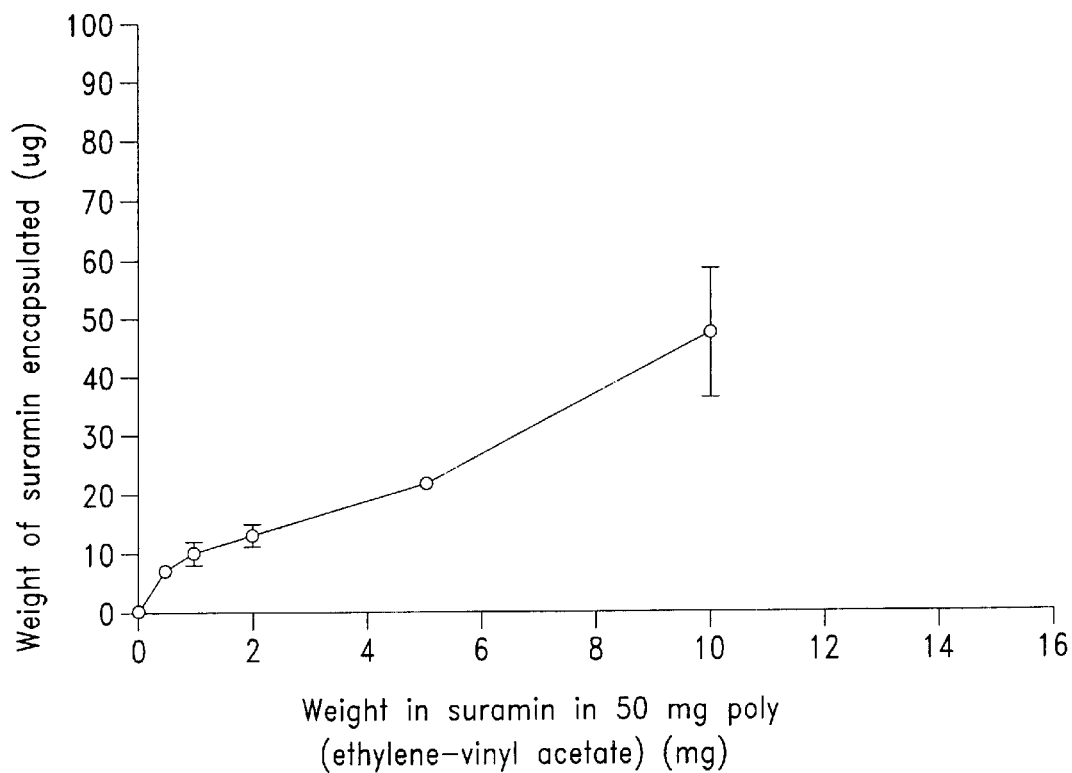
FIG. 7 is a graph which depicts the weight of encapsulation of Sodium Suramin in 50 mg poly (ethylene-vinyl acetate).
Figure 8:
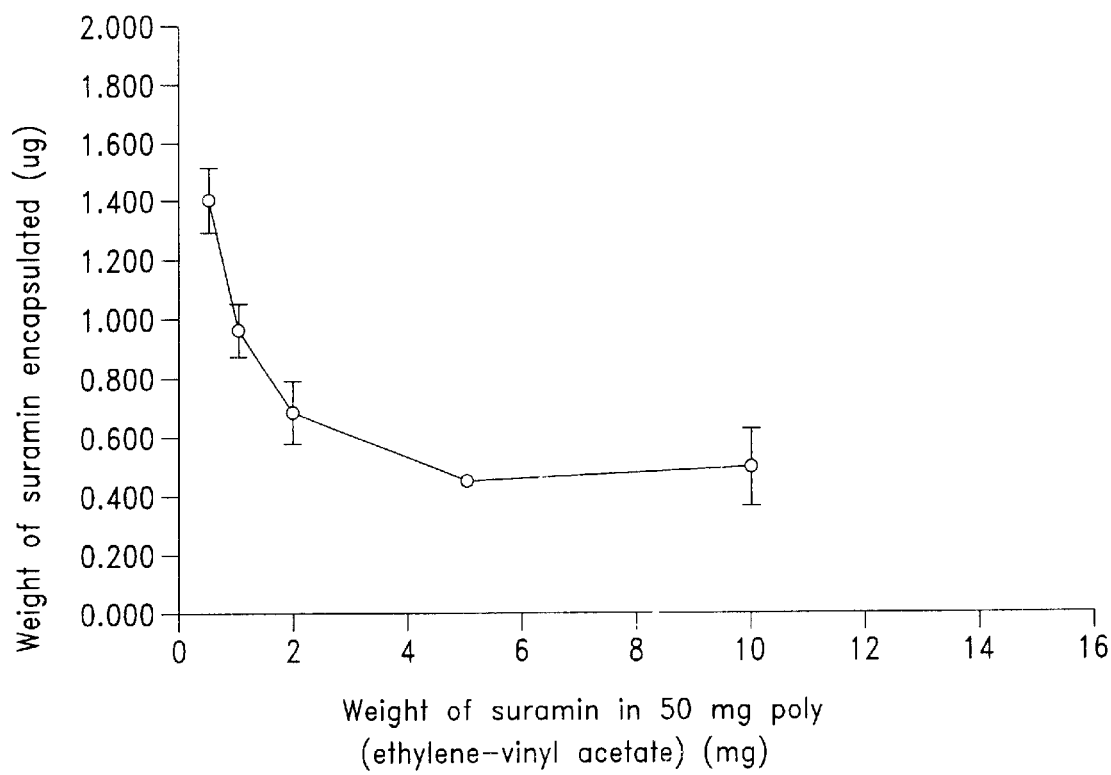
FIG. 8 is a graph which depicts the percent of encapsulation of Sodium Suramin in 50 mg poly (ethylene-vinyl acetate).
Figure 9:
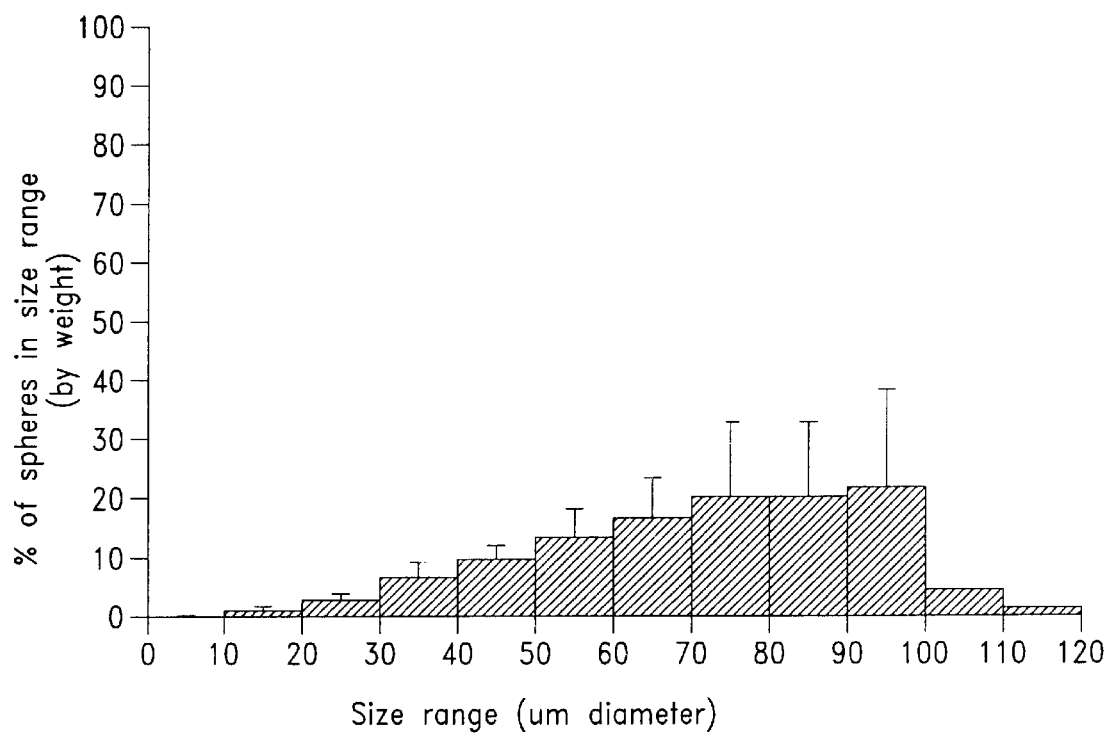
FIG. 9 is a bar graph which depicts the size distribution by weight of 5% ELVAX microspheres containing 10 mg sodium suramin made in 5% PVA containing 10% NaCl.
Figure 10:
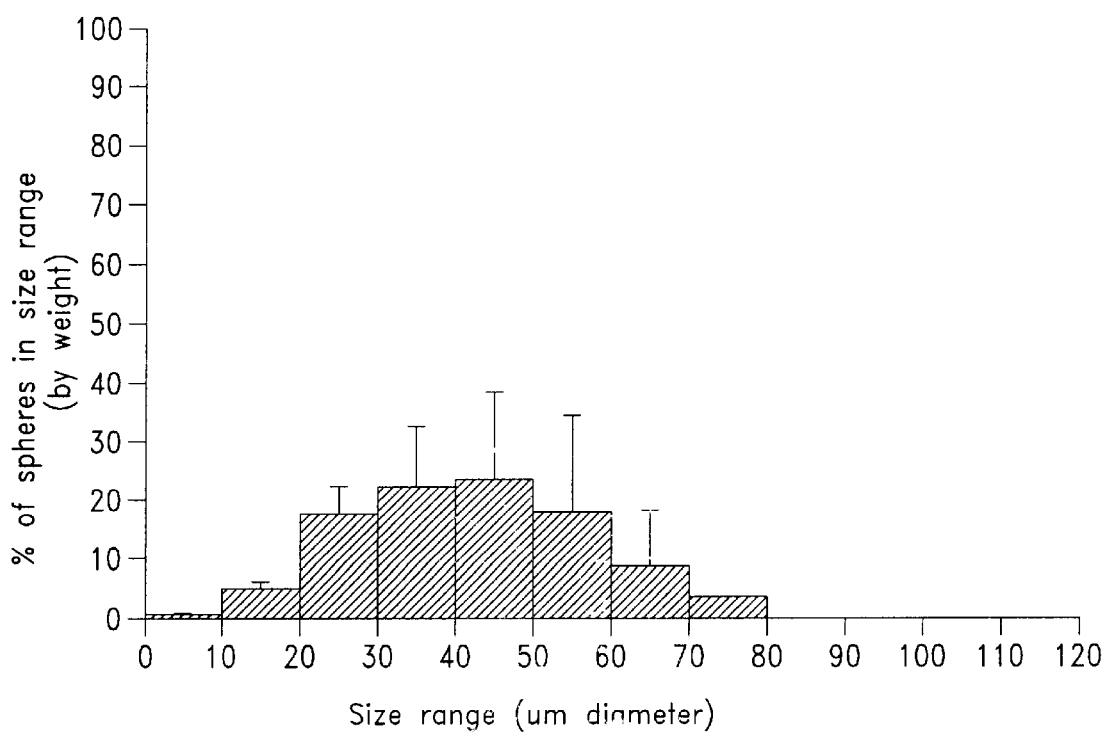
FIG. 10 is a bar graph which depicts the size distribution by weight of 5% microspheres containing 10 mg sodium suramin made in 5% PVA containing 10% NaCl.
Figure 11:
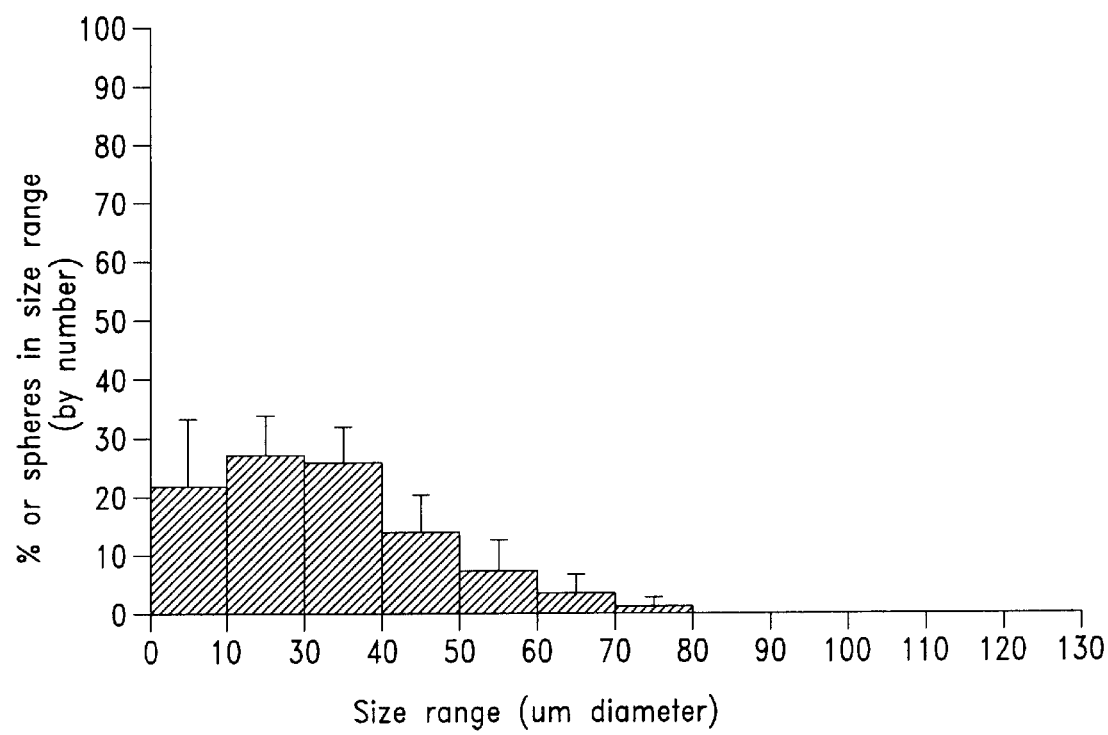
FIG. 11 is a bar graph which depicts the size distribution by number of 5% microspheres containing 10 mg sodium suramin made in 5% PVA containing 10% NaCl.
Figure 12:
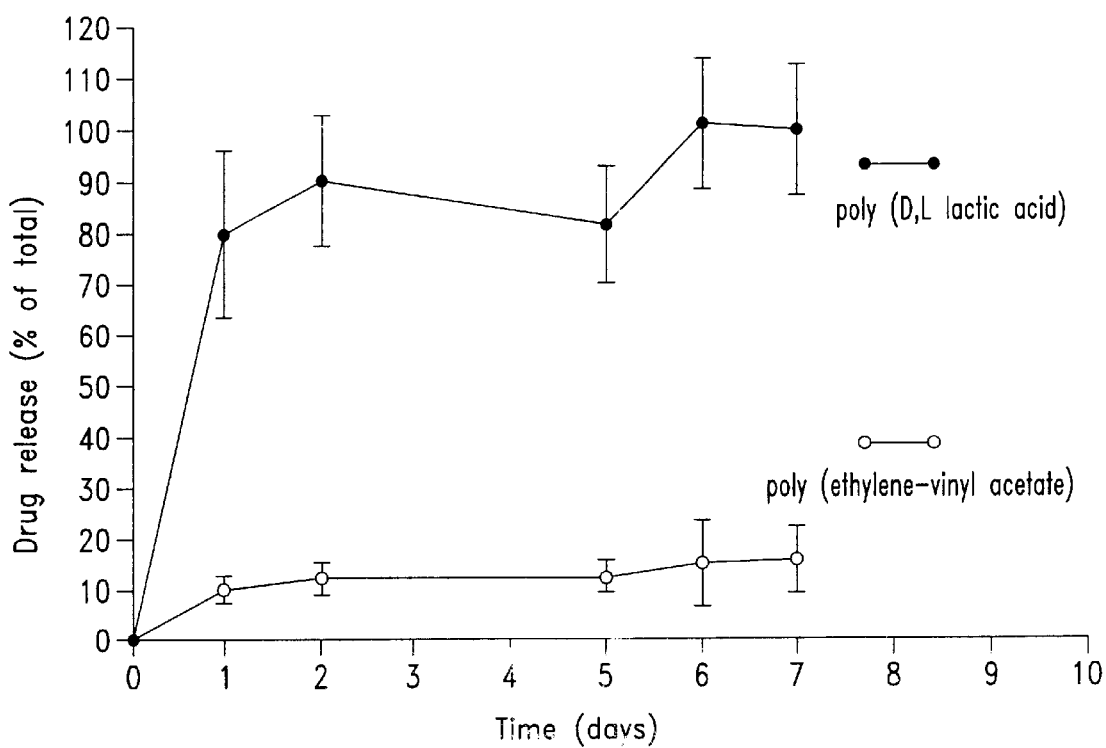
FIG. 12 is a line graph which depicts the time course of sodium suramin release.

The encapsulation of suramin is very low (<1%) (see FIG. 8). However as the weight of drug is increased in the DCM the total amount of drug encapsulated increased although the % encapsulation decreased. As is shown in FIG. 7, 50 ug of drug may be encapsulated in 50 mg of ELVAX. Encapsulation of sodium suramin in 2.5% PVA containing 10% NaCl is shown in FIG. 9 (size distribution by weight). Encapsulation of sodium suramin in 5% PVA containing 10% NaCl is shown in FIGS. 10 and 11 (size distribution by weight, and number, respectively).

Figure 28A:
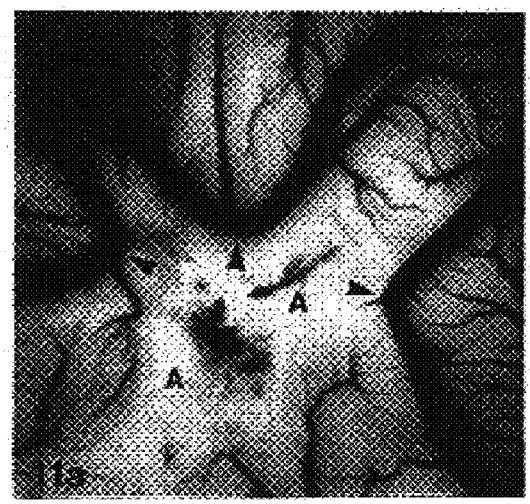
FIG. 28A is a photograph of Suramin and Cortisone Acetate on a CAM (Mag=8×). Briefly, this image shows an avascular zone treated with 20 $\mu$g of suramin and 70 $\mu$g of cortisone acetate in 0.5% methylcellulose. Note the blood vessels located at the periphery of the avascular zone which are being redirected away from the drug source.
Figure 28B:
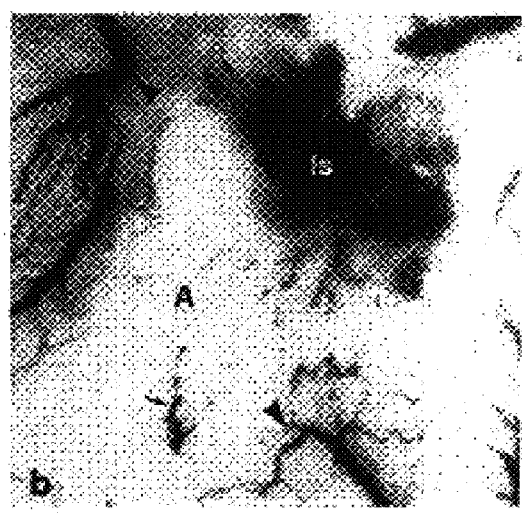
FIG. 28B is a photograph which shows the vascular detail of the effected region at a higher magnification (Mag=20×). Note the avascular regions and the typical "elbowing" effect of the blood vessels bordering the avascular zone.

To assess suramin and cortisone acetate as potential anti-angiogenic agents, each agent was mixed with 0.5% methylcellulose and applied the dried disks containing the agent onto the developing blood vessels of the 6-day old CAM. A combination treatment of suramin (70 μg) with cortisone acetate (20 g) was successful in inhibiting angiogenesis when tested on the CAM for 48 hours. The resulting avascular region measured 6 mm in diameter and revealed an absence of blood flow and the appearance of sparse blood islands (FIGS. 28A and 28B).

Example 4

Encapsulation of Paclitaxel

Five hundred micrograms of either paclitaxel or baccatin (a paclitaxel analog, available from Inflazyme Pharmaceuticals Inc., Vancouver, British Columbia, Canada) are dissolved in 1 ml of a 50:50 ELVAX:poly-1-lactic acid mixture in dcm. Microspheres are then prepared in a dissolution machine (Six-spindle dissolution tester, VanderKanp, Van Kell Industries Inc., U.S.A.) in triplicate at 200 rpm, 42° C., for 3 hours. Microspheres so prepared are washed twice in water and sized on the microscope.

Determination of paclitaxel encapsulation is undertaken in a uv/vis assay (uv/vis lambda max. at 237 nm, fluorescence assay at excitation 237, emission at 325 nm; Fluorescence results are presented in square brackets []). Utilizing the procedures described above, 58 μg (+/−12 μg) [75 μg (+/−25 μg)] of paclitaxel may be encapsulated from a total 500 μg of starting material. This represents 12% (+/−2.4%) [15% (+1−5%)] of the original weight, or 1.2% (+/−0.25%) [1.5% (+/−0.5%)] by weight of the polymer. After 18 hours of tumbling in an oven at 37° C., 10.3% (+/−10%) [6% (+/−5.6%)] of the total paclitaxel had been released from the microspheres.

For baccatin, 100+/−15 μg [83+/−231 g] of baccatin can be encapsulated from a total of 500 μg starting material. This represents a 20% (+/−3%) [17% (+/−5%) of the original weight of baccatin, and 2% (+/−0.3%) [1.7% (+/−0.5%)] by weight of the polymer. After 18 hours of tumbling in an oven at 37° C., 55% (+/−13%) [60% (+/−23%)] of the baccatin is released from the microspheres.

Example 5

Analysis of Surgical Paste Containing Anti-Angiogenic Compositions

Fisher rats weighing approximately 300 grams are anesthetized, and a 1 cm transverse upper abdominal incision is made. Two-tenths of a milliliter of saline containing $1 \times 10^6$ live 9L gliosarcoma cells (eluted immediately prior to use from tissue culture) are injected into 2 of the 5 hepatic lobes by piercing a 27 gauge needle 1 cm through the liver capsule. The abdominal wound is closed with 6.0 resorptible suture and skin clips and the GA terminated.

After 2 weeks, the tumor deposits will measure approximately 1 cm. At this time, both hepatic tumors are resected and the bare margin of the liver is packed with a hemostatic agent. The rats are divided into two groups: half is administered polymeric carrier alone, and the other half receives an anti-angiogenic composition.

Rats are sacrificed 2, 7, 14, 21 and 84 days post hepatic resection. In particular, the rats are euthanized by injecting Euthanyl into the dorsal vein of the tail. The liver, spleen, and both lungs are removed, and histologic analysis is performed in order to study the tumors for evidence of anti-angiogenic activity.

Example 6

Embolization of Rat Arteries

Fisher rats weighing approximately 300 grams are anesthetized. Utilizing aseptic procedures, a 1 cm transverse upper abdominal incision is made, and the liver identified. Two-tenths of a milliliter of saline containing 1 million live 9L gliosarcoma cells (eluted immediately prior from tissue culture) is injected into each of the 5 hepatic lobes by piercing a 27 gauge needle 1 cm through the liver capsule. One-tenth of a milliliter of normal saline is injected into the needle as it is withdrawn to ensure that there is no spillage of cells into the peritoneal cavity. A pledget of gelfoam is placed on each of the puncture sites to ensure hemostasis. The abdominal wound is closed with 6.0 resorptible suture with skin clips, and the anesthetic terminated. The rat is returned to the animal care facility to have a standard diet for 14 days, at which time each tumor deposit will measure 1 cm in diameter. The same procedure is repeated using Westar rats and a Colon Cancer cell line (Radiologic Oncology Lab, M. D. Anderson, Houston, Tex.). In this instance, 3 weeks are required post-injection for the tumor deposits to measure 1 cm in diameter each.

After 2 or 3 weeks, depending on the rat species, the same general anesthetic procedure is followed and a midline abdominal incision is performed. The duodenum is flipped and the gastroduodenal artery is identified and mobilized. Ties are placed above and below a cutdown site on the midportion of the gastroduodenal artery (GDA), and 0.038 inch polyethylene tubing is introduced in a retrograde fashion into the artery using an operating microscope. The tie below the insertion point will ligate the artery, while the one above will fix the catheter in place. Angiography is performed by injecting 0.5 ml of 60% radiopaque contrast material through the catheter as an x-ray is taken. The hepatic artery is then embolized by refluxing particles measuring 15–200 μm through the gastroduodenal artery catheter until flow, observed via the operating microscope, is seen to cease for at least 30 seconds. Occlusion of the hepatic artery is confirmed by repeating an angiogram through the GDA catheter. Utilizing this procedure, one-half of the rats receive 15–200 μm particles of polymer alone, and the other half receive 15–200 μm particles of the polymer-anti-angiogenic factor composition. The upper GDA ligature is tightened to occlude the GDA as the catheter is withdrawn to ensure hemostasis, and the hepatic artery (although embolized) is left intact. The abdomen is closed with 6.0 absorbable suture and surgical clips.

The rats are subsequently sacrificed at 2, 7, 14, 21 and 84 days post-embolization in order to determine efficacy of the anti-angiogenic factor. Briefly, general anesthetic is given, and utilizing aseptic precautions, a midline incision performed. The GDA is mobilized again, and after placing a ligature near the junction of the GDA and the hepatic artery (i.e., well above the site of the previous cutdown), a 0.038-inch polyethylene tubing is inserted via cutdown of the vessel and angiography is performed. The rat is then euthanized by injecting Euthanyl into the dorsal vein of the tail. Once euthanasia is confirmed, the liver is removed en bloc along with the stomach, spleen and both lungs.

Histologic analysis is performed on a prepared slide stained with hematoxylin and eosin ("H and E") stain. Briefly, the lungs are sectioned at 1 cm intervals to assess passage of embolic material through the hepatic veins and into the right side of circulation. The stomach and spleen are also sectioned in order to assess inadvertent immobilization from reflux of particles into the celiac access of the collateral circulation.

Example 7

Transplantation of Biliary Stents in Rats

General anesthetic is administered to 300 gram Fisher rats. A 1 cm transverse incision is then made in the upper abdomen, and the liver identified. In the most superficial lobe, 0.2 ml of saline containing 1 million cells of 9L gliosarcoma cells (eluted from tissue culture immediately prior to use) is injected via a 27 gauge needle to a depth of 1 cm into the liver capsule. Hemostasis is achieved after removal of the needle by placing a pledget of gelfoam at the puncture sites. Saline is injected as the needle is removed to ensure no spillage of cells into the peritoneal cavity or along the needle track. The general anesthetic is terminated, and the animal returned to the animal care center and placed on a normal diet.

Two weeks later, general anesthetic is administered, and utilizing aseptic precautions, the hepatic lobe containing the tumor is identified through a midline incision. A 16 gauge angiographic needle is then inserted through the hepatic capsule into the tumor, a 0.038-inch guidewire passed through the needle, and the needle withdrawn over the guidewire. A number 5 French dilator is passed over the guide into the tumor and withdrawn. A number 5 French delivery catheter is then passed over the wire containing a self-expanding stainless steel Wallstent (5 mm in diameter and 1 cm long). The stent is deployed into the tumor and the guidewire delivery catheter is removed. One-third of the rats have a conventional stainless steel stent inserted into the tumor, one-third a stainless steel stent coated with polymer, and one third a stent coated with the polymer-anti-angiogenic factor compound. The general anesthetic is terminated and the rat returned to the animal care facility.

A plain abdominal X-ray is performed at 2 days in order to assess the degree of stent opening. Rats are sacrificed at 2, 7, 14, 28 and 56 days post-stent insertion by injecting Euthanyl, and their livers removed en bloc once euthanasia is confirmed. After fixation in formaldehyde for 48 hours, the liver is sectioned at 0.5 mm intervals; including severing the stent transversely using a fresh blade for each slice. Histologic sections stained with H and E are then analyzed to assess the degree of tumor ingrowth into the stent lumen.

Example 8

Manufacture of Microspheres

Equipment which is preferred for the manufacture of microspheres described below include: 200 ml water jacketed beaker (Kimax or Pyrex), Haake circulating water bath, overhead stirrer and controller with 2 inch diameter (4 blade, propeller type stainless steel stirrer—Fisher brand), 500 ml glass beaker, hot plate/stirrer (Corning brand), 4×50 ml polypropylene centrifuge tubes (Nalgene), glass scintillation vials with plastic insert caps, table top centrifuge (GPR Beckman), high speed centrifuge—floor model (JS 21 Beckman), Mettler analytical balance (AJ 100, 0.1 mg), Mettler digital top loading balance (AE 163, 0.01 mg), automatic pipetter (Gilson). Reagents include Polycaprolactone ("PCL"—mol wt 10,000 to 20,000; Polysciences, Warrington Pa., USA), "washed" (see later method of "washing") Ethylene Vinyl Acetate ("EVA"), Poly(DL) lactic acid ("PLA"—mol wt 15,000 to 25,000; Polysciences), Polyvinyl Alcohol ("PVA"—mol wt 124,000 to 186,000; 99% hydrolyzed; Aldrich Chemical Co., Milwaukee Wis., USA), Dichloromethane ("DCM" or "methylene chloride"; HPLC grade Fisher scientific), and distilled water.

A. Preparation of 5% (w/v) Polymer Solutions

Depending on the polymer solution being prepared, 1.00 g of PCL or PLA, or 0.50 g each of PLA and washed EVA is weighed directly into a 20 ml glass scintillation vial. Twenty milliliters of DCM is then added, and the vial tightly capped. The vial is stored at room temperature (25° C.) for one hour (occasional shaking may be used), or until all the polymer has dissolved (the solution should be clear). The solution may be stored at room temperature for at least two weeks.

B. Preparation of 5% (w/v) Stock Solution of PVA

Twenty-five grams of PVA is weighed directly into a 600 ml glass beaker. Five hundred milliliters of distilled water is added, along with a 3 inch Teflon coated stir bar. The beaker is covered with glass to decrease evaporation losses, and placed into a 2000 ml glass beaker containing 300 ml of water (which acts as a water bath). The PVA is stirred at 300 rpm at 85° C. (Corning hot plate/stirrer) for 2 hours or until fully dissolved. Dissolution of the PVA may be determined by a visual check; the solution should be clear. The solution is then transferred to a glass screw top storage container and stored at 4° C. for a maximum of two months. The solution, however should be warmed to room temperature before use or dilution.

C. Procedure for Producing Microspheres

Based on the size of microspheres being made (see Table IV), 100 ml of the PVA solution (concentrations given in Table IV) is placed into the 200 ml water jacketed beaker. Haake circulating water bath is connected to this beaker and the contents are allowed to equilibrate at 27° C. (+/−1° C.) for 10 minutes. Based on the size of microspheres being made (see Table IV), the start speed of the overhead stirrer is set, and the blade of the overhead stirrer placed half way down in the PVA solution. The stirrer is then started, and 10 ml of polymer solution (polymer solution used based on type of microspheres being produced) is then dripped into the stirring PVA over a period of 2 minutes using a 5 ml automatic pipetter. After 3 minutes the stir speed is adjusted (see Table IV), and the solution stirred for an additional 2.5 hours. The stirring blade is then removed from the microsphere preparation, and rinsed with 10 ml of distilled water so that the rinse solution drains into the microsphere preparation. The microsphere preparation is then poured into a 500 ml beaker, and the jacketed water bath washed with 70 ml of distilled water, which is also allowed to drain into the microsphere preparation. The 180 ml microsphere preparation is then stirred with a glass rod, and equal amounts are poured into four polypropylene 50 ml centrifuge tubes. The tubes are then capped, and centrifuged for 10 minutes (force given in Table IV). A 5 ml automatic pipetter or vacuum suction is then utilized to draw 45 ml of the PVA solution off of each microsphere pellet.

TABLE IV

PVA concentrations, stir speeds, and centrifugal force requirements for each diameter range of microspheres.

| PRODUCTION STAGE | MICROSPHERE DIAMETER RANGES | | |
|---|---|---|---|
| | 30 µm to 100 µm | 10 µm to 30 µm | 0.1 µm to 3 µm |
| PVA concentration | 2.5% (w/v) (i.e.,) dilute 5% stock with distilled water | 5% (w/v) (i.e., undiluted stock) | 3.5% (w/v) (i.e., dilute 5% stock with distilled water |
| Starting Stir Speed | 500 rpm +/− 50 rpm | 500 rpm +/− 50 rpm | 3000 rpm +/− 200 rpm |
| Adjusted Stir Speed | 500 rpm +/− 50 rpm | 500 rpm +/− 50 rpm | 2500 rpm +/− 200 rpm |
| Centrifuge Force | 1000 g +/− 100 g (Table top model) | 1000 g +/− 100 g (Table top model) | 10000 g +/− 1000 g (High speed model) |

Five milliliters of distilled water is then added to each centrifuge tube, which is then vortexed to resuspend the microspheres. The four microsphere suspensions are then pooled into one centrifuge tube along with 20 ml of distilled water, and centrifuged for another 10 minutes (force given in Table IV). This process is repeated two additional times for a total of three washes. The microspheres are then centrifuged a final time, and resuspended in 10 ml of distilled water. After the final wash, the microsphere preparation is transferred into a preweighed glass scintillation vial. The vial is capped, and left overnight at room temperature (25° C.) in order to allow the microspheres to sediment out under gravity. Microspheres which fall in the size range of 0.1 um to 3 um do not sediment out under gravity, so they are left in the 10 ml suspension.

D. Drying of 10 μm to 30 μm or 30 μm to 100 μm Diameter Microspheres

After the microspheres have sat at room temperature overnight, a 5 ml automatic pipetter or vacuum suction is used to draw the supernatant off of the sedimented microspheres. The microspheres are allowed to dry in the uncapped vial in a drawer for a period of one week or until they are fully dry (vial at constant weight). Faster drying may be accomplished by leaving the uncapped vial under a slow stream of nitrogen gas (flow approx. 10 ml/min.) in the fume hood. When fully dry (vial at constant weight), the vial is weighed and capped. The labeled, capped vial is stored at room temperature in a drawer. Microspheres are normally stored no longer than 3 months.

E. Drying of 0.1 μm to 3 μm Diameter Microspheres

This size range of microspheres will not sediment out, so they are left in suspension at 4° C. for a maximum of four weeks. To determine the concentration of microspheres in the 10 ml suspension, a 200 μl sample of the suspension is pipetted into a 1.5 ml preweighed microfuge tube. The tube is then centrifuged at 10,000 g (Eppendorf table top microfuge), the supernatant removed, and the tube allowed to dry at 50° C. overnight. The tube is then reweighed in order to determine the weight of dried microspheres within the tube.

F. Manufacture of Paclitaxel Loaded Microsphere

In order to prepare paclitaxel containing microspheres, an appropriate amount of weighed paclitaxel (based upon the percentage of paclitaxel to be encapsulated) is placed directly into a 20 ml glass scintillation vial. Ten milliliters of an appropriate polymer solution is then added to the vial containing the paclitaxel, which is then vortexed until the paclitaxel has dissolved.

Microspheres containing paclitaxel may then be produced essentially as described above in steps (C) through (E).

Example 9

Manufacture of Stent Coating

Reagents and equipment which are utilized within the following experiments include (medical grade stents obtained commercially from a variety of manufacturers; e.g., the "Strecker" stent) and holding apparatus, 20 ml glass scintillation vial with cap (plastic insert type), TLC atomizer, Nitrogen gas tank, glass test tubes (various sizes from 1 ml and up), glass beakers (various sizes), Pasteur pipette, tweezers, Polycaprolactone ("PCL"—mol wt 10,000 to 20,000; Polysciences), Paclitaxel (Sigma Chemical Co., St. Louis, Mo., 95% purity), Ethylene vinyl acetate ("EVA"—washed—see previous), Poly(DL) lactic acid ("PLA"—mol wt 15,000 to 25,000; Polysciences), dichloromethane ("DCM"—HPLC grade, Fisher Scientific).

A. Procedure for Sprayed Stents

The following describes a typical method using a 3 mm crimped diameter interleaving metal wire stent of approximately 3 cm length. For larger diameter stents, larger volumes of polymer/drug solution are used.

Briefly, a sufficient quantity of polymer is weighed directly into a 20 ml glass scintillation vial, and sufficient DCM added in order to achieve a 2% w/v solution. The vial is then capped and mixed by hand in order to dissolve the polymer. The stent is then assembled in a vertical orientation, tying the stent to a retort stand with nylon. Position this stent holding apparatus 6 to 12 inches above the fume hood floor on a suitable support (e.g., inverted 2000 ml glass beaker) to enable horizontal spraying. Using an automatic pipette, a suitable volume (minimum 5 ml) of the 2% polymer solution is transferred to a separate 20 ml glass scintillation vial. An appropriate amount of paclitaxel is then added to the solution and dissolved by hand shaking.

To prepare for spraying, remove the cap of this vial and dip the barrel (only) of an TLC atomizer into the polymer solution. Note that the reservoir of the atomizer need not be used in this procedure: the 20 ml glass vial acts as a reservoir. Connect the nitrogen tank to the gas inlet of the atomizer. Gradually increase the pressure until atomization and spraying begins. Note the pressure and use this pressure throughout the procedure. To spray the stent use 5 second oscillating sprays with a 15 second dry time between sprays. After 5 sprays, rotate the stent 90° and spray that portion of the stent. Repeat until all sides of the stent have been sprayed. During the dry time, finger crimp the gas line to avoid wastage of the spray. Spraying is continued until a suitable amount of polymer is deposited on the stents. The amount may be based on the specific stent application in vivo. To determine the amount, weigh the stent after spraying has been completed and the stent has dried. Subtract the original weight of the stent from the finished weight and this produces the amount of polymer (plus paclitaxel) applied to the stent. Store the coated stent in a sealed container.

B. Procedure for Dipped Stents

The following describes a typical method using a 3 mm crimped diameter interleaving metal wire stent of approximately 3 cm length. For larger diameter stents, larger volumes of polymer/drug solution are used in larger sized test tubes.

Weigh 2 g of EVA into a 20 ml glass scintillation vial and add 20 ml of DCM. Cap the vial and leave it for 2 hours to dissolve (hand shake the vial frequently to assist the dissolving process). Weigh a known weight of paclitaxel directly into a 1 ml glass test tube and add 0.5 ml of the polymer solution. Using a glass Pasteur pipette, dissolve the paclitaxel by gently pumping the polymer solution. Once the paclitaxel is dissolved, hold the test tube in a near horizontal position (the sticky polymer solution will not flow out). Using tweezers, insert the stent into the tube all the way to the bottom. Allow the polymer solution to flow almost to the mouth of the test tube by angling the mouth below horizontal and then restoring the test tube to an angle slightly above the horizontal. While slowly rotating the stent in the tube, slowly remove the stent (approximately 30 seconds).

Hold the stent in a vertical position to dry. Some of the sealed perforations may pop so that a hole exists in the continuous sheet of polymer. This may be remedied by repeating the previous dipping procedure, however repetition of the procedure can also lead to further popping and a general uneven build up of polymer. Generally, it is better to dip the stent just once and to cut out a section of stent that has no popped perforations. Store the dipped stent in a sealed container.

Example 10

Manufacture of Surgical "Pastes"

As noted above, the present invention provides a variety of polymeric-containing drug compositions that may be utilized within a variety of clinical situations. For example, compositions may be produced: (1) as a "thermopaste" that is applied to a desired site as a fluid, and hardens to a solid of the desired shape at a specified temperature (e.g., body temperature); (2) as a spray (i.e., "nanospray") which may delivered to a desired site either directly or through a specialized apparatus (e.g., endoscopy), and which subsequently hardens to a solid which adheres to the tissue to which it is applied; (3) as an adherent, pliable, resilient, angiogeneis inhibitor-polymer film applied to a desired site either directly or through a specialized apparatus, and which preferably adheres to the site to which it is applied; and (4) as a fluid composed of a suspension of microspheres in an appropriate carrier medium, which is applied to a desired site either directly or via a specialized apparatus, and which leaves a layer of microspheres at the application site. Representative examples of each of the above embodiments is set forth in more detail below.

A. Procedure for Producing Thermopaste

Reagents and equipment which are utilized within the following experiments include a sterile glass syringe (1 ml), Corning hot plate/stirrer, 20 ml glass scintillation vial, moulds (e.g., 50 μl DSC pan or 50 ml centrifuge tube cap inner portion), scalpel and tweezers, Polycaprolactone ("PCL"—mol wt 10,000 to 20,000; Polysciences, Warrington, Pa. USA), and Paclitaxel (Sigma grade 95% purity minimum).

Weigh 5.00 g of polycaprolactone directly into a 20 ml glass scintillation vial. Place the vial in a 600 ml beaker containing 50 ml of water. Gently heat the beaker to 65° C. and hold it at that temperature for 20 minutes. This allows the polymer to melt. Thoroughly mix a known weight of paclitaxel, or other angiogenesis inhibitor into the melted polymer at 65° C. Pour the melted polymer into a pre-warmed (60° C. oven) mould. Use a spatula to assist with the pouring process. Allow the mould to cool so the polymer solidifies. Cut or break the polymer into small pieces (approximately 2 mm by 2 mm in size). These pieces must fit into a 1 ml glass syringe. Remove the plunger from the 1 ml glass syringe (do not remove the cap from the tip) and place it on a balance. Zero the balance.

Weigh 0.5 g of the pieces directly into the open end of the syringe. Place the glass syringe upright (capped tip downwards) into a 500 ml glass beaker containing distilled water at 65° C. (corning hot plate) so that no water enters the barrel. The polymer melts completely within 10 minutes in this apparatus. When the polymer pieces have melted, remove the barrel from the water bath, hold it horizontally and remove the cap. Insert the plunger into the barrel and compress the melted polymer into a sticky mass at the tip end of the barrel. Cap the syringe and allow it to cool to room temperature.

For application, the syringe may be reheated to 60° C. and administered as a liquid which solidifies when cooled to body temperature.

B. Procedure for Producing Nanospray

Nanospray is a suspension of small microspheres in saline. If the microspheres are very small (i.e., under 1 μm in diameter) they form a colloid so that the suspension will not sediment under gravity. As is described in more detail below, a suspension of 0.1 μm to 1 μm microparticles may be created suitable for deposition onto tissue through a finger pumped aerosol. Equipment and materials which may be utilized to produce nanospray include 200 ml water jacketed beaker (Kimax or Pyrex), Haake circulating water bath, overhead stirrer and controller with 2 inch diameter (4 blade, propeller type stainless steel stirrer; Fisher brand), 500 ml glass beaker, hot plate/stirrer (Corning brand), 4×50 ml polypropylene centrifuge tubes (Nalgene), glass scintillation vials with plastic insert caps, table top centrifuge (Beckman), high speed centrifuge—floor model (JS 21 Beckman), Mettler analytical balance (AJ 100, 0.1 mg), Mettler digital top loading balance (AE 163, 0.01 mg), automatic pipetter (Gilson), sterile pipette tips, pump action aerosol (Pfeiffer pharmaceuticals) 20 ml, laminar flow hood, Polycaprolactone ("PCL"—mol wt 10,000 to 20,000; Polysciences, Warrington, Pa. USA), "washed" (see previous) Ethylene Vinyl Acetate ("EVA"), Poly(DL)lactic acid ("PLA" mol wt 15,000 to 25,000; Polysciences), Polyvinyl Alcohol ("PVA"—mol wt 124,000 to 186,000; 99% hydrolyzed; Aldrich Chemical Co., Milwaukee, Wis. USA), Dichloromethane ("DCM" or "methylene chloride;" HPLC grade Fisher scientific), Distilled water, sterile saline (Becton and Dickenson or equivalent)

1. Preparation of 5% (w/v) Polymer Solutions

Depending on the polymer solution being prepared, weigh 1.00 g of PCL or PLA or 0.50 g each of PLA and washed EVA directly into a 20 ml glass scintillation vial. Using a measuring cylinder, add 20 ml of DCM and tightly cap the vial. Leave the vial at room temperature (25° C.) for one hour or until all the polymer has dissolved (occasional hand shaking may be used). Dissolving of the polymer can be determined by a visual check; the solution should be clear. Label the vial with the name of the solution and the date it was produced. Store the solutions at room temperature and use within two weeks.

2. Preparation of 3.5% (w/v) Stock Solution of PVA

The solution can be prepared by following the procedure given below, or by diluting the 5% (w/v) PVA stock solution prepared for production of microspheres (see Example 8). Briefly, 17.5 g of PVA is weighed directly into a 600 ml glass beaker, and 500 ml of distilled water is added. Place a 3 inch Teflon coated stir bar in the beaker. Cover the beaker with a cover glass to reduce evaporation losses. Place the beaker in a 2000 ml glass beaker containing 300 ml of water. This will act as a water bath. Stir the PVA at 300 rpm at 85° C. (Corning hot plate/stirrer) for 2 hours or until fully dissolved. Dissolving of the PVA can be determined by a visual check; the solution should be clear. Use a pipette to transfer the solution to a glass screw top storage container and store at 4° C. for a maximum of two months. This solution should be warmed to room temperature before use or dilution.

3. Procedure for Producing Nanospray

Place the stirring assembly in a fume hood. Place 100 ml of the 3.5% PVA solution in the 200 ml water jacketed beaker. Connect the Haake water bath to this beaker and allow the contents to equilibrate at 27° C. (+/−1° C.) for 10 minutes. Set the start speed of the overhead stirrer at 3000 rpm (+/−200 rpm). Place the blade of the overhead stirrer half way down in the PVA solution and start the stirrer. Drip 10 ml of polymer solution (polymer solution used based on type of nanospray being produced) into the stirring PVA over a period of 2 minutes using a 5 ml automatic pipetter. After 3 minutes, adjust the stir speed to 2500 rpm (+/−200 rpm) and leave the assembly for 2.5 hours. After 2.5 hours, remove the stirring blade from the nanospray preparation and rinse with 10 ml of distilled water. Allow the rinse solution to go into the nanospray preparation.

Pour the microsphere preparation into a 500 ml beaker. Wash the jacketed water bath with 70 ml of distilled water. Allow the 70 ml rinse solution to go into the microsphere preparation. Stir the 180 ml microsphere preparation with a glass rod and pour equal amounts of it into four polypropylene 50 ml centrifuge tubes. Cap the tubes. Centrifuge the capped tubes at 10000 g (+/−1000 g) for 10 minutes. Using a 5 ml automatic pipetter or vacuum suction, draw 45 ml of the PVA solution off of each microsphere pellet and discard it. Add 5 ml of distilled water to each centrifuge tube and use a vortex to resuspend the microspheres in each tube. Using 20 ml of distilled water, pool the four microsphere suspensions into one centrifuge tube. To wash the microspheres, centrifuge the nanospray preparation for 10 minutes at 10 000 g (+/−1000 g). Draw the supernatant off of the microsphere pellet. Add 40 ml of distilled water and use a vortex to resuspend the microspheres. Repeat this process two more times for a total of three washes. Do a fourth wash but use only 10 ml (not 40 ml) of distilled water when resuspending the microspheres. After the fourth wash, transfer the microsphere preparation into a preweighed glass scintillation vial.

Cap the vial and let it to sit for 1 hour at room temperature (25° C.) to allow the 2 $\mu$m and 3 $\mu$m diameter microspheres to sediment out under gravity. After 1 hour, draw off the top 9 ml of suspension using a 5 ml automatic pipetter. Place the 9 ml into a sterile capped 50 ml centrifuge tube. Centrifuge the suspension at 10 000 g (+/−1000 g) for 10 minutes. Discard the supernatant and resuspend the pellet in 20 ml of sterile saline. Centrifuge the suspension at 10 000 g (+/−1000 g) for 10 minutes. Discard the supernatant and resuspend the pellet in sterile saline. The quantity of saline used is dependent on the final required suspension concentration (usually 10% w/v). Thoroughly rinse the aerosol apparatus in sterile saline and add the nanospray suspension to the aerosol.

C. Manufacture of Paclitaxel Loaded Nanospray

To manufacture nanospray containing paclitaxel, use Paclitaxel (Sigma grade 95% purity). To prepare the polymer drug stock solution, weigh the appropriate amount of paclitaxel directly into a 20 ml glass scintillation vial. The appropriate amount is determined based on the percentage of paclitaxel to be in the nanospray. For example, if nanospray containing 5% paclitaxel was required, then the amount of paclitaxel weighed would be 25 mg since the amount of polymer added is 10 ml of a 5% polymer in DCM solution (see next step).

Add 10 ml of the appropriate 5% polymer solution to the vial containing the paclitaxel. Cap the vial and vortex or hand swirl it to dissolve the paclitaxel (visual check to ensure paclitaxel dissolved). Label the vial with the date it was produced. This is to be used the day it is produced.

Follow the procedures as described above, except that polymer/drug (e.g., paclitaxel) stock solution is substituted for the polymer solution.

D. Procedure for Producing Film

The term film refers to a polymer formed into one of many geometric shapes. The film may be a thin, elastic sheet of polymer or a 2 mm thick disc of polymer. This film is designed to be placed on exposed tissue so that any encapsulated drug is released from the polymer over a long period of time at the tissue site. Films may be made by several processes, including for example, by casting, and by spraying.

In the casting technique, polymer is either melted and poured into a shape or dissolved in dichloromethane and poured into a shape. The polymer then either solidifies as it cools or solidifies as the solvent evaporates, respectively. In the spraying technique, the polymer is dissolved in solvent and sprayed onto glass, as the solvent evaporates the polymer solidifies on the glass. Repeated spraying enables a build up of polymer into a film that can be peeled from the glass.

Reagents and equipment which were utilized within these experiments include a small beaker, Corning hot plate stirrer, casting moulds (e.g., 50 ml centrifuge tube caps) and mould holding apparatus, 20 ml glass scintillation vial with cap (Plastic insert type), TLC atomizer, Nitrogen gas tank, Polycaprolactone ("PCL"—mol wt 10,000 to 20,000; Polysciences), Paclitaxel (Sigma 95% purity), Ethanol, "washed" (see previous) Ethylene vinyl acetate ("EVA"), Poly(DL)lactic acid ("PLA"—mol wt 15,000 to 25,000; Polysciences), Dichloromethane (HPLC grade Fisher Scientific).

1. Procedure for Producing Films—Melt Casting

Weigh a known weight of PCL directly into a small glass beaker. Place the beaker in a larger beaker containing water (to act as a water bath) and put it on the hot plate at 70° C. for 15 minutes or until the polymer has fully melted. Add a known weight of drug to the melted polymer and stir the mixture thoroughly. To aid dispersion of the drug in the melted PCL, the drug may be suspended/dissolved in a small volume (<10% of the volume of the melted PCL) of 100% ethanol. This ethanol suspension is then mixed into the melted polymer. Pour the melted polymer into a mould and let it to cool. After cooling, store the film in a container.

2. Procedure for Producing Films—Solvent Casting

Weigh a known weight of PCL directly into a 20 ml glass scintillation vial and add sufficient DCM to achieve a 10% w/v solution. Cap the vial and mix the solution. Add sufficient paclitaxel to the solution to achieve the desired final paclitaxel concentration. Use hand shaking or vortexing to dissolve the paclitaxel in the solution. Let the solution sit for one hour (to diminish the presence of air bubbles) and then pour it slowly into a mould. The mould used is based on the shape required. Place the mould in the fume hood overnight. This will allow the DCM to evaporate. Either leave the film in the mould to store it or peel it out and store it in a sealed container.

3. Procedure for Producing Films—Sprayed

Weigh sufficient polymer directly into a 20 ml glass scintillation vial and add sufficient DCM to achieve a 2% w/v solution. Cap the vial and mix the solution to dissolve the polymer (hand shaking). Assemble the moulds in a vertical orientation in a suitable mould holding apparatus in the fume hood. Position this mould holding apparatus 6 to 12 inches above the fume hood floor on a suitable support (e.g., inverted 2000 ml glass beaker) to enable horizontal spraying. Using an automatic pipette, transfer a suitable volume (minimum 5 ml) of the 2% polymer solution to a separate 20 ml glass scintillation vial. Add sufficient paclitaxel to the solution and dissolve it by hand shaking the capped vial. To prepare for spraying, remove the cap of this vial and dip the barrel (only) of an TLC atomizer into the polymer solution. Note: the reservoir of the atomizer is not used in this procedure—the 20 ml glass vial acts as a reservoir.

Connect the nitrogen tank to the gas inlet of the atomizer. Gradually increase the pressure until atomization and spraying begins. Note the pressure and use this pressure throughout the procedure. To spray the moulds use 5 second oscillating sprays with a 15 second dry time between sprays. During the dry time, finger crimp the gas line to avoid wastage of the spray. Spraying is continued until a suitable thickness of polymer is deposited on the mould. The thickness is based on the request. Leave the sprayed films attached to the moulds and store in sealed containers.

E. Procedure for Producing Nanopaste

Nanopaste is a suspension of microspheres suspended in a hydrophilic gel. Within one aspect of the invention, the gel or paste can be smeared over tissue as a method of locating drug loaded microspheres close to the target tissue. Being water based, the paste will soon become diluted with bodily fluids causing a decrease in the stickiness of the paste and a tendency of the microspheres to be deposited on nearby tissue. A pool of microsphere encapsulated drug is thereby located close to the target tissue.

Reagents and equipment which were utilized within these experiments include glass beakers, Carbopol 925 (pharmaceutical grade, Goodyear Chemical Co.), distilled water, sodium hydroxide (1 M) in water solution, sodium hydroxide solution (5 M) in water solution, microspheres in the 0.1 lm to 3 lm size range suspended in water at 20% w/v (See previous).

1. Preparation of 5% w/v Carbopol Gel

Add a sufficient amount of carbopol to 1 M sodium hydroxide to achieve a 5% w/v solution. To dissolve the carbopol in the 1 M sodium hydroxide, allow the mixture to sit for approximately one hour. During this time period, stir the mixture using a glass rod. After one hour, take the pH of the mixture. A low pH indicates that the carbopol is not fully dissolved. The pH you want to achieve is 7.4. Use 5 M sodium hydroxide to adjust the pH. This is accomplished by slowly adding drops of 5 M sodium hydroxide to the mixture, stirring the mixture and taking the pH of the mixture. It usually takes approximately one hour to adjust the pH to 7.4. Once a pH of 7.4 is achieved, cover the gel and let it sit for 2 to 3 hours. After this time period, check the pH to ensure it is still at 7.4. If it has changed, adjust back to pH 7.4 using 5 M sodium hydroxide. Allow the gel to sit for a few hours to ensure the pH is stable at 7.4. Repeat the process until the desired pH is achieved and is stable. Label the container with the name of the gel and the date. The gel is to be used to make nanopaste within the next week.

2. Procedure for Producing Nanopaste

Add sufficient 0.1 μm to 3 μm microspheres to water to produce a 20% suspension of the microspheres. Put 8 ml of the 5% w/v carbopol gel in a glass beaker. Add 2 ml of the 20% microsphere suspension to the beaker. Using a glass rod or a mixing spatula, stir the mixture to thoroughly disperse the microspheres throughout the gel. This usually takes 30 minutes. Once the microspheres are dispersed in the gel, place the mixture in a storage jar. Store the jar at 4° C. It must be used within a one month period.

Example 11

Controlled Delivery of Paclitaxel from Microspheres Composed of a Blend of Ethylene-Vinyl-Acetate Copolymer and Poly (D,L Lactic Acid). In Vivo Testing of the Microspheres on the Cam Assay This example describes the preparation of paclitaxel-loaded microspheres composed of a blend of biodegradable poly (d,l-lactic acid) (PLA) polymer and nondegradable ethylene-vinyl acetate (EVA) copolymer. In addition, the in vitro release rate and anti-angiogenic activity of paclitaxel released from microspheres placed on a CAM are demonstrated.

Reagents which were utilized in these experiments include paclitaxel, which is purchased from Sigma Chemical Co. (St. Louis, Mo.); PLA (molecular weight 15,000–25,000) and EVA (60% vinyl acetate) (purchased from Polysciences (Warrington, Pa.); polyvinyl alcohol (PVA) (molecular weight 124,000–186,000, 99% hydrolysed, purchased from Aldrich Chemical Co. (Milwaukee, Wis.)) and Dichloromethane (DCM) (HPLC grade, obtained from Fisher Scientific Co). Distilled water is used throughout.

A. Preparation of Microspheres

Microspheres are prepared essentially as described in Example 8 utilizing the solvent evaporation method. Briefly, 5% w/v polymer solutions in 20 mL DCM are prepared using blends of EVA:PLA between 35:65 to 90:10. To 5 mL of 2.5% w/v PVA in water in a 20 mL glass vial is added 1 mL of the polymer solution dropwise with stirring. Six similar vials are assembled in a six position overhead stirrer, dissolution testing apparatus (Vanderkamp) and stirred at 200 rpm. The temperature of the vials is increased from room temperature to 40° C. over 15 min and held at 40° C. for 2 hours. Vials are centrifuged at 500× g and the microspheres washed three times in water. At some EVA:PLA polymer blends, the microsphere samples aggregated during the washing stage due to the removal of the dispersing or emulsifying agent, PVA. This aggregation effect could be analyzed semi-quantitatively since aggregated microspheres fused and the fused polymer mass floated on the surface of the wash water. This surface polymer layer is discarded during the wash treatments and the remaining, pelleted microspheres are weighed.

The % aggregation is determined from $$\% \text{ aggregation} = \frac{1 - (\text{weight of pelleted microshperes}) \times 100}{\text{initial polymer weight}}$$

Paclitaxel loaded microspheres (0.6% w/w paclitaxel) are prepared by dissolving the paclitaxel in the 5% w/v polymer solution in DCM. The polymer blend used is 50:50 EVA:PLA. A "large" size fraction and "small" size fraction of microspheres are produced by adding the paclitaxel/polymer solution dropwise into 2.5% w/v PVA and 5% w/v PVA, respectively. The dispersions are stirred at 40° C. at 200 rpm for 2 hours, centrifuged and washed 3 times in water as described previously. Microspheres are air dried and samples are sized using an optical microscope with a stage micrometer. Over 300 microspheres are counted per sample. Control microspheres (paclitaxel absent) are prepared and sized as described previously.

B. Encapsulation Efficiency

Known weights of paclitaxel-loaded microspheres are dissolved in 1 mL DCM, 20 mL of 40% acetonitrile in water at 50° C. are added and vortexed until the DCM had been evaporated. The concentration of paclitaxel in the 40% acetonitrile is determined by HPLC using a mobile phase of water:methanol:acetonitrile (37:5:58) at a flow rate of 1 mL/min (Beckman isocratic pump), a C8 reverse phase column (Beckman) and UV detection at 232 nm. To determine the recovery efficiency of this extraction procedure, known weights of paclitaxel from 100–1000 μg are dissolved in 1 mL of DCM and subjected to the same extraction procedure in triplicate as described previously. Recoveries are always greater than 85% and the values of encapsulation efficiency are corrected appropriately.

C. Drug Release Studies

In 15 mL glass, screw capped tubes are placed 10 mL of 10 mM phosphate buffered saline (PBS), pH 7.4 and 35 mg paclitaxel-loaded microspheres. The tubes are tumbled at 37° C. and at given time intervals, centrifuged at 1500× g for 5 min and the supernatant saved for analysis. Microsphere pellets are resuspended in fresh PBS (10 mL) at 37° C. and reincubated. Paclitaxel concentrations are determined by extraction into 1 mL DCM followed by evaporation to dryness under a stream of nitrogen, reconstitution in 1 μL of 40% acetonitrile in water and analysis using HPLC as previously described.

D. Scanning Electron Microscopy (SEM)

Microspheres are placed on sample holders, sputter coated with gold and micrographs obtained using a Philips 501B SEM operating at 15 kV.

E. CAM Studies

Fertilized, domestic chick embryos are incubated for 4 days prior to shell-less culturing. The egg contents are incubated at 90% relative humidity and 3% $CO_2$ for 2 days. On day 6 of incubation, 1 mg aliquots of 0.6% paclitaxel loaded or control (paclitaxel free) microspheres are placed directly on the CAM surface. After a 2 day exposure the vasculature is examined using a stereomicroscope interfaced with a video camera; the video signals are then displayed on a computer and video printed.

F. Results

Microspheres prepared from 100% EVA are freely suspended in solutions of PVA but aggregated and coalesced or fused extensively on subsequent washing in water to remove the PVA. Blending EVA with an increasing proportion of PLA produced microspheres showing a decreased tendency to aggregate and coalesce when washed in water, as described in FIG. 15A. A 50:50 blend of EVA:PLA formed microspheres with good physical stability, that is the microspheres remained discrete and well suspended with negligible aggregation and coalescence.

The size range for the "small" size fraction microspheres is determined to be >95% of the microsphere sample (by weight) between 10–30 um and for the "large" size fraction, >95% of the sample (by weight) between 30–100 um. Representative scanning electron micrographs of paclitaxel loaded 50:50 EVA:PLA microspheres in the "small" and "large" size ranges are shown in FIGS. 15B and 15C, respectively. The microspheres are spherical with a smooth surface and with no evidence of solid drug on the surface of the microspheres. The efficiency of loading 50:50 EVA:PLA microspheres with paclitaxel is between 95–100% at initial paclitaxel concentrations of between 100–1000 mg paclitaxel per 50 mg polymer. There is no significant difference (Student t-test, $p<0.05$) between the encapsulation efficiencies for either "small" or "large" microspheres.

Figure 15A:
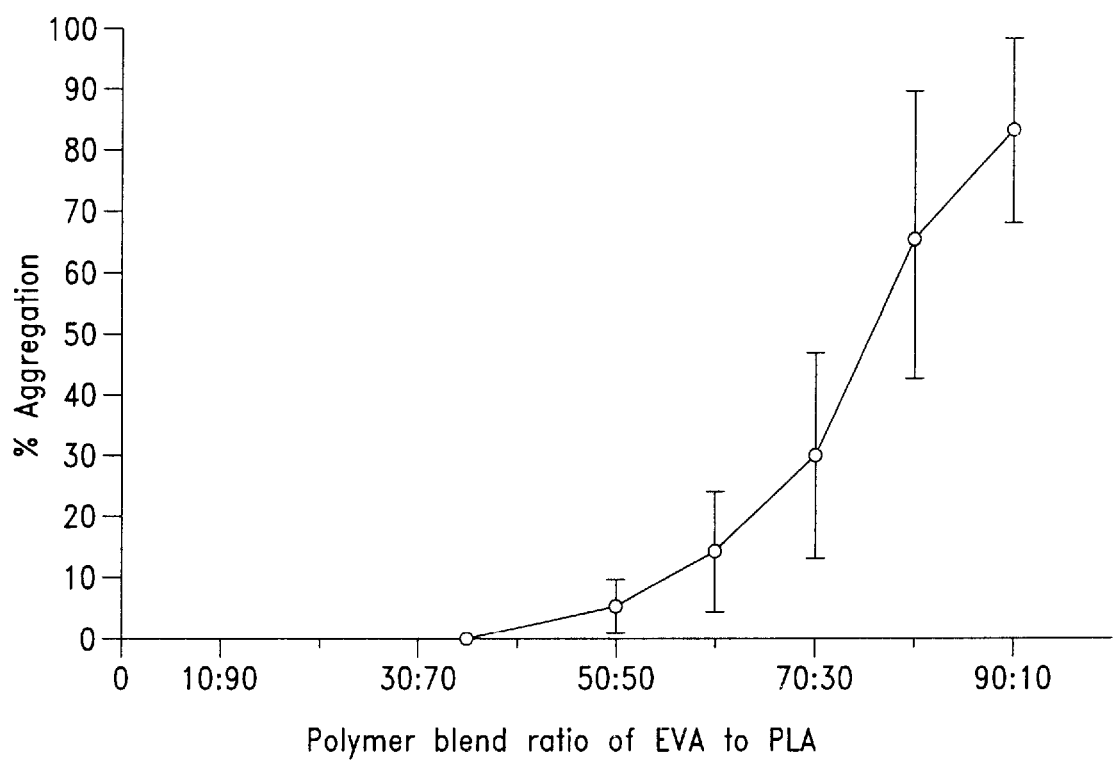
FIG. 15A is a graph which shows the effect of the EVA:PLA polymer blend ratio upon aggregation of microspheres.
Figure 15B:
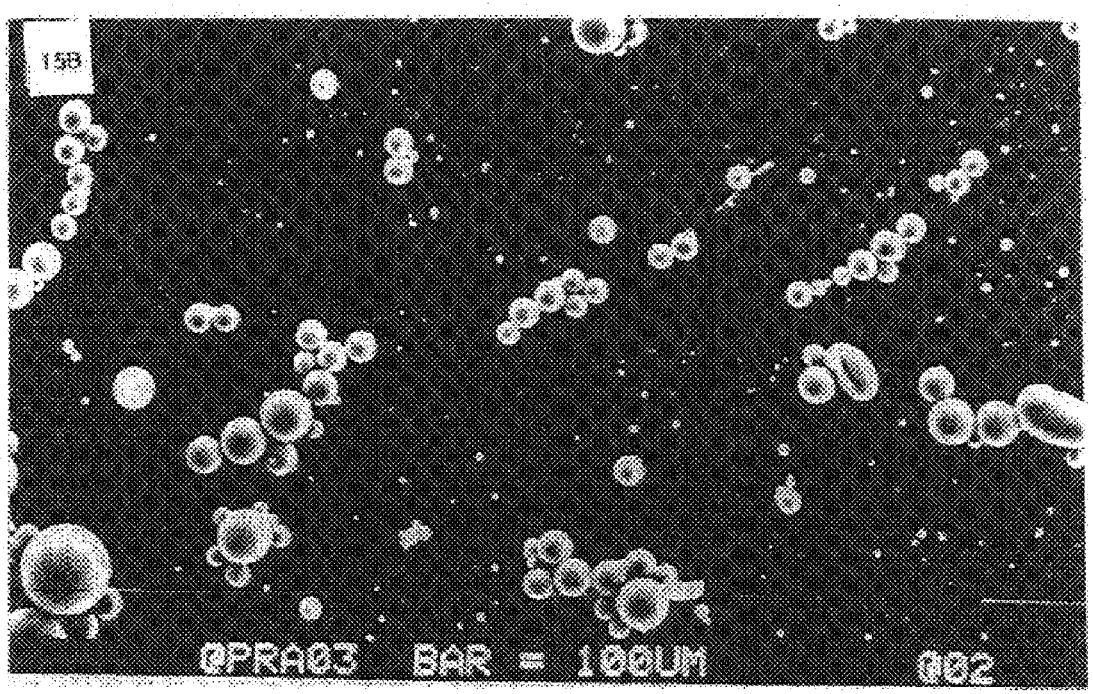
FIG. 15B is a scanning electron micrograph which shows the size of "small" microspheres.
Figure 15C:
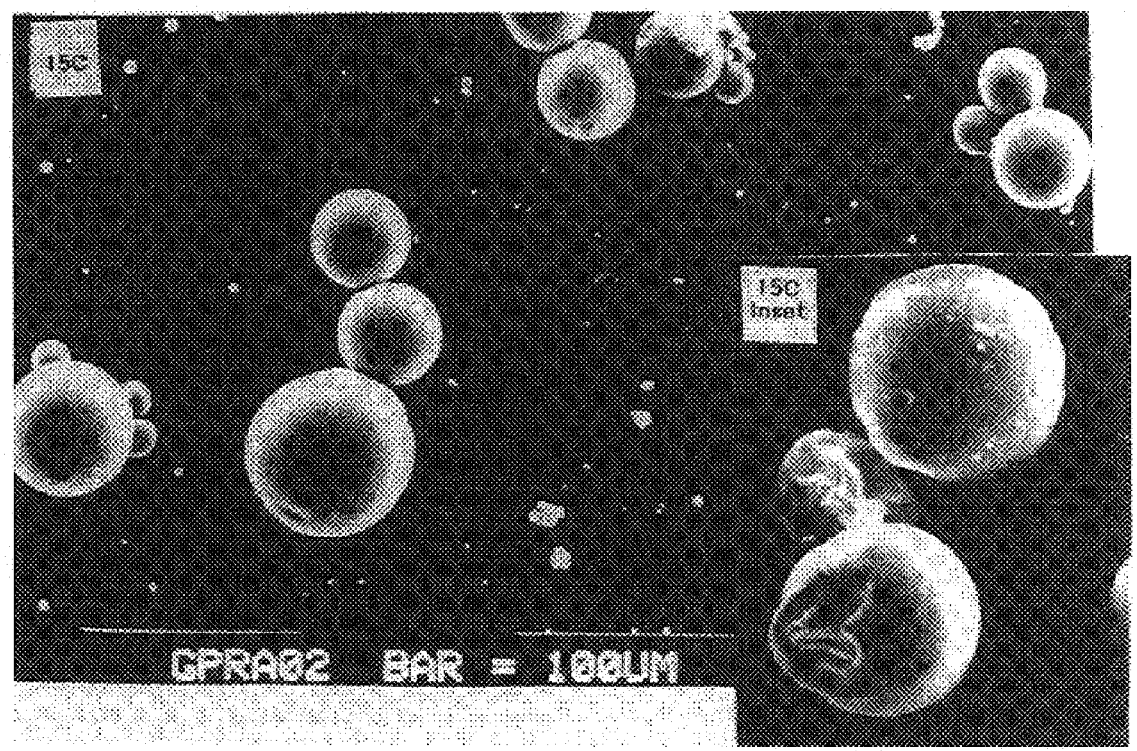
FIG. 15C (which includes a magnified inset—labelled "15C-inset") is a scanning electron micrograph which shows the size of "large" microspheres.
Figure 15D:
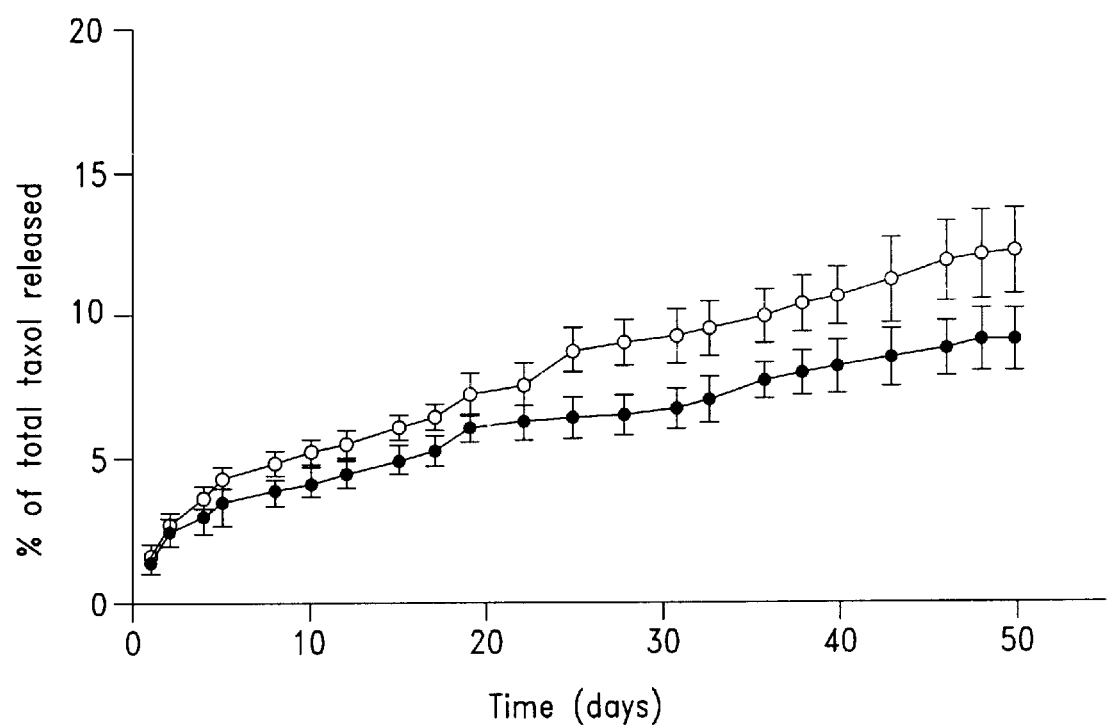
FIG. 15D is a graph which depicts the time course of in vitro paclitaxel release from 0.6% w/v paclitaxel-loaded 50:50 EVA:PLA polymer blend microspheres into phosphate buffered saline (pH 7.4) at 37° C. Open circles are "small" sized microspheres, and closed circles are "large" sized microspheres.

The time course of paclitaxel release from 0.6% w/v loaded 50:50 EVA:PLA microspheres is shown in FIG. 15D for "small" size (open circles) and "large" size (closed circles) microspheres. The release rate studies are carried out in triplicate tubes in 3 separate experiments. The release profiles are biphasic with an initial rapid release of paclitaxel or "burst" phase occurring over the first 4 days from both size range microspheres. This is followed by a phase of much slower release. There is no significant difference between the release rates from "small" or "large" microspheres. Between 10–13% of the total paclitaxel content of the microspheres is released in 50 days.

Figure 15E:
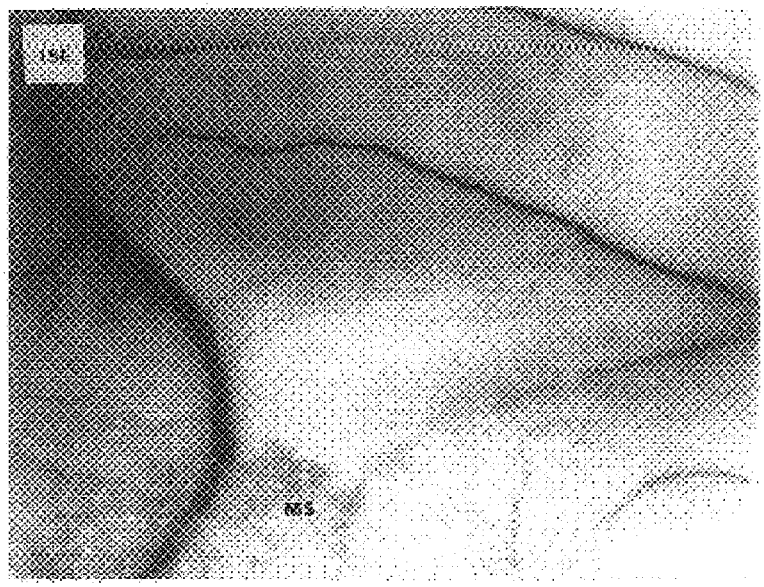
FIG. 15F is a photograph of a CAM which shows the results of paclitaxel release by microspheres ("MS").
Figure 15F:
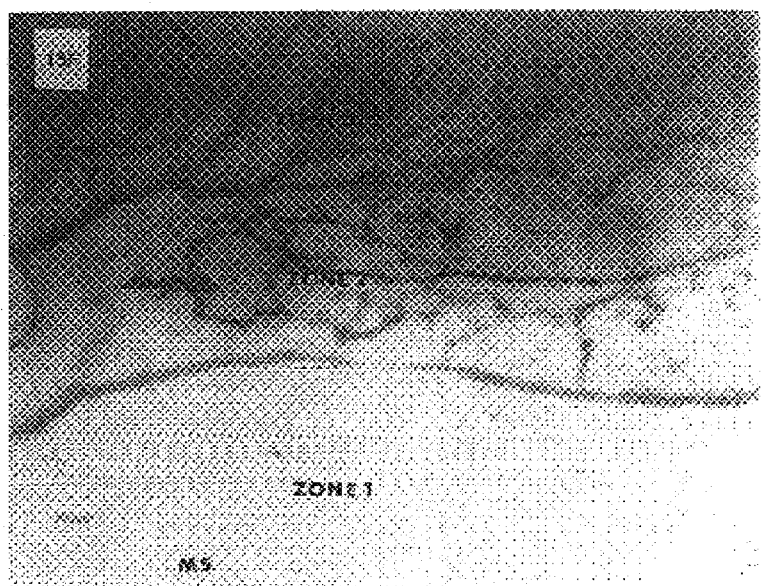

The paclitaxel loaded microspheres (0.6% w/v loading) are tested using the CAM assay and the results are shown in FIG. 15E. The paclitaxel microspheres released sufficient drug to produce a zone of avascularity in the surrounding tissue (FIG. 15F). Note that immediately adjacent to the microspheres ("MS" in FIGS. 15E and 15F) is an area in which blood vessels are completely absent (Zone 1); further from the microspheres is an area of disrupted, non-functioning capillaries (Zone 2); it is only at a distance of approximately 6 mm from the microspheres that the capillaries return to normal. In CAMs treated with control microspheres (paclitaxel absent) there is a normal capillary network architecture (figure not shown.)

Discussion

Arterial chemoembolization is an invasive surgical technique. Therefore, ideally, a chemoembolic formulation of an anti-angiogenic drug such as paclitaxel would release the drug at the tumor site at concentrations sufficient for activity for a prolonged period of time, of the order of several months. EVA is a tissue compatible nondegradable polymer which has been used extensively for the controlled delivery of macromolecules over long time periods (>100 days).

EVA is initially selected as a polymeric biomaterial for preparing microspheres with paclitaxel dispersed in the polymer matrix. However, microspheres prepared with 100% EVA aggregated and coalesced almost completely during the washing procedure.

Polymers and copolymers based on lactic acid and glycolic acid are physiologically inert and biocompatible and degrade by hydrolysis to toxicologically acceptable products. Copolymers of lactic acid and glycolic acids have faster degradation rates than PLA and drug loaded microspheres prepared using these copolymers are unsuitable for prolonged, controlled release over several months. Dollinger and Sawan blended PLA with EVA and showed that the degradation lifetime of PLA is increased as the proportion of EVA in the blend is increased. They suggested that blends of EVA and PLA should provide a polymer matrix with better mechanical stability and control of drug release rates than PLA.

FIG. 15A shows that increasing the proportion of PLA in a EVA:PLA blend decreased the extent of aggregation of the microsphere suspensions. Blends of 50% or less EVA in the EVA:PLA matrix produced physically stable microsphere suspensions in water or PBS. A blend of 50:50 EVA:PLA is selected for all subsequent studies.

Different size range fractions of microspheres could be prepared by changing the concentration of the emulsifier, PVA, in the aqueous phase. "Small" microspheres are produced at the higher PVA concentration of 5% w/v whereas "large" microspheres are produced at 2.5% w/v PVA. All other production variables are the same for both microsphere size fractions. The higher concentration of emulsifier gave a more viscous aqueous dispersion medium and produced smaller droplets of polymer/paclitaxel/DCM emulsified in the aqueous phase and thus smaller microspheres. The paclitaxel loaded microspheres contained between 95–100% of the initial paclitaxel added to the organic phase encapsulated within the solid microspheres. The low water solubility of paclitaxel favoured partitioning into the organic phase containing the polymer.

Release rates of paclitaxel from the 50:50 EVA:PLA microspheres are very slow with less than 15% of the loaded paclitaxel being released in 50 days. The initial burst phase of drug release may be due to diffusion of drug from the superficial region of the microspheres (close to the microsphere surface).

The mechanism of drug release from nondegradable polymeric matrices such as EVA is thought to involve the diffusion of water through the dispersed drug phase within the polymer, dissolution of the drug and diffusion of solute through a series of interconnecting, fluid filled pores. Blends of EVA and PLA have been shown to be immiscible or bicontinuous over a range of 30 to 70% EVA in PLA. In degradation studies in PBS buffer at 37° C., following an induction or lag period, PLA hydrolytically degraded and eroded from the EVA:PLA polymer blend matrix leaving an inactive sponge-like skeleton. Although the induction period and rate of PLA degradation and erosion from the blended matrices depended on the proportion of PLA in the matrix and on process history, there is consistently little or no loss of PLA until after 40–50 days.

Although some erosion of PLA from the 50:50 EVA:PLA microspheres may have occurred within the 50 days of the in vitro release rate study (FIG. 15C), it is likely that the primary mechanism of drug release from the polymer blend is diffusion of solute through a pore network in the polymer matrix.

At the conclusion of the release rate study, the microspheres are analyzed from the amount of drug remaining. The values for the percent of paclitaxel remaining in the 50 day incubation microsphere samples are 94% +/−9% and 89% +/−12% for "large" and "small" size fraction microspheres, respectively.

Microspheres loaded with 6 mg per mg of polymer (0.6%) provided extensive inhibition of angiogenesis when placed on the CAM of the embryonic chick (FIGS. 15E and 15F).

Example 12

Paclitaxel Encapsulation in Poly(E-Caprolactone) Microspheres. Inhibition of Angiogenesis on the Cam Assay by Paclitaxel-Loaded Microspheres This example evaluates the in vitro release rate profile of paclitaxel from biodegradable microspheres of poly(e-caprolactone) and demonstrates the anti-angiogenic activity of paclitaxel released from these microspheres when placed on the CAM.

Reagents which were utilized in these experiments include: poly(e-caprolactone) ("PCL") (molecular weight 35,000–45,000; purchased from Polysciences (Warrington, Pa.)); dichloromethane ("DCM") from Fisher Scientific Co., Canada; polyvinyl alcohol (PVP) (molecular weight 12,000–18,000, 99% hydrolysed) from Aldrich Chemical Co. (Milwaukee, Wis.), and paclitaxel from Sigma Chemical Co. (St. Louis, Mo.). Unless otherwise stated all chemicals and reagents are used as supplied. Distilled water is used throughout.

A. Preparation of microspheres

Microspheres are prepared essentially as described in Example 8 utilizing the solvent evaporation method. Briefly, 5% w/w paclitaxel loaded microspheres are prepared by dissolving 10 mg of paclitaxel and 190 mg of PCL in 2 ml of DCM, adding to 100 ml of 1% PVP aqueous solution and stirring at 1000 rpm at 25° C. for 2 hours. The suspension of microspheres is centrifuged at 1000×g for 10 minutes (Beckman GPR), the supernatant removed and the microspheres washed three times with water. The washed microspheres are air-dried overnight and stored at room temperature. Control microspheres (paclitaxel absent) are prepared as described above. Microspheres containing 1% and 2% paclitaxel are also prepared. Microspheres are sized using an optical microscope with a stage micrometer.

B. Encapsulation Efficiency

A known weight of drug-loaded microspheres (about 5 mg) is dissolved in 8 ml of acetonitrile and 2 ml distilled water is added to precipitate the polymer. The mixture is centrifuged at 1000 g for 10 minutes and the amount of paclitaxel encapsulated is calculated from the absorbance of the supernatant measured in a UV spectrophotometer (Hewlett-Packard 8452A Diode Array Spectrophotometer) at 232 nm.

C. Drug Release Studies

About 10 mg of paclitaxel-loaded microspheres are suspended in 20 ml of 10 mM phosphate buffered saline, pH 7.4 (PBS) in screw-capped tubes. The tubes are tumbled end-over-end at 37° C. and at given time intervals 19.5 ml of supernatant is removed (after allowing the microspheres to settle at the bottom), filtered through a 0.45 um membrane filter and retained for paclitaxel analysis. An equal volume of PBS is replaced in each tube to maintain sink conditions throughout the study. The filtrates are extracted with 3×1 ml DCM, the DCM extracts evaporated to dryness under a stream of nitrogen, redissolved in 1 ml acetonitrile and analyzed by HPLC using a mobile phase of water:methanol:acetonitrile (37:5:58) at a flow rate of 1 ml min$^{-1}$ (Beckman Isocratic Pump), a C8 reverse phase column (Beckman), and UV detection (Shimadzu SPD A) at 232 nm.

D. CAM Studies

Fertilized, domestic chick embryos are incubated for 4 days prior to shell-less culturing. On day 6 of incubation, 1 mg aliquots of 5% paclitaxel-loaded or control (paclitaxel-free) microspheres are placed directly on the CAM surface. After a 2-day exposure the vasculature is examined using a stereomicroscope interfaced with a video camera; the video signals are then displayed on a computer and video printed.

E. Scanning Electron Microscopy

Microspheres are placed on sample holders, sputter-coated with gold and then placed in a Philips 501B Scanning Electron Microscope operating at 15 kV. is F. Results The size range for the microsphere samples is between 30–100 um, although there is evidence in all paclitaxel-loaded or control microsphere batches of some microspheres falling outside this range. The efficiency of loading PCL microspheres with paclitaxel is always greater than 95% for all drug loadings studied. Scanning electron microscopy demonstrated that the microspheres are all spherical and many showed a rough or pitted surface morphology. There appeared to be no evidence of solid drug on the surface of the microspheres.

Figure 16A:
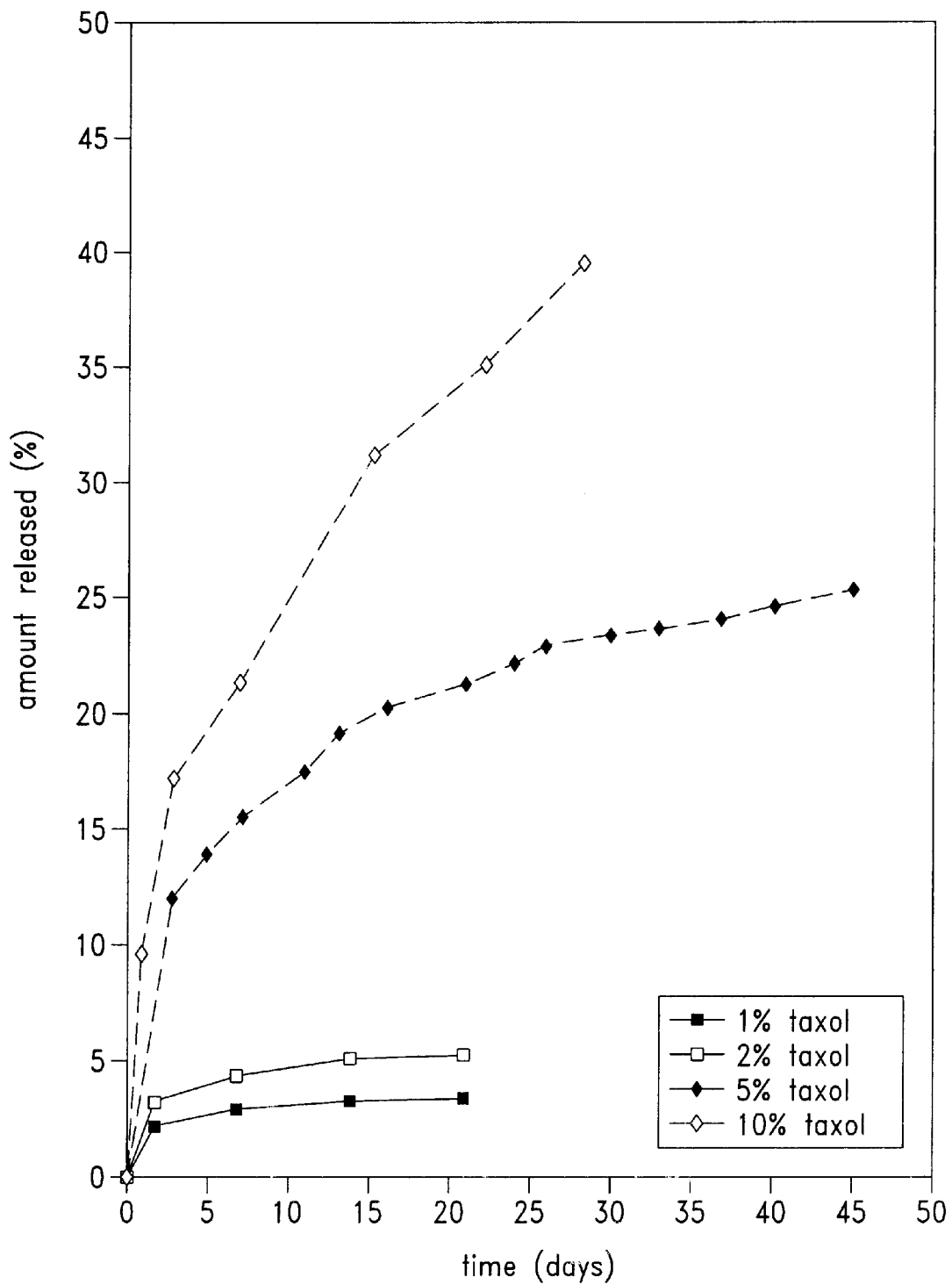
FIG. 16 is a graph which shows release rate profiles from polycaprolactone microspheres containing 1%, 2%, 5% or 10% paclitaxel into phosphate buffered saline at 37° C.
FIG. 16B is a photograph which shows a CAM treated with control microspheres.
FIG. 16C is a photograph which shows a CAM treated with 5% paclitaxel loaded microspheres.

The time courses of paclitaxel release from 1%, 2% and 5% loaded PCL microspheres are shown in FIG. 16A. The release rate profiles are bi-phasic. There is an initial rapid release of paclitaxel or "burst phase" at all drug loadings. The burst phase occurred over 1–2 days at 1% and 2% paclitaxel loading and over 3–4 days for 5% loaded microspheres. The initial phase of rapid release is followed by a phase of significantly slower drug release. For microspheres containing 1% or 2% paclitaxel there is no further drug release after 21 days. At 5% paclitaxel loading, the microspheres had released about 20% of the total drug content after 21 days.

Figure 16B:
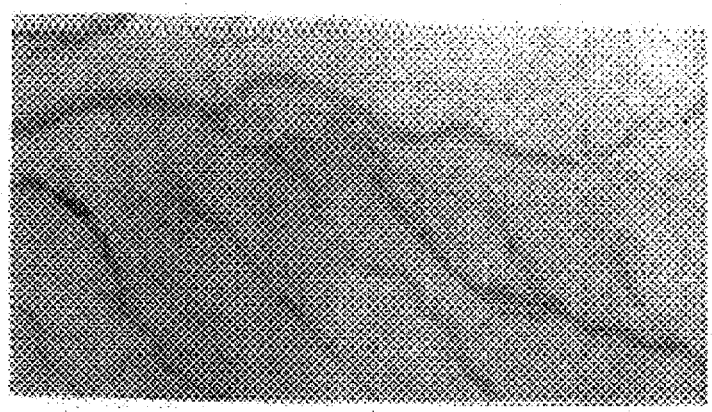
Figure 16C:
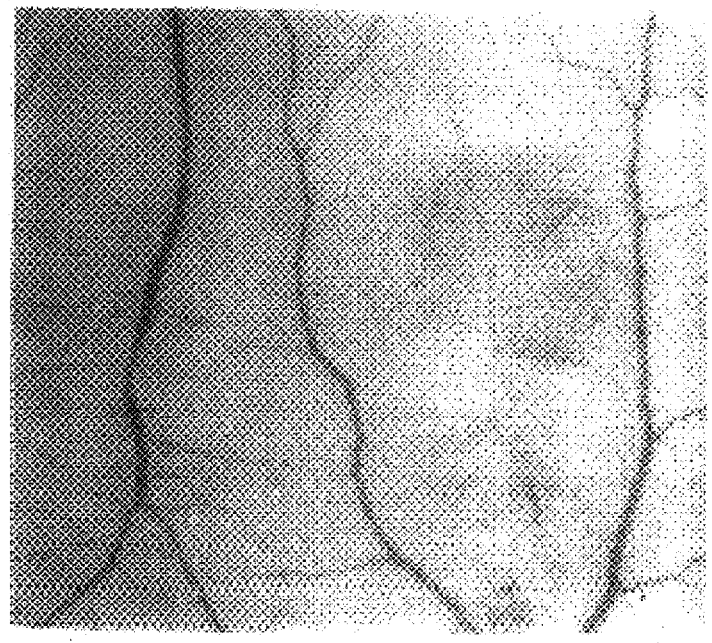

FIG. 16B shows CAMs treated with control PCL microspheres, and FIG. 16C shows treatment with 5% paclitaxel loaded microspheres. The CAM with the control microspheres shows a normal capillary network architecture. The CAM treated with paclitaxel-PCL microspheres shows marked vascular regression and zones which are devoid of a capillary network.

G. Discussion

The solvent evaporation method of manufacturing paclitaxel-loaded microspheres produced very high paclitaxel encapsulation efficiencies of between 95–100%. This is due to the poor water solubility of paclitaxel and its hydrophobic nature favouring partitioning in the organic solvent phase containing the polymer.

The biphasic release profile for paclitaxel is typical of the release pattern for many drugs from biodegradable polymer matrices. Poly(e-caprolactone) is an aliphatic polyester which can be degraded by hydrolysis under physiological conditions and it is non-toxic and tissue compatible. The degradation of PCL is significantly slower than that of the extensively investigated polymers and copolymers of lactic and glycolic acids and is therefore suitable for the design of long-term drug delivery systems. The initial rapid or burst phase of paclitaxel release is thought to be due to diffusional release of the drug from the superficial region of the microspheres (close to the microsphere surface). Release of paclitaxel in the second (slower) phase of the release profiles is not likely due to degradation or erosion of PCL because studies have shown that under in vitro conditions in water there is no significant weight loss or surface erosion of PCL over a 7.5-week period. The slower phase of paclitaxel release is probably due to dissolution of the drug within fluid-filled pores in the polymer matrix and diffusion through the pores. The greater release rate at higher paclitaxel loading is probably a result of a more extensive pore network within the polymer matrix.

Paclitaxel microspheres with 5% loading have been shown to release sufficient drug to produce extensive inhibition of angiogenesis when placed on the CAM. The inhibition of blood vessel growth resulted in an avascular zone as shown in FIG. 16C.

Example 13

Paclitaxel-Loaded Polymeric Films Composed of Ethylene Vinyl Acetate and a Surfactant Two types of films are investigated within this example: pure EVA films loaded with paclitaxel and EVA/surfactant blend films loaded with paclitaxel.

The surfactants being examined are two hydrophobic surfactants (Span 80 and Pluronic L101) and one hydrophilic surfactant (Pluronic F127). The pluronic surfactants are themselves polymers, which is an attractive property since they can be blended with EVA to optimize various drug delivery properties. Span 80 is a smaller molecule which is in some manner dispersed in the polymer matrix, and does not form a blend.

Figure 17A:
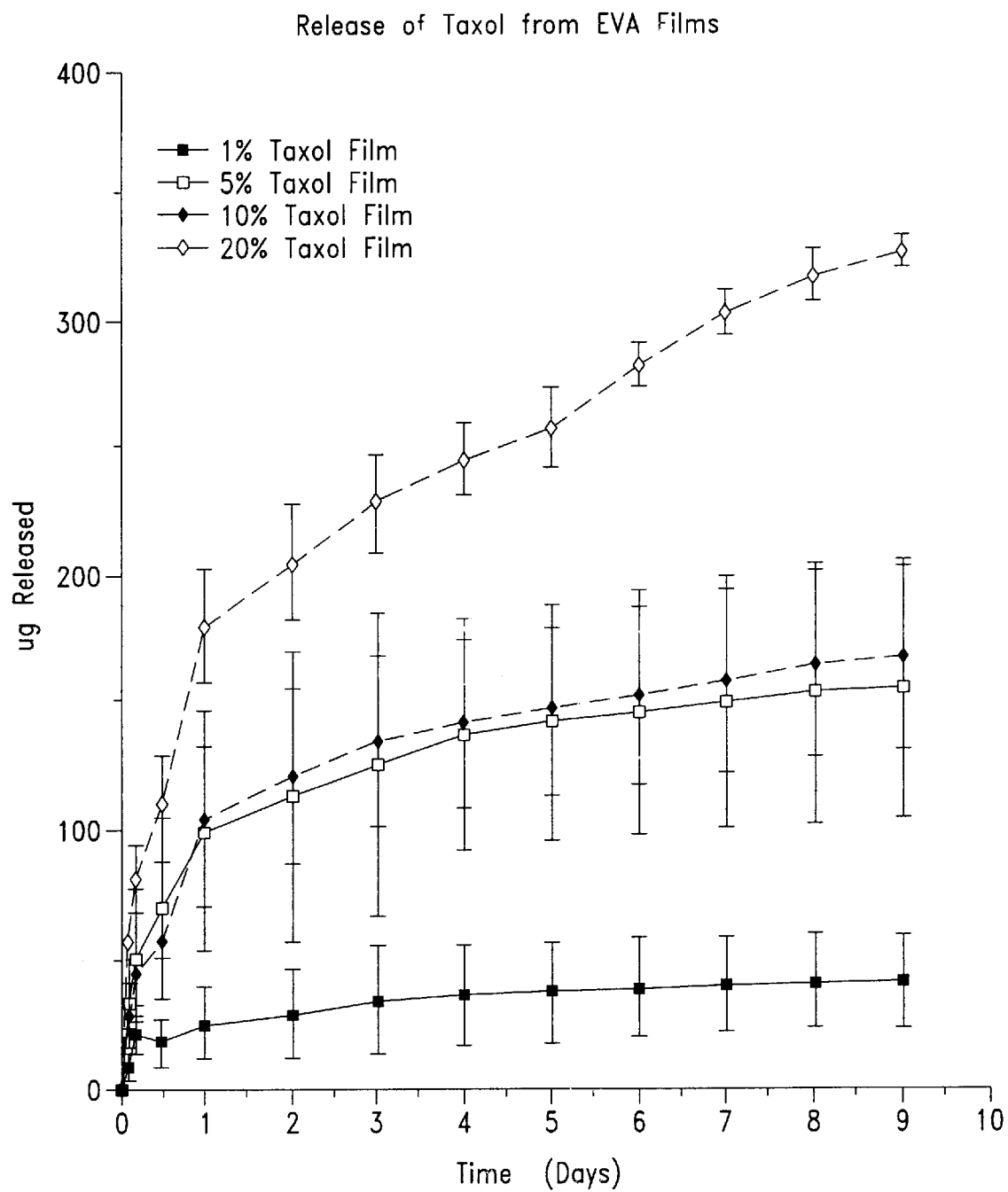
FIGS. 17A and 17B, respectively, are two graphs which show the release of paclitaxel from EVA films, and the percent paclitaxel remaining in those same films over time.
Figure 17B:
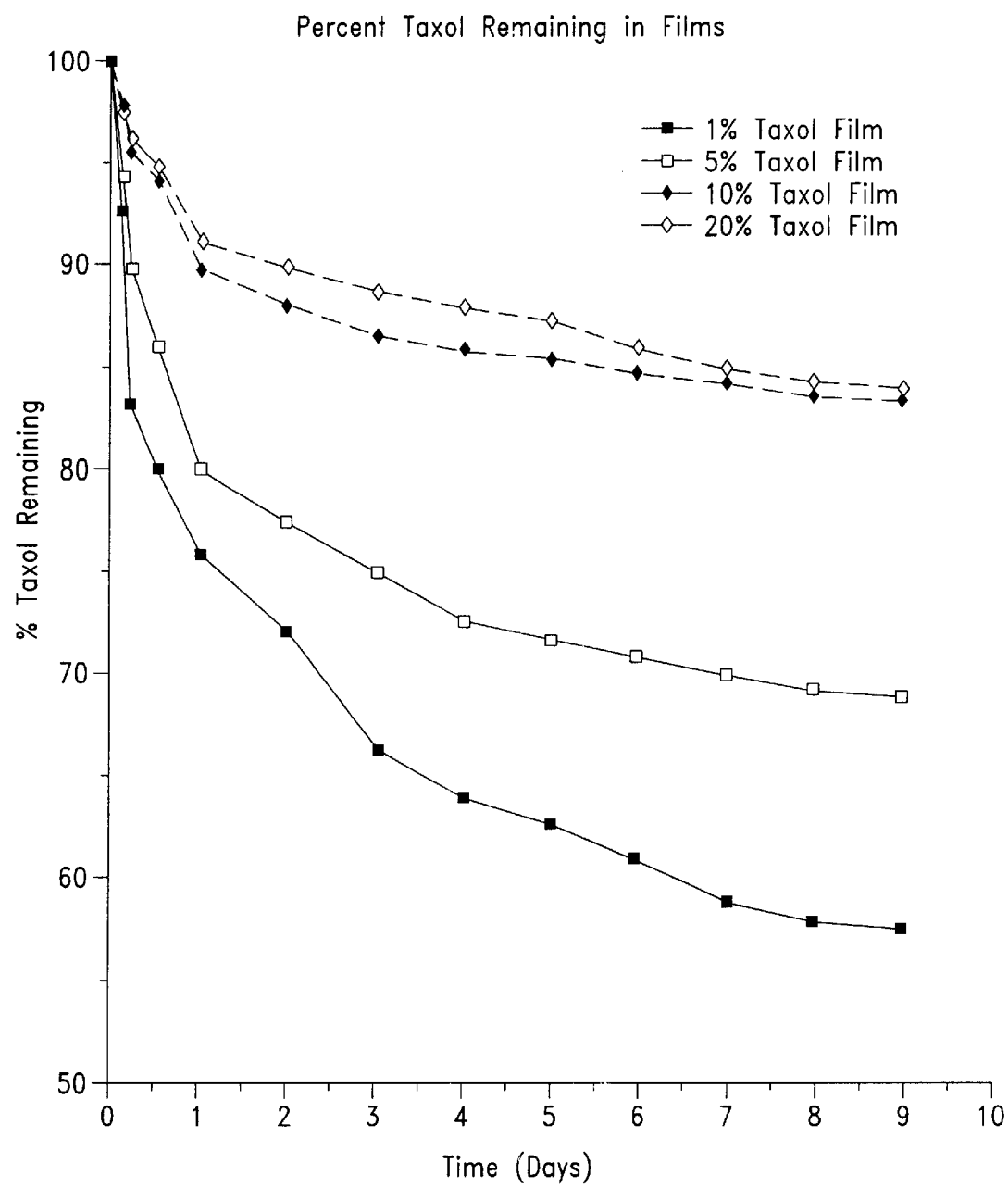
Figure 17C:
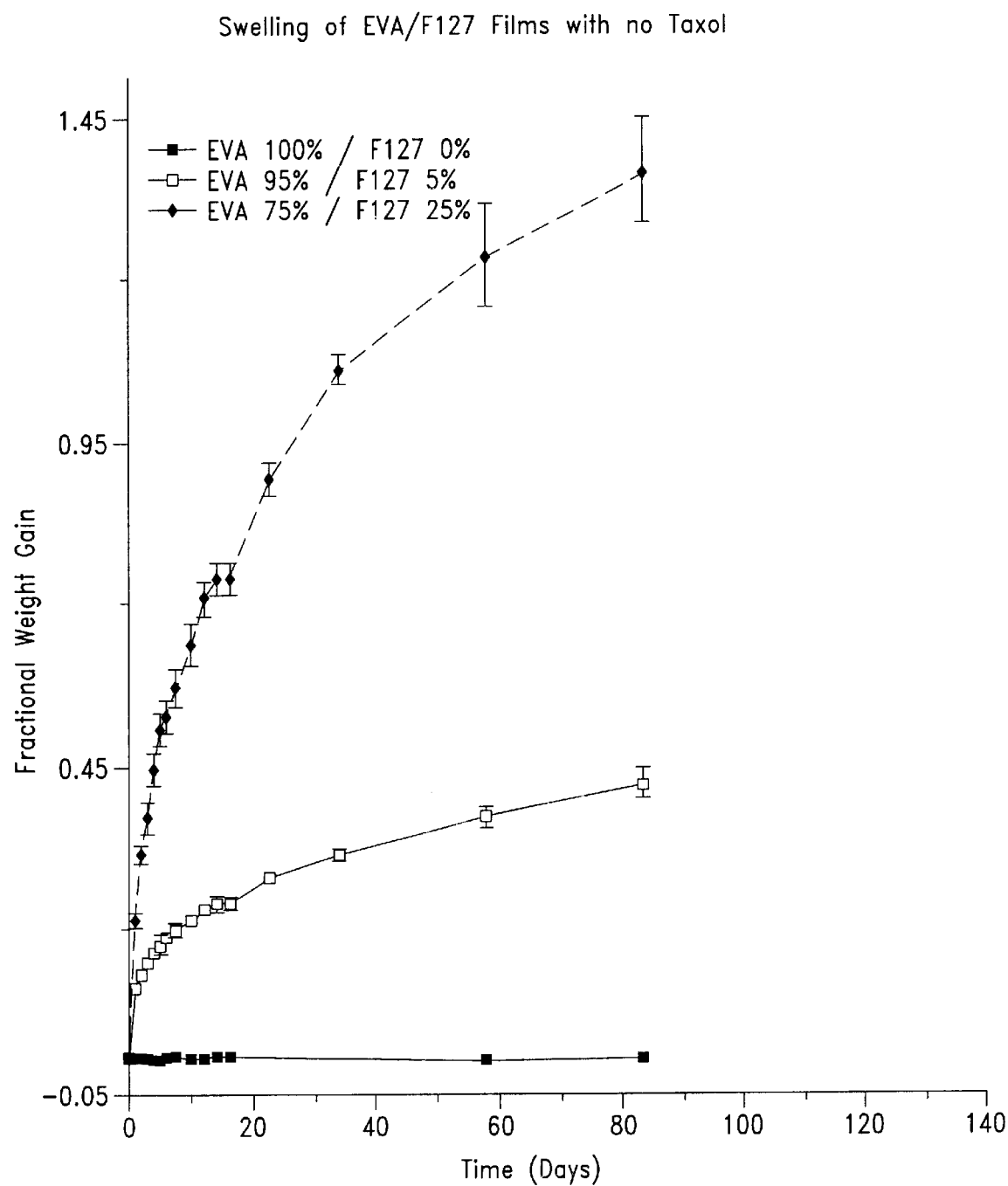
FIG. 17C is a graph which shows the swelling of EVA/F127 films with no paclitaxel over time.
Figure 17D:
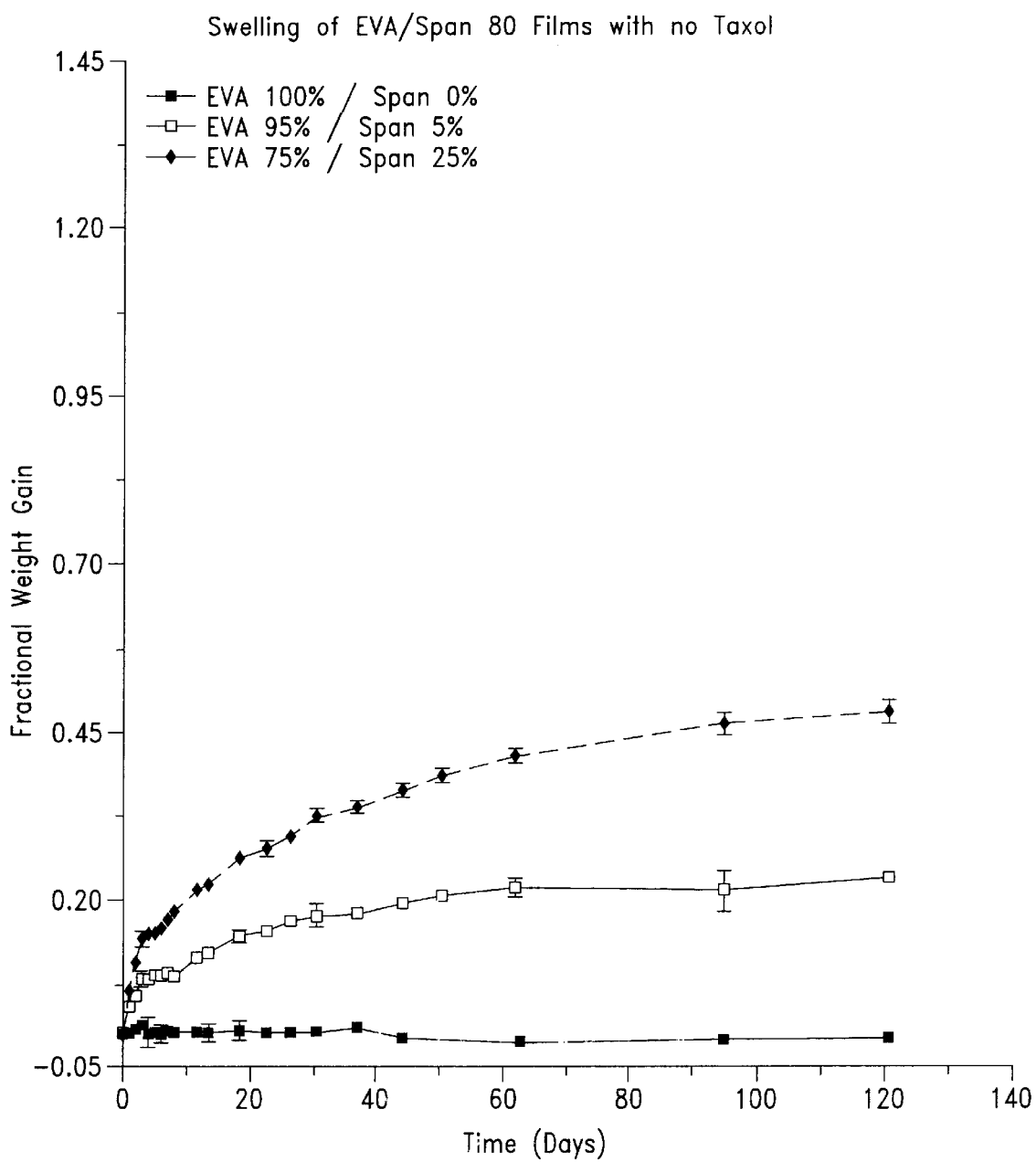
FIG. 17D is a graph which shows the swelling of EVA/Span 80 films with no paclitaxel over time.

Surfactants is useful in modulating the release rates of paclitaxel from films and optimizing certain physical parameters of the films. One aspect of the surfactant blend films which indicates that drug release rates can be controlled is the ability to vary the rate and extent to which the compound will swell in water. Diffusion of water into a polymer-drug matrix is critical to the release of drug from the carrier. FIGS. 17C and 17D show the degree of swelling of the films as the level of surfactant in the blend is altered. Pure EVA films do not swell to any significant extent in over 2 months. However, by increasing the level of surfactant added to the EVA it is possible to increase the degree of swelling of the compound, and by increasing hydrophilicity swelling can also be increased.

Results of experiments with these films are shown below in FIGS. 17A–E. Briefly, FIG. 17A shows paclitaxel release (in mg) over time from pure EVA films. FIG. 17B shows the percentage of drug remaining for the same films. As can be seen from these two figures, as paclitaxel loading increases (i.e., percentage of paclitaxel by weight is increased), drug release rates increase, showing the expected concentration dependence. As paclitaxel loading is increased, the percent paclitaxel remaining in the film also increases, indicating that higher loading may be more attractive for long-term release formulations.

Figure 17E:
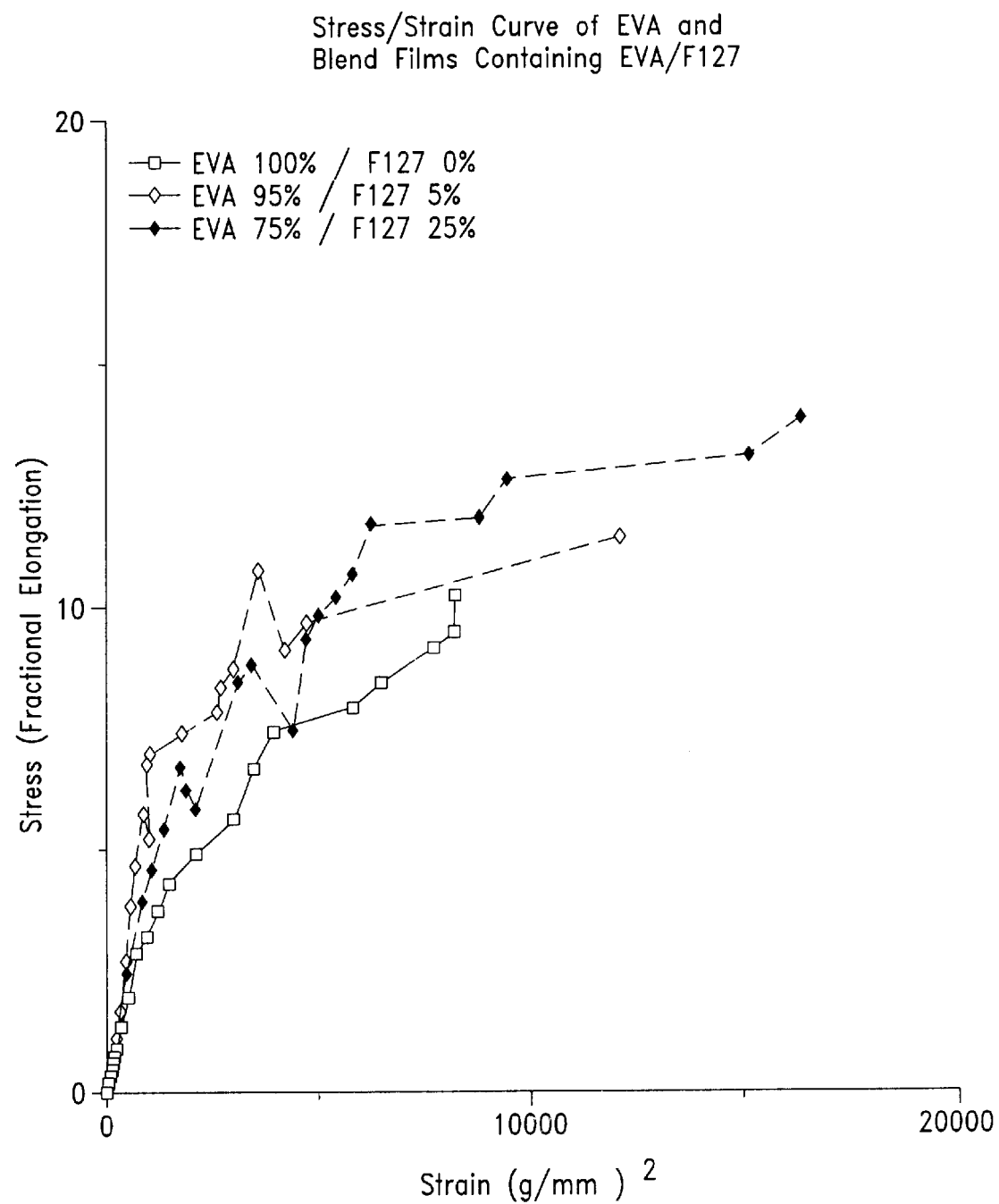
FIG. 17E is a graph which depicts a stress vs. strain curve for various EVA/F127 blends.

Physical strength and elasticity of the films is assessed in FIG. 17E. Briefly, FIG. 17E shows stress/strain curves for pure EVA and EVA-Surfactant blend films. This crude measurement of stress demonstrates that the elasticity of films is increased with the addition of Pluronic F127, and that the tensile strength (stress on breaking) is increased in a concentration dependent manner with the addition of Pluronic F127. Elasticity and strength are important considerations in designing a film which can be manipulated for particular clinical applications without causing permanent deformation of the compound.

The above data demonstrates the ability of certain surfactant additives to control drug release rates and to alter the physical characteristics of the vehicle.

Example 14

Incorporating Methoxypolyethylene Glycol 350 (MePEG) into Poly(e-Caprolactone) to Develop a Formulation for the Controlled Delivery of Paclitaxel from a Paste Reagents and equipment which were utilized within these experiments include methoxypolyethylene glycol 350 ("MePEG"—Union Carbide, Danbury, Conn.). MePEG is liquid at room temperature, and has a freezing point of 10° to −5° C.

A. Preparation of a MePEG/PCL Paclitaxel-Containing Paste

MePEG/PCL paste is prepared by first dissolving a quantity of paclitaxel into MePEG, and then incorporating this into melted PCL. One advantage with this method is that no DCM is required.

B. Analysis of Melting Point

Figure 18A:
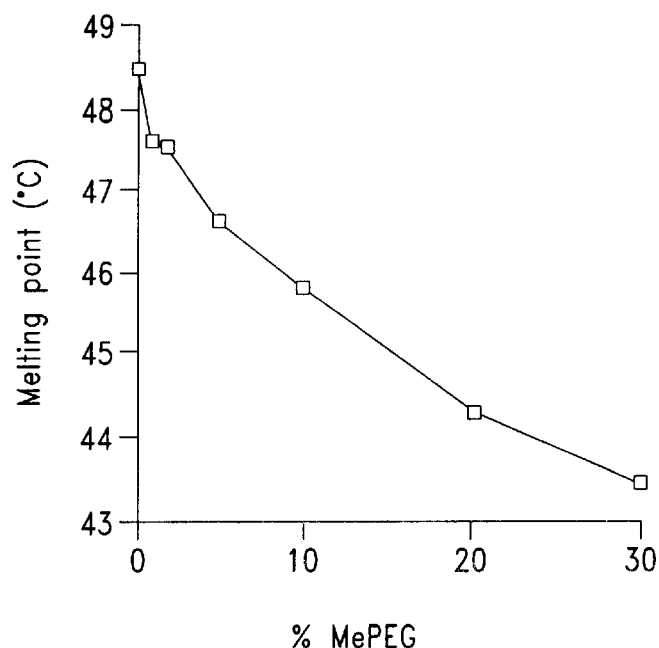
FIGS. 18A and 18B are two graphs which show the melting point of PCL/MePEG polymer blends as a function of % MePEG in the formulation (18A), and the percent increase in time needed for PCL paste at 60° C. to being to solidify as a function of the amount of MePEG in the formulation (18B).
Figure 18B:
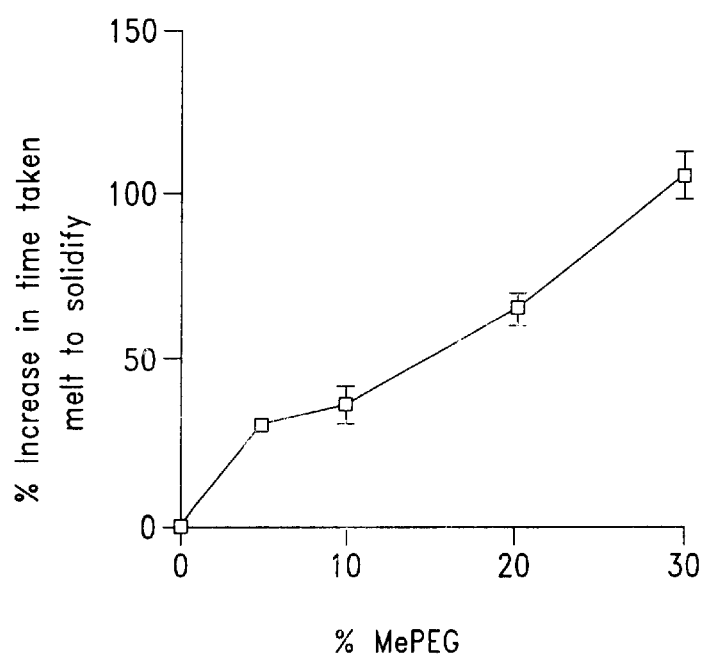

The melting point of PCL/MePEG polymer blends may be determined by differential scanning calorimetry from 30° C. to 70° C. at a heating rate of 2.5° C. per minute. Results of this experiment are shown in FIGS. 18A and 18B. Briefly, as shown in FIG. 18A the melting point of the polymer blend (as determined by thermal analysis) is decreased by MePEG in a concentration dependent manner. The melting point of the polymer blends as a function of MePEG concentration is shown in FIG. 18A. This lower melting point also translates into an increased time for the polymer blends to solidify from melt as shown in FIG. 18B. A 30:70 blend of MePEG-:PCL takes more than twice as long to solidify from the fluid melt than does PCL alone.

C. Measurement of Brittleness

Figure 18C:
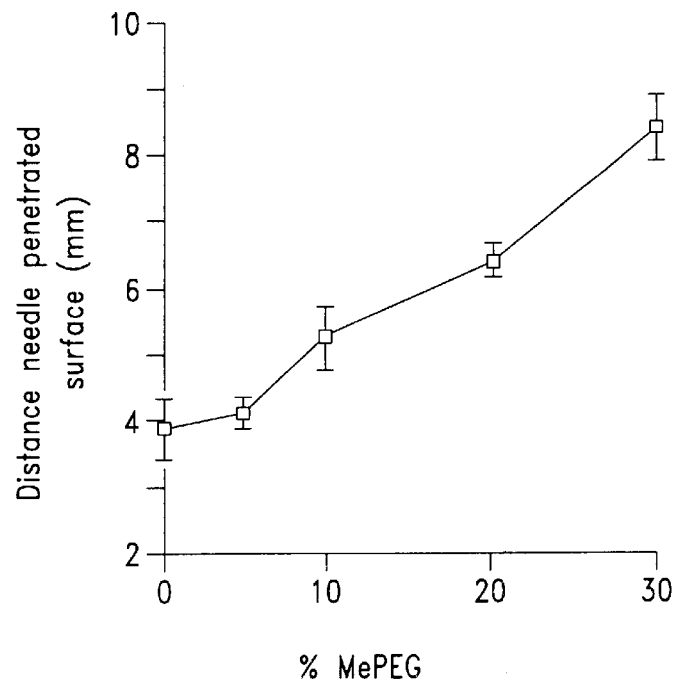
FIG. 18C is a graph which depicts the softness of varying PCL/MePEG polymer blends.

Incorporation of MePEG into PCL appears to produce a less brittle solid, as compared to PCL alone. As a "rough" way of quantitating this, a weighted needle is dropped from an equal height into polymer blends containing from 0% to 30% MePEG in PCL, and the distance that the needle penetrates into the solid is then measured. The resulting graph is shown as FIG. 18C. Points are given as the average of four measurements +/−1 S.D.

For purposes of comparison, a sample of paraffin wax is also tested and the needle penetrated into this a distance of 7.25 mm+/−0.3 mm.

D. Measurement of Paclitaxel Release

Figure 18D:
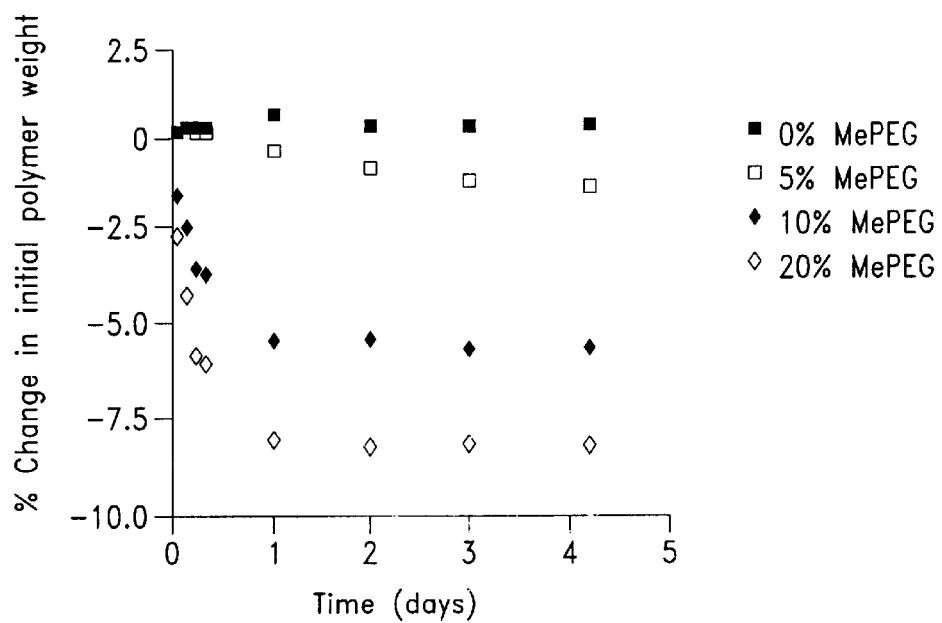
FIG. 18D is a graph which shows the percent weight change over time for polymer blends of various MePEG concentrations.

Pellets of polymer (PCL containing 0%, 5%, 10% or 20% MePEG) are incubated in phosphate buffered saline (PBS, pH 7.4) at 37° C., and % change in polymer weight is measured over time. As can be seen in FIG. 18D, the amount of weight lost increases with the concentration of MePEG originally present in the blend. It is likely that this weight loss is due to the release of MePEG from the polymer matrix into the incubating fluid. This would indicate that paclitaxel will readily be released from a MePEG/PCL blend since paclitaxel is first dissolved in MePEG before incorporation into PCL.

E. Effect of Varying Quantities of MePEG on Paclitaxel Release

Figure 18E:
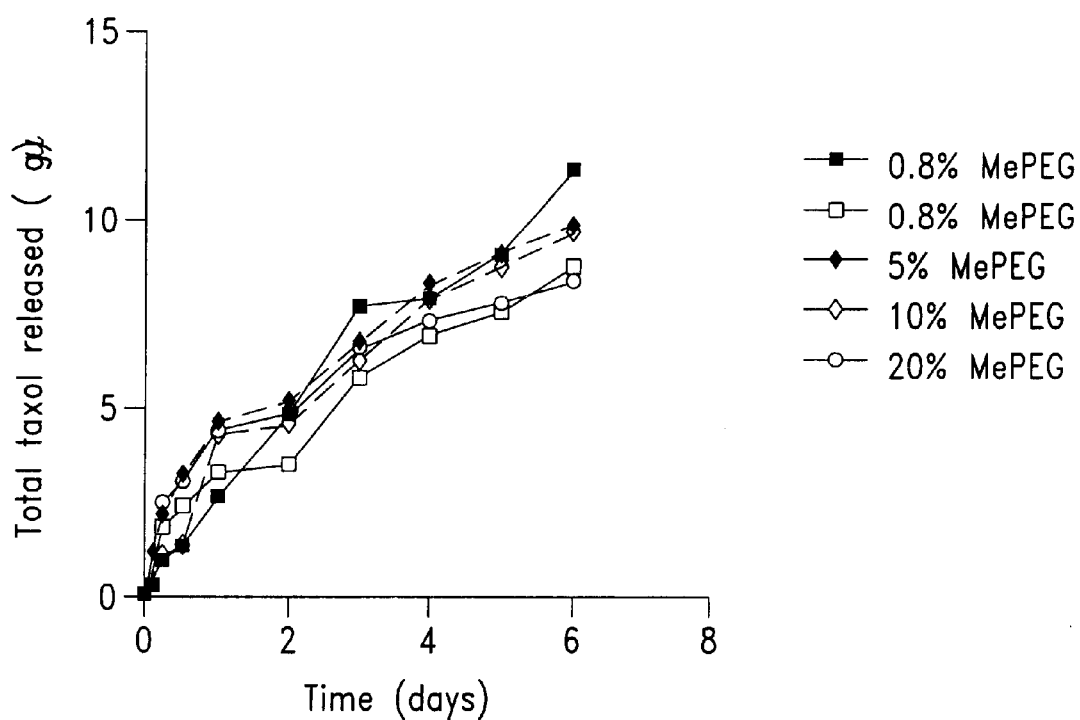
FIG. 18E is a graph which depicts the rate of paclitaxel release over time from various polymer blends loaded with 1% paclitaxel.

Thermopastes are made up containing between 0.8% and 20% MePEG in PCL. These are loaded with 1% paclitaxel. The release of paclitaxel over time from 10 mg pellets in PBS buffer at 37° C. is monitored using HPLC. As is shown in FIG. 18E, the amount of MePEG in the formulation does not affect the amount of paclitaxel that is released.

Figure 18F:
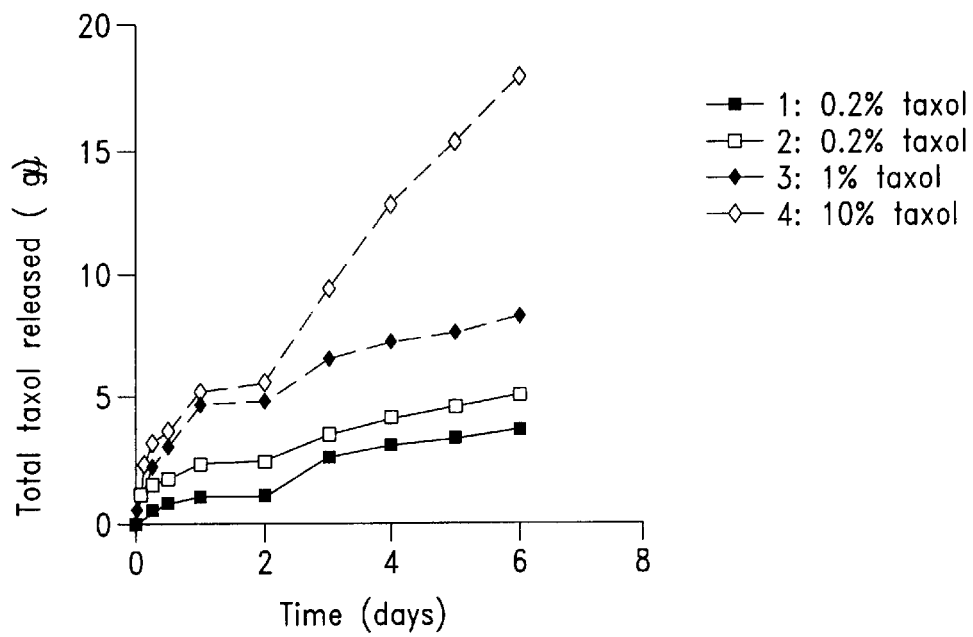
FIGS. 18F and 18G are graphs which depict the effect of varying quantities of paclitaxel on the total amount of paclitaxel released from a 20% MePEG/PCL blend.
Figure 18G:
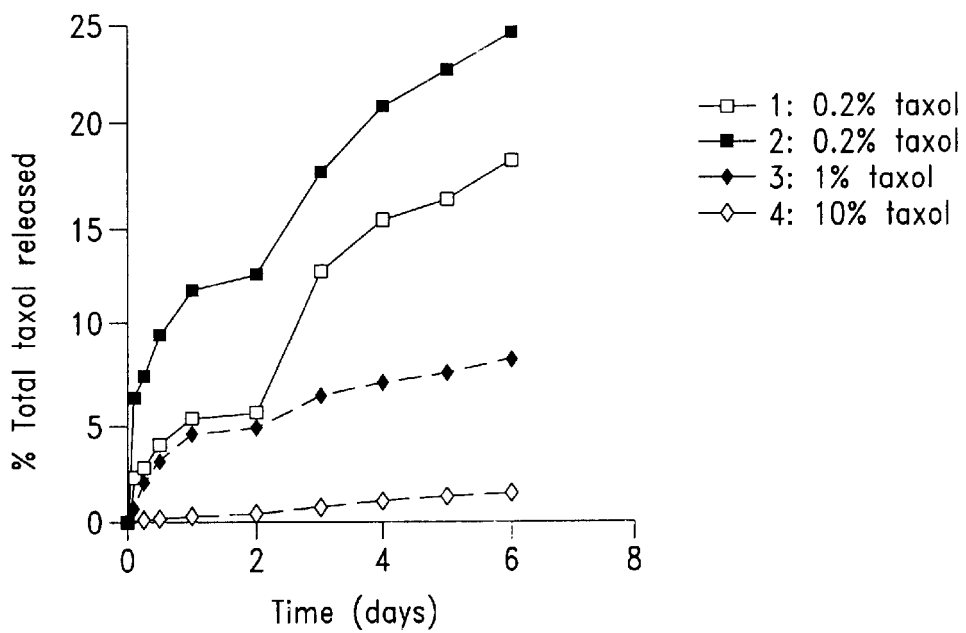

F. Effect of Varying Quantities of Paclitaxel on the Total Amount of Paclitaxel Released From a 20% MePEG/PCL Blend Thermopastes are made up containing 20% MePEG in PCL and loaded with between 0.2% and 10% paclitaxel. The release of paclitaxel over time is measured as described above. As shown in FIG. 18F, the amount of paclitaxel released over time increases with increased paclitaxel loading. When plotted as the percent total paclitaxel released, however, the order is reversed (FIG. 18G). This gives information about the residual paclitaxel remaining in the paste and allows for a projection of the period of time over which paclitaxel may be released from the 20% MePEG Thermopaste.

G. Strength Analysis of Various MePEG/PCL Blends

A CT-40 mechanical strength tester is used to measure the strength of solid polymer "tablets" of diameter 0.88 cm and an average thickness of 0.560 cm. The polymer tablets are blends of MePEG at concentrations of 0%, 5%, 10% or 20% in PCL.

Figure 18H:
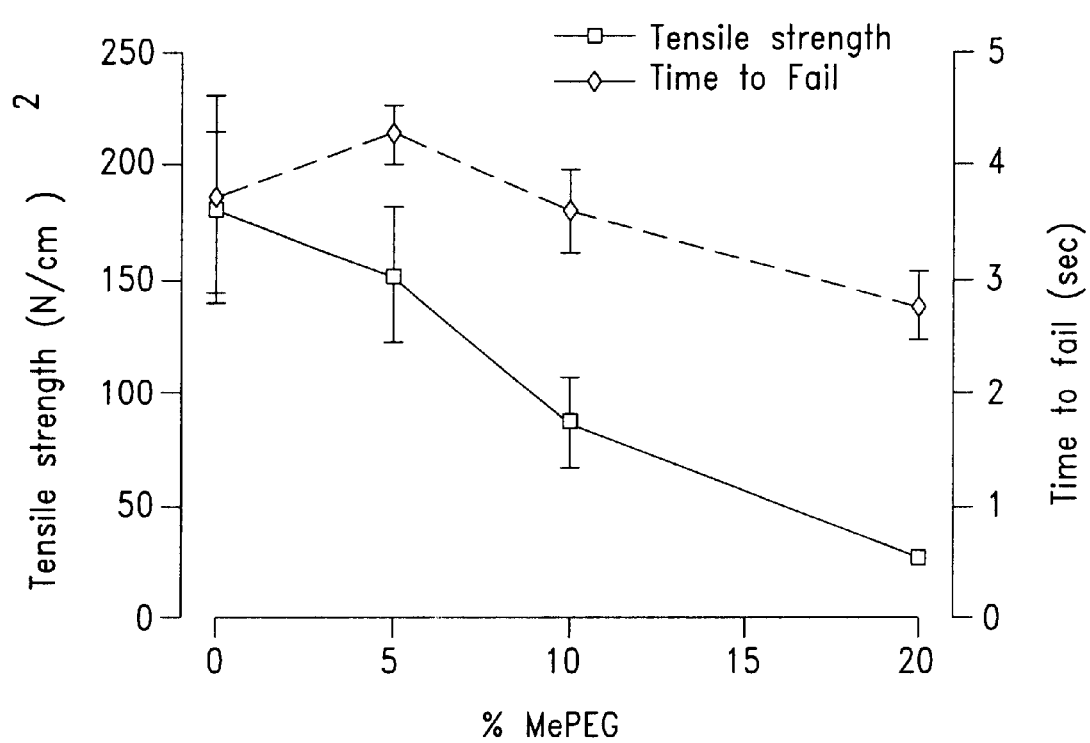
FIG. 18H is a graph which depicts the effect of MePEG on the tensile strength of a MePEG/PCL polymer.

Results of this test are shown in FIG. 18H, where both the tensile strength and the time to failure are plotted as a function of % MePEG in the blend. Single variable ANOVA indicated that the tablet thicknesses within each group are not different. As can be seen from FIG. 18H, the addition of MePEG into PCL decreased the hardness of the resulting solid.

Example 15

Effect of Paclitaxel-Loaded Thermopaste on Angiogenesis in Vivo

Fertilized, domestic chick embryos were incubated for 4 days prior to shell-less culturing as described in Example 2. The egg contents are removed from the shell and emptied into roundbottom sterilized glass bowls and covered with petri dish covers.

Paclitaxel is incorporated into thermopaste at concentrations of 0.05%, 0.1%, 0.25%, 0.5%, 1.0%, 5%, 10%, and 20% (w/v) essentially as described above (see Example 10), and used in the following experiments on the CAM. Dried thermopaste disks weighing 3 mg were made by heating the paste to 60° C., forming drop size aliquots, and then allowing it to cool.

In addition, unloaded thermopaste and thermopaste containing 20% paclitaxel were also heated to 60° C. and placed directly on the growing edge of each CAM at day 6 of incubation; two animals each were treated in this manner. There was no observable difference in the results obtained using the different methods of administration indicating that the temperature of the paste at the time of application was not a factor in the outcome.

Each concentration of paclitaxel-loaded thermopaste (0.05%, 0.1%, 0.25%, 0.5%, 1.0%, 5%, 10%, and 20%) was tested on 4 to 9 embryos at day 6 of development (see Table III). After a 2 day exposure (day 8 of incubation) the vasculature was examined with the aid of a stereomicroscope. Liposyn II, a white opaque solution, was injected into the CAM which increases the visibility of the vascular details.

Figure 19A:
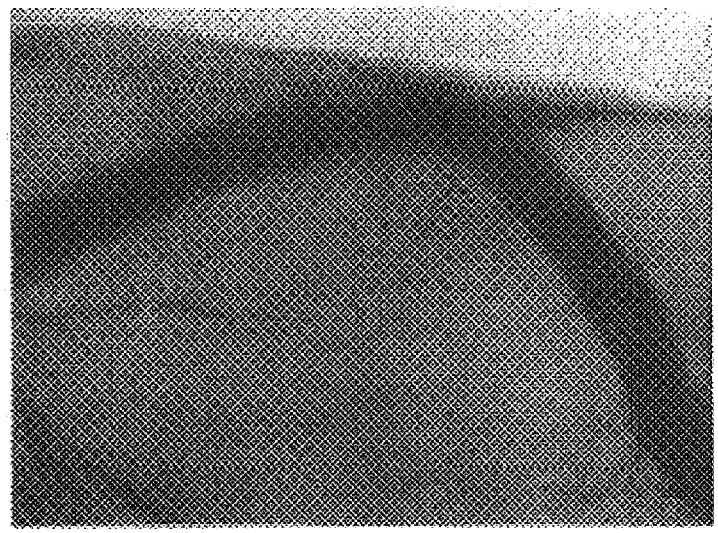
FIG. 19A is a photograph which shows control (unloaded) thermopaste on a CAM. Note that both large vessels and small vessels (capillaries) are found immediately adjacent to the paste. Blood flow in the area around and under the paste is unaffected.
Figure 19B:
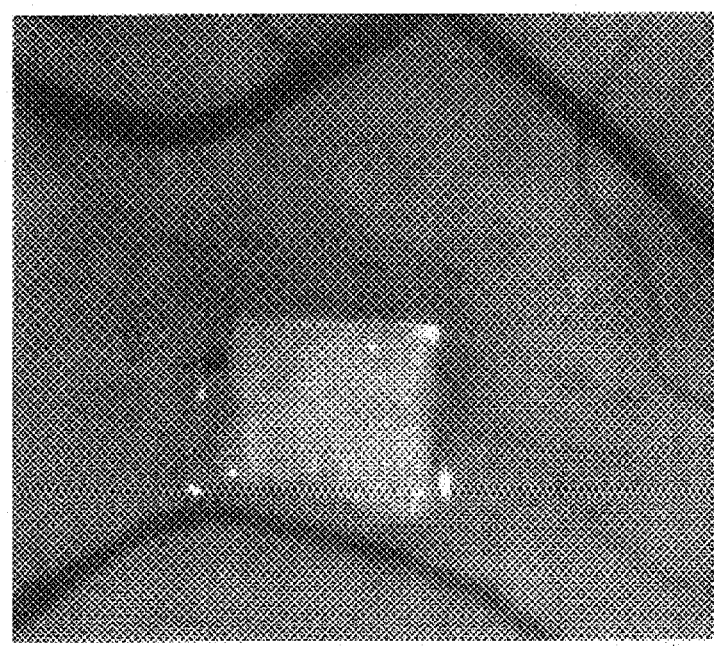
FIG. 19B is a photograph of 20% paclitaxel-loaded thermopaste on a CAM. Note the disruption of the vasculature when compared to the surrounding tissues. The drug loaded paste has blocked the growth of the capillaries, caused regression of the larger vessels, and created a region of avascularity on the CAM assay.

The 20% paclitaxel-loaded thermopaste induced an extensive area of avascularity (see FIG. 19B) in all 6 of the CAMs receiving this treatment. The highest degree of inhibition was defined as a region of avascularity covering an area of 6 mm in diameter. All of the CAMs treated with 20% paclitaxel-loaded thermopaste displayed this degree of angiogenesis inhibition.

In the animals treated with 5% paclitaxel-loaded paste, 4 animals demonstrated maximum inhibition of angiogenesis. Of the animals treated with 10% paclitaxel-loaded thermopaste, only 5 illustrated maximal inhibition.

Figure 19C:
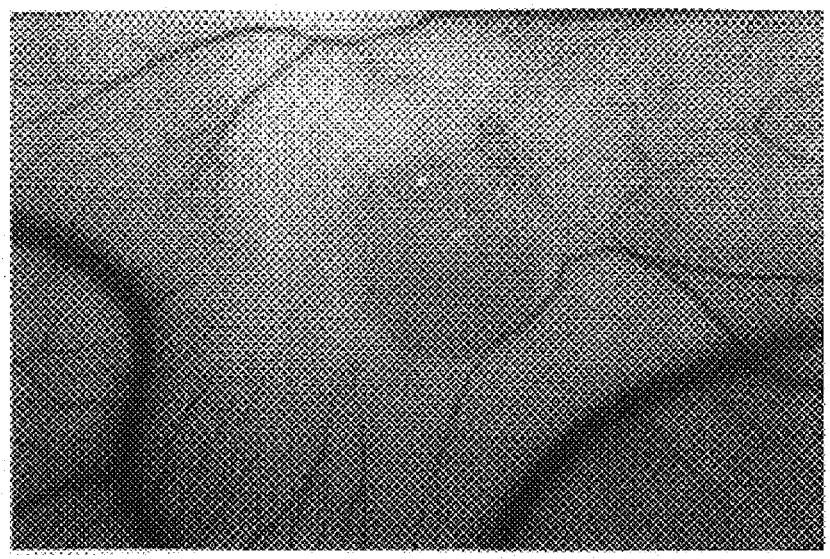
FIG. 19C is a photograph of 0.5% paclitaxel-loaded thermopaste on a CAM (Mag.–40×). Briefly, the paclitaxel-loaded thermopaste disk induced an avascular zone measuring 6 mm in diameter on the CAM. This avascular region was induced by blocking new capillary growth and occluding, disrupting, and regressing the existing blood vessels found within the treated region.
Figure 19D:
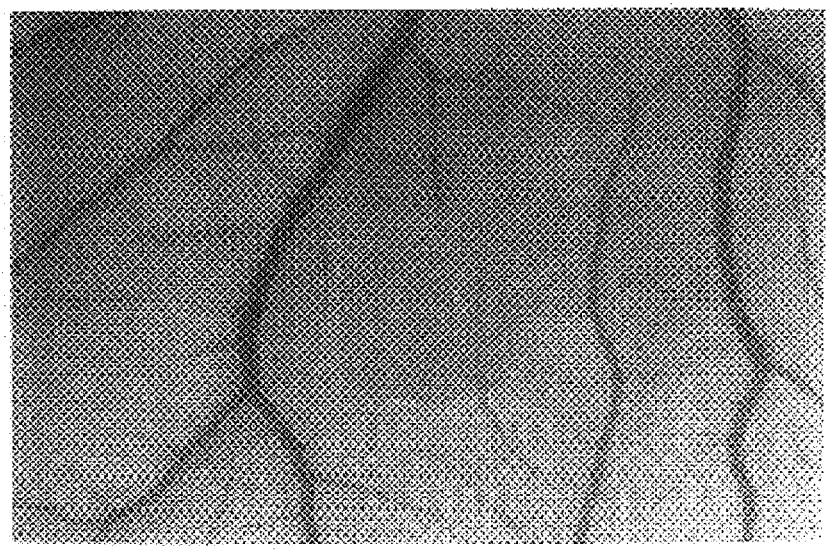
FIG. 19D is a photograph of control (unloaded) Thermopaste on a CAM. Briefly, after a 2 day exposure, the blood vessel organization of the CAM (Mag=50×) treated with the control paste shows normal blood vessel organization. Functional vessels are located immediately adjacent to the unloaded paste.

The results of this study also show that paclitaxel-loaded thermopaste, as low as 0.25%, can release a significant amount of drug to induce angiogenesis inhibition on the CAM. (Table IV, FIGS. 19C and 19D).

By comparison, the control (unloaded) thermopaste did not inhibit angiogenesis on the CAM (see FIG. 19A); this higher magnification view (note that the edge of the paste is seen at the top of the image) demonstrates that the vessels adjacent to the paste are unaffected by the thermopaste. This suggests that the avascular effect observed is due to the sustained release of paclitaxel and is not due to the polymer itself or due to a secondary pressure effect of the paste on the developing vasculature.

This study also demonstrates that thermopaste releases sufficient quantities of angiogenesis inhibitor (in this case paclitaxel) to inhibit the normal development of the CAM vasculature.

TABLE IV

Angiogenic Inhibition of Paclitaxel-Loaded Thermopaste

| Paclitaxel-loaded Thermopaste (%) | Embryos Evaluated (positive/n) |
| --- | --- |
| 0.05 | 0/9 |
| 0.1 | 1/8 |
| 0.25 | 4/4 |
| 0.5 | 4/4 |
| 1 | 8/8 |
| 5 | 4/4 |
| 10 | 5/5 |
| 20 | 6/6 |
| 0 (control) | 0/30 |

Example 16

Effect of Paclitaxel-Loaded Thermopaste on Tumor Growth and Tumor Angiogenesis in Vivo Fertilized domestic chick embryos are incubated for 3 days prior to having their shells removed. The egg contents are emptied by removing the shell located around the airspace, severing the interior shell membrane, perforating the opposite end of the shell and allowing the egg contents to gently slide out from the blunted end. The contents are emptied into round-bottom sterilized glass bowls, covered with petri dish covers and incubated at 90% relative humidity and 3% carbon dioxide (see Example 2).

MDAY-D2 cells (a murine lymphoid tumor) is injected into mice and allowed to grow into tumors weighing 0.5–1.0 g. The mice are sacrificed, the tumor sites wiped with alcohol, excised, placed in sterile tissue culture media, and diced into 1 mm pieces under a laminar flow hood. Prior to placing the dissected tumors onto the 9-day old chick embryos, CAM surfaces are gently scraped with a 30 gauge needle to insure tumor implantation. The tumors are then placed on the CAMs after 8 days of incubation (4 days after deshelling), and allowed to grow on the CAM for four days to establish a vascular supply. Four embryos are prepared utilizing this method, each embryo receiving 3 tumors. For these embryos, one tumor receives 20% paclitaxel-loaded thermopaste, the second tumor unloaded thermopaste, and the third tumor no treatment. The treatments are continued for two days before the results were recorded.

The explanted MDAY-D2 tumors secrete angiogenic factors which induce the ingrowth of capillaries (derived from the CAM) into the tumor mass and allow it to continue to grow in size. Since all the vessels of the tumor are derived from the CAM, while all the tumor cells are derived from the explant, it is possible to assess the effect of therapeutic interventions on these two processes independently. This assay has been used to determine the effectiveness of paclitaxel-loaded thermopaste on: (a) inhibiting the vascularization of the tumor and (b) inhibiting the growth of the tumor cells themselves.

Figure 20A:
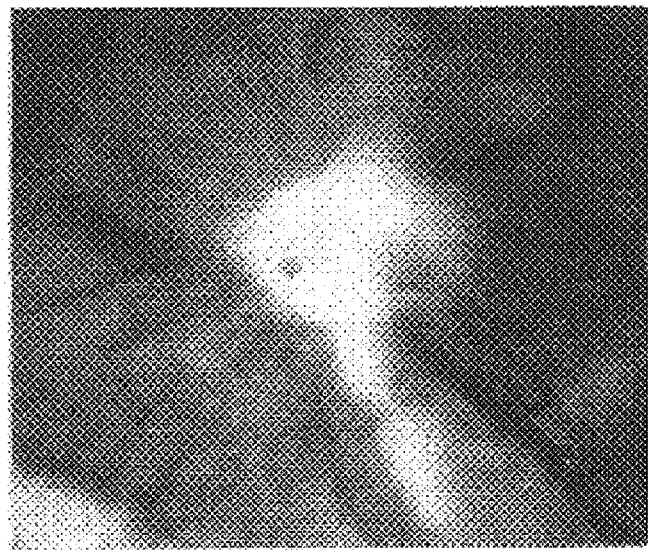
FIGS. 20A and 20B are two photographs of a CAM having a tumor treated with control (unloaded) thermopaste. Briefly, in FIG. 20A the central white mass is the tumor tissue. Note the abundance of blood vessels entering the tumor from the CAM in all directions. The tumor induces the ingrowth of the host vasculature through the production of "angiogenic factors." The tumor tissue expands distally along the blood vessels which supply it.
Figure 20B:
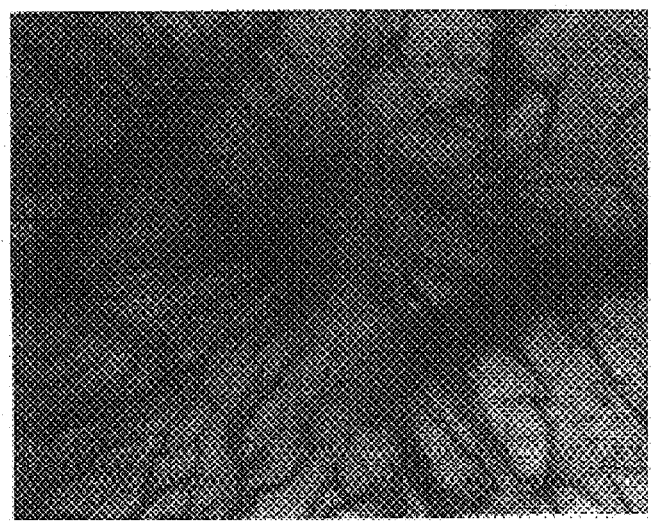
Figure 20C:
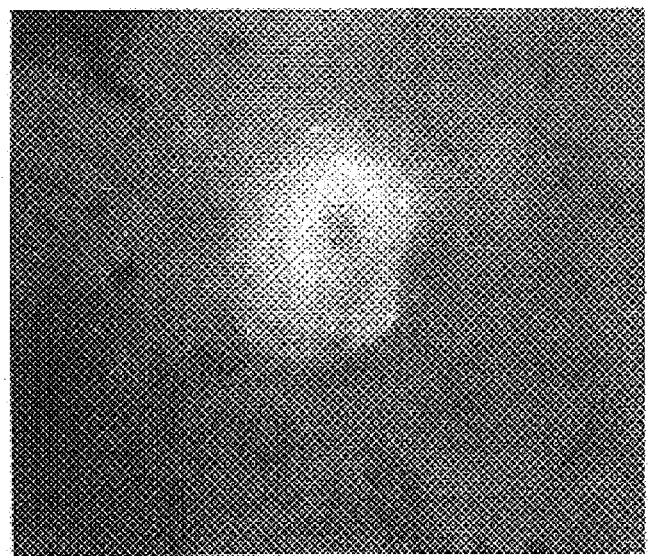
FIGS. 20C and 20D are two photographs of a CAM having a tumor treated with 20% paclitaxel-loaded thermopaste. Briefly, in FIG. 20C the central white mass is the tumor tissue. Note the paucity of blood vessels in the vicinity of the tumor tissue. The sustained release of the angiogenesis inhibitor is capable of overcoming the angiogenic stimulus produced by the tumor. The tumor itself is poorly vascularized and is progressively decreasing in size.
Figure 20D:

Direct in vivo stereomicroscopic evaluation and histological examination of fixed tissues from this study demonstrated the following. In the tumors treated with 20% paclitaxel-loaded thermopaste, there was a reduction in the number of the blood vessels which supplied the tumor (see FIGS. 20C and 20D), a reduction in the number of blood vessels within the tumor, and a reduction in the number of blood vessels in the periphery of the tumor (the area which is typically the most highly vascularized in a solid tumor) when compared to control tumors. The tumors began to decrease in size and mass during the two days the study was conducted. Additionally, numerous endothelial cells were seen to be arrested in cell division indicating that endothelial cell proliferation had been affected. Tumor cells were also frequently seen arrested in mitosis. All 4 embryos showed a consistent pattern with the 20% paclitaxel-loaded thermopaste suppressing tumor vascularity while the unloaded thermopaste had no effect.

By comparison, in CAMs treated with unloaded thermopaste, the tumors were well vascularized with an increase in the number and density of vessels when compared to that of the normal surrounding tissue, and dramatically more vessels than were observed in the tumors treated with paclitaxel-loaded paste. The newly formed vessels entered the tumor from all angles appearing like spokes attached to the center of a wheel (see FIGS. 20A and 20B). The control tumors continued to increase in size and mass during the course of the study. Histologically, numerous dilated thin-walled capillaries were seen in the periphery of the tumor and few endothelial were seen to be in cell division. The tumor tissue was well vascularized and viable throughout.

As an example, in two similarly-sized (initially, at the time of explantation) tumors placed on the same CAM the following data was obtained. For the tumor treated with 20% paclitaxel-loaded thermopaste the tumor measured 330 mm×597 mm; the immediate periphery of the tumor has 14 blood vessels, while the tumor mass has only 34 small capillaries. For the tumor treated with unloaded thermopaste the tumor size was 623 mm×678 mm; the immediate periphery of the tumor has 54 blood vessels, while the tumor mass has 12–14 small blood vessels. In addition, the surrounding CAM itself contained many more blood vessels as compared to the area surrounding the paclitaxel-treated tumor.

This study demonstrates that thermopaste releases sufficient quantities of angiogenesis inhibitor (in this case paclitaxel) to inhibit the pathological angiogenesis which accompanies tumor growth and development. Under these conditions angiogenesis is maximally stimulated by the tumor cells which produce angiogenic factors capable of inducing the ingrowth of capillaries from the surrounding tissue into the tumor mass. The 20% paclitaxel-loaded thermopaste is capable of blocking this process and limiting the ability of the tumor tissue to maintain an adequate blood supply. This results in a decrease in the tumor mass both through a cytotoxic effect of the drug on the tumor cells themselves and by depriving the tissue of the nutrients required for growth and expansion.

Example 17

Effect of Angiogenesis Inhibitor-Loaded Thermopaste on Tumor Growth in Vivo in a Murine Tumor Model The murine MDAY-D2 tumor model may be used to examine the effect of local slow release of the chemotherapeutic and anti-angiogenic compounds such as paclitaxel on tumor growth, tumor metastasis, and animal survival. The MDAY-D2 tumor cell line is grown in a cell suspension consisting of 5% Fetal Calf Serum in alpha mem media. The cells are incubated at 37° C. in a humidified atmosphere supplemented with 5% carbon dioxide, and are diluted by a factor of 15 every 3 days until a sufficient number of cells are obtained. Following the incubation period the cells are examined by light microscopy for viability and then are centrifuged at 1500 rpm for 5 minutes. PBS is added to the cells to achieve a dilution of 1,000,000 cells per ml.

Ten week old DBA/2 j female mice are acclimatized for 34 days after arrival. Each mouse is then injected subcutaneously in the posteriolateral flank with 100,000 MDAY-D2 cells in 100 ml of PBS. Previous studies have shown that this procedure produces a visible tumor at the injection site in 3–4 days, reach a size of 1.0–1.7 g by 14 days, and produces visible metastases in the liver 19–25 days post-injection. Depending upon the objective of the study a therapeutic intervention can be instituted at any point in the progression of the disease.

Using the above animal model, 20 mice are injected with 140,000 MDAY-D2 cells s.c. and the tumors allowed to grow. On day 5 the mice are divided into groups of 5. The tumor site was surgically opened under anesthesia, the local region treated with the drug-loaded thermopaste or control thermopaste without disturbing the existing tumor tissue, and the wound was closed. The groups of 5 received either no treatment (wound merely closed), polymer (PCL) alone, 10% paclitaxel-loaded thermopaste, or 20% paclitaxel-loaded thermopaste (only 4 animals injected) implanted adjacent to the tumor site. On day 16, the mice were sacrificed, the tumors were dissected and examined (grossly and histologically) for tumor growth, tumor metastasis, local and systemic toxicity resulting from the treatment, effect on wound healing, effect on tumor vascularity, and condition of the paste remaining at the incision site.

The weights of the tumors for each animal is shown in the table below:

TABLE V

| | Tumor Weights (gm) | | | |
| --- | --- | --- | --- | --- |
| | Control (empty) | Control (PCL) | 10% Paclitaxel Thermopaste | 20% Paclitaxel Thermopaste |
| Animal No. | | | | |
| 1 | 1.387 | 1.137 | 0.487 | 0.114 |
| 2 | 0.589 | 0.763 | 0.589 | 0.192 |
| 3 | 0.461 | 0.525 | 0.447 | 0.071 |
| 4 | 0.606 | 0.282 | 0.274 | 0.042 |
| 5 | 0.353 | 0.277 | 0.362 | |
| Mean | 0.6808 | 0.6040 | 0.4318 | 0.1048 |
| Std. Deviation | 0.4078 | 0.3761 | 0.1202 | 0.0653 |
| P Value | | 0.7647 | 0.358 | 0.036 |

Figure 21A:
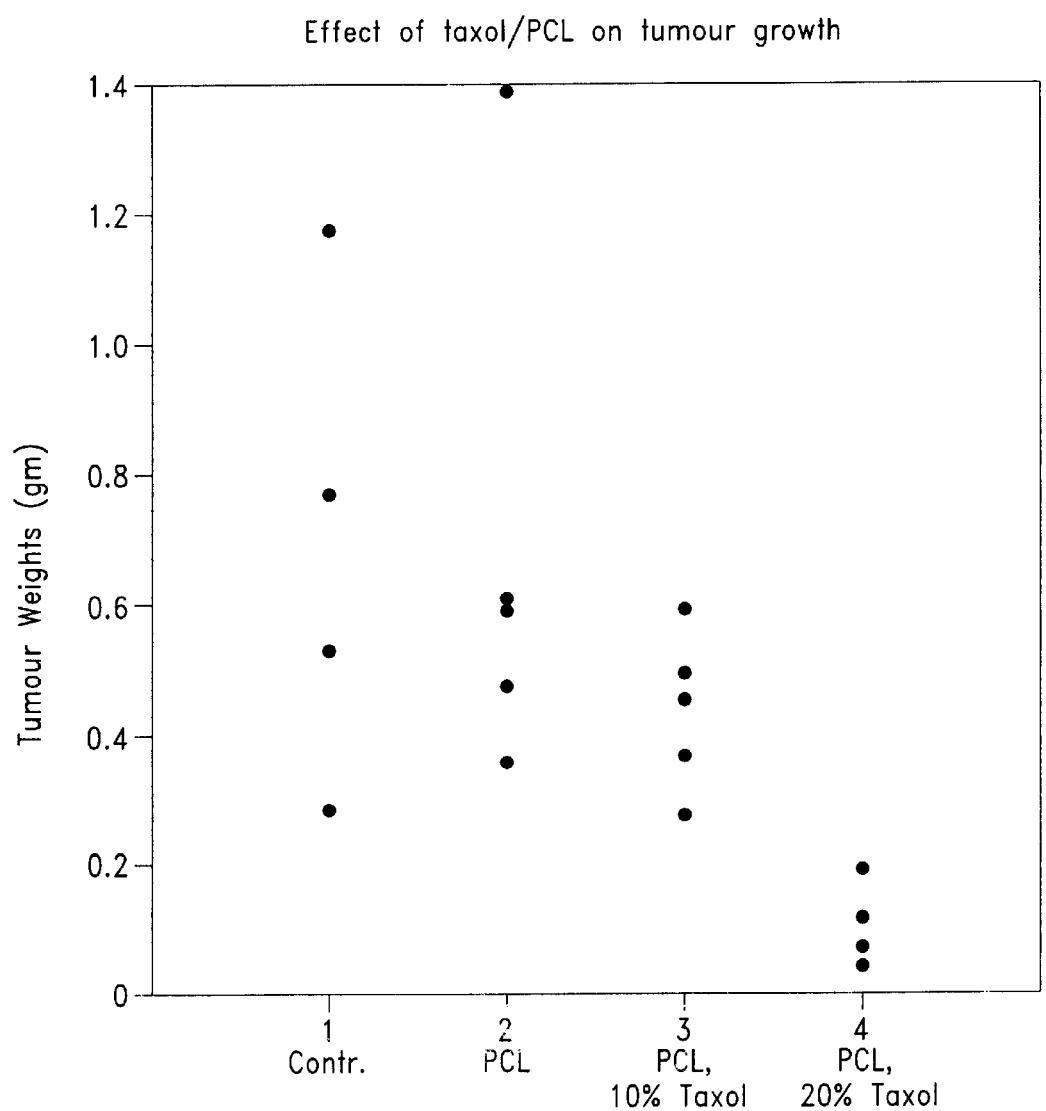
FIG. 21A is a graph which shows the effect of paclitaxel/PCL on tumor growth.
Figure 21B:
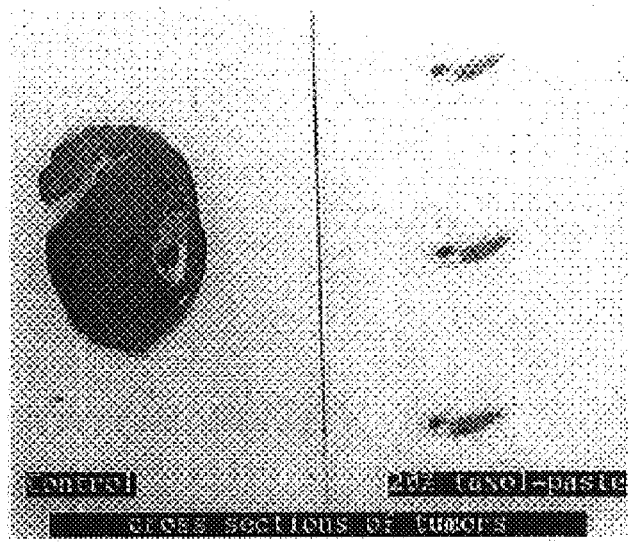
FIGS. 21B and 21C are two photographs which show the effect of control, 10% and 20% paclitaxel-loaded thermopaste on tumor growth.
Figure 21C:
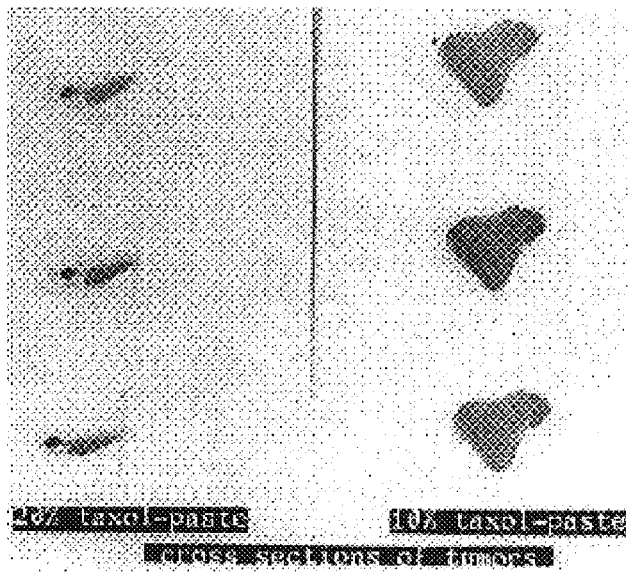

Thermopaste loaded with 20% paclitaxel reduced tumor growth by over 85% (average weight 0.105) as compared to control animals (average weight 0.681). Animals treated with thermopaste alone or thermopaste containing 10% paclitaxel had only modest effects on tumor growth; tumor weights were reduced by only 10% and 35% respectively (FIG. 21A). Therefore, thermopaste containing 20% paclitaxel was more effective in reducing tumor growth than thermopaste containing 10% paclitaxel (see FIG. 21C; see also FIG. 21B).

Thermopaste was detected in some of the animals at the site of administration. Polymer varying in weight between 0.026 g to 0.078 g was detected in 8 of 15 mice. Every animal in the group containing 20% paclitaxel-loaded thermopaste contained some residual polymer suggesting that it was less susceptible to dissolution. Histologically, the tumors treated with paclitaxel-loaded thermopaste contained lower cellularity and more tissue necrosis than control tumors. The vasculature was reduced and endothelial cells were frequently seen to be arrested in cell division. The paclitaxel-loaded thermopaste did not appear to affect the integrity or cellularity of the skin or tissues surrounding the tumor. Grossly, wound healing was unaffected.

Example 18

The use of Angiogenesis-Inhibitor Loaded Surgical Films in the Prevention of Iatrogenic Metastatic Seeding of Tumor Cells During Cancer Resection Surgery As discussed above, sterile, pliable, stretchable drug-polymer compounds (e.g., films) may be utilized in accordance with the methods described herein in order to isolate normal surrounding tissues from malignant tissue during resection of cancer. Such material prevents iatrogenic spread of the disease to adjacent organs through inadvertent contamination by cancer cells. Such polymers may be particularly useful if placed around the liver and/or other abdominal contents during bowel cancer resection surgery in order to prevent intraperitoneal spread of the disease to the liver.

A. Materials and Methods

Preparation of Surgical Film. Surgical films are prepared as described in Example 10. Thin films measuring approximately 1 cm×1 cm are prepared containing either polymer alone (PCL) or PCL loaded with 5% paclitaxel.

Rat Hepatic Tumor Model. In an initial study Wistar rats weighing approximately 300 g underwent general anesthesia and a 3–5 cm abdominal incision is made along the midline. In the largest hepatic lobe, a 1 cm incision is made in the hepatic parenchyma and part of the liver edge is resected. A concentration of 1 million live 9L Glioma tumor cells (eluted from tissue culture immediately prior to the procedure) suspended in 100 ml of phosphate buffered saline are deposited onto the cut liver edge with a 30 gauge needle. The surgical is then placed over the cut liver edge containing the tumor cells and affixed in place with Gelfoam. Two animals received PCL films containing 5% paclitaxel and two animals received films containing PCL alone. The abdominal wall is closed with 3.0 Dexon and skin clips. The general anesthetic is terminated and the animal is allowed to recover. Ten days later the animals are sacrificed and the livers examined histologically.

B. Results

Local tumour growth is seen in the 2 livers treated with polymer alone. Both livers treated with polymer plus paclitaxel are completely free of tumour when examined histologically. Also of importance, the liver capsule had regenerated and grown completely over the polymeric film and the cut surface of the liver indicating that there is no significant effect on wound healing. There is no evidence of local hepatic toxicity surrounding any (drug-loaded or drug-free) of the surgical films.

C. Discussion

This study indicates that surgical films placed around normal tissues and incision sites during surgery may be capable of decreasing the incidence of accidental implantation of tumor cells into normal surrounding tissue during resection of malignant tumors.

Example 19

Intra-Articular Injection of Angiogenesis-Inhibitor-Loaded Biodegradable Microspheres in the Treatment of Arthritis Articular damage in arthritis is due to a combination of inflammation (including WBCs and WBC products) and pannus tissue development (a tissue composed on neovascular tissue, connective tissue, and inflammatory cells). Paclitaxel has been chosen for the initial studies because it is a potent inhibitor of neovascularization. In this manner, paclitaxel in high local concentrations will prove to be a disease modifying agent in arthritis.

In order to determine whether microspheres have a deleterious effect on joints, the following experiments are conducted. Briefly, plain PCL and paclitaxel-loaded microspheres are prepared as described previously in Example 8. Three rabbits are injected intra-articularly with 0.5–5.0 $\mu$m, $10^{-30}$ $\mu$m, or 30–80 $\mu$m microspheres in a total volume of 0.2 mls (containing 0.5 mg of microspheres). The joints are assessed visually (clinically) on a daily basis. After two weeks the animals are sacrificed and the joints examined histologically for evidence of inflammation and depletion of proteoglycans.

The rabbit inflammatory arthritis and osteoarthritis models may be utilized in order to evaluate the use of microspheres in reducing synovitis and cartilage degradation. Briefly, degenerative arthritis is induced by a partial tear of the cruciate ligament and meniscus of the knee. After 4 to 6 weeks, the rabbits develop erosions in the cartilage similar to that observed in human osteoarthritis. Inflammatory-arthritis is induced by immunizing rabbits with bovine serum albumen (BSA) in Complete Freund's Adjuvant (CFA). After 3 weeks, rabbits containing a high titer of anti-BSA antibody receive an intra-articular injection of BSA (5 mg). Joint swelling and pronounced synovitis is apparent by seven days, a proteoglycan depletion is observed by 7 to 14 days, and cartilage erosions are observed by 4 to 6 weeks.

Inflammatory arthritis is induced as described above. After 4 days, the joints are injected with microspheres containing 5% paclitaxel or vehicle. One group of animals is sacrificed on day 14 and another on day 28. The joints are examined histologically for inflammation and cartilage degradation. The experiment is designed to determine if paclitaxel microspheres can affect joint inflammation and cartilage matrix degradation.

Angiogenesis-inhibitor microspheres may be further examined in an osteoarthritis model. Briefly, degenerative arthritis is induced in rabbits as described above, and the joints receive an intra-articular injection of microspheres (5% paclitaxel or vehicle only) on day 4. The animals are sacrificed on day 21 and day 42 and the joints examined histologically for evidence of cartilage degradation.

Results

Figure 22A:
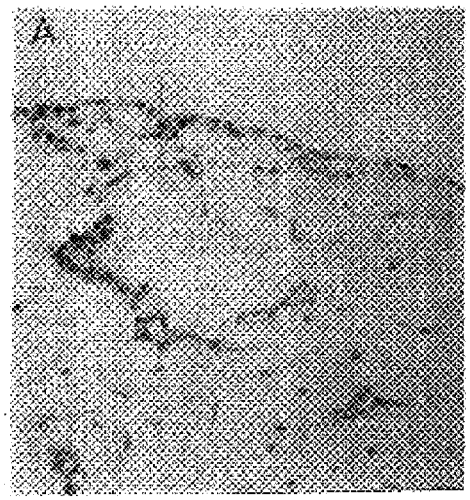
FIG. 22A is a photograph of synovium from a PBS injected joint.
Figure 22B:
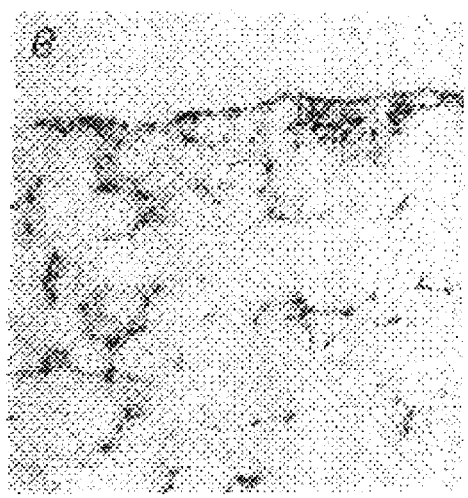
FIG. 22B is a photograph of synovium from a microsphere injected joint.
Figure 22C:
FIG. 22C is a photograph of cartilage from joints injected with PBS.
Figure 22D:
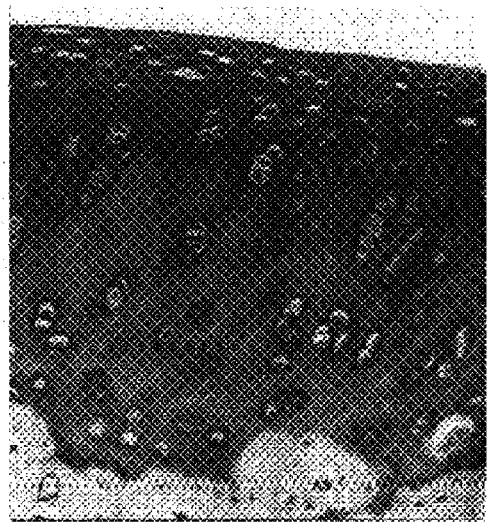
FIG. 22D is a photograph of cartilage from joints injected with microspheres.

Unloaded PCL microspheres of differing sizes (0.5–5.0 μm, 10–30 μm, or 30–80 μm) are injected intra-articularly into the rabbit knee joint. Results of these experiments are shown in FIGS. 22A to 22D. Briefly, FIG. 22A is a photograph of synovium from PBS injected joints. FIG. 22B is a photograph of joints injected with microspheres. FIG. 22C is a photograph of cartilage from joints injected with PBS, and FIG. 22D is a photograph of cartilage from joints injected with microspheres.

As can be seen from these photographs, histologically, there is no difference between joints receiving a microsphere injection and those which did not. Clinically, there was no evidence of joint inflammation during the 14 days the experiment was conducted. Grossly, there is no evidence of joint inflammation or cartilage damage in joints where microspheres are injected, as compared to untreated normal joints.

Conclusions

Microspheres can be injected intra-articularly without causing any discernible changes to the joint surface. This indicates that this method may be an effective means of delivering a targeted, sustained-release of disease-modifying agents to diseased joints, while minimizing the toxicity which could be associated with the systemic administration of such biologically active compounds.

As discussed above, microspheres can be formulated into specific sizes with defined drug release kinetics. It has also been demonstrated that paclitaxel is a potent inhibitor of angiogenesis and that it is released from microspheres in quantities sufficient to block neovascularization on the CAM assay. Therefore, angiogenesis-inhibitor-loaded (e.g., paclitaxel-loaded) microspheres may be administered intra-articularly in order to block the neovascularization that occurs in diseases such as rheumatoid arthritis. In this manner the drug-loaded microspheres can act as a "chondroprotective" agent which protects the cartilage from irreversible destruction from invading neovascular pannus tissue.

Example 20

The Anti-Angiogenic Effects of Paclitaxel in an Ophthalmic Suspension

In order to test whether paclitaxel would inhibit the pathogenesis of corneal neovascularization, an ophthalmic suspension of 0.3% paclitaxel and a 10% paclitaxel microsphere suspension was first prepared and tested on the CAM in order to determine whether sufficient quantities of paclitaxel could be released to inhibit angiogenesis.

Briefly, fertilized, chick eggs were incubated for 4 days prior to shell-less culturing as described previously in Example 2. The egg contents are removed from the shell and emptied into round-bottom sterilized glass bowls and covered with petri dish covers.

On day 6 of development, the ophthalmic drops were tested on the CAM. To deliver the ophthalmic suspensions, a 0.5 mL syringe was sliced into rings measuring 1 mm thick. These rings, which formed wells when placed onto the CAM were used to localize a 15 μL aliquot of ophthalmic suspension to the CAMs blood vessels. The paclitaxel (0.3%) suspension was tested on 11 embryos, whereas the 10% paclitaxel-loaded microsphere suspension was tested on 4 other embryos. The control (unloaded) ophthalmic suspension was tested on the remaining 5 CAMs. After a 48 hour period, Liposyn II, a white opaque solution, was injected into the CAM which increased the visibility of the vascular details when observed with a stereomicroscope.

Figure 23A:
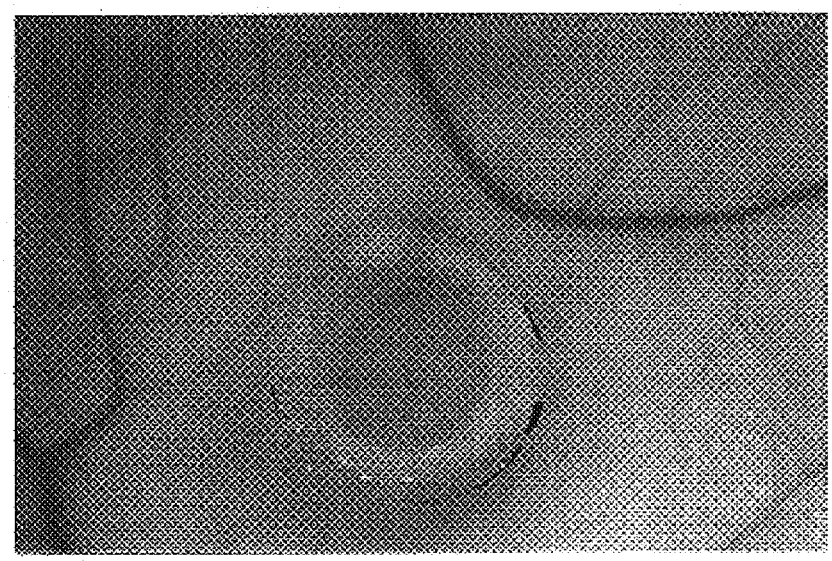
FIG. 23A is a photograph of a 0.3% Paclitaxel Ophthalmic Drop Suspension on a CAM (Mag.=32×). The plastic ring was used to localize the drug treatment to the CAM. Note the lack of blood vessels located within and immediately adjacent to the ring. The functional blood vessels bordering the avascular zone are defined by their "elbowing" morphology away form the drug source.

Within 48 hours, the 0.3% paclitaxel suspension inhibited angiogenesis on 11/11 CAMs tested and the 10% paclitaxel-loaded microsphere suspension inhibited angiogenesis on 4/4 of the embryos tested. This was evident by the presence of avascular zones measuring 6 mm in diameter in the vicinity of the treated area (FIG. 23A); in many cases the avascular zone exceeded the size of the application ring. This avascular zone was defined as a region containing disrupted blood vessel fragments and discontinuous blood flow. The functional vessels adjacent to the avascular zone were modified in such a way to redirect the blood flow away from the drug source; these vessels possessed an angular architecture which was not evident in the control (unloaded) thermopaste treated CAMs.

Figure 23B:
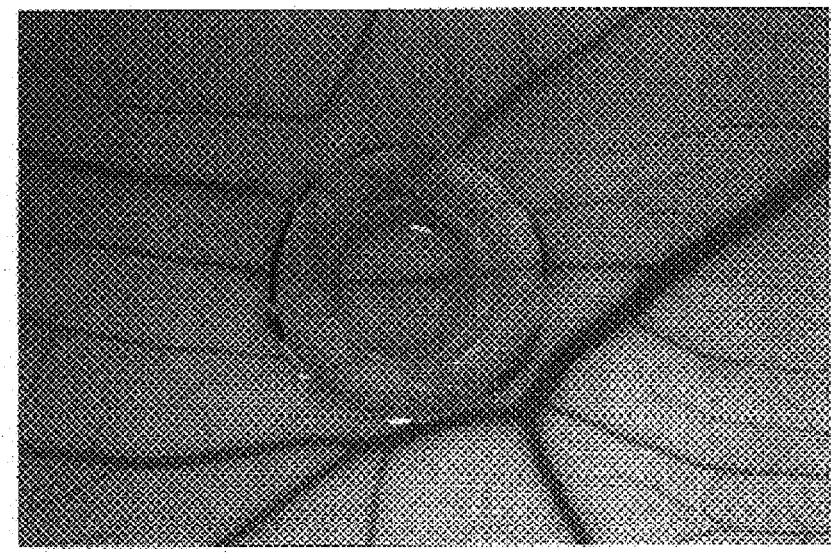
FIG. 23B is a photograph of a control (unloaded) Ophthalmic Drop Suspension on a CAM (Mag=32×). Note the normal organization of the CAM blood vessels and the abundance of functional vessels located within the ring.

In comparison, the control (unloaded) ophthalmic vehicle did not inhibit angiogenesis on any of the 5 CAMs tested; this was evident by the functional vessels visible within the center of the application ring (FIG. 23B). In some cases, there was some reduction in the amount of microvessels located in the control treated CAMs although this was only due to the aqueous suspension vehicle in which paclitaxel was administered.

In summary, paclitaxel was sufficiently released from the ophthalmic drop suspension to inhibit angiogenesis on the CAM. Therefore, since paclitaxel can be released from this vehicle system, it may likewise be utilized in the treatment of neovascular disease of the eye, such as corneal neovascularization.

Example 21

The Anti-Angiogenic Effects of Paclitaxel-Loaded Stent Coating

A. Testing of Paclitaxel-Loaded Stents on a CAM

As noted above, stents are currently used for the prevention of luminal closure induced by a disease process, such as biliary tumor ingrowth. Although stents prevent tumor ingrowth temporarily, tumor ingrowth eventually recurs. In this study, strecker stents were coated with an EVA polymer containing paclitaxel at concentrations of 33%, 10%, and 2.5% and were tested for their ability to inhibit angiogenesis on the CAM.

Briefly, paclitaxel-coated stent tynes (3 mm in size) were placed onto the growing vessels of the CAM at day 6 of development. Of these CAMs, 3 received 33% paclitaxel-loaded stent coating, 5 CAMs received 2.5% paclitaxel, and 1 CAM received 10% paclitaxel-loaded stent coating. In addition, control stents, coated with unloaded EVA, were tested on a total of 6 CAMs. After 48 hours, Liposyn II was injected within the CAM to increase the vascular details during observations.

Figure 24A:
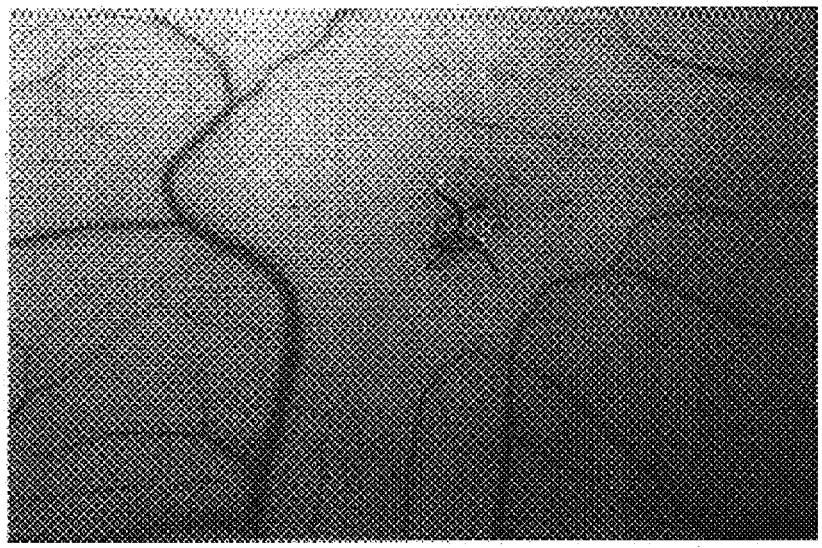
FIG. 24A is a photograph of a 2.5% Paclitaxel-Loaded Stent Coating (Mag=26×). Briefly, the blood vessels surrounding the avascular zone are morphologically redirected away from the paclitaxel source; this produces an avascular zone which can measure up to 6 mm in diameter. The disrupted vascular remnants which represent vascular regression can be seen within the avascular zone.

All 3 different paclitaxel concentrations of the stent coating inhibited angiogenesis on the CAM within the 48 hour period. The CAMs were maximally inhibited which was characterized by the induction of avascular zones measuring 6 mm in diameter (FIG. 24A).

B. Testing of Control Stents in Tumors

Figure 25:
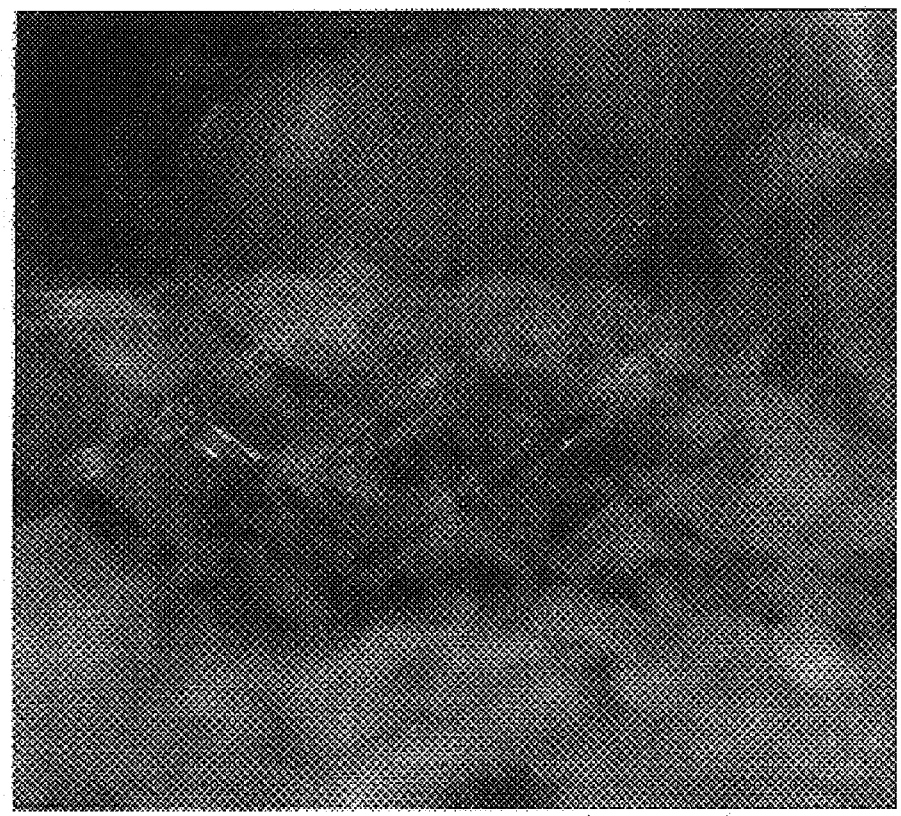
FIG. 25 is a photograph of a control stent. Briefly, this image shows the longitudinal orientation of a nylon stent incorporated within gliosarcoma tissue of the rat liver. Ingrowth within the nylon stent is evident.
Figure 26:
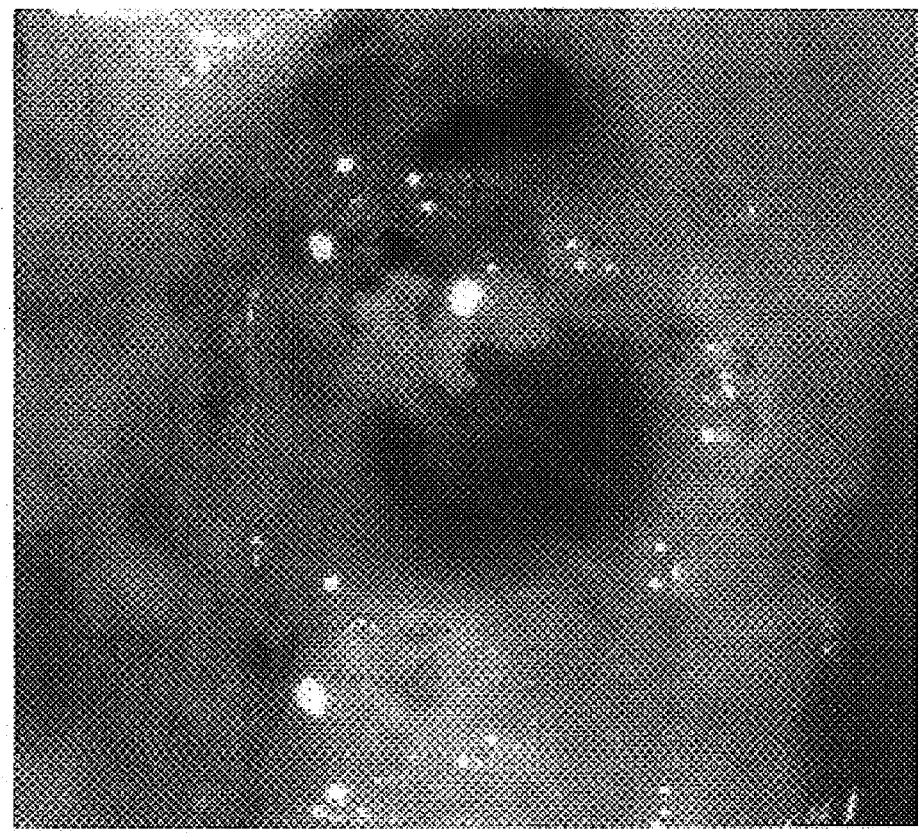
FIG. 26 is a photograph of a control stent. Briefly, this image also illustrates tumor ingrowth within the lumen of the nylon stent.
Figure 27:
FIG. 27 is a photograph of a lung. Briefly, in addition to large liver tumors, metastasis to the lung is common. Such metastases are evident by the presence of small white lobules seen throughout the lung.

Similar to above, control stents were prepared as described above and placed into established gliosarcoma tumors of the rat liver. After a 7 day period, these rats were sedated and perfused with a 2.0% glutaraldehyde in sodium cacodylate solution. The livers were excised and the stents were dissected away from the surrounding tissue. Images of the gross anatomy revealed that the nylon stents had become incorporated into the tumor and tumor ingrowth had been established within the lumen of the stent (FIGS. 25 and 26). FIG. 27 shows that metastasis had occurred within the lung.

Figure 24B:
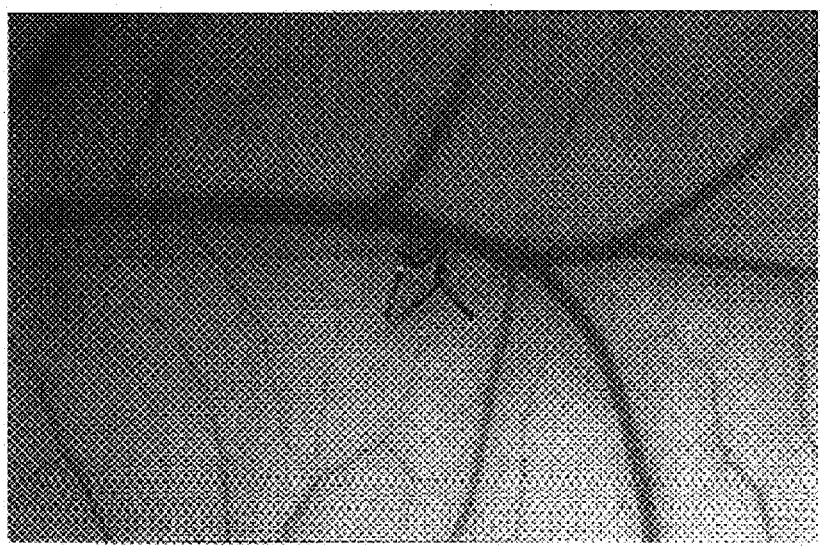
FIG. 24B is a control (unloaded) Stent Coating (Mag=26×). Briefly, the blood vessels of the CAM are found immediately adjacent to the stent and do not illustrate any morphological alterations.

Unlike the paclitaxel-loaded stent coating, the control coating did not inhibit angiogenesis and maintained its normal architecture in all of the 6 CAMs which were tested (FIG. 24B).

In summary, since paclitaxel coated stents have the capability of releasing sufficient drug to inhibit angiogenesis on the CAM, paclitaxel coated stents may likewise be utilized for a variety of applications in order to prevent tumor ingrowth within the binary lumen.

Example 22

Effect of Paclitaxel on Neutrophil Activity

The example describes the effect of paclitaxel on the response of neutrophils stimulated with opsonized CPPD crystals or opsonized zymosan. As shown by experiments set forth below, paclitaxel is a strong inhibitor of particulate inducted neutrophil activation as measured by chemiluminescence, superoxide anion production and degranulation in response to plasma opsonized microcrystals or zymosan.

A. Materials and Methods

Hanks buffered salt solution (HBSS) pH 7.4 was used throughout this study. All chemicals were purchased from Sigma Chemical Co (St. Louis,) unless otherwise stated. All experiments were performed at 37° C. unless otherwise stated.

1. Preparation and Characterization of Crystals

CPPD (triclinic) crystals were prepared. The size distribution of the crystals was approximately 33% less than 10 $\mu$m, 58% between 10 and 20 $\mu$m and 9% greater than 20 $\mu$m. Crystals prepared under the above conditions are pyrogen free and crystals produced under sterile, pyrogen free conditions produced the same magnitude of neutrophil response as crystals prepared under normal, non-sterile laboratory conditions.

2. Opsonization of Crystals and Zymosan

All experiments that studied neutrophil responses to crystals or zymosan in the presence of paclitaxel were performed using plasma opsonized CPPD or zymosan. Opsonization of crystals or zymosan was done with 50% heparinized plasma at a concentration of 75 mg of CPPD or 12 mg of zymosan per ml of 50% plasma. Crystals or zymosan were incubated with plasma for 30 min. at 37° C. and then washed in excess HBSS.

3. Neutrophil Preparation

Neutrophils were prepared from freshly collected human citrated whole blood. Briefly, 400 ml of blood were mixed with 80 ml of 4% dextran T500 (Phamacia LKB, Biotechnology AB Uppsala, Sweden) in HBSS and allowed to settle for 1 h. Plasma was collected continuously and 5 ml applied to 5 ml of Ficoll Paque (Pharmacia) in 15 ml polypropylene tubes (Coming, N.Y.). Following centrifugation at 500× g for 30 min, the neutrophil pellets were washed free of erythrocytes by 20 s of hypotonic shock. Neutrophils were resuspended in HBSS, kept on ice and used for experiments within 3 h. Neutrophil viability and purity was always greater than 90%.

4. Incubation of Neutrophils with Paclitaxel

A stock solution of paclitaxel at 12 mM in DMSO was freshly prepared before each experiment. This stock solution was diluted in DMSO to give solutions of paclitaxel in the 1 to 10 mM concentration range. Equal volumes of these diluted paclitaxel solutions was added to neutrophils at 5,000,000 cells per ml under mild vortexing to achieve concentrations of 0 to 50 $\mu$M with a final DMSO concentration of 0.5%. Cells were incubated for 20 minutes at 33° C. then for 10 minutes at 37° C. before addition to crystals or zymosan.

5. Chemiluminescence Assay

All chemiluminescence studies were performed at a cell concentration of 5,000,000 cells/ml in HBSS with CPPD (50 mg/ml). In all experiments 0.5 ml of cells was added to 25 mg of CPPD or 0.5 mg of zymosan in 1.5 ml capped Eppendorf tubes. 10 $\mu$l of luminol dissolved in 25% DMSO in HBSS was added to a final concentration of 1 $\mu$M and the samples were mixed to initiate neutrophil activation by the crystals or zymosan. Chemiluminescence was monitored using an LKB Luminometer (Model 1250.) at 37° C. with shaking immediately prior to measurements to resuspend the crystals or zymosan. Control tubes contained cells, drug and luminol (crystals absent).

6. Superoxide Anion Generation

Superoxide anion concentrations were measured using the superoxide dismutase inhibitable reduction of cytochrome c assay. Briefly, 25 mg of crystals or 0.5 mg of zymosan was placed in a 1.5 ml capped Eppendorf tube and warmed to 37° C. 0.5 ml of cells at 37° C. were added together with ferricytochrome c (final concentration 1.2 mg/ml) and the cells were activated by shaking the capped tubes. At appropriate times tubes were centrifuged at 10,000 g for 10 seconds and the supernatant collected for assay be measuring the absorbance of 550 nm. Control tubes were set up under the same conditions with the inclusion of superoxide dismutase at 600 units per ml.

7. Neutrophil Degranulation Assay

One and a half milliliter Eppendorf tubes containing either 25 mg of CPPD or 1 mg of zymosan were preheated to 37° C. 0.5 ml of cells at 37° C. were added followed by vigorous shaking to initiate the reactions. At appropriate times, tubes were centrifuged at 10,000× g for 10 seconds and 0.4 ml of supernatant was stored at −20° C. for later assay.

Lysozyme was measured by the decrease in absorbance at 450 nm of a *Micrococcus lysodeikticus* suspension. Briefly, *Micrococcus lysodeikticus* was suspended at 0.1 mg/ml in 65 mM potassium phosphate buffer, pH 6.2 and the absorbance at 450 nm was adjusted to 0.7 units by dilution. The crystal (or zymosan) and cell supernatant (100 $\mu$l) was added to 2.5 ml of the Micrococcus suspension and the decrease in absorbance was monitored. Lysozyme standards (chicken egg white) in the 0 to 2000 units/ml range were prepared and a calibration graph of lyzozyme concentration against the rate of decrease in the absorbance at 450 nm was obtained.

Myeloperoxidase (MPO) activity was measured by the increase in absorbance at 450 nm that accompanies the oxidation of dianisidine. 7.8 mg of dianisidine was dissolved in 100 ml of 0.1 M citrate buffer, pH 5.5 at 3.2 mM by sonication. To a 1 ml cuvette, 0.89 mL of the dianisidine solution was added, followed by 50 µl of 1% Triton×100, 10 µl of a 0.05% hydrogen peroxide in water solution and 50 µl of crystal-cell supernatant. MPO activity was determined from the change in absorbance (450 nm) per minute, Delta A 450, using the following equation:

Dianisidine oxidation $(nmol/min) = 50 \times \text{Delta } A\ 450$

8. Neutrophil Viability

To determine the effect of paclitaxel on neutrophil viability the release of the cytoplasmic marker enzyme, Lactate Dehydrogenase (LDH) was measured. Control tubes containing cells with drug (crystals absent) from degranulation experiments were also assayed for LDH.

B. Results

In all experiments statistical significance was determined using Students' t-test and significance was claimed at $p<0.05$. Where error bars are shown they describe one standard deviation about the mean value for the n number given.

1. Neutrophil Viability

Neutrophils treated with paclitaxel at 46 µM for one hour at 37° C. did not show any increased level of LDH release (always less than 5% of total) above controls indicating that paclitaxel did not cause cell death.

2. Chemiluminescence

Figure 29A:
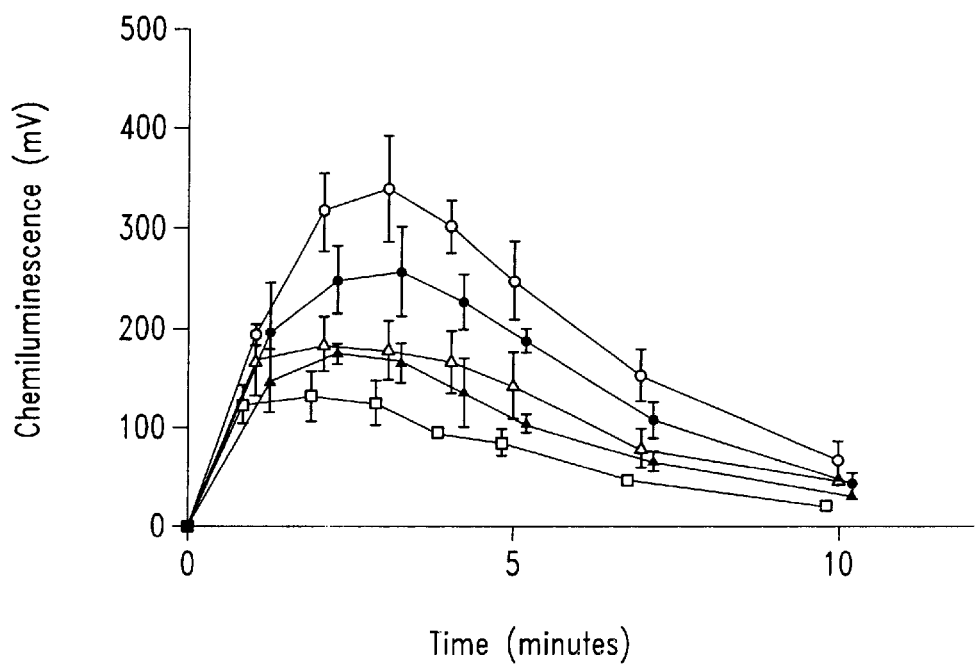
FIG. 29A is a graph which shows the chemiluminescence response of neutrophils ($5 \times 10^6$ cells/ml) to plasma opsonized CPPD crystals (50 mg/ml). Effect of paclitaxel at (○) no paclitaxel, (●) 4.5 $\mu$M, (Δ) 14 $\mu$M, (▲) 28 $\mu$M, (□) 46 $\mu$M; n=3.
Figure 29B:
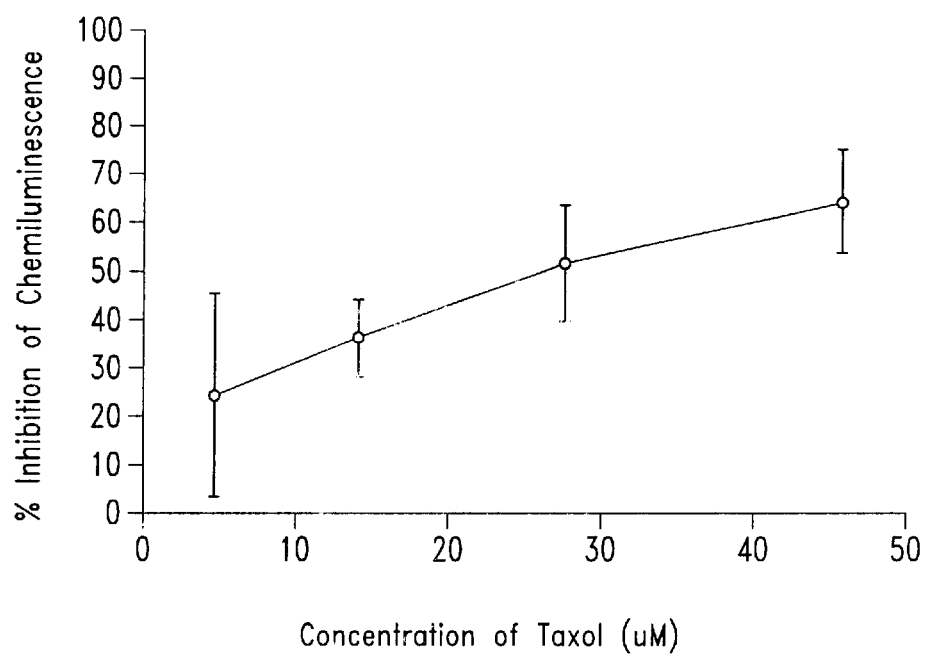
FIG. 29B is a graph which shows the time course concentration dependence of paclitaxel inhibition of plasma opsonized CPPD crystal induced neutrophil chemiluminescence.

Paclitaxel at 28 µM produced strong inhibition of both plasma opsonized CPPD and plasma opsonised zymosan induced neutrophil chemiluminescence as shown in FIGS. 29A, 29B and 33A respectively. The inhibition of the peak chemiluminescence response was 52% (+/−12%) and 45% (+1−11%) for CPPD and zymosan respectively. The inhibition by paclitaxel at 28 µM of both plasma opsonized CPPD and plasma opsonized zymosan induced chemiluminescence was significant at all times from 3 to 16 minutes (FIGS. 29A, 29B and 33A). FIGS. 29A and 29B show the concentration dependence of paclitaxel inhibition of plasma opsonized CPPD induced neutrophil chemiluminescence. In all experiments control samples never produced chemiluminescence values of greater than 5 mV and the addition of paclitaxel at all concentrations used in this study had no effect on the chemiluminescence values of controls.

3. Superoxide Generation

Figure 30A:
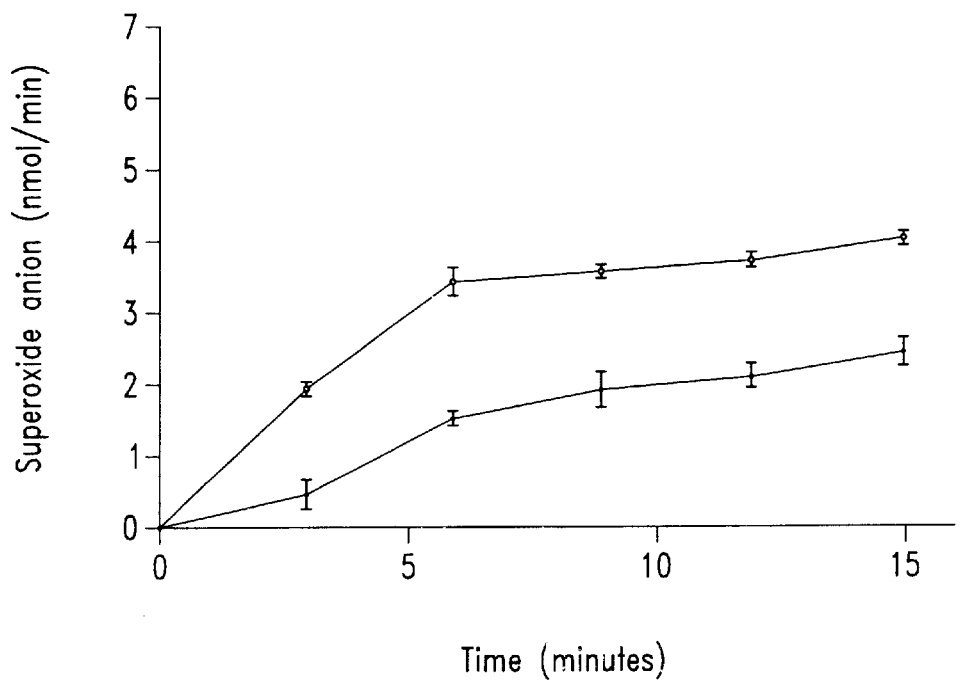
FIG. 30A is a graph which shows superoxide anion production by neutrophils ($5 \times 10^6$ cells/ml) in response to plasma opsonized CPPD crystals (50 mg/ml). Effect of paclitaxel at (○) no paclitaxel, (●) 28 $\mu$M, (Δ) Control (cells alone); n=3.
Figure 30B:
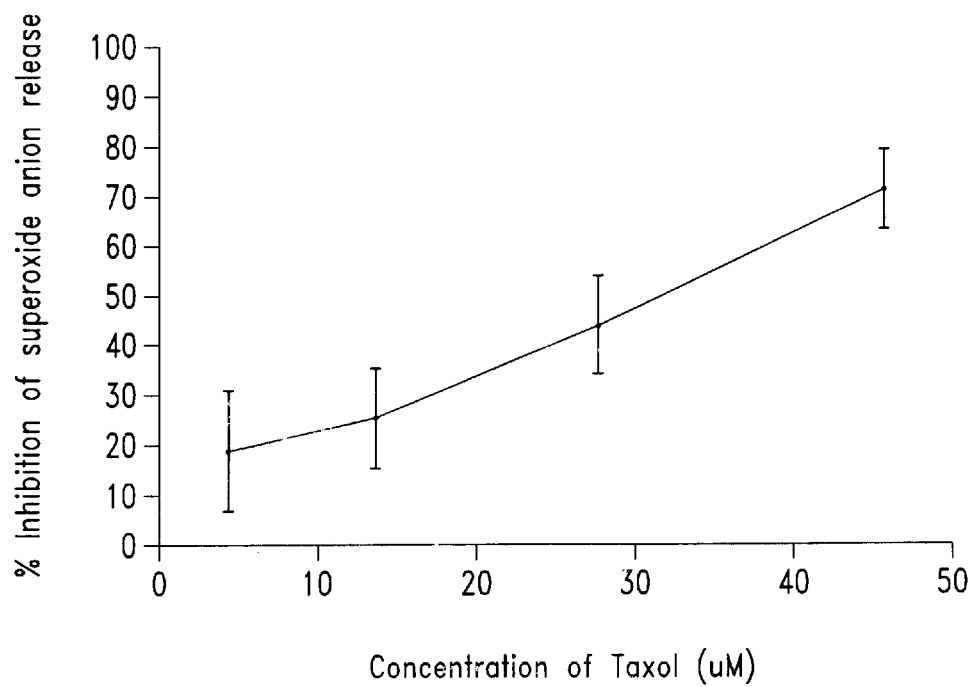
FIG. 30B is a graphic which shows the time course concentration dependence of paclitaxel inhibition of plasma opsonized CPPD crystal induced neutrophil superoxide anion production; n 3.
Figure 31A:
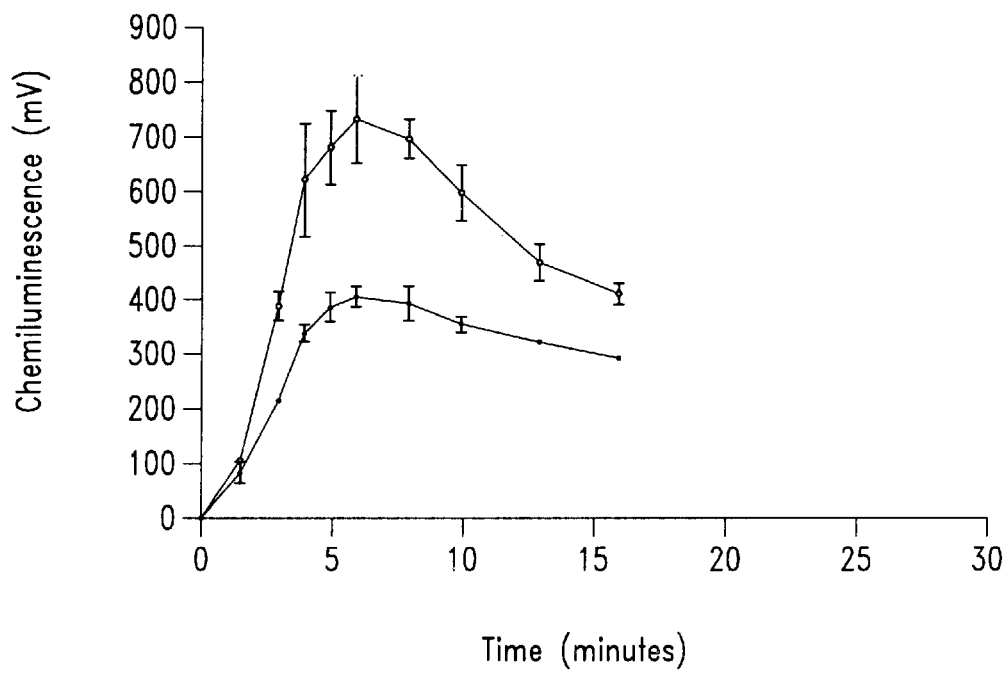
FIG. 31A is a graph which shows the chemiluminescence response of neutrophils ($5 \times 10^6$ cells/ml) in response to plasma opsonized zymozan (1 mg/ml). Effect of paclitaxel at (○) no drug, (●) 28 $\mu$M; n=3.
Figure 31B:
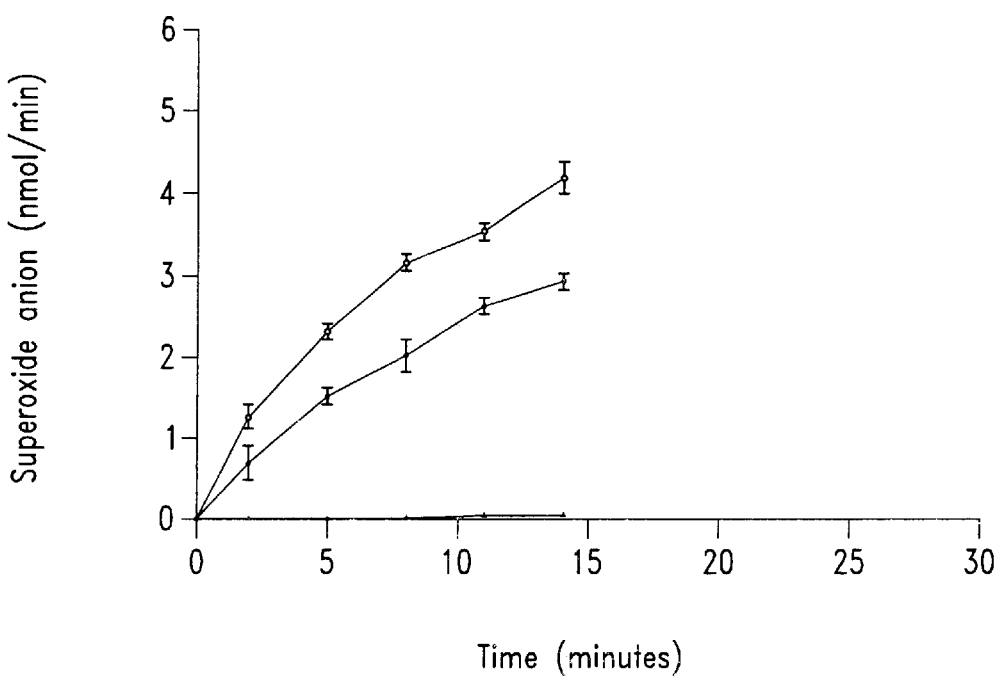
FIG. 31B is a graph which shows plasma opsonized zymosan induced neutrophil superoxide anion production. Effect of paclitaxel at (○) no paclitaxel, (●) 28 $\mu$M, (Δ) Control (cells alone); n 3.

The time course of plasma opsonised CPPD crystal induced superoxide anion production, as measured by the superoxide dismutase (SOD) inhibitable reduction of cytochrome c, is shown in FIG. 2. Treatment of the cells with paclitaxel at 28 µM produced a decrease in the amount of superoxide generated at all times. This decrease was significant at all times shown in FIG. 30A. The concentration dependence of this inhibition is shown in FIG. 30B. Stimulation of superoxide anion production by opsonised zymosan (FIG. 31B) showed a similar time course to CPPD induced activation. The inhibition of zymosan induced superoxide anion production by paclitaxel at 28 µM was less dramatic than the inhibition of CPPD activation but was significant at all times shown in FIG. 31B.

4. Neutrophil Degranulation

Figure 32A:
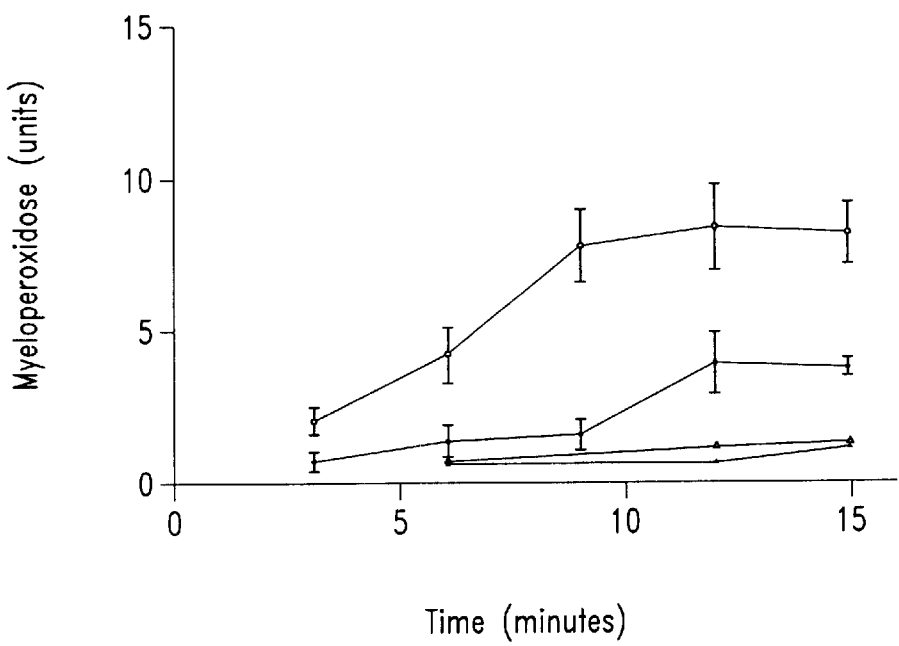
FIG. 32A is a graph which shows myeloperoxidase release from neutrophils ($5 \times 10^6$ cells/ml) in response to plasma opsonized CPPD crystals (50 mg/ml). Effect of paclitaxel at (○) no paclitaxel, (●) 28 $\mu$M. (Δ) Control (cells alone), (▲) Control (cells with paclitaxel at 28 $\mu$M); n=3.
Figure 32B:
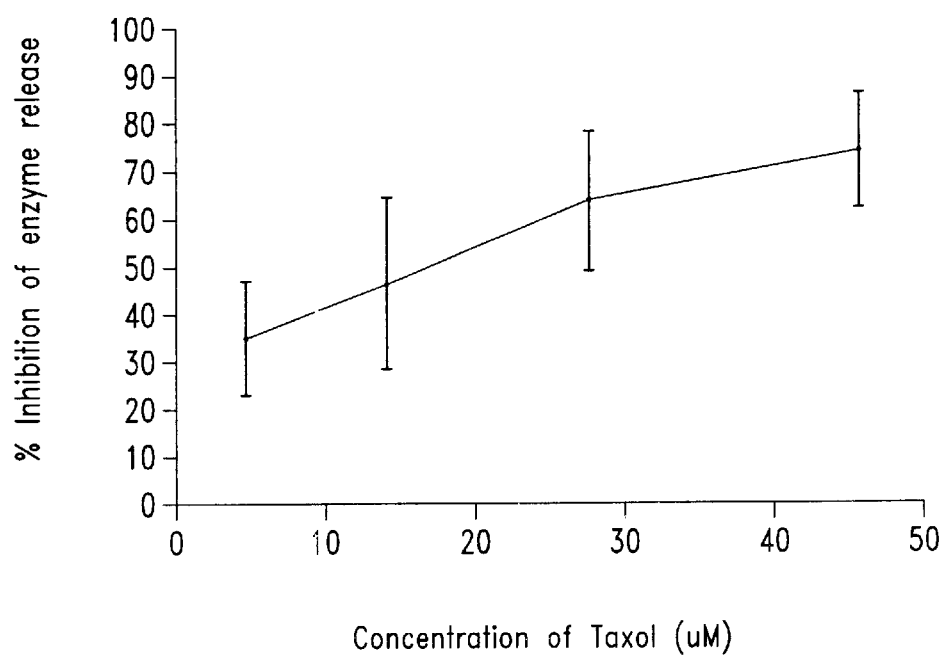
FIG. 32B is a graph which shows the concentration dependence of paclitaxel inhibition of myeloperoxidase release from neutrophils in response to plasma opsonized CPPD crystals; n 3.
Figure 33:
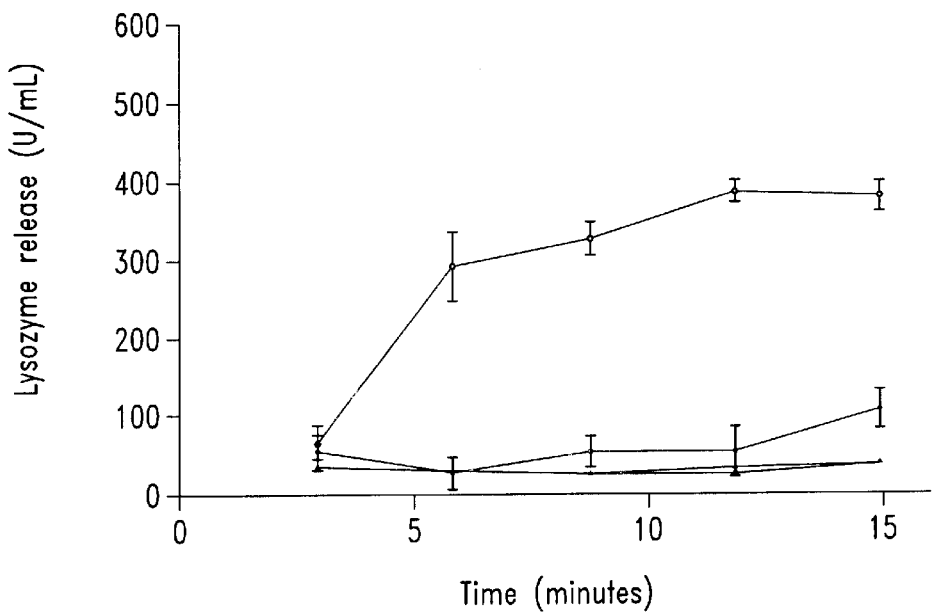
FIG. 33 is a graph which shows lysozyme release from neutrophils ($5 \times 10^6$/ml) in response to plasma opsonized CPPD crystals (50 mg/ml). Effect of paclitaxel at (○) no paclitaxel, (●) 28 $\mu$M, (Δ) Control (cells alone), (▲) Control (cells and paclitaxel at 28 $\mu$M); n 3.

Neutrophil degranulation was monitored by the plasma opsonized CPPD crystal induced release of myeloperoxidase and lysozyme or the plasma opsonized zymosan induced release of myeloperoxidase. It has been shown that sufficient amounts of these two enzymes are released into the extracellular media when plasma coated CPPD crystals are used to stimulate neutrophils without the need for the addition of cytochalasin B to the cells. FIGS. 32 and 33 show the time course of the release of MPO and lysozyme respectively, from neutrophils stimulated by plasma coated CPPD. FIG. 32A shows that paclitaxel inhibits myeloperoxidase release from plasma opsonized CPPD activated neutrophils in the first 9 minutes of the crystal-cell incubation. Paclitaxel significantly inhibited CPPD induced myeloperoxidase release at all times as shown in FIG. 32A. FIG. 32B shows the concentration dependence of paclitaxel inhibition of CPPD induced myeloperoxidase release.

Paclitaxel at 28 µM reduced lysozyme release and this inhibition of degranulation was significant at all times as shown in FIG. 33.

Only minor amounts of MPO and lysozyme were released when neutrophils were stimulated with opsonized zymosan. Despite these low levels it was possible to monitor 50% inhibition of MPO release after 9 minutes incubation in the presence of paclitaxel at 28 µM that was statistically significant ($p<0.05$) (data not shown).

C. Discussion

These experiments demonstrate that paclitaxel is a strong inhibitor of crystal induced neutrophil activation. In addition, by showing similar levels of inhibition in neutrophil responses to another form of particulate activator, opsonized zymozan, it is evident that the inhibitory activity of paclitaxel is not limited to neutrophil responses to crystals.

Example 23

Effect of Paclitaxel on Synoviocyte Proliferation

Two experiments were conducted in order to assess the effect of differing concentrations of paclitaxel on tritiated thymidine incorporation (a measurement of synoviocyte DNA synthesis) and synoviocyte proliferation in vitro.

A. Materials and Methods

1. $^3$H-Thymidine Incorporation into Synoviocytes

Synoviocytes were incubated with different concentrations of paclitaxel ($10^{-5}$ M, $10^{-6}$ M, $10^{-7}$ M, and $10^{-8}$ M) continuously for 6 or 24 hours in vitro. At these times, $1 \times 10^{-6}$ cpm of $^3$H-thymidine was added to the cell culture and incubated for 2 hours at 37° C. The cells were placed through a cell harvester, washed through a filter, the filters were cut, and the amount of radiation contained in the filter sections determined. Once the amount of thymidine incorporated into the cells was ascertained, it was used to determine the rate of cell proliferation. This experiment was repeated three times and the data collated together.

2. Synoviocyte Proliferation

Bovine synovial fibroblasts were grown in the presence and absence of differing concentrations ($10^{-5}$ M, $10^{-6}$ M, $10^{-7}$ M and $10^{-8}$ M) of paclitaxel for 24 hours. At the end of this time period the total number of viable synoviocyte cells was determined visually by dye exclusion counting using Trypan blue staining. This experiment was conducted 4 times and the data collated.

B. Results

1. $^3$H-Thymidine Incorporation into Synoviocytes

Figure 34:
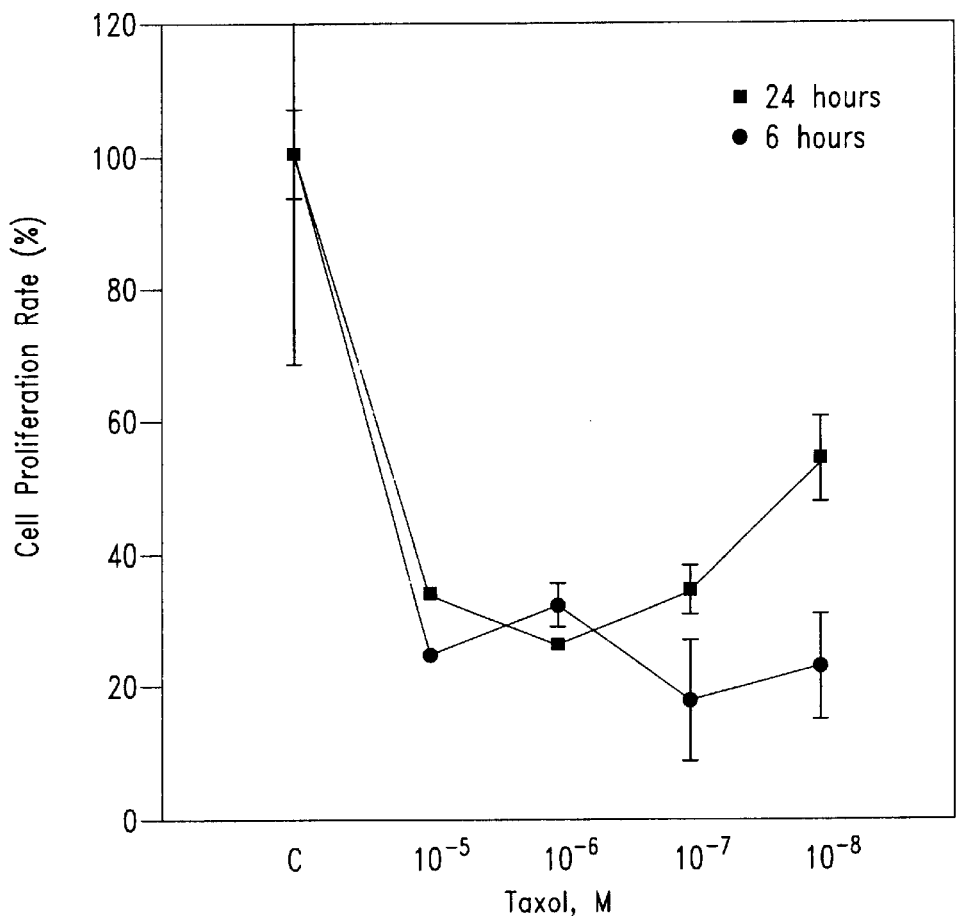
FIG. 34 is a graph which depicts proliferation of synoviocytes at various concentrations of paclitaxel.

This study demonstrated that paclitaxel at low concentrations inhibits the incorporation of 3H-thymidine (and by extension DNA synthesis) in synoviocytes at concentrations as low as $10^{-8}$ M. At six hours there was no significant difference in the between the degree of inhibition produced by the higher versus the lower concentrations of paclitaxel (see FIG. 34). However, by 24 hours some of the effect was lost at lower concentrations of the drug ($10^{-8}$ M), but was still substantially lower than that seen in control animals.

2. Synoviocyte Proliferation

Figure 35:
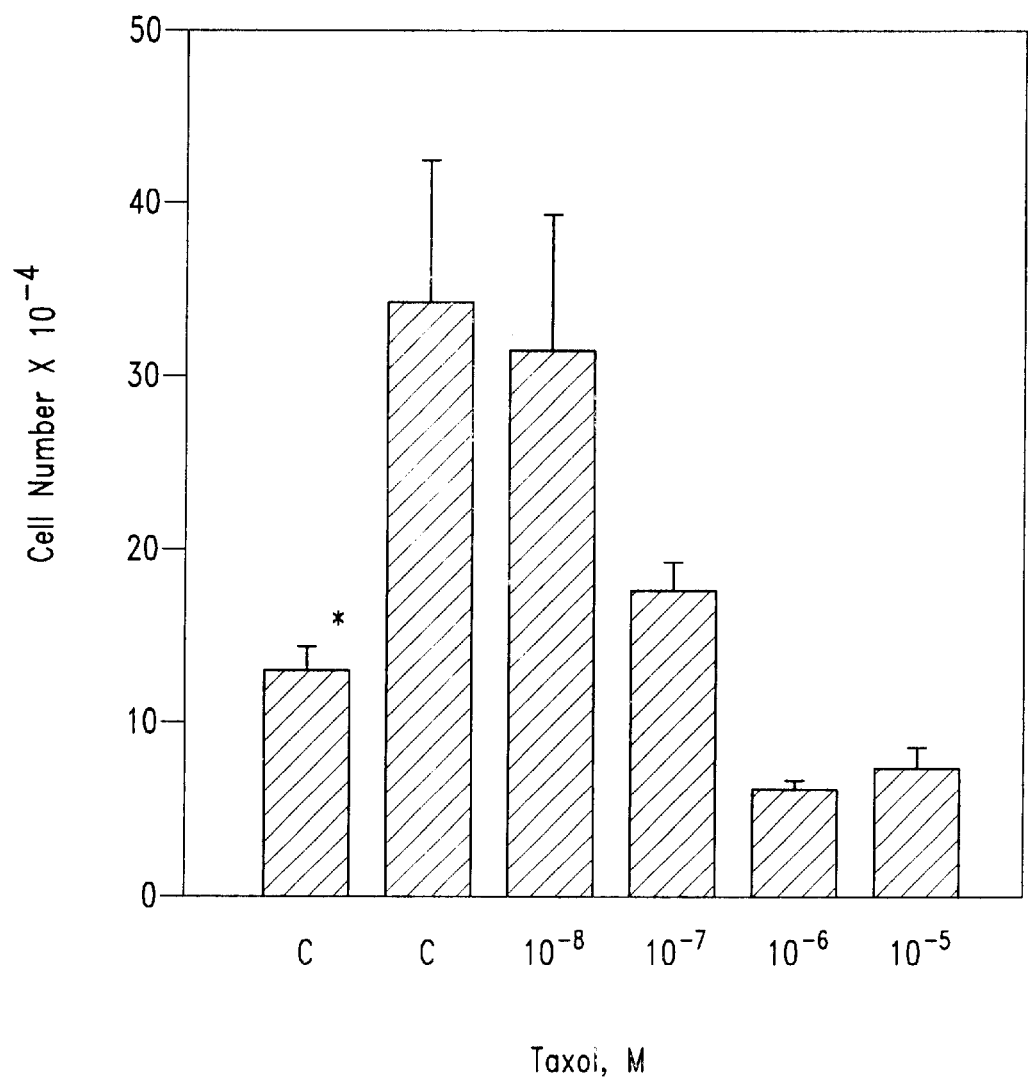
FIG. 35 is a bar graph which depicts the cytotoxicity of paclitaxel at various concentrations to proliferating synoviocytes.

This study demonstrated that paclitaxel was cytotoxic to proliferating synovial fibroblasts in a concentration dependent manner. Paclitaxel at concentrations as low as $10^{-7}$ M is capable of inhibiting proliferation of the synoviocytes (see FIG. 35). At higher concentrations of paclitaxel ($10^{-6}$ M and $10^{-5}$ M) the drug was toxic to the synovial fibroblasts in vitro.

C. Discussion

The above study demonstrates that paclitaxel is capable of inhibiting the proliferation of synovial fibroblasts at relatively low concentrations in vitro. Therefore, given the role of these cells in the development of pannus tissue and their growth during the pathogenesis of rheumatoid arthritis, blocking synoviocyte proliferation can be expected to favorably affect the outcome of the disease in vivo.

Example 24

Effect of Paclitaxel on Collagenase Expression

As noted above, collagenase production by a variety of tissues (synovial fibroblasts, endothelial cells, chondrocytes, and white blood cells) plays an critical role in the development of the pathology of arthritis. Degradation of the cartilage matrix by proteolytic enzymes represents an irreversible step in the development of the disease resulting in irreparable damage to the articular cartilage. Numerous attempts have been made to restore the balance between the enzymes which degrade connective tissue (matrix metalloproteinases—MMPs; collagenase is an important member of this family) and those which inhibit degradation (tissue inhibitors of metalloproteinases—TIMPs). Evidence suggests that the imbalance of proteolytic versus inhibitory activity which results in cartilage destruction is due to an excess of MMP activity as opposed to a paucity of TIMP activity. Treatment that decreases the amount of MMP activity may thus favorably influence the outcome of the disease.

C-fos is an oncogene transcription factor shown to be involved and required for the induction of genes involved in cell proliferation and collagenase expression. In cultured chondrocytes, both interleukin-1 (IL-1) and tumor necrosis factor (TNF) have been shown to stimulate c-fos expression and produce all of the signals necessary to induce the expression of collagenase. When IL-1 is administered to chondrocytes in vitro there is a transient increase in fos mRNA levels which peak 30–60 minutes later, while collagenase mRNA is detected 9 hours later and continues to increase up to 12 hours (data not shown) after IL-1 stimulation. The fos and collagenase mRNA can be detected using the respective cDNA probes and analyzed by Northern blot analysis. This allows the determination of agents capable of inhibiting collagenase production and an approximation of the step in the collagenase synthetic pathway that is affected by the treatment.

A. Materials and Methods

1. Effect of Paclitaxel on c-fos Expression

Chondrocytes were treated with different concentrations of paclitaxel ($10^{-6}$ M, $10^{-7}$ M, and $10^{-8}$ M) for 2 hours and then treated with TNFα (Sigma Chemical Co., St. Louis, Mo.) at 30 ng/ml for 1 hour. Human recombinant TNFα was dissolved in phosphate buffered saline (PBS) with 0.1% bovine serum albumin (BSA). Total RNA from bovine articular chondrocytes was isolated by the acidified guanidine isothiocyanate method and the levels of c-fos mRNA determined by Northern blot analysis. Denatured RNA samples (12 μg) were analyzed by gel electrophoresis in a denaturing 1% agarose gel, transferred to a nylon membrane (Bio-Rad), cross-linked with an ultraviolet cross-linker (Stratagene UV stratalinker 1800), and hybridized with $^{32}$P-labeled rat c-fos DNA. mRNA for tubulin and total RNA were used as controls. To determine tubulin mRNA, the blots described above were subsequently stripped of DNA and re-probed with $^{32}$P-labeled rat P-tubulin cDNA. This experimented was conducted three times and the data collated.

2. Effect of Paclitaxel on Collagenase Expression

Chondrocytes were treated with different concentrations of paclitaxel ($10^{-6}$ M and $10^{-7}$ M,) for 2 hours prior to the addition of IL-1 (20 ng/ml). The cells were then incubated for a further 16 hours. Total RNA from bovine articular chondrocytes was isolated by the acidified guanidine isothiocyanate method and the collagenase mRNA determined by Northern blot analysis. The RNA samples were prepared as described above using $^{32}$P-labeled rat collagenase cDNA.

B. Results

1. Effect of Paclitaxel on c-fos Expression

Figure 36A:
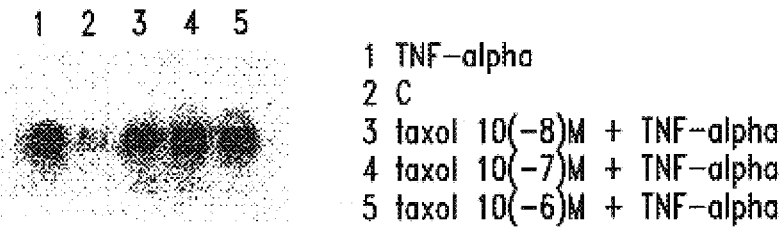
FIGS. 36A, 36B, and 36C are photographs of a series of gels which show the effect of various concentrations of paclitaxel on c-FOS expression.
Figure 36B:
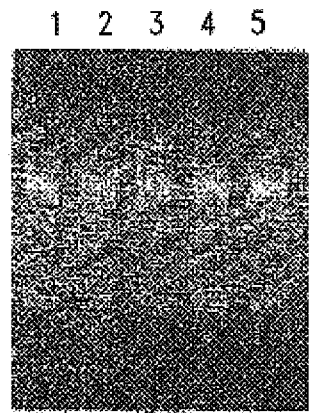
Figure 36C:
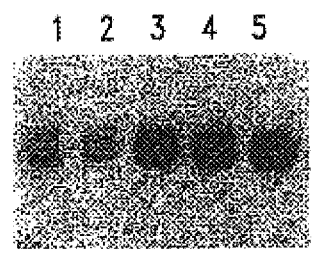

This experiment demonstrates that paclitaxel does not alter c-fos expression at any concentration (see FIG. 36). Comparable levels of c-fos mRNA were detectable in the controls and all of the experimental groups regardless of the paclitaxel concentration present. Total RNA and tubulin expression was similarly unaffected.

2. Effect of Paclitaxel on Collagenase Expression

Figure 37A:
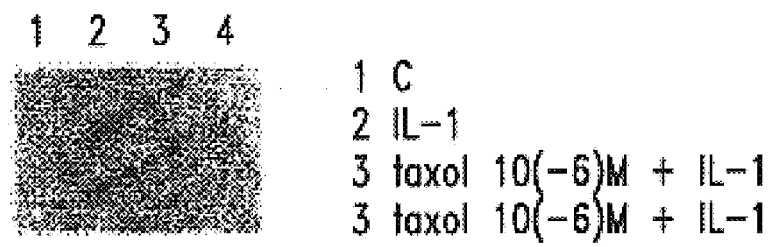
FIGS. 37A and 37B are photographs of a series of gels which show the effect of various concentrations of paclitaxel on collagenase expression.
Figure 37B:
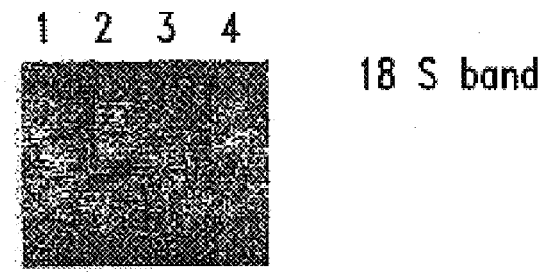

This experiment demonstrates that paclitaxel at a concentration of $10^{-6}$ M completely inhibited IL-1 induced collagenase expression. Collagenase mRNA was not detectable above background at this concentration of paclitaxel in vitro (see FIG. 37).

C. Discussion

Paclitaxel is capable of inhibiting collagenase production by chondrocytes in vitro at concentrations of $10^{-6}$M. This inhibition occurs downstream from the transcription factor activity of c-fos, but still represents a secondary gene response, as collagenase mRNA production is affected. As such, paclitaxel inhibition of collagenase production is not strictly due to interruption of the microtubules involved in the protein secretory pathway (which is dependent upon microtubular function for the movement of secretory granules), but acts at the level of the gene response to stimulation of collagenase production. Regardless of the mechanism of action, paclitaxel is capable of inhibiting collagenase production by at least one cell type known to produce this enzyme in the arthritic disease process.

Example 25

Effect of Paclitaxel on Chondrocyte Viability

While it is important that a disease modifying agent be capable of strongly inhibiting a variety of inappropriate cellular activities (proliferation, inflammation, proteolytic enzyme production) which occur in excess during the development of RA, it must not be toxic to the normal joint tissue. It is particularly critical that normal chondrocytes not be damaged, as this would hasten the destruction of the articular cartilage and lead to progression of the disease. In this example, the effect of paclitaxel on normal chondrocyte viability in vitro was examined.

Briefly, chondrocytes were incubated in the presence ($10^{-5}$ M, $10^{-7}$ M, and $10^{-9}$ M) or absence (control) of paclitaxel for 72 hours. At the end of this time period, the total number of viable chondrocytes was determined visually by dye exclusion counting using Trypan blue staining. This experiment was conducted 4 times and the data collated.

Figure 38:
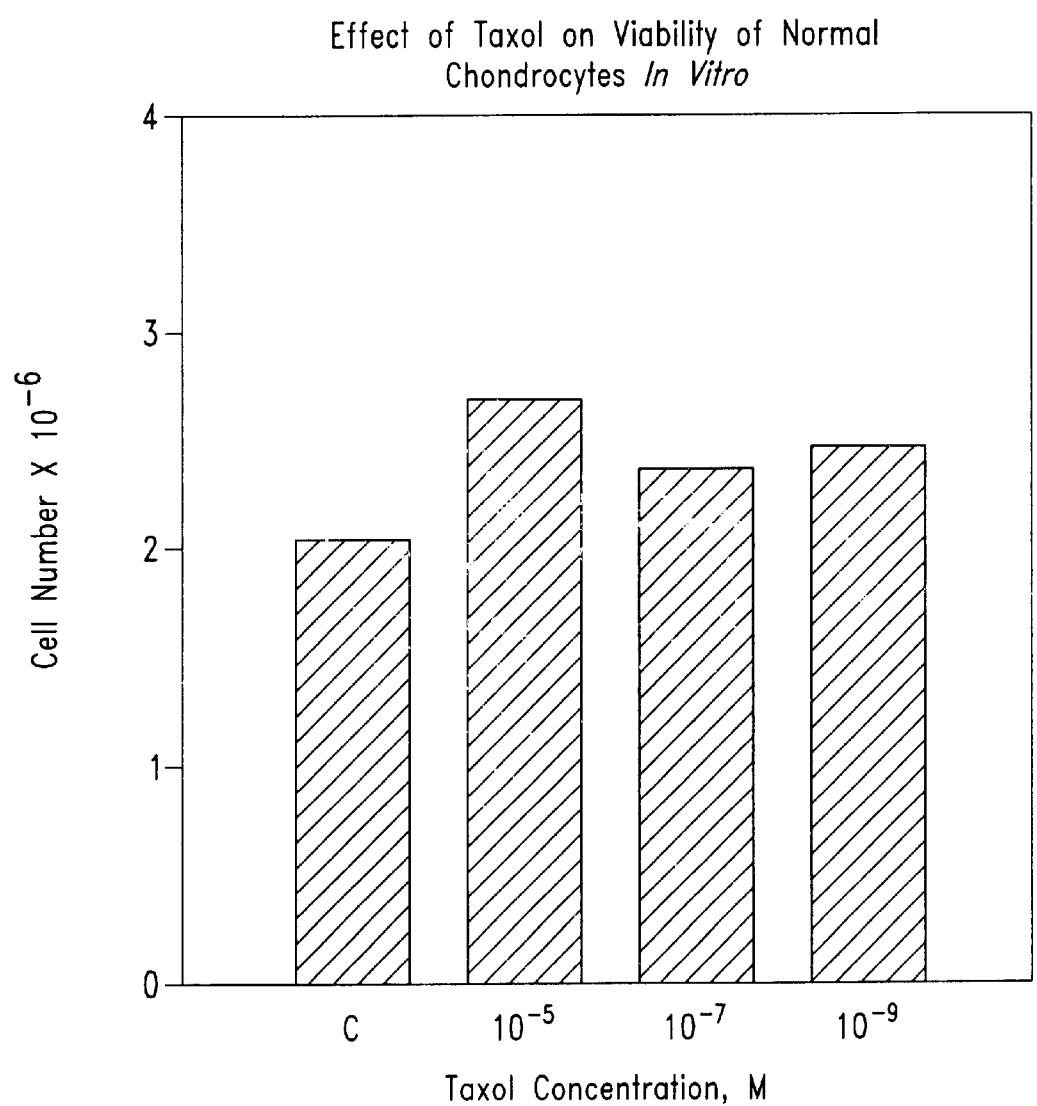
FIG. 38 is a bar graph which depicts the effects of paclitaxel on viability of normal chondrocytes in vitro.

Results of this experiment are shown in FIG. 38. Briefly, as is evident from FIG. 38, paclitaxel does not affect the viability of normal chondrocytes in vitro even at high concentrations ($10^{-5}$ M) of paclitaxel. More specifically, even at drug concentrations sufficient to block the pathological processes described in the preceding examples, there is no cytotoxicity to normal chondrocytes.

Example 26

Ophthalmic Drops Containing Paclitaxel or Prednisolone Acetate

Figure 48:
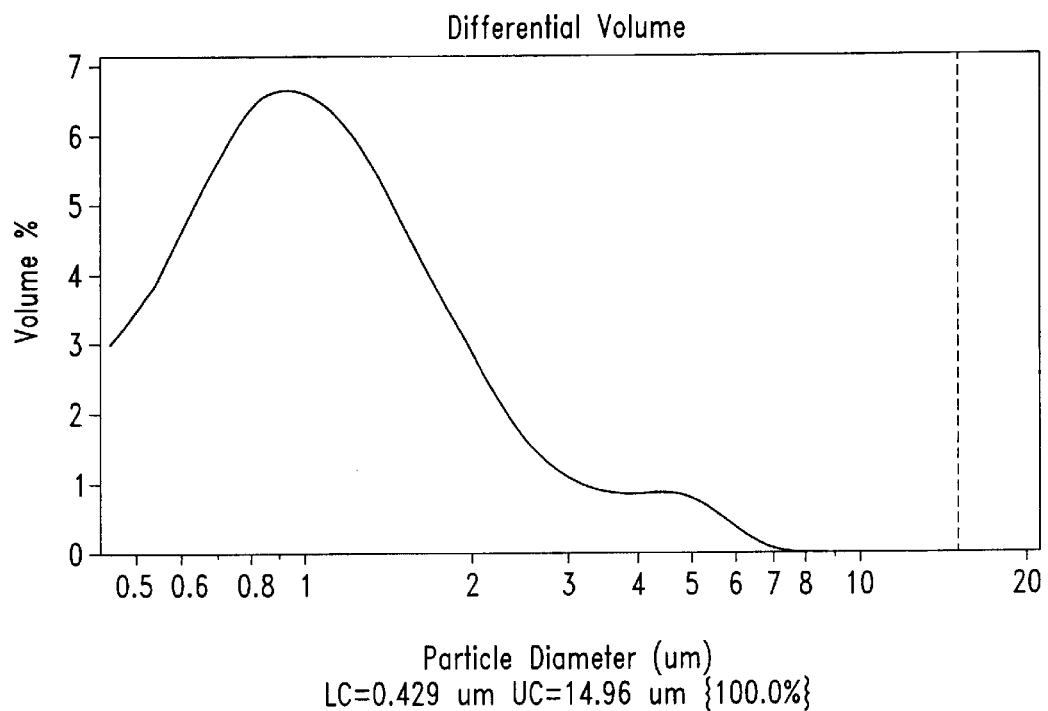
FIG. 48 is a graph of particle diameter ($\mu$m) determined by a Coulter® LS130 Particle Size Analysis.

Three formulations containing 0.3% paclitaxel for ophthalmic use were prepared. The particle size distribution of paclitaxel as received from a supplier was not within acceptable limits for ophthalmic use. In particular, for ophthalmic drops at least 90% of the particles should preferably be below 10 μm, with no particle above 20 μm. Two methods were used to reduce the particle size. The first method involved precipitating paclitaxel from its solution in acetone. Briefly, 150 mg of paclitaxel was dissolved in 5 ml of acetone. This solution was added in a gentle stream, with stirring, to 20 ml of Sterile water USP to precipitate the drug. The suspension was homogenized with the Dounce homogenizer until about 90% of the drug was under 10 μm. The suspension was allowed to stand for about 1 hour. The larger particles settled and were separated from the smaller ones by decantation. The larger particles were again reduced until all particles were under 20 μm (see FIG. 48). This suspension was added to the one previously decanted and the acetone was evaporated by heating at 50° C. for 2 hours and then in a vacuum oven at 30° C. and 25 torr overnight to remove the residual acetone. Sodium chloride (0.45 g) was dissolved in 5 ml Sterile water USP. This solution and 20 ml of 5% PVA solution were mixed with the paclitaxel suspension, made up to 50 ml with sterile water and bottled.

Figure 49:
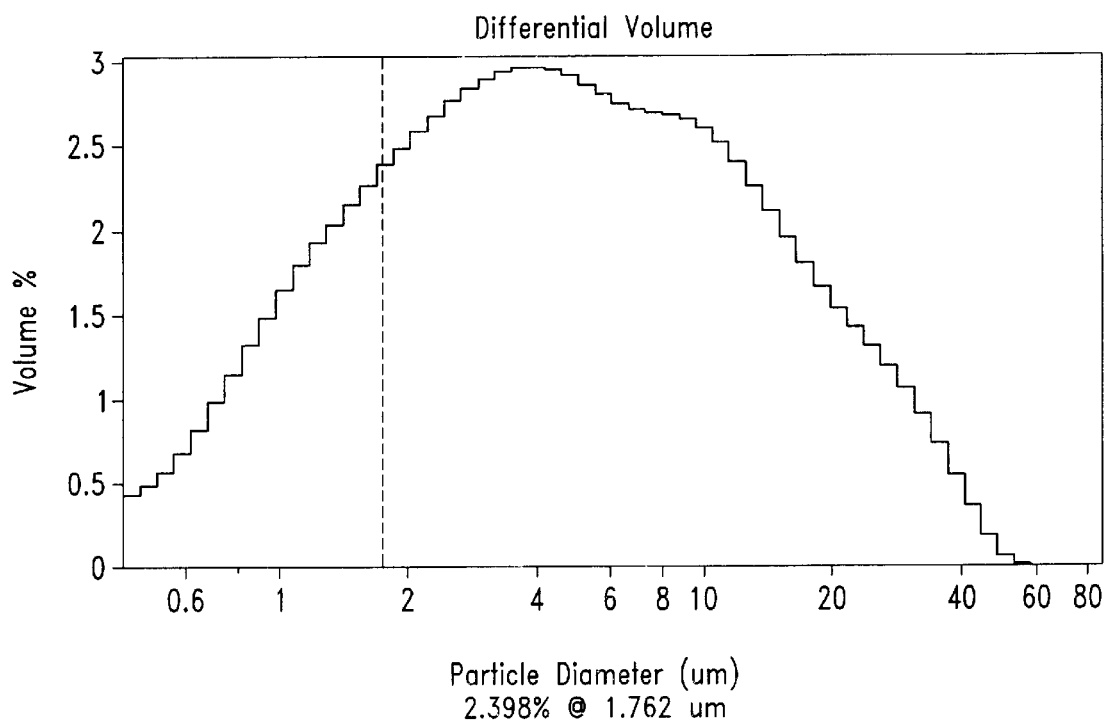
FIG. 49 is a graph of particle diameter ($\mu$m) determined by a Coulter® LS 130 Particle Size Analysis.

Paclitaxel suspension (0.3%) was also prepared by adding 150 mg of paclitaxel to 10 ml of sterile water and comminuted using the Fritsch Pulverizer for 15 minutes. It was not possible to produce particles lower than 60 μm with this method probably because the solid paclitaxel was not hard and brittle (see FIG. 49). The suspension was mixed with 5 ml sterile water containing 0.45 g of NaCl and 20 ml of 5% PVA solution and made up to 50 ml with sterile water.

Paclitaxel microspheres containing 10% paclitaxel in PCL were also prepared. Briefly, paclitaxel (60 mg) and PCL (540 mg) were dissolved in 3 ml of DCM, 20 ml of 3% PVA solution was added and homogenized with the Polytron homogenizer at point 3 setting for about 1 minute. The emulsion was poured into a 30 ml beaker and stirred until the microspheres were formed (about 3 hours). This suspension was placed in a vacuum oven, at 30° C. and 25 torr, overnight to remove residual DCM. The small microsphere suspension (15 ml) was decanted and evaporated under vacuum to about 5 ml and assayed for paclitaxel. This suspension was mixed with 2 ml solution of NaCl (0.45 g) solution and made up to 10 ml with sterile water.

Prednisolone acetate suspension containing 1% drug was prepared by homogenizing the appropriate amount of the drug (as received) in 20 ml of 5% PVA, NaCl solution was added and made up to volume with sterile water.

Example 27

Paclitaxel in an Animal Model of Corneal Neovascularization

Induction of Corneal Neovascularization

Corneal angiogenesis is induced in male New Zealand white rabbits (2.5 to 3.0 kg) essentially as described by Scroggs et al., *Invest. Ophthalmol. Vis. Sc.* 32:2105–2111, 1991. Briefly, rabbits are anesthetized with a subcutaneous injection of 0.15 cc of a 1:1 mixture of ketamine (80 mg/ml) and xylazine (4 mg/ml), and the eyes cauterized by applying the tip of a new silver-potassium nitrate applicator (75% silver nitrate: 25% potassium nitrate; Graham-Field, Hauppage, N.Y.) 3 to 4 millimeters from the corneo-scleral limbus.

Immediately following chemical cauterization, one drop of the study solution (e.g., the study solutions may be vehicle alone, prednisolone acetate 1%, or 0.3% paclitaxel in suspension) is applied to the cauterized eyes. Gentamicin ophthalmic ointment is then applied to the treated eyes. Over the next two weeks, one drop of the study solution is applied four times daily.

In a second study, 0.5 ml aliquots of a 10% paclitaxel-loaded microsphere suspension and a 20% paclitaxel-loaded thermopaste is administered via subconjuctival injection to the experimental animals.

On the eighth day and fourteenth following cauterization of the corneas, all animals are re-anesthetized as described above, and the corneas photographed using a Nikon biomicroscope and Kodak ASA 180 tungsten film under microscope incandescent illumination. The highest magnification that incorporates the entire cornea is used.

The photographs are randomly presented to a masked observer who grades the corneal vessels based upon a 0 to 4 scale of vessel density, and who measures the total extent in clock hours of circumferential corneal neovascularization. Vessel density grade is based on two standard photographs obtained from pilot experiments that had been assigned grades 2 (moderate vessel density) and 4 (severe vessel density) respectively. Grades 1 and 3 were established be interpolation; grade 0 is applied to corneas that demonstrate a central cautery scar, but the absence of new vessel growth.

Differences in both corneal vessel density and extent, in terms of clock hours of involvement, is analyzed using non-paired Student's t tests. Tests are two-tailed, with a p value of $\leq 0.05$ considered significant. Measures are reported as mean±standard deviation.

Example 28

Modification of Paclitaxel Release from Thermopaste Using Low Molecular Weight Poly(D, L, Lactic Acid)

As discussed above, depending on the desired therapeutic effect, either quick release or slow release polymeric carriers may be desired. For example, polycaprolactone (PCL) and mixtures of PCL with poly(ethylene glycol) (PEG) produce compositions which release paclitaxel over a period of several months. In particular, the diffusion of paclitaxel in the polymers is very slow due to its large molecular size and extreme hydrophobicity.

On the other hand, low molecular weight poly(DL-lactic acid) (PDLLA) gives fast degradation, ranging from one day to a few months depending on its initial molecular weight.

The release of paclitaxel, in this case, is dominated by polymer degradation. Another feature of low molecular weight PDLLA is its low melting temperature, (i.e., 40° C.–60° C.), which makes it suitable material for making Thermopaste. As described in more detail below, several different methods can be utilized in order to control the polymer degradation rate, including, for example, by changing molecular weight of the PDLLA, and/or by mixing it with high mol wt. PCL, PDLLA, or poly(lactide-co-glyocide) (PLGA).

A. Experimental Materials

D,L-lactic acid was purchased from Sigma Chemical Co., St. Louis, Mo. PCL (molecular weight $10^{-20,000}$) was obtained from Polysciences, Warrington, Pa. High molecular weight PDLLA (intrinsic viscosity 0.60 dl/g) and PLGA (50:50 composition, viscosity 0.58 dl/g) were from Birmingham Polymers.

B. Synthesis of Low Molecular Weight PDLLA

Low molecular weight PDLLA was synthesized from DL-lactic acid through polycondensation. Briefly, DL-lactic acid was heated in a glass beaker at 200° C. with nitrogen purge and magnetic stirring for a desired time. The viscosity increased during the polymerization, due to the increase of molecular weight. Three batches were obtained with different polymerization times, i.e., 40 min (molecular weight 800), 120 min, 160 min.

C. Formulation of Paclitaxel Thermopastes

Paclitaxel was loaded, at 20%, into the following materials by hand mixing at a temperature about 60° C.

1. low molecular weight PDLLA with polymerization time of 40 min.
2. low molecular weight PDLLA with polymerization time of 120 min.
3. low mol. wt PDLLA with polymerization time of 160 min.
4. a mixture of 50:50 high molecular weight PDLLA and low molecular weight PDLLA 40 min.
5. a mixture of 50:50 high molecular weight PLGA and low molecular weight PDLLA 40 min.
6. mixtures of high molecular weight PCL and low molecular weight. PDLLA 40 min with PCL:PDLLA of 10:90, 20:80, 40:60, 60:40, and 20:80. Mixtures of high molecular weight PDLLA or PLGA with low molecular weight. PDLLA were obtained by dissolving the materials in acetone followed by drying.

D. Release Study

The release of paclitaxel into PBS albumin buffer at 37° C. was measured as described above with HPLC at various times.

E. Results

Low molecular weight PDLLA 40 min was a soft material with light yellow color. The color is perhaps due to the oxidation during the polycondensation. Low molecular weight PDLLA 120 min (yellow) and 160 min (brown) were brittle solids at room temperature. They all become melts at 60° C. Mixtures of 50:50 high molecular weight PDLLA or PLGA with low molecular weight PDLLA 40 min also melted about 60° C.

During the release, low molecular weight PDLLA 40 min and 120 min broke up into fragments within one day, other materials were intact up to this writing (3 days).

Figure 50:
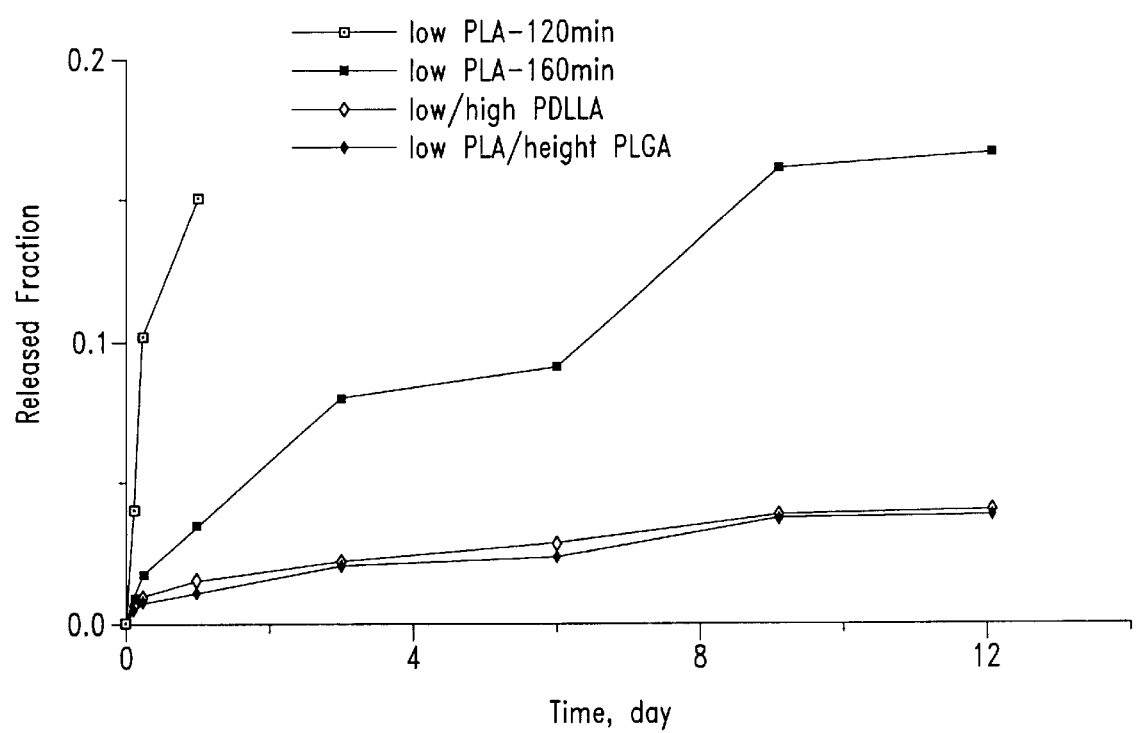
FIG. 50 is a graph which shows paclitaxel release from various polymeric formulations.

The release of paclitaxel from formulations 2–5 were shown in FIG. 50. Low molecular weight PDLLA 40 min and 120 min gave the fastest release due to the break up of the paste. The release was perhaps solubility limited. Low molecular weight PDLLA 160 min. also gave a fast release yet maintained an intact pellet. For example, 10% of loaded paclitaxel was released with one day. The 50:50 mixtures of high molecular weight PDLLA or PLGA with low molecular weight PDLLA 40 min were slower, i.e., 3.4% and 2.2% release within one day.

Although not specifically set forth above, a wide variety of other polymeric carriers may be manufactured, including for example, (1) low molecular weight (500–10,000) poly (D,L-lactic acid), poly(L-lactic acid), poly(glycolic acid), poly(6-hydroxycaproic acid), poly(5-hydroxyvaleric acid), poly(4-hydroxybutyric acid), and their copolymers; (2) blends of above (#1) above; (3) blends of (#1) above with high molecular weight poly(DL-lactic acid), poly(L-lactic acid), poly(glycolic acid), poly(6-hydroxycaproic acid), poly(5-hydroxyvaleric acid), poly(4-hydroxybutyric acid), and their copolymers; and (4) copolymers of poly(ethylene glycol) and pluronics with poly(D,L-lactic acid), poly(L-lactic acid), poly(glycolic acid), poly(6-hydroxycaproic acid), poly(5-hydroxyvaleric acid), poly(4-hydroxybutyric acid), and their copolymers.

Example 29

Surfactant Coated Microspheres

A. Materials and Methods

Microspheres were manufactured from Poly (DL) lactic acid (PLA), poly methylmethacrylate (PMMA), polycaprolactone (PCL) and 50:50 Ethylene vinyl acetate (EVA):PLA essentially as described in Example 8. Size ranged from 10 to 100 um with a mean diameter 45 um.

Human blood was obtained from healthy volunteers. Neutrophils (white blood cells) were separated from the blood using dextran sedimentation and Ficoll Hypaque centrifugation techniques. Neutrophils were suspended at 5 million cells per ml in Hanks Buffered Salt Solution ("HBSS").

Neutrophil activation levels were determined by the generation of reactive oxygen species as determined by chemiluminescence. In particular, chemiluminescence was determined by using an LKB luminometer with 1 uM luminol enhancer. Plasma precoating (or opsonization) of microspheres was performed by suspending 10 mg of microspheres in 0.5 ml of plasma and tumbling at 37° C. for 30 min.

Microspheres were then washed in 1 ml of HBSS and the centrifuged microsphere pellet added to the neutrophil suspension at 37° C. at time t=0. Microsphere surfaces were modified using a surfactant called Pluronic F127 (BASF) by suspending 10 mg of microspheres in 0.5 ml of 2% w/w solution of F127 in HBSS for 30 min at 37° C. Microspheres were then washed twice in 1 ml of HBSS before adding to neutrophils or to plasma for further precoating.

B. Results

Figure 51:
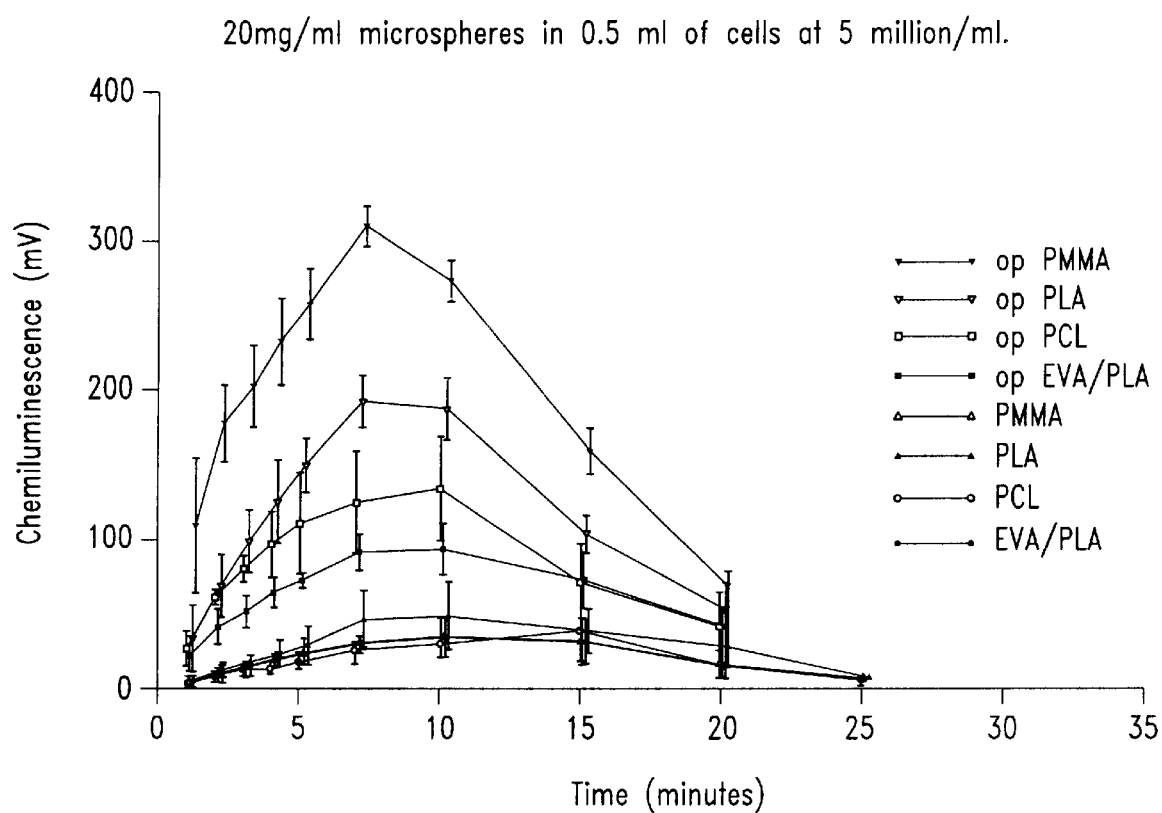
FIG. 51 is a graph which shows the effect of plasma opsonization of polymeric microspheres on the chemiluminescence response of neutrophils (20 mg/ml microspheres in 0.5 ml of cells (conc. $5 \times 10^6$ cells/ml) to PCL microspheres.
Figure 52:
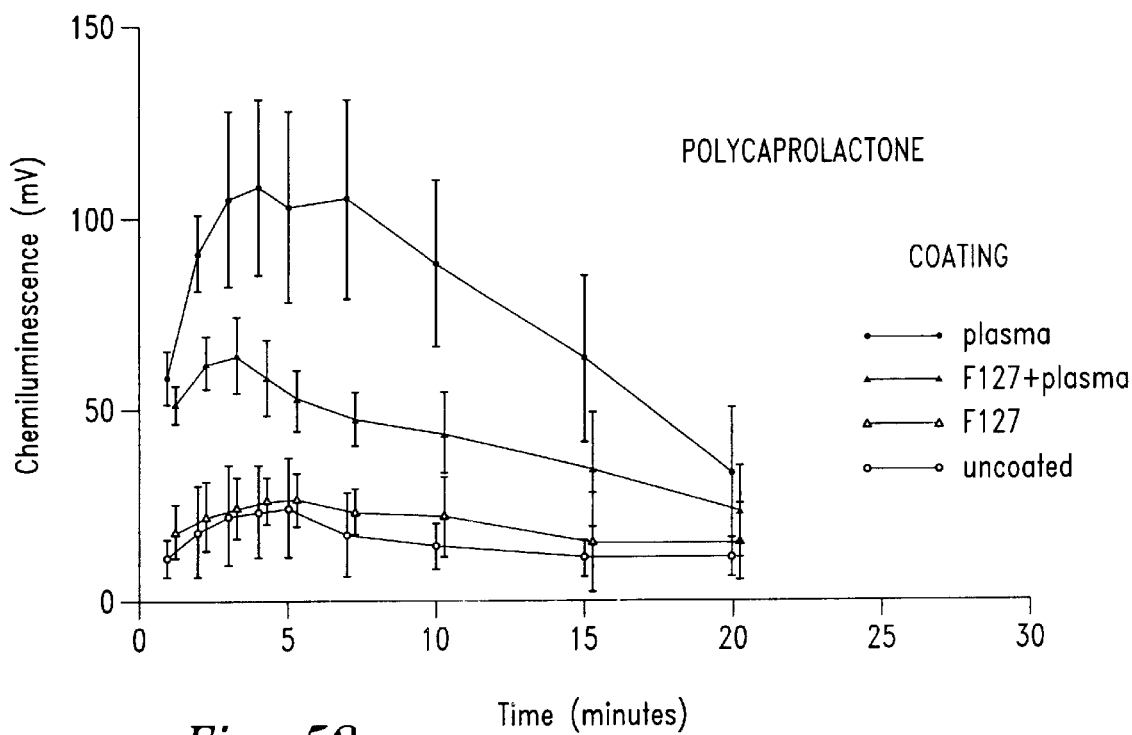
FIG. 52 is a graph which shows the effect of precoating plasma +/−2% pluronic F127 on the chemiluminescence response of neutrophils ($5 \times 10^6$ cells/ml) to PCL microspheres.
Figure 53:
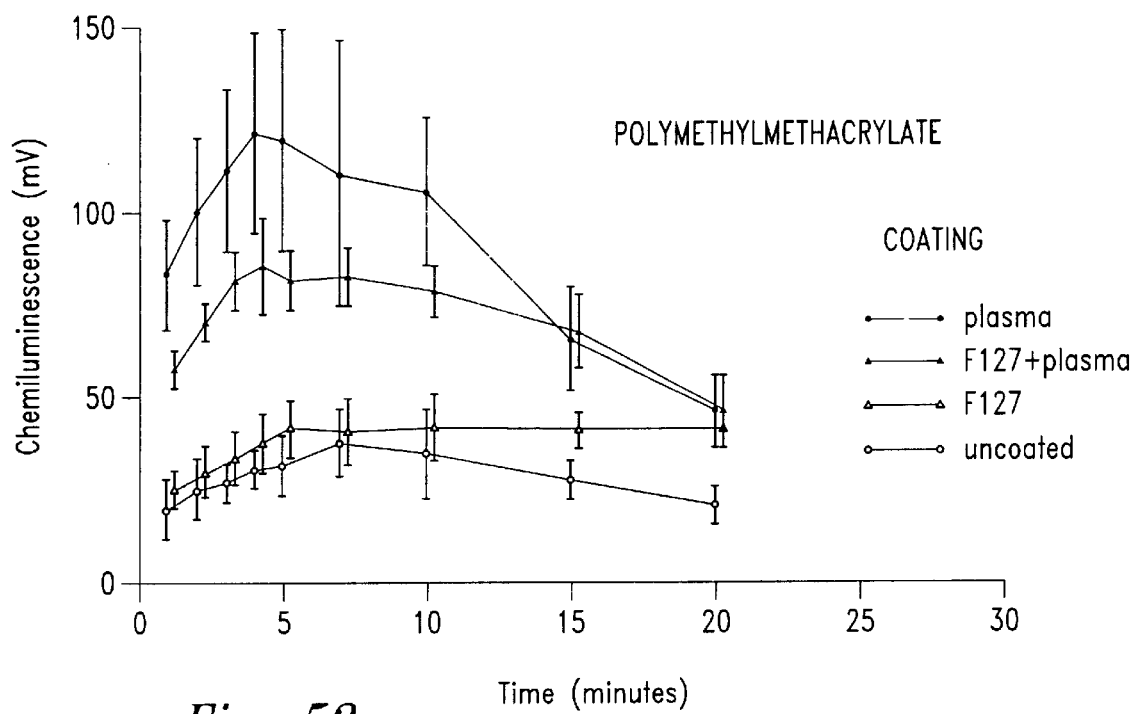
FIG. 53 is a graph which shows the effect of precoating plasma +/−2% pluronic F127 on the chemiluminescence response of neutrophils (5×10⁶ cells/ml) to PMMA microspheres.
Figure 54:
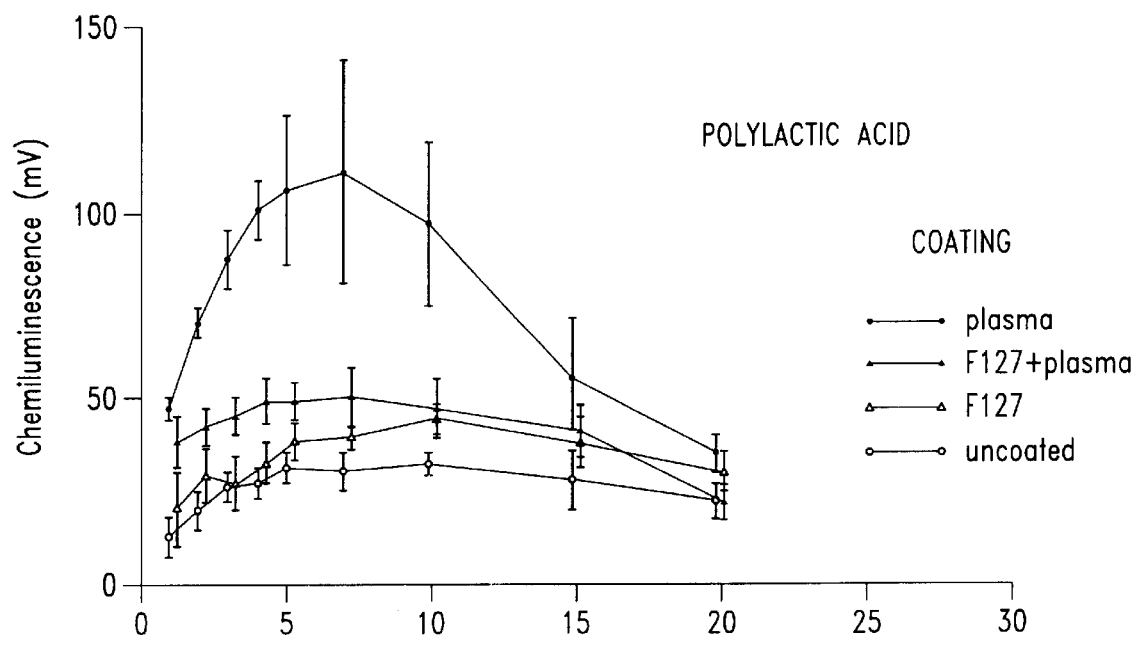
FIG. 54 is a graph which shows the effect of precoating plasma +/−2% pluronic F127 on the chemiluminescence response of neutrophils (5×10⁶ cells/ml) to PLA microspheres.
Figure 55:
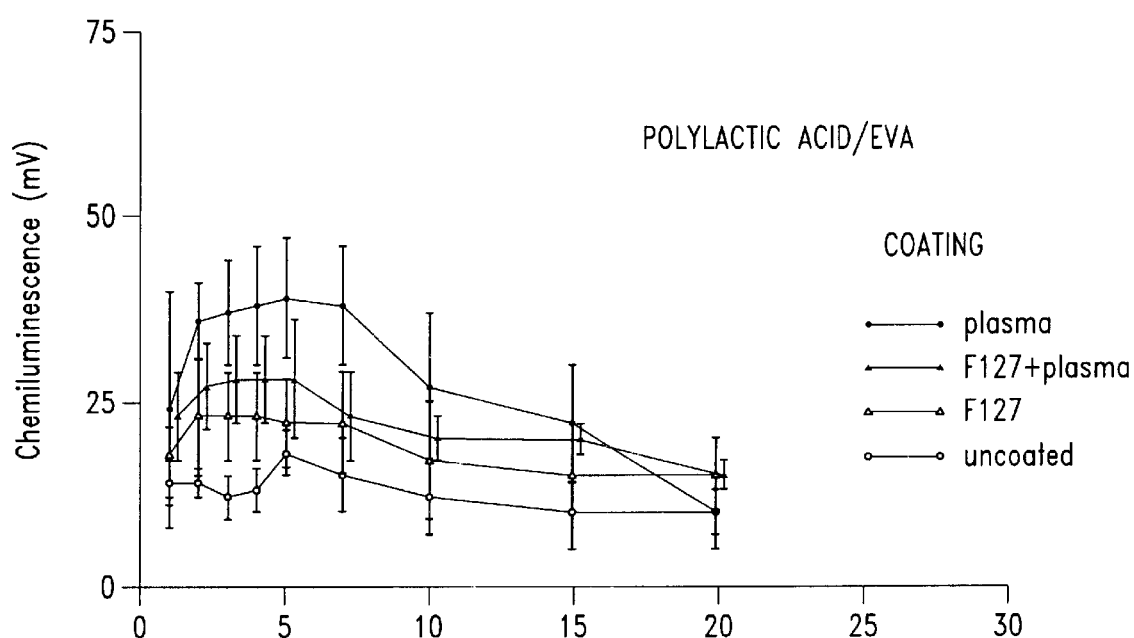
FIG. 55 is a graph which shows the effect of precoating plasma +/−2% pluronic F127 on the chemiluminescence response of neutrophils (5×10⁶ cells/ml) to EVA:PLA microspheres.
Figure 56:
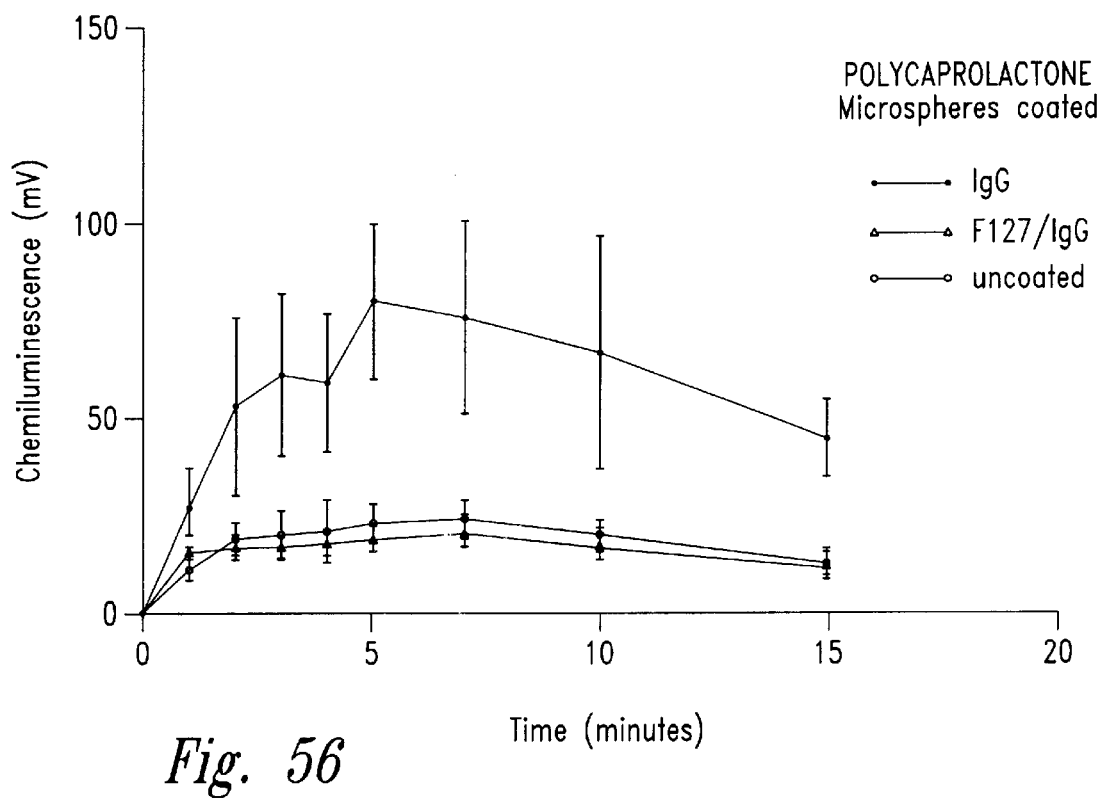
FIG. 56 is a graph which shows the effect of precoating IgG (2 mg/ml), or 2% pluronic F127 then IgG (2 mg/ml) on the chemiluminescence response of neutrophils to PCL microspheres.
Figure 57:
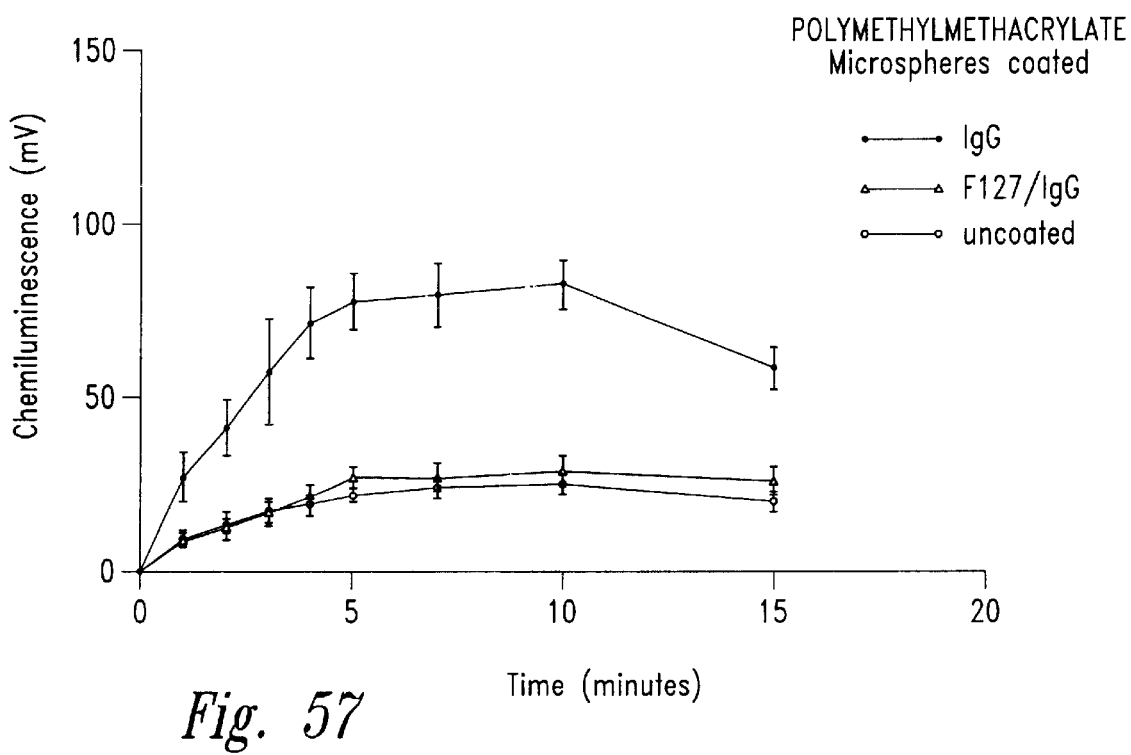
FIG. 57 is a graph which shows the effect of precoating IgG (2 mg/ml), or 2% pluronic F127 then IgG (2 mg/ml) on the chemiluminescence response of neutrophils to PMMA microspheres.
Figure 58:
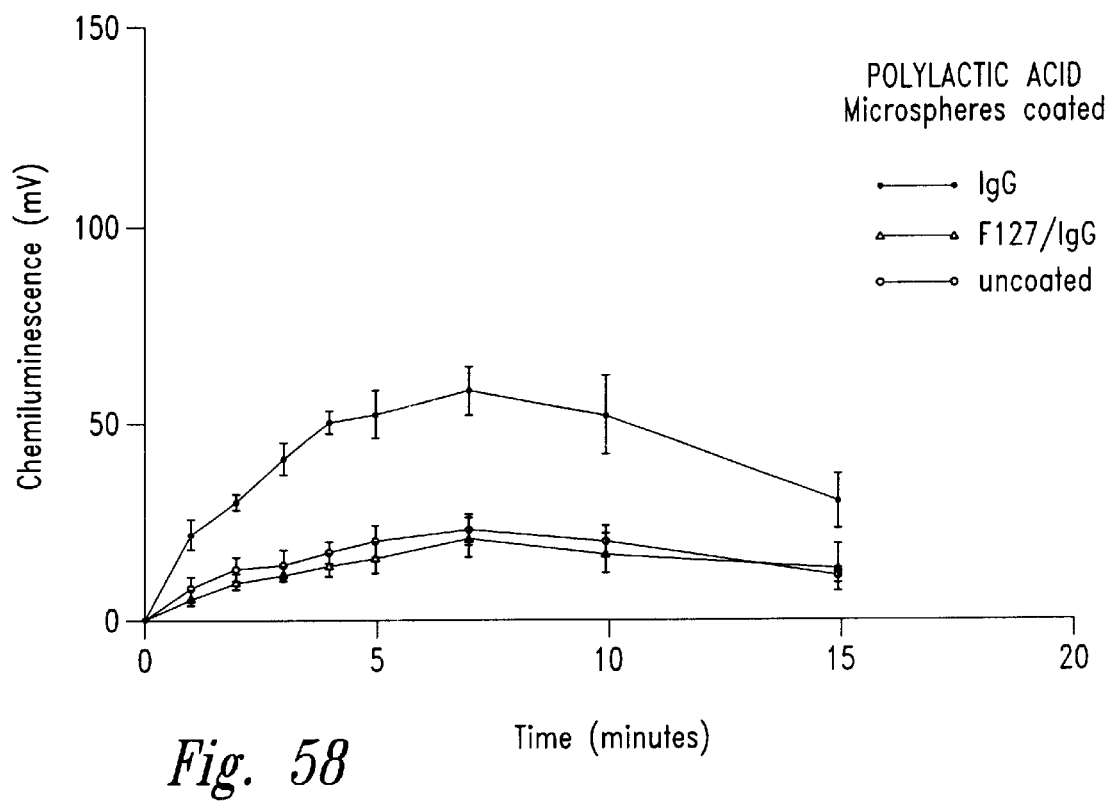
FIG. 58 is a graph which shows the effect of precoating IgG (2 mg/ml), or 2% pluronic F127 then IgG (2 mg/ml) on the chemiluminescence response of neutrophils to PVA microspheres.
Figure 59:
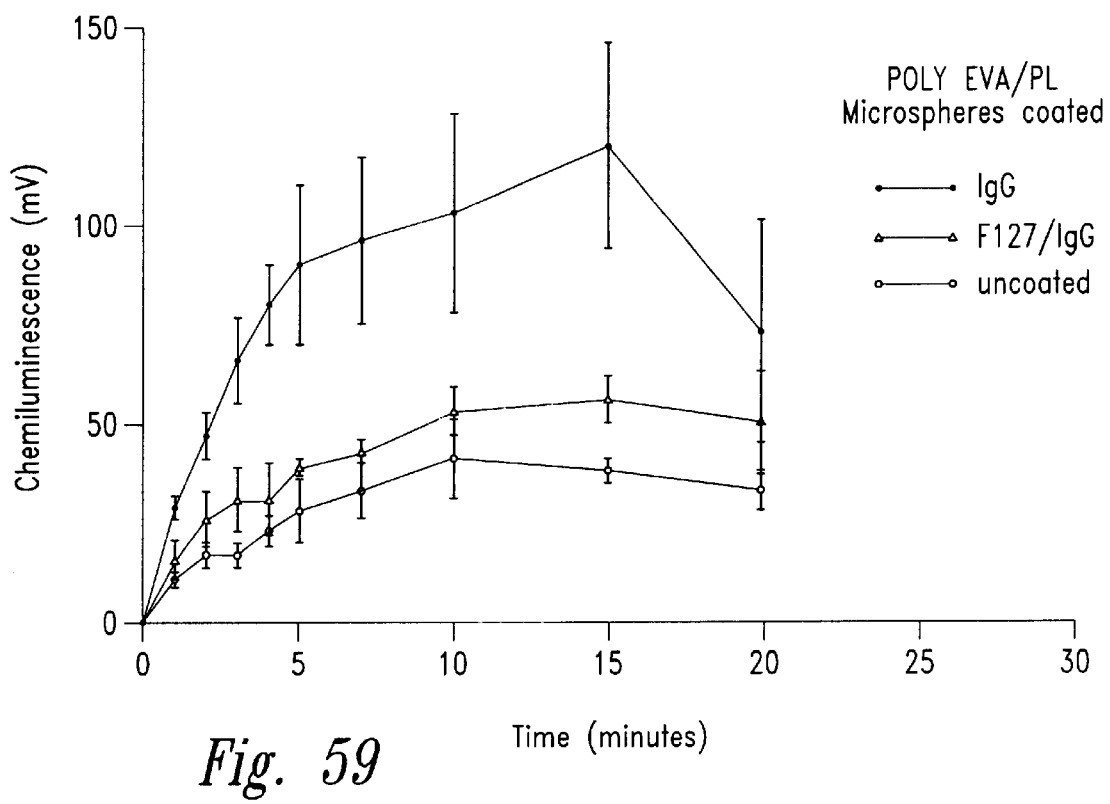
FIG. 59 is a graph which shows the effect of precoating IgG (2 mg/ml), or 2% pluronic F127 then IgG (2 mg/ml) on the chemiluminescence response of neutrophils to EVA:PLA microspheres.

FIG. 51 shows that the untreated microspheres give chemiluminescence values less than 50 mV. These values represent low levels of neutrophil activation. By way of comparison, inflammatory microcrystals might give values close to 1000 mV, soluble chemical activators might give values close to 5000 mV. However, when the microspheres are precoated with plasma, all chemiluminescence values are amplified to the 100 to 300 mV range (see FIG. 51). These levels of neutrophil response or activation can be considered mildly inflammatory. PMMA gave the biggest response and could be regarded as the most inflammatory. PLA and PCL both become three to four times more potent in activating neutrophils after plasma pretreatment (or opsonization) but there is little difference between the two polymers in this regard. EVA:PLA is not likely to be used in angiogenesis formulations since the microspheres are difficult to dry and resuspend in aqueous buffer. This effect of plasma is termed opsonization and results from the adsorption of antibodies or complement molecules onto the surface. These adsorbed species interact with receptors on white blood cells and cause an amplified cell activation.

FIGS. 52–55 describe the effects of plasma precoating of PCL, PMMA, PLA and EVA:PLA respectively as well as showing the effect of pluronic F127 precoating prior to plasma precoating of microspheres. These figures all show the same effect: (1) plasma precoating amplifies the response; (2) Pluronic F127 precoating has no effect on its own; (3) the amplified neutrophil response caused by plasma precoating can be strongly inhibited by pretreating the microsphere surface with 2% pluronic F127.

The nature of the adsorbed protein species from plasma was also studied by electrophoresis. Using this method, it was shown that pretreating the polymeric surface with Pluronic F127 inhibited the adsorption of antibodies to the polymeric surface.

FIGS. 56–59 likewise show the effect of precoating PCL, PMMA, PLA or EVA:PLA microspheres (respectively) with either IgG (2 mg/ml) or 2% pluronic F127 then IgG (2 mg/ml). As can be seen from these figures, the amplified response caused by precoating microspheres with IgG can be inhibited by treatment with pluronic F127.

This result shows that by pretreating the polymeric surface of all four types of microspheres with Pluronic F127, the "inflammatory" response of neutrophils to microspheres may be inhibited.

Example 30

Preparation of Low Molecular Weight Poly(D,L-Lactic Acid)

Five hundred grams of D,L-lactic acid (Sigma Chemical Co., St. Louis, Mo.) was heated in a heating mantle at 190° C. for 90 minutes under a stream of nitrogen gas. This process produced 400 g of poly(D,L-lactic acid) with a molecular weight of 700–800 as determined by end group titration and gel permeation chromatography (Fukusaki et al, Eur. Polym. J. 25(10):1019–1026, 1989).

Example 31

Preparation of Polymeric Compositions Containing Gelatinized Paclitaxel

A. Preparation of Polymers

Two hundred milligrams of gelatin (Type B, bloom strength 225, Fisher Scientific) 200 mg of NaCl, or 100 mg of gelatin and 100 mg of NaCl were dissolved in 0.5 mL of water. Next, 200 mg of paclitaxel was dissolved in 0.5 mL of ethanol. The dissolved gelatin, salt, or gelatin and salt were then added to the paclitaxel and triturated on a petri dish incubating in a water bath at 80° C., until dry. The precipitate was then ground in a mortar and pestle and sieved through either no. 60 or no. 140 mesh (Endecott, London, England). (No. 60 mesh produces larger granules and no. 140 mesh produces smaller granules.)

Polycaprolactone was then heated to 60° C., and granules added to a final ratio of 40:60 (w/w). The polymeric composition was placed into a 1 ml syringe and extruded.

B. Analysis of Paclitaxel Release

Figure 39:
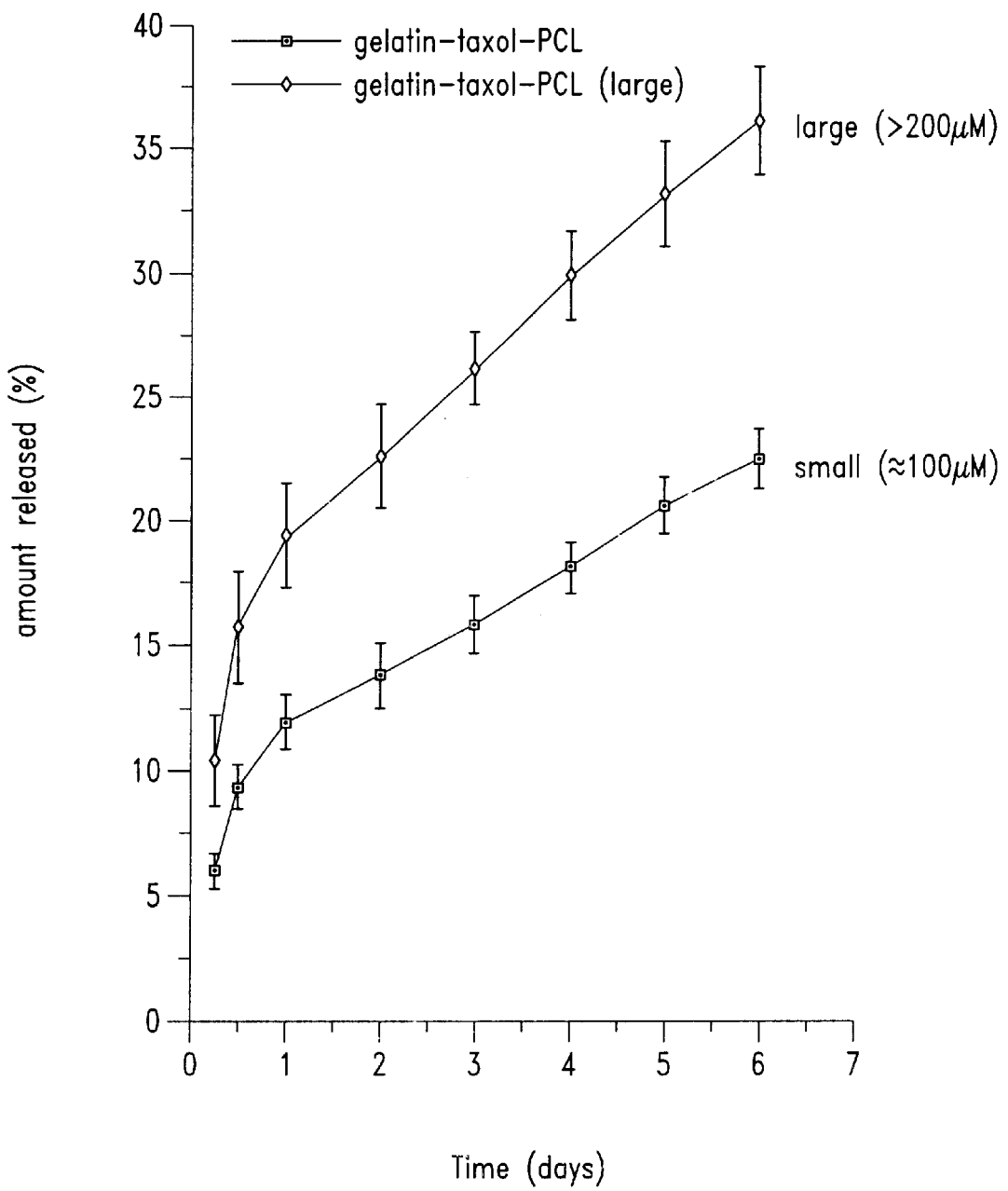
FIG. 39 is a graph which shows the percentage of paclitaxel release based upon gelatinized-paclitaxel of either a large (7200 $\mu$m) or small (2100 $\mu$m) size.
Figure 40:
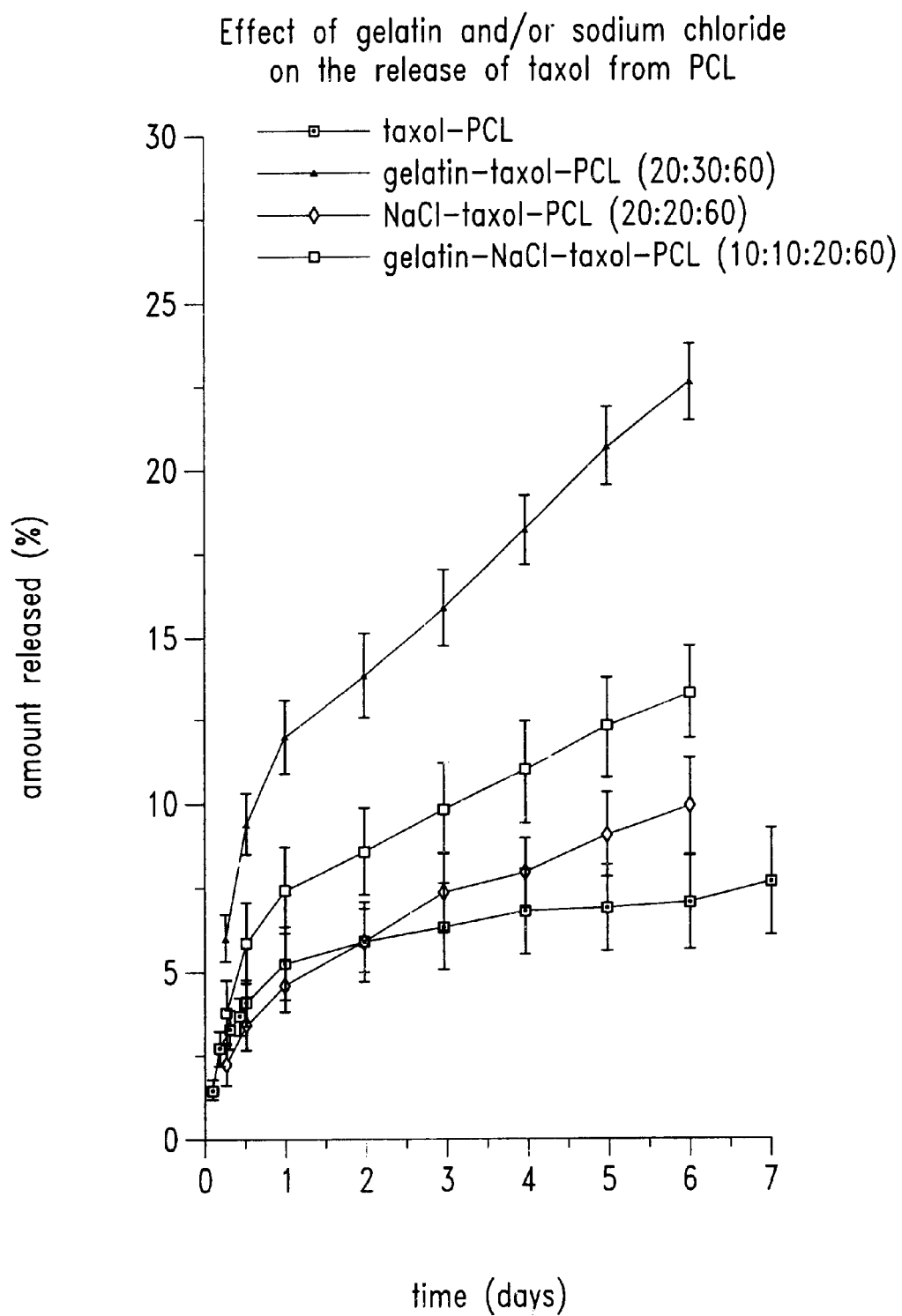
FIG. 40 is a graph which shows the effect of gelatin and/or sodium chloride on the release of paclitaxel from PCL.

A measured amount of the cylindrical polymeric composition is then added into an albumin buffered solution, and, over a time course, aliquots are removed and paclitaxel extracted with DCM. The extracts are then analyzed by HPLC. Results of these experiments are shown in FIGS. 39 and 40. Briefly, FIG. 38 shows a greater percentage of paclitaxel released when large gelatinized particles (>200 μm) are utilized. FIG. 39 shows that addition of NaCl is not preferred when higher amounts of paclitaxel release is desired.

Example 32

Copolymerization of Poly(D,L-Lactic Acid) and Polyethylene Glycol

D,L,lactide (Aldrich Chemical Co.) was added to polyethylene glycol (molecular weight 8,000; Sigma Chemical Co., St. Louis, Mo.) in a tube and heated with 0.5% stannous octoate (Sigma Chemical Co.) for 4 hours at 150° C. in an oven.

Figure 41:
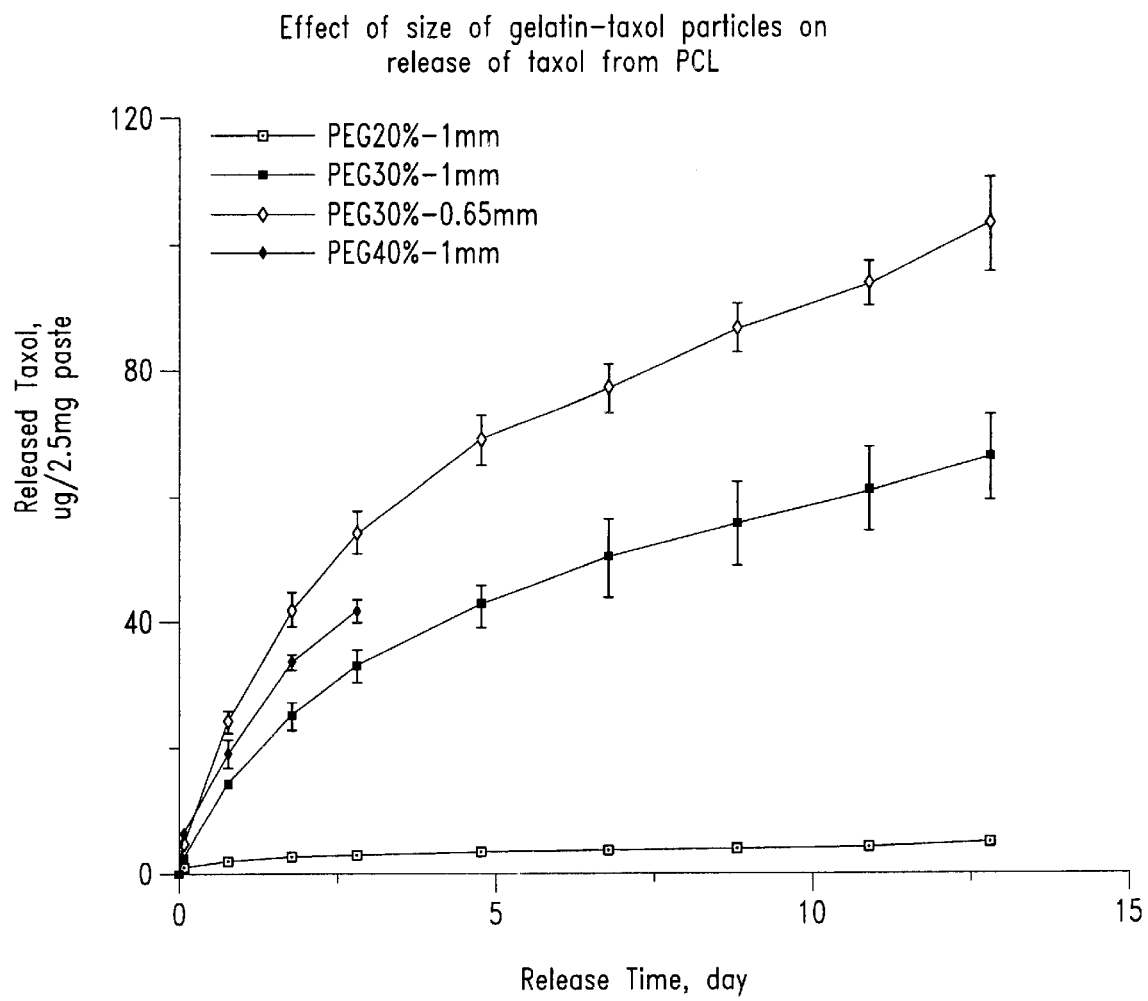
FIG. 41 is a graph which shows the release of paclitaxel from PDLLA-PEG-PDLLA cylinders containing 20% paclitaxel.

This process produces a copolymer of poly(D,L-lactic acid) with polyethylene glycol as a triblock polymer (i.e., PDLLA-PEG-PDLLA). Paclitaxel release from this polymer is shown in FIG. 41.

Example 33

Analysis of Drug Release

A known weight of a polymer (typically a 2.5 mg pellet) is added to a 15 ml test tube containing 14 ml of a buffer containing 10 mm $Na_2HPO_4$—$NaH_2PO_4$, 0.145 m NaCl and 0.4 g/l bovine serum albumin. The tubes are capped and tumbled at 37° C. At specific times all the 14 ml of the liquid buffer are removed and replaced with fresh liquid buffer.

The liquid buffer is added to 1 milliliter of methylene chloride and shaken for 1 minute to extract all the paclitaxel into the methylene chloride. The aqueous phase is then removed and the methylene chloride phase is dried under nitrogen. The residue is then dissolved in 60% acetonitrile: 40% water and the solution is injected on to a HPLC system using the following conditions: C8 column (Beckman Instruments USA), mobile phase of 58%:5%:37% acetonitrile:methanol:water at a flow rate of 1 minute per minute.

For paclitaxel the collected buffer is then analyzed at 232 nm. For MTX the collected buffer is applied directly to the HPLC column with no need for extraction in methylene chloride. MTX is analyzed at 302 nm. For Vanadium containing compounds the liquid buffer is analyzed directly using a UV/VIS spectrometer in the 200 to 300 nm range.

Example 34

Manufacture of Polymeric Compositions Containing PCL and MePEG

A. Paclitaxel Release from PCL

Figure 42A:
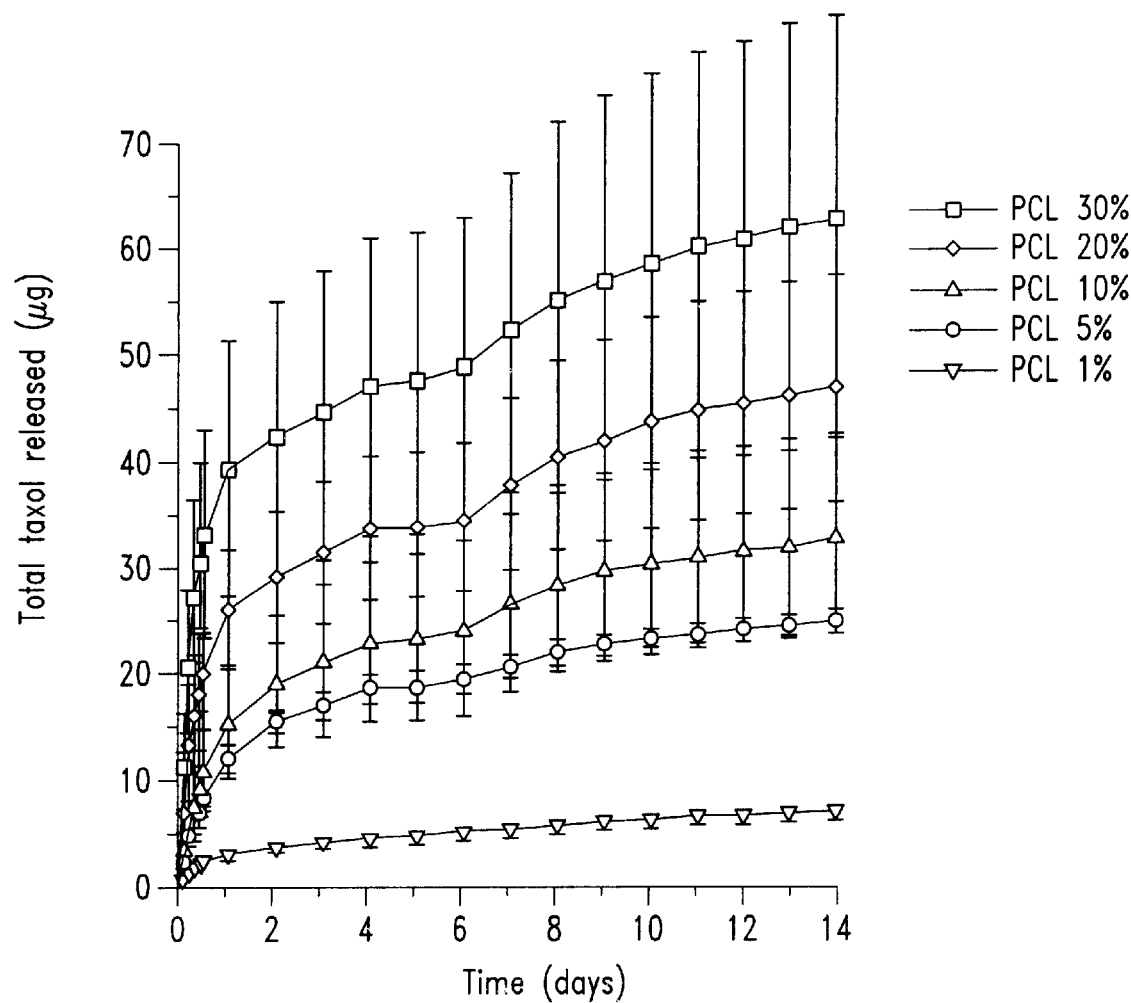
FIG. 42A is a graph which depicts the time course of paclitaxel release from 2.5 mg pellets of PCL.
Figure 42B:
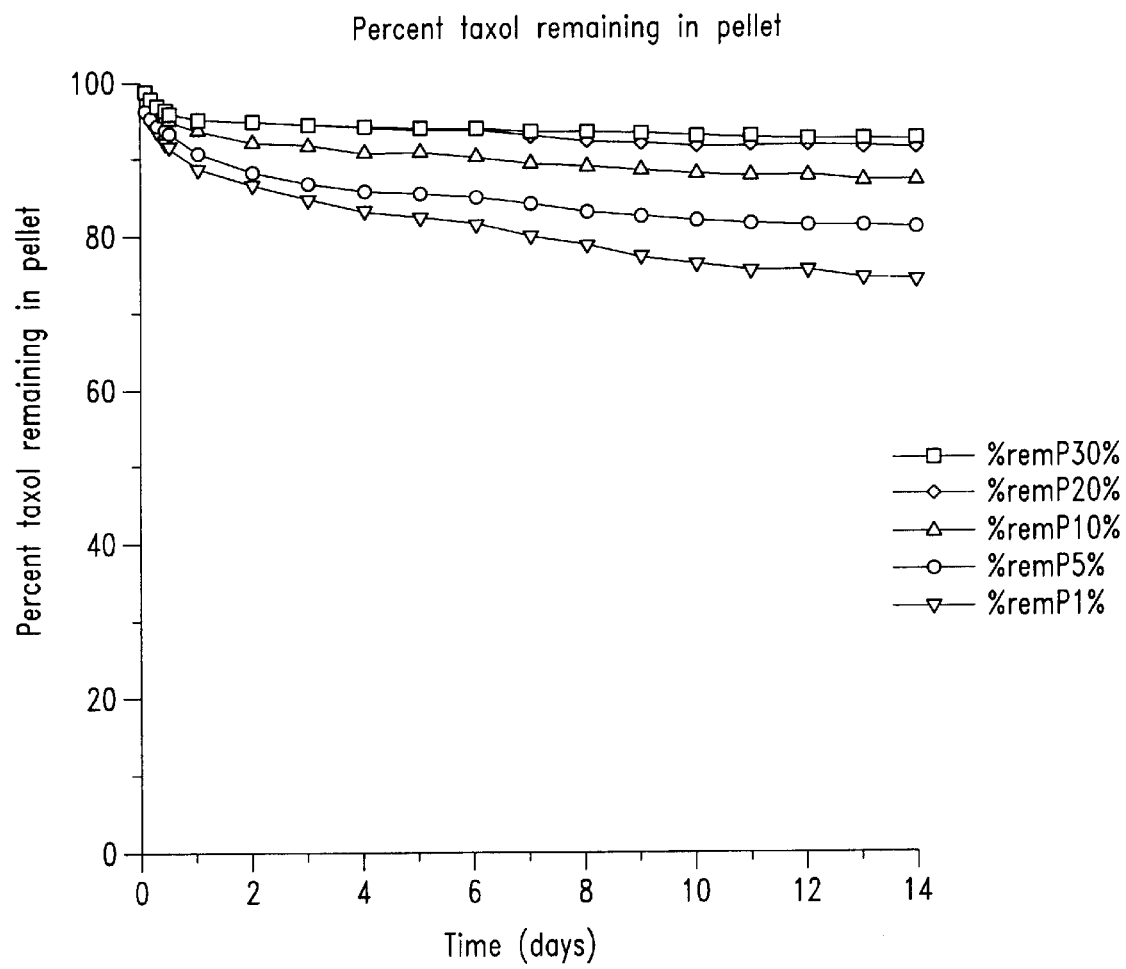
FIG. 42B is a graph which shows the percent paclitaxel remaining in the pellet, over time.

Polycaprolactone containing various concentrations of paclitaxel was prepared as described in Example 10. The release of paclitaxel over time was measured by HPLC essentially as described above. Results are shown in FIG. 42.

B. Effect of MePEG on Paclitaxel Release

Figure 43A:
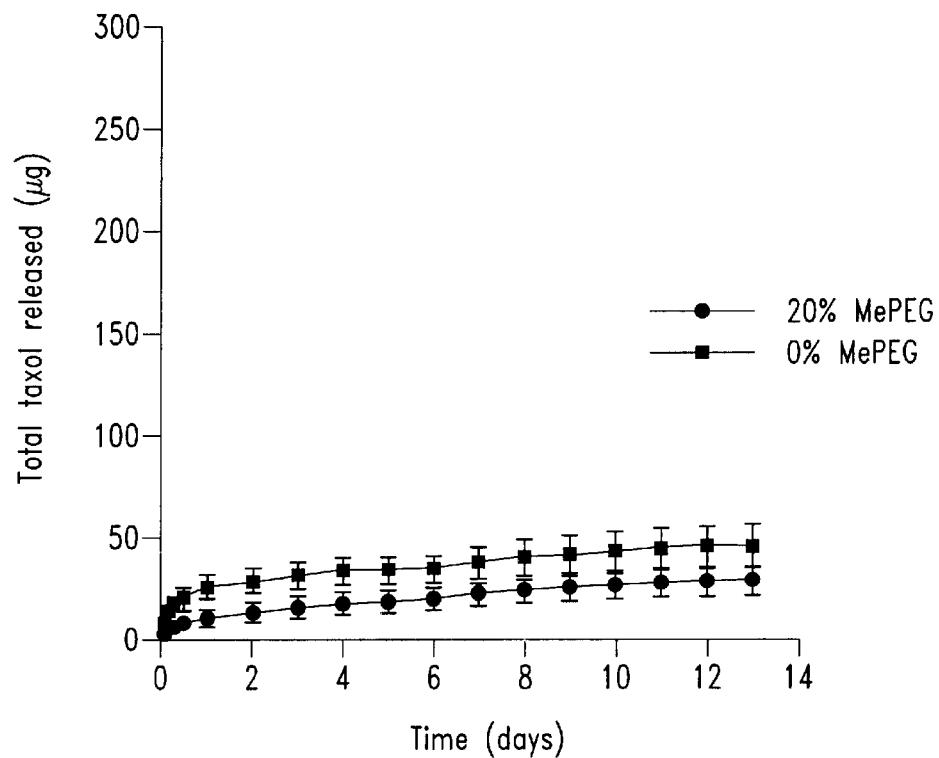
FIG. 43A is a graph which shows the effect of MePEG on paclitaxel release from PCL paste leaded with 20% paclitaxel.
Figure 43B:
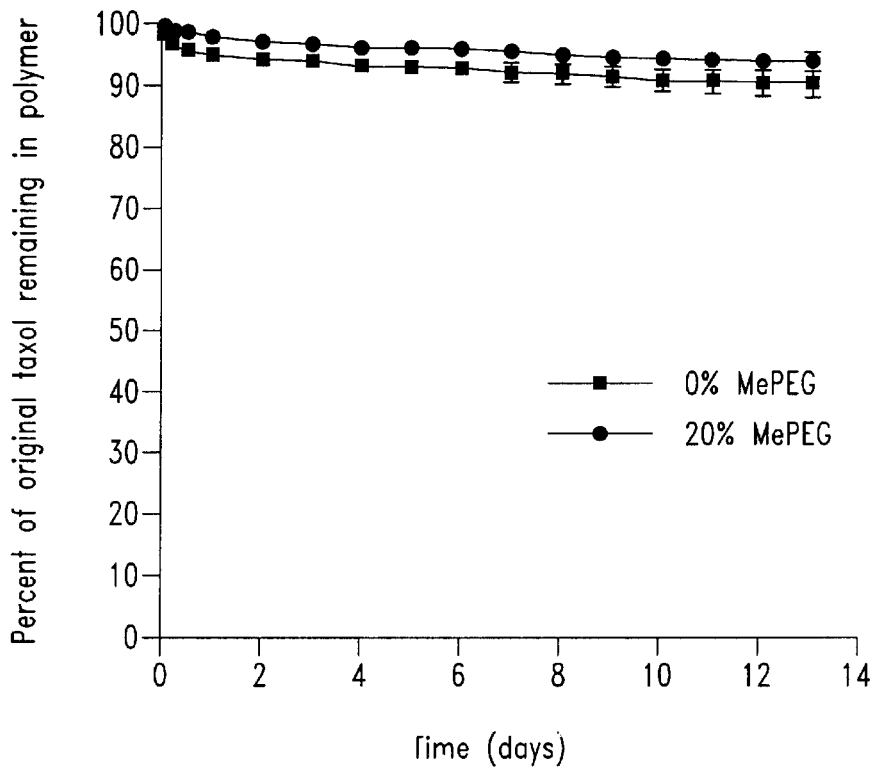
FIG. 43B is a graph which shows the percent paclitaxel remaining in the pellet, over time.

MePEG at various concentrations was formulated into PCL paste containing 20% paclitaxel, utilizing the methods described in Example 10. The release of paclitaxel over time was measured by HPLC essentially as described above. Results of this study are shown in FIG. 43.

C. Effect of MePEG on the Melting Point of PCL

Figure 44A:
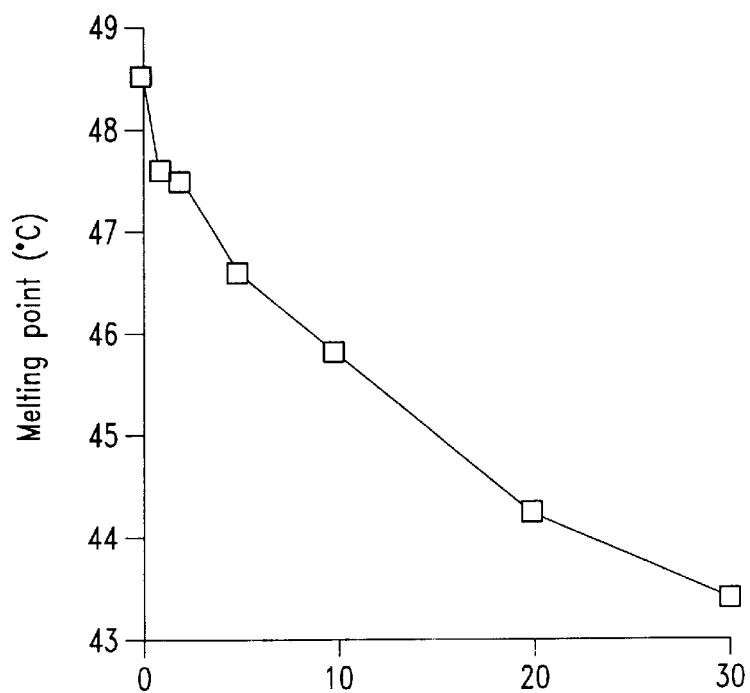
FIGS. 44A and 44B are graphs which show the effect of various concentrations of MePEG in PCL in terms of melting point (44A) and time to solidify (44B).
Figure 44B:
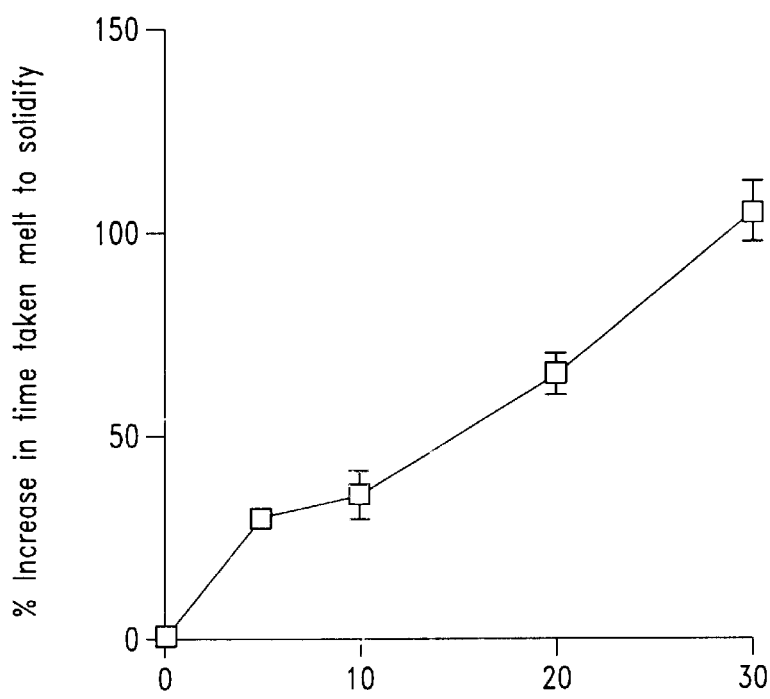

MePEG at various concentrations (formulated into PCL paste containing 20% paclitaxel) was analyzed for melting point using DSC analysis at a heating rate of 2.5° C. per minute. Results are shown in FIGS. 44A (melting point vs. % MePEG) and 44B (percent increase in time to solidify vs. % MePEG).

D. Tensile Strength of MePEG Containing PCL

Figure 45:
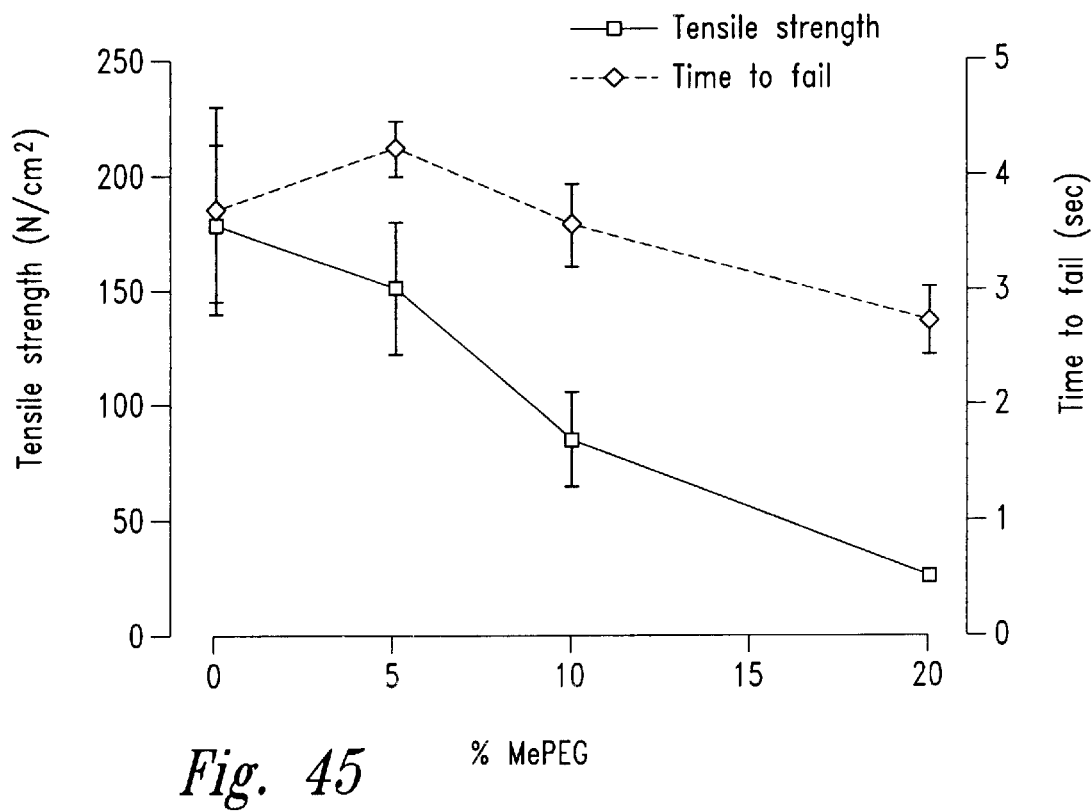
FIG. 45 is a graph which shows the effect of MePEG incorporation into PCL on the tensile strength and time to fail of the polymer.

PCL containing MePEG at various concentrations was tested for tensile strength and time to fail by a CT-40 Mechanical Strength Tester. Results are shown in FIG. 45.

E. Effect of γ-irradiation or the Release of Paclitaxel

Figure 46:
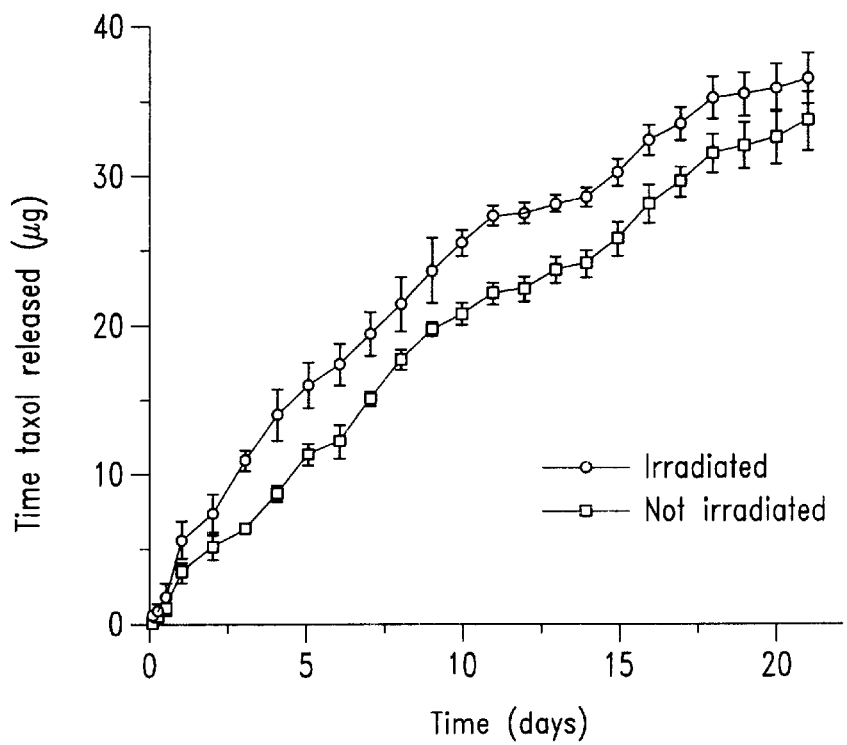
FIG. 46 is a graph which shows the effect of irradiation on paclitaxel release.

PCL:MePEG (80:20) paste loaded with 20% paclitaxel was γ-irradiated and analyzed for paclitaxel release over time. Results are set forth in FIG. 46.

In summary, based on the above experiments it can be concluded that the addition of MePEG makes the polymer less brittle and more wax like, reduces the melting point and increases the solidification time of the polymer. All these factors improve the application properties of the paste. At low concentrations (20%) MePEG has no effect on the release of paclitaxel from PCL. Gamma-irradiation appears to have little effect on paclitaxel release.

Example 35

Methotrexate-Loaded Paste

A. Manufacture of Methotrexate-Loaded Paste

Methotrexate ("MTX"; Sigma Chemical Co.) is ground in a pestle and mortar to reduce the particle size to below 5 microns. It is then mixed as a dry powder with polycaprolactone (molecular wt 18000 Birmingham Polymers, AL USA). The mixture is heated to 65° C. for 5 minutes and the molten polymer/methotrexate mixture is stirred into a smooth paste for 5 minutes. The molten paste is then taken into a 1 mL syringe, and extruded as desired.

B. Results

Figure 47A:
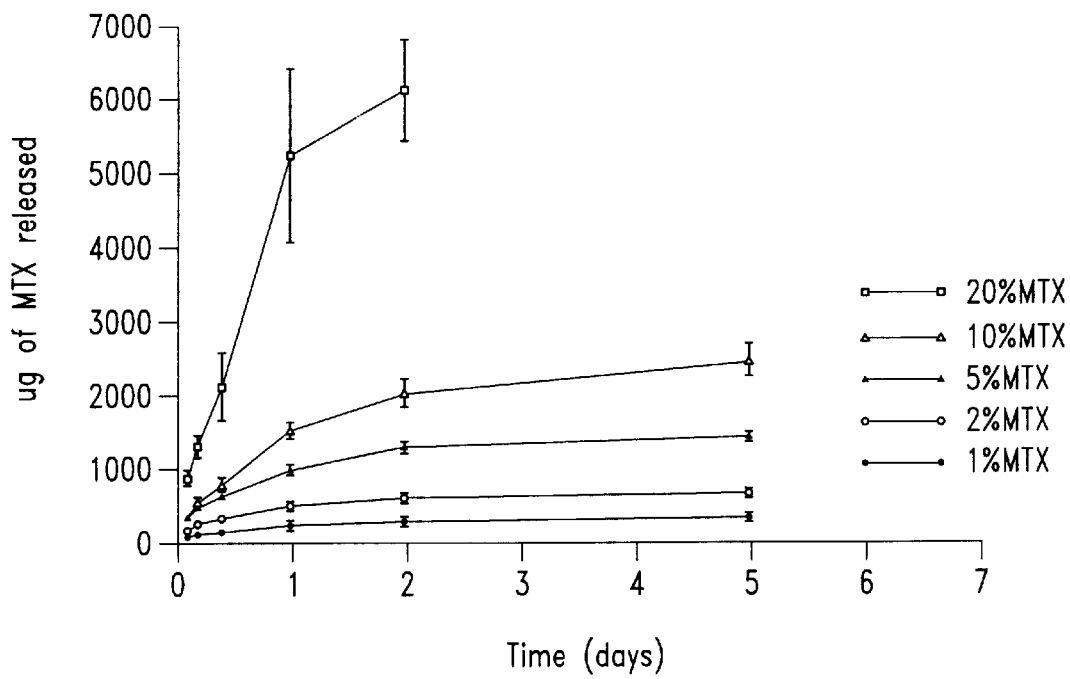
FIGS. 47A, B, C, D and E show the effect of MTX release from PCL over time.
Figure 47B:
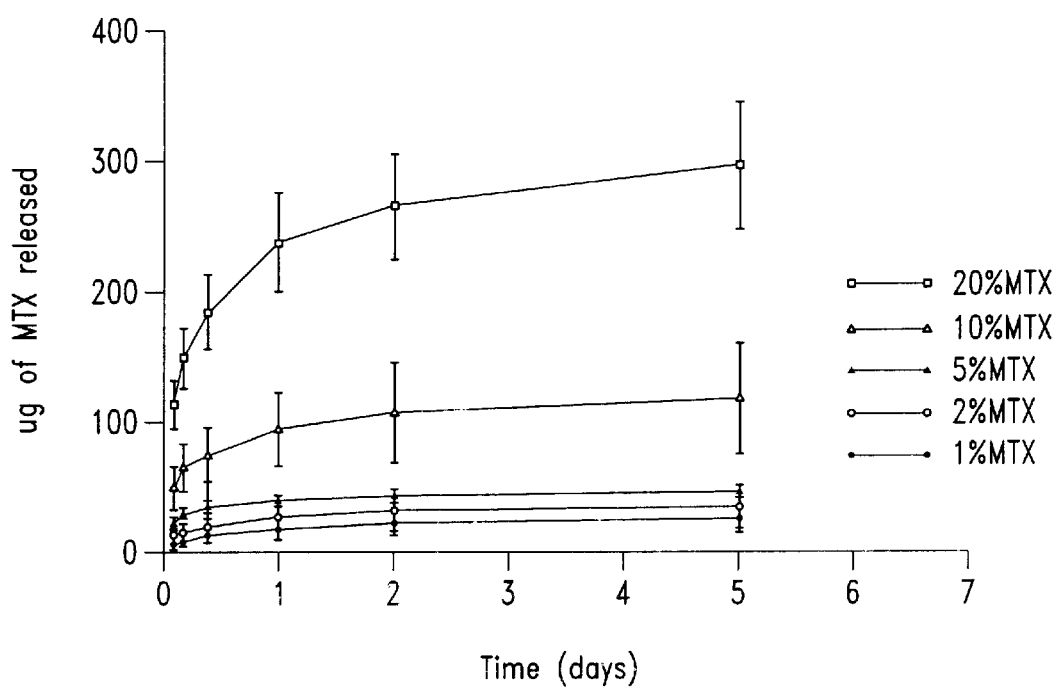
Figure 47C:
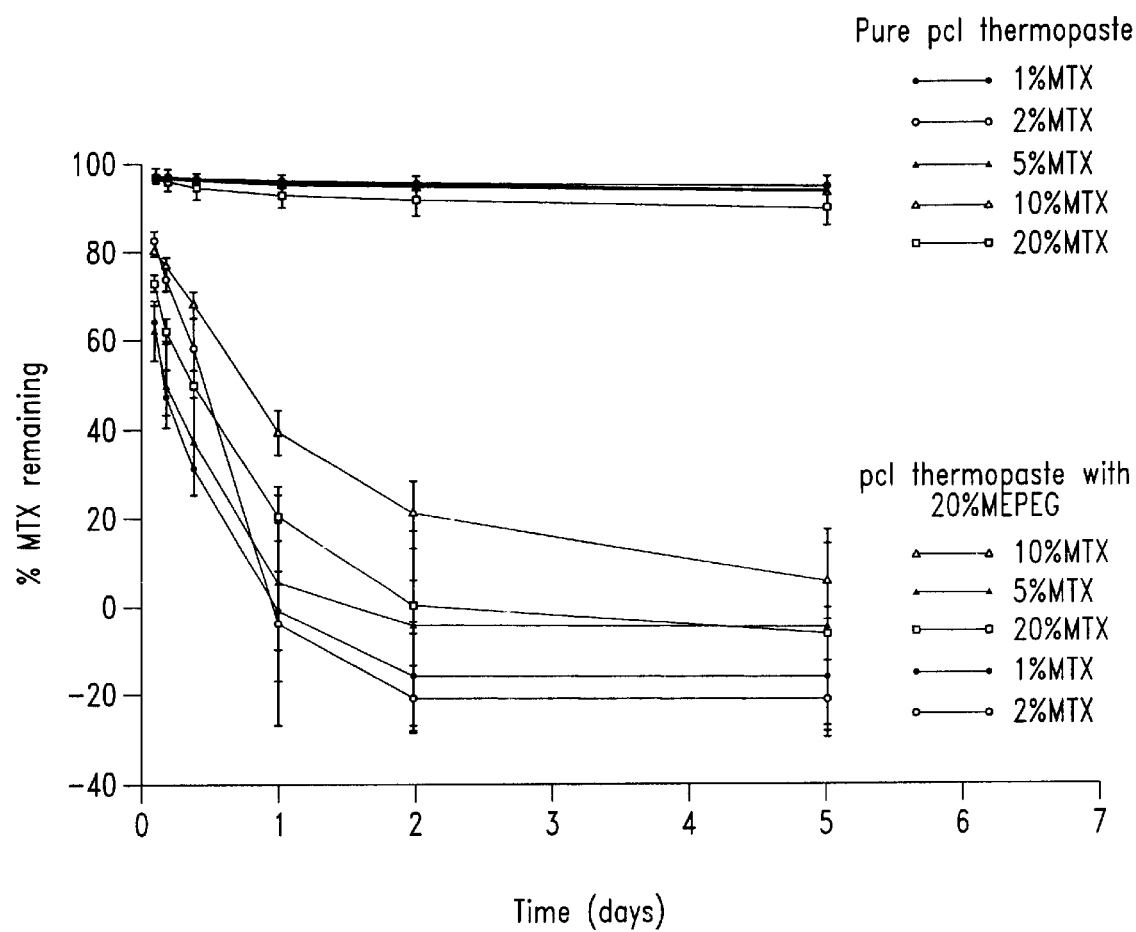

Results are shown in FIGS. 47A–E. Briefly, FIG. 47A shows MTX release from PCL discs containing 20% MePEG and various concentrations of MTX. FIG. 47B shows a similar experiment for paste which does not contain MePEG. FIGS. 47C, D, and E show the amount of MTX remaining in the disk.

As can be seen by the above results, substantial amounts of MTX can be released from the polymer when high MePEG concentrations are utilized.

Example 36

Manufacture of Microspheres Containing Methotrexate

A. Microspheres With MTX Alone

Methotrexate (Sigma) was ground in a pestle and mortar to reduce the particle size to below 5 microns. One hundred milliliters of a 2.5% PVA (w/v) (Aldrich or Sigma) in water was stirred for 15 minutes with 500 mg of unground MTX at 25° C. to saturate the solution with MTX. This solution was then centrifuged at 2000 rpm to remove undissolved MTX and the supernatant used in the manufacture of microspheres.

Briefly, 10 ml of a 5% w/v solution of poly(DL) lactic acid (molecular weight 500,000; Polysciences), Polylactic:glycolic acid (50:50 IV 0.78 polysciences) or polycaprolactone (molecular weight 18,000, BPI) containing 10:90 w/w MTX (ground):POLYMER were slowly dripped into 100 mL of the MTX saturated 2.5% w/v solution of PVA (Aldrich or Sigma) with stirring at 600 rpm. The mixture was stirred at 25° C. for 2 hours and the resulting microspheres were washed and dried.

Using this method MTX loaded microspheres can be reproducibly manufactured in the 30 to 160 micron size range.

Figure 60:
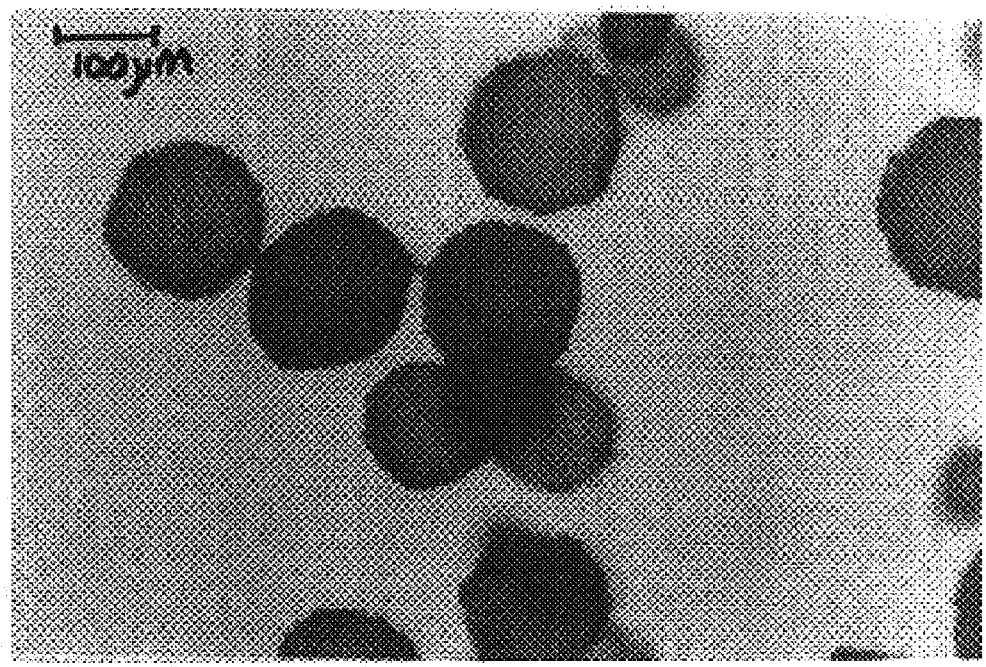
FIG. 60 is a photograph of 10% methotrexate ("MTX") loaded microspheres made from a 50:50 ratio of PLA:GA (IV 0.78).

FIG. 60 depicts the results for 10% methotrexate-loaded microspheres made from PLA:GA (50:50); Inherent Viscosity "IV"=0.78.

B. Microspheres with MTX and Hyaluronic Acid

MTX loaded microspheres can be made using hyaluronic acid ("HA") as the carrier by a water in oil emulsion manufacture method, essentially as described below. Briefly, 50 ml of Parafin oil (light oil; Fisher Scientific) is warmed to 60° C. with stirring at 200 rpm. A 5 mL solution of sodium hyaluronate (20/mL); source=rooster comb; Sigma) in water containing various amounts MTX is added dropwise into the Parafin oil. The mixture is stirred at 200 rpm for 5 hours, centrifuged at 500× g for 5 minutes. The resulting microspheres are washed in hexane four times, and allowed to dry.

Example 37

Manufacture of Polymeric Compositions Containing Vanadium Compounds

A. Polymeric Paste Containing Vanadyl Sulfate

Vanadyl Sulfate (Fisher Scientific) is first ground in a pestle and mortar to reduce the particle size, then dispersed into melted PCL as described above for MTX. It is then taken up into a syringe to solidify and is ready for use.

Drug release was determined essentially as described above in Example 33, except that a 65 mg pellet of a 10% w/w $VOSO_4$:PCL was suspended in 10 ml of water and the supernatant analyzed for released Vanadyl Sulphate using UV/Vis absorbance spectroscopy of the peak in the 200 to 300 nm range.

Figure 61:
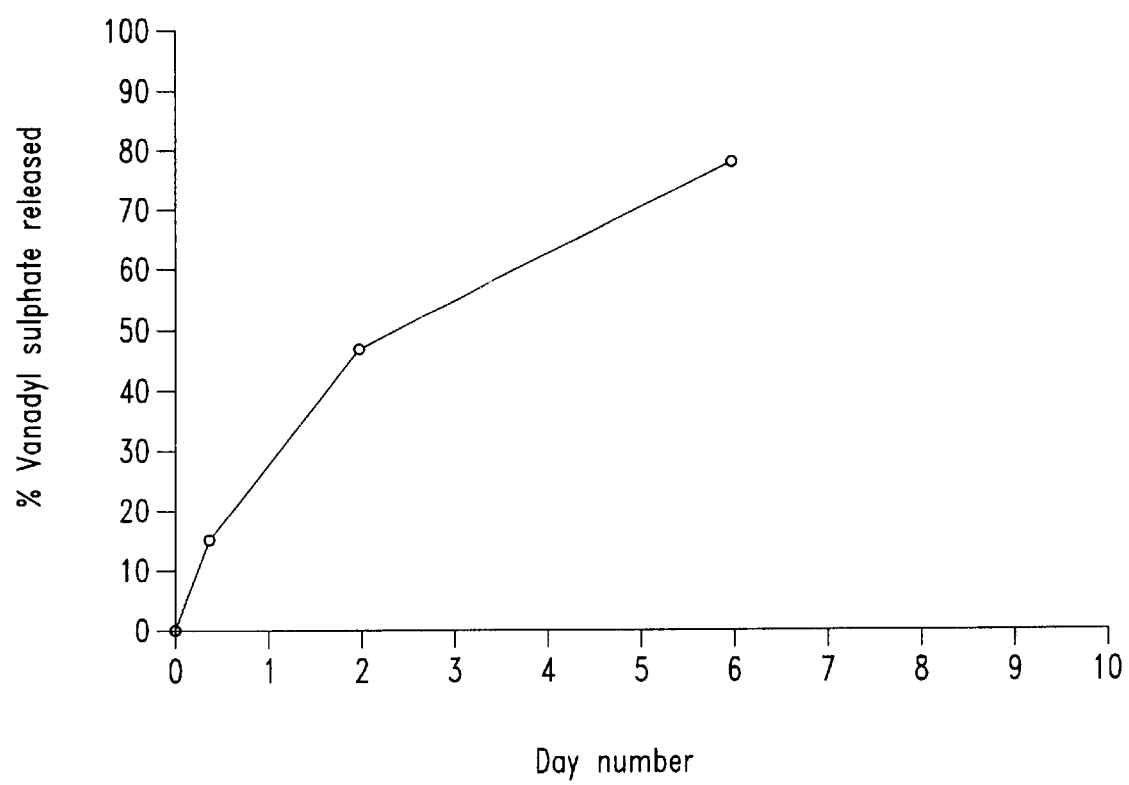
FIG. 61 is a graph which depicts the release of 10% loaded vanadyl sulfate from PCL.

Results are shown in FIG. 61. Briefly, from a polymeric composition containing 10% $VOSO_4$, 1 mg of $VOSO_4$ was released in 6 hours, 3 mg after 2 days and 5 mg by day 6.

B. Polymeric Microspheres Containing Vanadyl Sulfate

Figure 62:
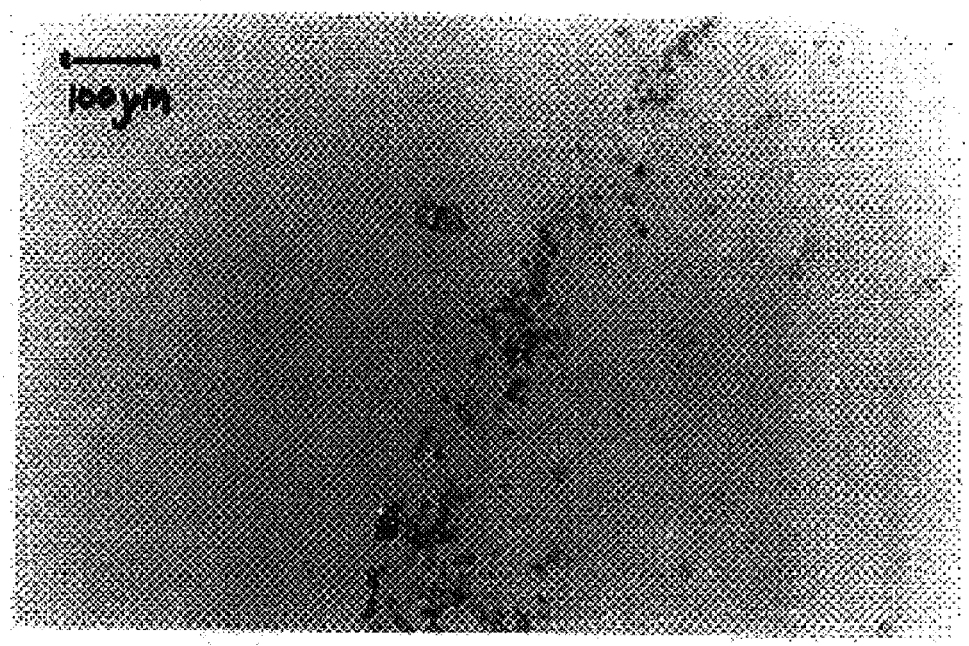
FIG. 62 is a photograph of hyaluronic acid microspheres containing vanadium sulfate.

Vanadyl sulfate was incorporated into microspheres of polylactic acid or hyaluronic acid essentially as described in Example 36B. Results are shown in FIG. 62.

C. Polymeric Paste Containing Organic Vanadate

Figure 63A:
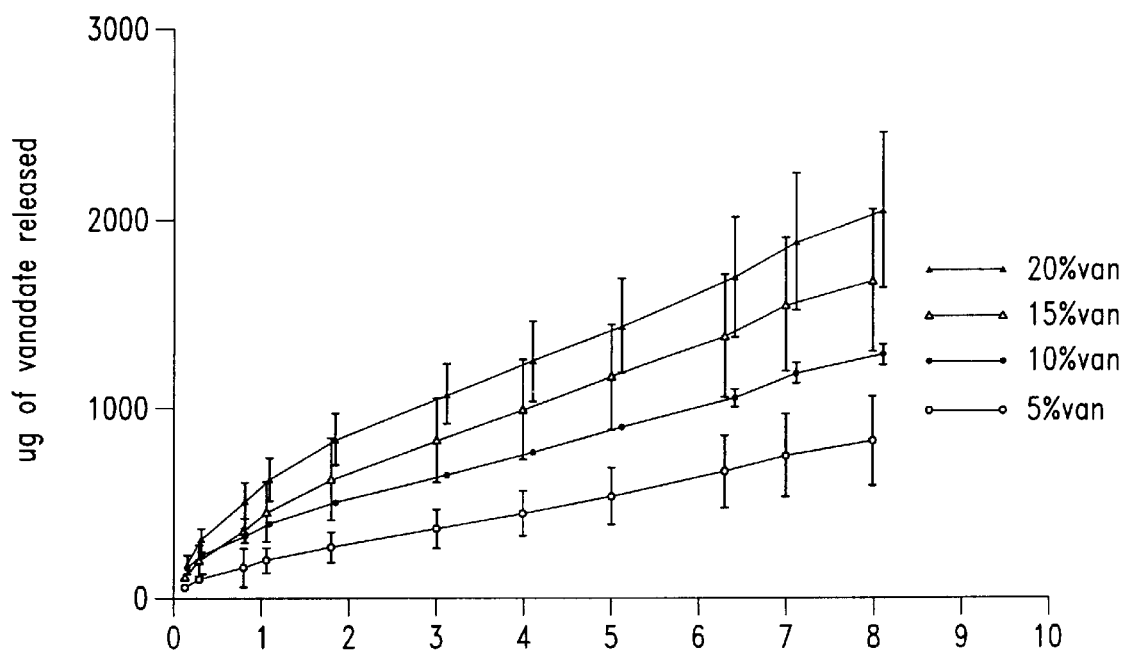
FIG. 63A is a graph which depicts the release of organic vanadate from PCL.
Figure 63B:
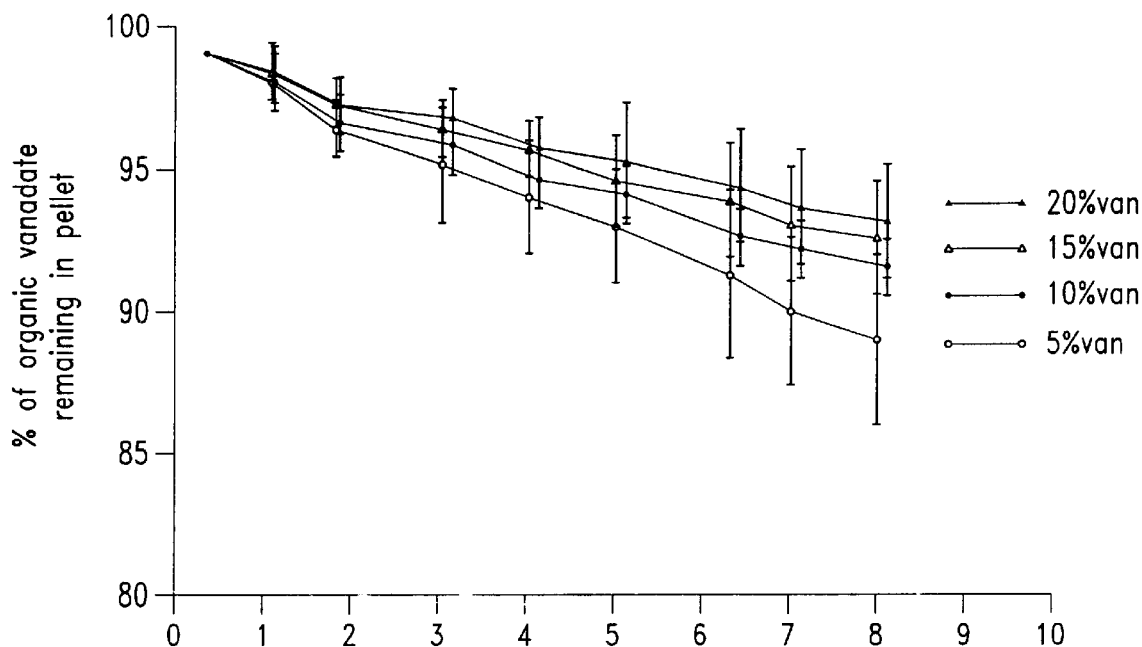
FIG. 63B depicts the percentage of organic vanadate remaining over a time course.

Organic vanadate is loaded into a PCL paste essentially as described above in Example 35. Vanadate release from the microspheres was determined as described above and in Example 33. Results are shown in FIGS. 63A and 63B.

D. Organic Vanadate Containing Microspheres

Figure 64:
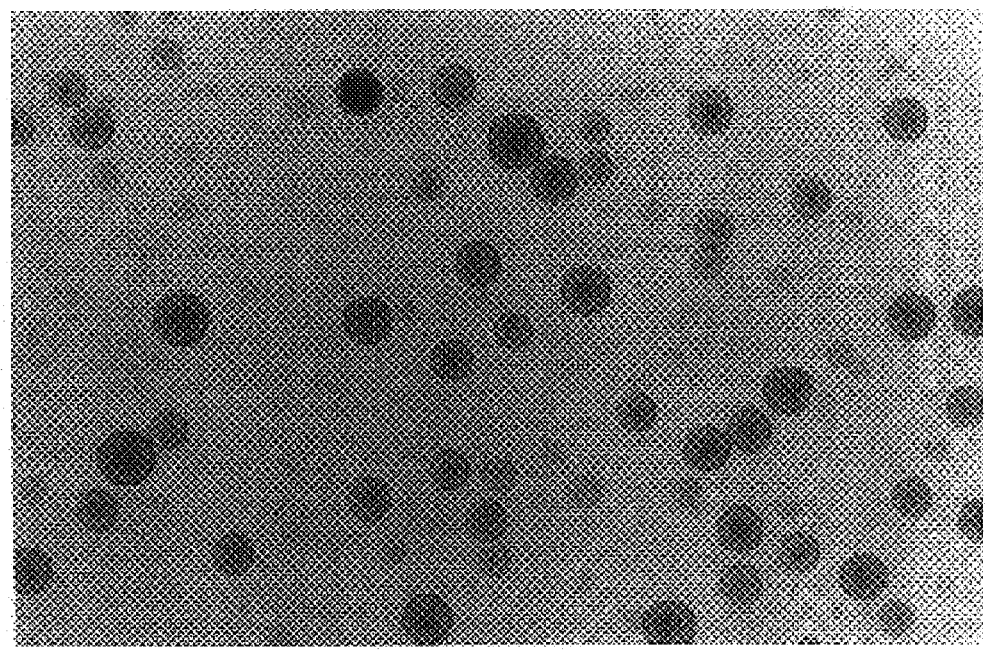
FIG. 64 is a photograph showing poly D,L, lactic acid microspheres containing organic vanadate.

Organic vanadate may also be loaded into microspheres essentially as described in Example 36A. Such microspheres are shown in FIG. 64 for poly D,L lactic acid (M.W. 500,000; Polysciences).

Example 38

Polymeric Compositions with Increased Concentrations of Paclitaxel

PDLLA-MePEG and PDLLA-PEG-PDLLA are block copolymers with hydrophobic (PDLLA) and hydrophilic (PEG or MePEG) regions. At appropriate molecular weights and chemical composition, they may form tiny aggregates of hydrophobic PDLLA core and hydrophilic MePEG shell. Paclitaxel can be loaded into the hydrophobic core, thereby providing paclitaxel with an increased "solubility".

A. Materials

D,L-lactide was purchased from Aldrich, Stannous octoate, poly (ethylene glycol) (mol. wt. 8,000), MePEG (mol. wt. 2,000 and 5,000) were from Sigma. MePEG (mol. wt. 750) was from Union Carbide. The copolymers were synthesized by a ring opening polymerization procedure using stannous octoate as a catalyst (Deng et al, *J. Polym. Sci., Polym, Lett.* 28:411–416, 1990; Cohn et al, *J. Biomed, Mater. Res.* 22: 993–1009, 1988).

For synthesizing PDLLA-MePEG, a mixture of DL-lactide/MePEG/stannous octoate was added to a 10 milliliter glass ampoule. The ampoule was connected to a vacuum and sealed with flame. Polymerization was accomplished by incubating the ampoule in a 150° C. oil bath for 3 hours. For synthesizing PDLLA-PEG-PDLLA, a mixture of D,L-lactide/PEG/stannous octoate was transferred into a glass flask, sealed with a rubber stopper, and heated for 3 hours in a 150° C. oven. The starting compositions of the copolymers are given in Tables V and VI. In all the cases, the amount of stannous octoate was 0.5%–0.7%.

B. Methods

The polymers were dissolved in acetonitrile and centrifuged at 10,000 g for 5 minutes to discard any non-dissolvable impurities. Paclitaxel acetonitrile solution was then added to each polymer solution to give a solution with paclitaxel (paclitaxel+polymer) of 10%-wt. The solvent acetonitrile was then removed to obtain a clear paclitaxel/PDLLA-MePEG matrix, under a stream of nitrogen and 60° C. warming. Distilled water, 0.9% NaCl saline, or 5% dextrose was added at four times weight of the matrix. The matrix was finally "dissolved" with the help of vortex mixing and periodic warming at 60° C. Clear solutions were obtained in all the cases. The particle sizes were all below 50 nm as determined by a submicron particle sizer, NICOMP Model 270. The formulations are given in Table V.

TABLE V

Formulations of Paclitaxel/PDLLA-MePEG*

| PDLLA-MePEG | Dissolving Media | Paclitaxel Loading (final paclitaxel concentrate) |
|---|---|---|
| 2000/50/50 | water | 10% (20 mg/ml) |
| 2000/40/60 | water | 10% (20 mg/ml) |
| 2000/50/50 | 0.9% saline | 5% (10 mg/ml) |
| 2000/50/50 | 0.9% saline | 10% (20 mg/ml) |
| 2000/50/50 | 5% dextrose | 10% (10 mg/ml) |
| 2000/50/50 | 5% dextrose | 10% (20 mg/ml) |

In the case of PDLLA-PEG-PDLLA, since the copolymers cannot dissolve in water, paclitaxel and the polymer were co-dissolved in acetone. Water or a mixture of water/acetone was gradually added to this paclitaxel polymer solution to induce the formation of paclitaxel/polymer spheres.

TABLE VI

Composition of PDLLA-PEG-PDLLA

| Copolymer Name | Wt. of PEG (g) | Wt. of DL-lactide (g) |
|---|---|---|
| PDLLA-PEG-PDLLA 90/10 | 1 | 9 |
| PDLLA-PEG-PDLLA 80/20 | 2 | 8 |
| PDLLA-PEG-PDLLA 70/30 | 3 | 7 |
| PDLLA-PEG-PDLLA 60/40 | 4 | 6 |
| PDLLA-PEG-PDLLA 30-/70 | 14 | 6 |

* PEG molecular weight 8,000

C. Results

Many of the PDLLA-MePEG compositions form clear solutions in water, 0.9% saline, or 5% dextrose, indicating the formation of tiny aggregates in the range of nanometers. Paclitaxel was loaded into PDLLA-MePEG nanoparticles successfully. For example, at % loading (this represents 10 mg paclitaxel in 1 ml paclitaxel/PDLLA-MePEG/aqueous system), a clear solution was obtained from 2000-50/50 and 200040/60. The particle size was about 20 nm.

Example 39

Insertion of Control and Paclitaxel Coated Stents into Microswine

As discussed above, various tubes within the body can be occluded by disease processes. One method for treating such occlusion is to insert an endoluminal stent within the tube in order to relieve the obstruction. Unfortunately, the stents themselves are often overgrown by epithelial cells, thus limiting the duration and effectiveness of the treatment. As described in more detail below, stainless steel stents were coated with paclitaxel-loaded EVA polymer and placed into the biliary duct of microswine in order to assess prevention of benign epithelial overgrowth.

A. Materials and Methods

Yucatan microswine were placed under general anesthetic and a 5 cm transverse upper abdominal incision performed. The gallbladder was grasped and sewn to the anterior abdominal wall and a tiny incision was made in the gallbladder fundus. A 5F catheter was inserted into the gallbladder and radiopaque contrast injected to outline the biliary tree. A hydrophilic guidewire was advanced through the cystic duct into the common bile duct, and over this a 7F (purpose—built, reusable) delivery catheter containing a stainless steel (5 mm diameter×4.2 cm long) was advanced and deployed in the common bile duct. The delivery catheter was withdrawn into the gallbladder and a repeat cholangiogram performed. The gallbladder incision was closed, a radiopaque staple was fixed at the incision site, and then the abdominal incision was closed. The swine was randomized into groups of receiving uncoated stents, polymer coated stents, and paclitaxel-loaded (33%) polymer coated stents. Tantalum (strecker) stainless steel stents and stainless steel Wallstents were used for each of these studies. Swines from each group were sacrificed at 14, 28, 56, and 112 days post-stent insertion by injecting Euthanyl. After sacrifice, the gallbladder was cannulated percutaneously under X-ray by puncturing at the staple and radiopaque contrast injected to outline the biliary tree. X-rays were taken and analyzed for narrowing at or adjacent to the stent. The liver and biliary tree were removed en bloc. The portion of bile duct containing the stent was sectioned transversely at 1 cm intervals and the histologic sections were used to assess the degree of overgrowth of the stent. The liver was also examined histologically for signs of chronic obstruction or inflammation.

B. Results

Figure 65A:
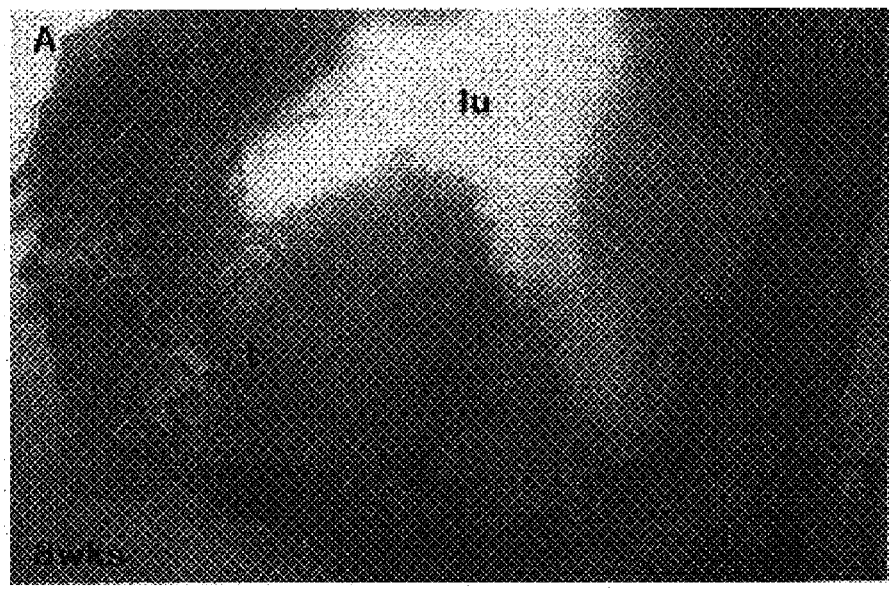
FIGS. 65A and 65B are photographs of control (uncoated) stents which show typical epithelial ingrowth seen at both 8 weeks (A) and at 16 weeks (B). Indentations of the stent tines (t) and narrowing of the lumen (lu) are shown. There is progressive epithelial overgrowth of the stent surface over this time by fibrous and inflammatory tissue.
Figure 65B:
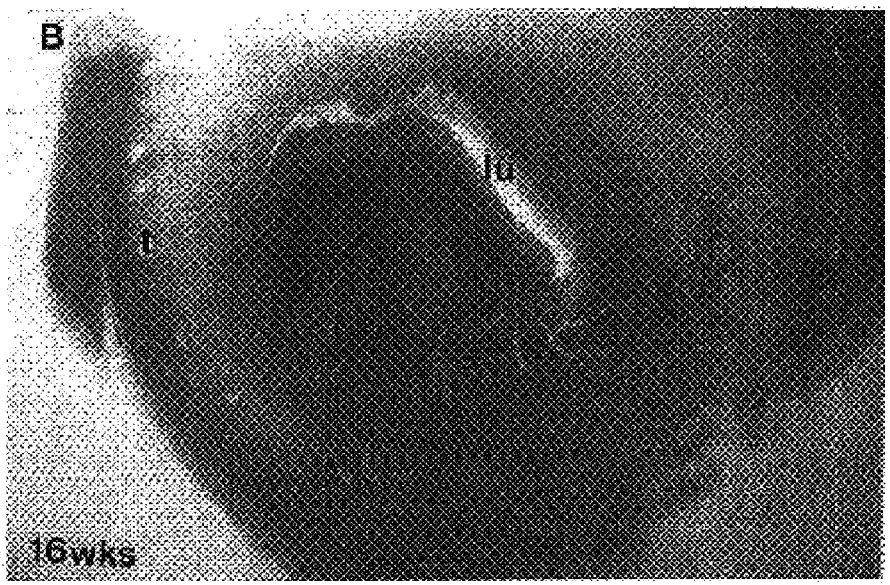
Figure 66A:
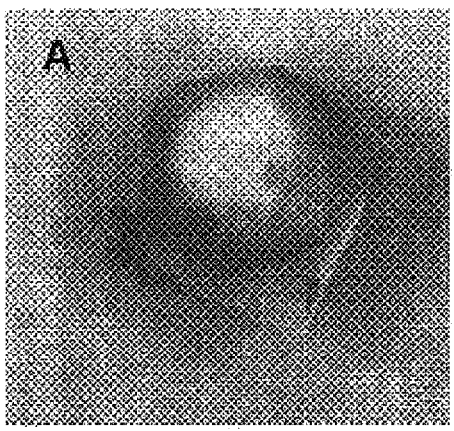
FIGS. 66A, 66B, 66C, and 66D are a series of photographs which show control and paclitaxel-coated biliary stents.
Figure 66C:
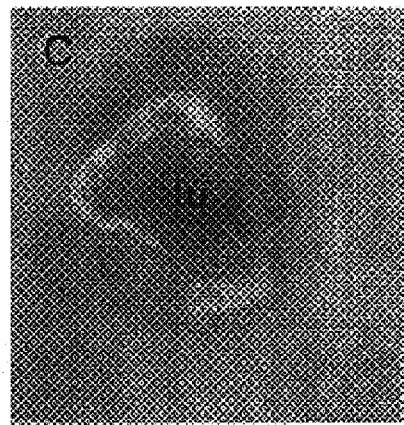
Figure 66B:

Control, uncoated stainless steel stents were inserted into microswine as described above, and sacrificed at various times. At two weeks, the bile mucosa appeared normal in 2 of the sacrificed pigs, while one presented a small non-obstructive bile concretion within the biliary lumen, and a slight indentation in the bile duct mucosa at the site of the tines. At 4 weeks, of the 3 pigs which were sacrificed a small bile concretion was present on the distal stent, as well as mucosal indentations of the stent tine within the bile duct mucosa. At 8 weeks, the bile duct mucosa at the site of stent insertion in the sacrificed pigs partially overgrew the stent tines in a crescentic manner over approximately 25–30% of the radius of the stent (FIGS. 65A, 66A, and 66B). In addition, one pig contained thick bile containing inflammatory cells within the lumen. At 16 weeks, pigs which were sacrificed presented a stent which was completely overgrown distally by fibrous tissue, and no evidence of a lumen (FIG. 65B). Histologically, the tissue was uniformly fibrous. Surprisingly, the liver biopsy of all of the control treated swines were normal and there was no evidence of obstructive changes.

Figure 66D:

In another group of microswine, stents coated with ethylene vinyl acetate and 33% paclitaxel were inserted into the biliary duct. After an 8 week exposure, one pig was sacrificed and showed a slight indentation of the bile duct mucosa at the site of the stent tines and no indication of overgrowth (FIGS. 66C and 66D). The underlying mucosa was normal apart from some inflammatory cell infiltration. Non-obstructive bile concretions were noted in the lumen of the stent. The liver biopsy was normal, with no evidence of obstructive changes.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for embolizing a blood vessel, comprising delivering into said vessel a therapeutically effective amount of a composition comprising a compound which disrupts microtubule function, wherein said compound is paclitaxel, or an analogue or derivative thereof, such that said blood vessel is effectively occluded.

2. The method according to claim 1 wherein said paclitaxel, or an analogue or derivative thereof is paclitaxel.

3. The method according to claim 1 or 2 wherein said composition further comprises a polymeric carrier.

4. The method according to claim 3 wherein said composition is formed into microspheres.

5. The method according to claim 3 wherein said polymeric carrier is poly(ethylene-vinyl acetate) crosslinked with 40% vinyl acetate.

6. The method according to claim 3, wherein said polymeric carrier is poly(lactic-co-glycolic acid).

7. The method according to claim 3 wherein said polymeric carrier is poly(caprolactone).

8. The method according to claim 3 wherein said polymeric carrier is poly(lactic acid).

9. The method according to claim 3 wherein said polymeric carrier is a copolymer of poly(lactic acid) and poly(caprolactone).

10. The method according to claim 3 wherein said polymeric carrier is a copolymer of poly(ethylene-vinyl acetate) crosslinked with 40% vinyl acetate, and poly(lactic acid).

11. The method according to claim 1 or 2 wherein said blood vessel nourishes a tumor.

12. The method according to claim 1 or 2 wherein said blood vessel nourishes a non-tumorigenic, angiogenesis-dependent disease.

13. The method according to claim 3 wherein said blood vessel nourishes a tumor.

14. The method according to claim 3 wherein said blood vessel nourishes a non-tumorigenic, angiogenesis-dependent disease.

15. The method according to claim 3 wherein said polymeric carrier is biodegradable.

* * * * *

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 9 amino acids
      (B) TYPE: amino acid
      (C) STRANDEDNESS:
      (D) TOPOLOGY: linear (xi) SEQUENCE DESCRIPTION: SEQ ID NO: 1:

```
Cys Asp Pro Gly Tyr Ile Gly Ser Arg
1               5
```